United States Patent [19]

Gee

[11] Patent Number: 4,927,453
[45] Date of Patent: May 22, 1990

[54] HERBICIDAL SULFONAMIDES

[75] Inventor: Stephen K. Gee, Wilmington, Del.

[73] Assignee: E. I. Du Pont de Nemours and Company, Wilmington, Del.

[21] Appl. No.: 238,108

[22] Filed: Aug. 30, 1988

Related U.S. Application Data

[63] Continuation-in-part of Ser. No. 85,852, Aug. 17, 1987, abandoned, which is a continuation of Ser. No. 920,051, Oct. 17, 1986, abandoned.

[51] Int. Cl.$^5$ .................... A01N 43/54; C07D 239/69
[52] U.S. Cl. .............................. 71/92; 71/90; 71/86; 71/87; 544/296; 544/243; 544/321; 544/323; 544/324; 544/331; 544/332; 544/229
[58] Field of Search ........................ 71/86, 87, 90, 92; 544/295, 243, 321, 323, 324, 331, 332, 229

[56] References Cited

U.S. PATENT DOCUMENTS

| | | | |
|---|---|---|---|
| 4,310,346 | 1/1982 | Levitt et al. | 71/92 |
| 4,332,611 | 6/1982 | Peterson | 71/92 |
| 4,348,219 | 9/1982 | Levitt | 71/92 |
| 4,348,220 | 9/1982 | Schwing | 71/92 |
| 4,424,377 | 1/1984 | Schwing | 564/91 |
| 4,443,243 | 4/1984 | Fory et al. | 71/93 |
| 4,454,335 | 6/1984 | Levitt | 560/12 |
| 4,478,635 | 10/1984 | Meyer et al. | 71/92 |
| 4,480,101 | 10/1984 | Meyer | 544/320 |
| 4,510,325 | 4/1985 | Meyer et al. | 564/89 |
| 4,515,626 | 7/1985 | Szczepanski | 71/93 |
| 4,540,782 | 9/1985 | Meyer | 544/194 |
| 4,545,811 | 10/1985 | Meyer et al. | 71/93 |
| 4,559,078 | 12/1985 | Maier et al. | 71/87 |
| 4,579,584 | 4/1986 | Meyer et al. | 71/93 |
| 4,594,097 | 6/1986 | Schurter et al. | 71/93 |
| 4,632,693 | 12/1986 | Hillemann | 71/93 |
| 4,659,369 | 4/1987 | Levitt | 71/92 |
| 4,662,932 | 5/1987 | Dumas | 71/91 |
| 4,671,819 | 6/1987 | Meyer et al. | 71/93 |
| 4,677,217 | 6/1987 | Maier et al. | 558/190 |
| 4,678,498 | 7/1987 | Artz | 71/87 |

FOREIGN PATENT DOCUMENTS

| | | |
|---|---|---|
| 3043384 | 1/1985 | Australia . |
| 0204513 | 12/1986 | European Pat. Off. . |
| 83/6449 | 2/1984 | South Africa . |
| 83/8416 | 5/1984 | South Africa . |
| 842722 | 6/1985 | South Africa . |

*Primary Examiner*—John M. Ford

[57] ABSTRACT

This invention relates to a novel class of sulfonylureas and their use as herbicides and plant growth regulants.

24 Claims, No Drawings

HERBICIDAL SULFONAMIDES

RELATED APPLICATIONS

This application is a continuation in part of application Ser. No. 085,852, filed on Aug. 17, 1987, now abandoned which was a continuation in part of U.S. application Ser. No. 920,051, filed Oct. 17, 1986, now abandoned.

BACKGROUND OF THE INVENTION

The compounds of this invention are highly active, novel 3-substituted methyl sulfonylureas which are useful as herbicides and plant growth regulators.

EP-A-44,209 (Cognate) discloses herbicidal sulfonamides of formula

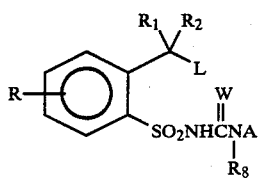

wherein
  R is H, F, Cl, Br, $NO_2$, $CF_3$, $C_1$-$C_3$ alkyl or $C_1$-$C_3$ alkoxy;
  $R_1$ is H, Cl or $C_1$-$C_4$ alkyl;
  $R_2$ is H or $CH_3$; and
  L is, among other values, $CO_2R_{10}$, $CONR_3R_4$, CN, Cl, Br, $NR_3R_4$, $S(O)_nR_7$, $SO_2NR_3R_4$, $OR_9$ and $OC(O)R_{11}$.

EP-A-112,803 discloses, in part, herbicidal sulfonamides of formula

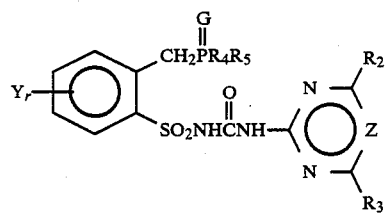

South African patent application No. 84/2722 discloses herbicidal sulfonamides of formula

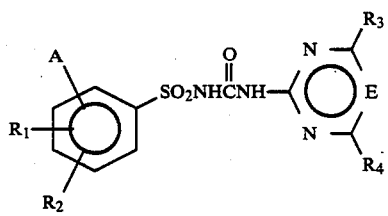

wherein
  A is $CR_6R_7XR_8$, $CR_9R_{10}R_{11}$ or $CHR_7SCQR_{21}$;
  $R_9$ and $R_{10}$ are, among other values, H or $CH_3$;
  $R_{11}$ is $COR_{24}$ or a $C_1$-$C_4$ alkyl group substituted with, among other values, CN, $NO_2$, OH, $C_1$-$C_4$ alkoxy, $C_1$-$C_4$ alkylthio, $C_1$-$C_4$ alkylsulfinyl, $C_1$-$C_4$ alkylsulfonyl, $C_1$-$C_4$ haloalkoxy, $NR_{12}R_{13}$, $SO_2NR_{15}R_{16}$, $SC(O)R_{18}$, $OC(O)R_{18}$ and $OSO_2R_{17}$;
  $R^1$ includes H, halogen, $NO_2$, CN, $C_1$-$C_4$ haloalkyl and $COR^{18}$; and
  $R^2$ includes H, halogen, $C_1$-$C_4$ alkyl and $C_1$-$C_4$ alkoxy.

EP-A-162,723 discloses 2,5-substituted herbicidal sulfonamides of formula

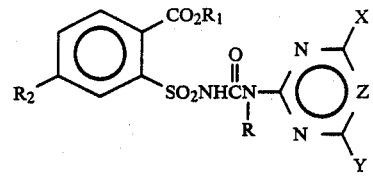

wherein
  R is H or $CH_3$;
  $R_1$ is $C_1$-$C_3$ alkyl; and
  $R_2$ is $C_2$-$C_6$ alkoxy, $C_1$-$C_6$ alkylthio, $C_3$-$C_6$ alkenyl, $C_3$-$C_6$ alkenyloxy, $C_3$-$C_6$ alkenylthio, $C_3$-$C_6$ alkynyloxy, $C_3$-$C_6$ alkynylthio, $OCH_2CH_2OCH_3$, $OCH_2CH_2SCH_3$, $CH_2F$, $CHF_2$, $OCF_2H$, $OCH_2CH_2F$, $OCH_2CHF_2$, $OCH_2CF_3$, $OCH_2CH_2Cl$, $C_2$-$C_6$ alkyl substituted with 1-3 atoms of F or Cl or $C_1$-$C_4$ alkyl substituted with $C_1$-$C_2$ alkoxy or $C_1$-$C_2$ alkylthio;

South African patent application No. 84/5216 discloses herbicidal sulfonylureas of the formula

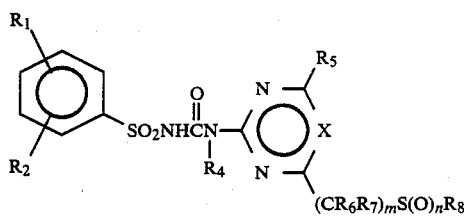

wherein
  $R_1$ and $R_2$ independently include H, $C_1$-$C_4$ alkyl, $C_1$-$C_4$ alkoxy or $C_{1-4}$ alkylthio which are optionally substituted by halogen, $NO_2$, $OSO_2(C_{1-4}$ alkyl), $OSO_2CF_3$ or $C_1$-$C_4$ alkoxycarbonyl;
  X is CH or N;
  $R_6$ and $R_7$ include H or $C_1$-$C_4$ alkyl; and
  $R_8$ is $C_1$-$C_4$ alkyl, $C_2$-$C_4$ alkenyl or benzyl.

EP-A-204,513, published 12/10/86 discloses herbicidal sulfonylureas of the formula

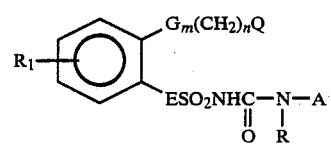

wherein
  G is O, S, SO or $SO_2$;
  m is 0 or 1;
  n is 0, 1 or 2;
  E is a single bond, $CH_2$ or O;
  Q is a tetrazole or tetrazolinone;
  A includes pyrimidines and triazines; and
  $R_1$ includes H, $C_1$ to $C_3$ alkyl, $C_1$ to $C_3$ haloalkyl and $C_1$-$C_2$ alkyl substituted by $C_1$-$C_2$ alkoxy, $C_1$-$C_2$ haloalkoxy, $C_1$-$C_2$ alkylthio, $C_1$-$C_2$ haloalkylthio, $C_1$-$C_2$ haloalkylthio or CN.

EP-A-205,348, published Dec. 17, 1986, discloses herbicidal sulfonylureas of the formula

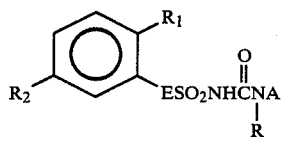

wherein
- $R_1$ includes halogen, $C_1$-$C_4$ alkyl, $C_1$-$C_4$ alkoxy, $CO_2R_3$, $CONR_4R_5$, $SO_2NR_4R_5$ and certain heterocyclic aromatic moieties;
- $R_2$ includes a variety of substituted methyl moieties; and
- A is one of seven heteroaromatic radicals.

U.S. Pat. No. 4,515,626 discloses herbicidal 4-cyclopropyl pyrimidinyl and triazinyl benzenesulfonylureas.

U.S. Pat. No. 4,545,811 discloses herbicidal 4-(haloalkoxy or haloalkylthio)pyrimidinyl and triazinyl benzenesulfonylureas.

U.S. Pat. No. 4,510,325 discloses herbicidal compounds of the formula

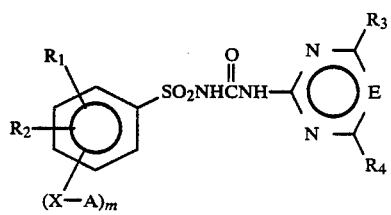

wherein
- X is O, S, SO or $SO_2$;
- A includes substituted $C_1$-$C_6$ alkyl and optionally substituted $C_2$-$C_6$ alkenyl; and
- $R_2$ includes H, halogen, $C_1$-$C_5$ alkyl and $C_1$-$C_4$ haloalkyl.

EP-A-192,489 discloses herbicidal compounds of the formula

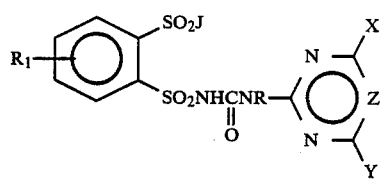

wherein
J is $NHR_2$, $NR_3R_4$ or $NR_2'NR_3'R_4'$.

U.S. Pat. No. 4,594,097 discloses herbicidal alkynyl-substituted benzenesulfonylureas.

U.S. Pat. No. 4,443,243 discloses herbicidal alkoxyalkynyl and thioalkynyl benzenesulfonylureas.

South African patent application No. 82/7439 discloses 4-aminopyrimidinyl and triazinyl benzenesulfonylureas.

South African patent application No. 83/6449 discloses herbicidal substituted-alkenyl benzenesulfonylureas.

EP-A-111,442 discloses herbicidal orthoheterocyclic benzenesulfonylureas.

South African patent application No. 84/2245 discloses herbicidal compounds of the formula

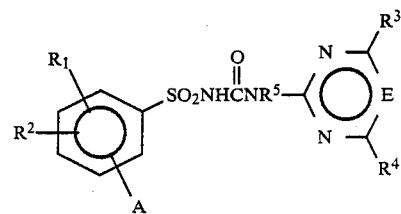

wherein
- A is $C_1$-$C_6$ haloalkyl; provided that A is not $CF_3$ or $CR^aR^bR^c$;
- $R^a$ is H, Cl or $C_1$-$C_4$ alkyl;
- $R^b$ is H or $CH_3$; and
- $R^c$ is Cl or Br.

U.S. Pat. No. 4,310,346 discloses herbicidal o-sulfonamide sulfonylureas.

SUMMARY OF THE INVENTION

This application pertains to novel compounds of Formula I, agriculturally suitable compositions containing them and their method-of-use as preemergent and/or postemergent herbicides or plant growth regulants.

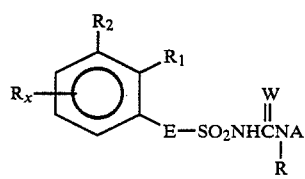

I wherein
- E is $CH_2$ or a single bond;
- W is O or S;
- R is H or $CH_3$;
- $R_X$ is H, F, Cl, $CH_3$, $OCH_3$, $N(CH_3)_2$ or $OCHF_2$;
- $R_1$ is F, Cl, Br, $NO_2$, $C_1$-$C_4$ alkyl, $C_2$-$C_4$ alkenyl, $C_2$-$C_4$ haloalkenyl, $C_2$-$C_4$ alkynyl, $C_1$-$C_4$ haloalkyl, $C_1$-$C_4$ alkoxy, $OCH_2CH_2OCH_3$, $C_1$-$C_4$ haloalkoxy, $C_3$-$C_4$ alkenyloxy, $C_2$-$C_4$ haloalkenyloxy, $C_3$-$C_4$ alkynyloxy, $CO_2R_3$, $CONR_4R_5$, $SO_2NR_4'R_5'$, $S(O)_nR_6$, $OSO_2R_7$, $C_1$-$C_2$ alkyl substituted with $C_1$-$C_2$ alkoxy, OH or $C_1$-$C_2$ alkylthio, $CH_2CN$, $C_6H_5$,

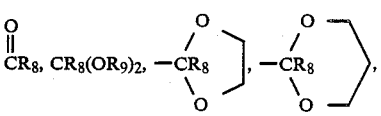

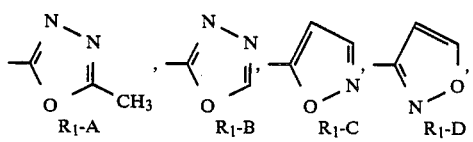

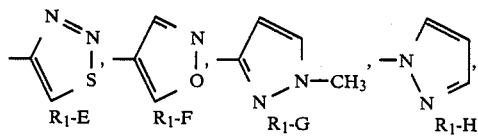

-continued

R₁-I, R₁-J, R₁-K, R₁-L, R₁-M,

R₁-N, R₁-O, R₁-P, R₁-Q, R₁-R,

R₁-S, R₁-T, R₁-U, R₁-V,

R₁-W, R₁-X, R₁-Y,

R₁-Z, R₁-AA, R₁-AB,

R₁-AC, R₁-AD;

R₂ is $-CH(R_{16})CN$, $-CH(R_{17})SCN$, $-CH(R_{17})\overset{O}{\overset{\|}{P}}R_{10}R_{11}$, $-CH(R_{17})\overset{S}{\overset{\|}{P}}R_{10}R_{11}$, $-CH(R_{17})NR_{12}R_{13}$, $-CH(R_{17})SeR_{14}$, $-CH(R_{17})N_3$, $-CH(R_{17})NO_2$, $-CH(R_{17})NC$, $-\overset{O}{\overset{\|}{C}}R_{17}$, $-C(OR_{18})_2$, $-C(SR_{18})_2$, $-\underset{R_{17}}{C}\overset{S}{\underset{S}{\diagdown}}(\phantom{\big|})_p$, $-\underset{R_{17}}{C}\overset{O}{\underset{O}{\diagdown}}(\phantom{\big|})_p$, $-\underset{R_{17}}{\overset{CN}{C}}OR_{19}$, $-\underset{R_{17'}}{C}=N-OR_{20}$, $-CH(OCCH_3)_2$, $-\underset{R_{17}}{CH}O\overset{O}{\overset{\|}{C}}R_{22}$, $-\underset{R_{23}}{C(R_{17})}Cl$, $-\underset{R_{24}}{C(R_{17})}Br$ or $-\underset{R_{17}}{CH}OSO_2CH_3$;

R₃ is C₁–C₄ alkyl, C₃–C₄ alkenyl, C₃–C₄ alkynyl, $-CH_2-\triangleleft$,

CH₂CH₂Cl, CH₂CH₂F, or C₁–C₂ alkyl substituted with OCH₃, SCH₃ or CN;
R₄ is C₁–C₃ alkyl or C₁–C₂ alkoxy;
R₄' is C₁–C₃ alkyl or C₁–C₂ alkoxy;
R₅ is H or C₁–C₃ alkyl;
R₅' is H or C₁–C₃ alkyl;
R₄ and R₅ may be taken together to form —(CH₂)₃— or —(CH₂)₄—;
R₄' and R₅' may be taken together to form —(CH₂)₃— or —(CH₂)₄—;
R₆ is C₁–C₃ alkyl, —CH₂CH=CH₂ or CH₂C≡CH;
R₇ is C₁–C₃ alkyl or N(CH₃)₂;
R₈ is H, C₁–C₄ alkyl, C₃–C₄ alkenyl, C₃–C₄ alkynyl, CH₂CH₂Cl, CH₂CH₂F, C₁–C₂ alkyl substituted with OCH₃ or SCH₃ or C₃–C₆ cycloalkyl;
R₉ is C₁–C₂ alkyl;
R₁₀ and R₁₁ are independently C₁–C₂ alkyl, C₁–C₂ alkoxy, C₁–C₂ alkylthio, NHCH₃ or N(CH₃)₂;
R₁₂ and R₁₃ are independently H or C₁–C₂ alkyl;
R₁₄ is C₁–C₃ alkyl;
R₁₅ is H or CH₃;
R₁₆ is H, C₁–C₂ alkyl or F;
R₁₇ is H or C₁–C₂ alkyl;
R₁₇ is H, C₁–C₂ alkyl, CN, Cl, OCH₃, SCH₃ or N(CH₃)₂;
R₁₈ is C₁–C₂ alkyl;
R₁₉ is H, Si(CH₃)₃ or C₁–C₂ alkyl;
R₂₀ is H or C₁–C₂ alkyl;
R₂₁ is H, C₁–C₃ alkyl or allyl;
R₂₂ is C₁–C₂ alkyl or C₁–C₂ haloalkyl;
R₂₃ is H, CH₃, Cl or Br;
R₂₄ is H or CH₃;
p is 1 or 2;
n is 0, 1 or 2;
A is

A-1, A-2, A-3,

A-4, A-5

-continued

[Structures A-6 and A-7 shown: A-6 is $-CH_2-$ attached to a ring with $OCH_3$, N, N, $X_3$; A-7 is a ring with NC, $X_4$, N, $Y_4$]

X is H, $C_1$–$C_4$ alkyl, $C_1$–$C_4$ alkoxy, $C_1$–$C_4$ haloalkoxy, $C_1$–$C_4$ haloalkyl, $C_1$–$C_4$ haloalkylthio, $C_1$–$C_4$ alkylthio, halogen, $C_2$–$C_5$ alkoxyalkyl, $C_2$–$C_5$ alkoxyalkoxy, amino, $C_1$–$C_3$ alkylamino or di($C_1$–$C_3$ alkyl)amino;

Y is H, $C_1$–$C_4$ alkyl, $C_1$–$C_4$ alkoxy, $C_1$–$C_4$ haloalkoxy, $C_1$–$C_4$ haloalkylthio, $C_1$–$C_4$ alkylthio, $C_2$–$C_5$ alkoxyalkyl, $C_2$–$C_5$ alkoxyalkoxy, amino, $C_1$–$C_3$ alkylamino, di($C_1$–$C_3$ alkyl)amino, $C_3$–$C_4$ alkenyloxy, $C_3$–$C_4$ alkynyloxy, $C_2$–$C_5$ alkylthioalkyl, $C_2$–$C_5$ alkylsulfinylalkyl, $C_2$–$C_5$ alkylsulfonylalkyl, $C_1$–$C_4$ haloalkyl, $C_2$–$C_4$ alkynyl, $C_3$–$C_5$ cycloalkyl, azido, cyano,

[Structures shown involving $CR_a$, $Q_1$, $Q_2$, $R_a$, $R_b$, $R_c$, $(CH_2)_m$, and $N(OCH_3)CH_3$]

m is 2 or 3;
$Q_1$ and $Q_2$ are independently O or S;
$R_a$ is H or $C_1$–$C_3$ alkyl;
$R_b$ and $R_c$ are independently $C_1$–$C_3$ alkyl;
Z is CH, N, $CCH_3$, $CC_2H_5$, CCl or CBr;
$Y_1$ is O or $CH_2$;
$X_1$ is $CH_3$, $OCH_3$, $OC_2H_5$ or $OCF_2H$;
$X_2$ is $CH_3$, $C_2H_5$ or $CH_2CF_3$;
$Y_2$ is $OCH_3$, $OC_2H_5$, $SCH_3$, $SC_2H_5$, $CH_3$ or $CH_2CH_3$;
$X_3$ is $CH_3$ or $OCH_3$;
$Y_3$ is H or $CH_3$;
$X_4$ is $CH_3$, $OCH_3$, $OC_2H_5$, $CH_2OCH_3$ or Cl;
$Y_4$ is $CH_3$, $OCH_3$, $OC_2H_5$ or Cl;
and their agriculturally suitable salts; provided that (1) when X is halogen, then Z is CH and Y is $OCH_3$, $OC_2H_5$, $NH_2$, $NHCH_3$, $N(CH_3)_2$, $OCF_2H$, $OCF_2Br$ or $N(OCH_3)CH_3$;

(2) when X or Y is $C_1$ haloalkoxy, then Z is CH;

(3) when W is S, then R is H, A is A-1, Z is CH or N, and Y is $CH_3$, $OCH_3$, $OC_2H_5$, $CH_2OCH_3$, $C_2H_5$, $CF_3$, $SCH_3$, $OCH_2CH=CH_2$, $OCH_2C\equiv CH$, $OCH_2CH_2OCH_3$, $CH(OCH_3)_2$ or

[structure: $-CH$ with $-O-$, $-O-$ forming ring]

(4) when the total number of carbon atoms of X and Y is greater than four, then the combined number of carbons of $R_1$ and $R_2$ is less than or equal to six;

(5) when $R_2$ is $-C(O)R_{17}$, $-C(R_{23})(R_{17})Cl$ or $-C(R_{24})(R_{17})Br$ then Y is other than cyclopropyl;

(6) when Y is $C_2$–$C_5$ alkylthioalkyl, $C_2$–$C_5$ alkylsulfinylalkyl or $C_2$–$C_5$ alkylsulfonylalkyl, then $R_2$ is other than $-CH(R_{17})NO_2$, $$-\underset{R_{23}}{\underset{|}{C}}(R_{17})Cl, \quad -\underset{R_{24}}{\underset{|}{C}}(R_{17})Br \text{ and } -\underset{R_{17}}{\underset{|}{C}}HOSO_2CH_3.$$

(7) $X_4$ and $Y_4$ are not simultaneously Cl;

(8) when $R_4'$ is $C_1$–$C_2$ alkoxy and $R_5'$ is H, then $R_2$ is other than $CH(R_{17})CN$, $C(R_{23})(R_{17})Cl$ and $C(R_{24})(R_{17})Br$;

(9) when $R_2$ is $C(O)R_{17}$, $C(R_{23})(R_{17})Cl$ or $C(R_{24})(R_{17})Br$, then $R_1$ is other than $C_1$–$C_4$ haloalkyl or $C_2$ alkyl substituted with $C_1$–$C_2$ alkoxy, OH or $C_1$–$C_2$ alkylthio;

(10) when $R_2$ is $C(R_{23})(R_{17})Cl$ or $C(R_{24})(R_{17})Br$, then X and Y are other than $C_1$–$C_4$ haloalkoxy or $C_1$–$C_4$ haloalkylthio;

(11) when $R_2$ is $C(R_{23})(R_{17})Cl$ or $C(R_{24})(R_{17})Br$, then $R_1$ is other than $C_1$–$C_4$ haloalkoxy, $C_3$–$C_4$ alkenyloxy, $C_2$–$C_4$ haloalkenyloxy, $C_2$–$C_4$ alkynyl, $C_3$–$C_4$ alkynyloxy, $C_2$–$C_4$ haloalkenyl and $R_1$—A through $R_1$—W;

(12) when $R_1$ is $R_1$—X, $R_1$—Y, $R_1$—Z, $R_1$—AA, $R_1$—AB, $R_1$—AC or $R_1$—AD, then $R_2$ is other than $CH(R_{16})CN$, $C(R_{23})$—$(R_{17})Cl$ and $C(R_{24})(R_{17})Br$;

(13) when $R_2$ is $C(O)R_{17}$, then $R_1$ is other than $SO_2NR_4'R_5'$; and

(14) when $R_1$ is $CO_2R_3$ then both $R_{12}$ and $R_{13}$ are other than H.

In the above definitions, the term "alkyl", used either alone or in compound words such as "alkylthio" or "haloalkyl", denotes straight chain or branched alkyl, e.g., methyl, ethyl, n-propyl, isopropyl or the different butyl isomers.

Alkoxy denotes methoxy, ethoxy, n-propoxy, isopropoxy and the different butoxy isomers.

Alkenyl denotes straight chain or branched alkenes, e.g., vinyl, 1-propenyl, 2-propenyl, 3-propenyl and the different butenyl isomers.

Alkynyl denotes straight chain or branched alkynes, e.g., ethynyl, 1-propynyl, 2-propynyl and the different butynyl isomers.

Cycloalkyl denotes cyclopropyl, cyclobutyl, cyclopentyl and cyclohexyl.

The term "halogen", either alone or in compound words such as "haloalkyl", denotes fluorine, chlorine, bromine or iodine. Further, when used in compound words such as "haloalkyl" said alkyl may be mono-halogenated or fully substituted with halogen atoms, which may be the same or different. Examples of haloalkyl include $CH_2CH_2F$, $CF_2CF_3$ and $CH_2CHFCl$. Similarly, haloalkoxy, haloalkylthio, haloalkenyl and haloalkenyloxy would be defined as mono- or poly-substituted with the same or different halogen atoms.

The total number of carbon atoms in a substituent group is indicated by the $C_i$–$C_j$ prefix where i and j are numbers from 1 to 5. For example, $C_1$–$C_3$ alkylsulfonyl would designate methylsulfonyl through propylsulfonyl, $C_2$ alkoxyalkoxy would designate $OCH_2OCH_3$; $C_4$ alkoxyalkoxy would designate the various isomers of an alkoxy group substituted with a second alkoxy group containing a total of 4 carbon atoms, examples including $OCH_2OCH_2CH_2CH_3$ and $OCH_2CH_2OCH_2CH_3$; as a further example, $C_2$ cyanoalkyl would designate CH₂CN and C₃ cyanoalkyl would designate CH₂CH₂CN and CH(CN)CH₃.

PREFERRED COMPOUNDS

Preferred for reasons of increased ease of synthesis and/or greater herbicidal efficacy are:
1. Compounds of Formula I where
W is O.
2. Compounds of Preferred 1 where
E is a single bond;
X is $C_1$-$C_2$ alkyl, $C_1$-$C_2$ alkoxy, Cl, F, Br, I, $OCF_2H$, $CH_2F$, $CF_3$, $OCH_2CH_2F$, $OCH_2CHF_2$, $OCH_2CF_3$, $CH_2Cl$ or $CH_2Br$; and
Y is H, $C_1$-$C_2$ alkyl, $C_1$-$C_2$ alkoxy, $CH_2OCH_3$, $CH_2OCH_2CH_3$, $NHCH_3$, $N(OCH_3)CH_3$, $N(CH_3)_2$, $CF_3$, $SCH_3$, $OCH_2CH=CH_2$, $OCH_2C\equiv CH$, $OCH_2CH_2OCH_3$, $CH_2SCH_3$,

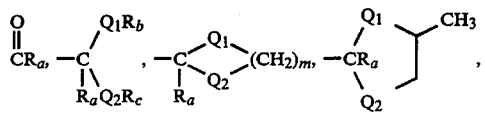

$OCF_2H$, $SCF_2H$, $OCF_2Br$, cyclopropyl, C≡CH or C≡CCH₃;
Z is CH or N;
$R_a$ is H or $CH_3$;
$R_{23}$ is H; and
$R_{24}$ is H.
3. Compounds of Preferred 2 where
$R_2$ is —$CH_2CN$, —$CH_2N_3$,

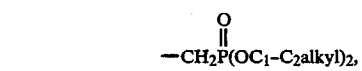

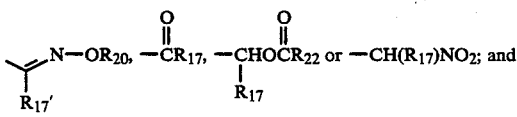

$R_{17}'$ is H, $C_1$-$C_2$ alkyl, Cl or CN.
4. Compounds of Preferred 3 where A is A-1.
5. Compounds of Preferred 4 where
$R_1$ is F, Cl, Br, $NO_2$, $C_1$-$C_3$ alkyl, $C_1$-$C_2$ alkyl substituted with 1-3 F or Cl or 1 Br, $C_2$-$C_3$ alkenyl, $C_2$-$C_3$ alkenyl substituted with 1-3 F or Cl, $C_1$-$C_2$ alkoxy, $C_1$-$C_2$ alkoxy substituted with 1-3 F or Cl or 1-Br, allyloxy, propargyloxy, OC(Cl)=CHCl, $CO_2CH_3$, $CO_2C_2H_5$, $CO_2CH_2CH=CH_2$, $CO_2CH_2CH_2Cl$, $CO_2CH_2CH_2OCH_3$, CONH($C_1$-$C_2$ alkyl), CONCH₃($C_1$-$C_2$ alkyl), SO₂N(OCH₃)CH₃, SO₂NH($C_1$-$C_2$ alkyl), SO₂N($C_1$-$C_2$ alkyl)₂, S(O)ₙ$C_1$-$C_3$ alkyl, OSO₂$C_1$-$C_3$ alkyl, $C_1$-$C_2$ alkyl substituted with OCH₃ or SCH₃, $C_6H_5$ and $R_1$—A, $R_1$—B, $R_1$—C, $R_1$—D, $R_1$—E, $R_1$—F, $R_1$—G, $R_1$—H, $R_1$—I, $R_1$—J, $R_1$—K, $R_1$—L, $R_1$—M, $R_1$—N, $R_1$—O, $R_1$—P, $R_1$—Q, $R_1$—R, $R_1$—S, $R_1$—T, $R_1$—U, $R_1$—V, $R_1$—W, $R_1$—X, $R_1$—Y, $R_1$—Z, $R_1$—AA, $R_1$—AB, $R_1$—AC or $R_1$—AD;
6. Compounds of Preferred 5 where
X is $CH_3$, $OCH_3$, $OCH_2CH_3$, Cl, $OCF_2H$ or $OCH_2CF_3$; and
Y is $CH_3$, $OCH_3$, $C_2H_5$, $CH_2OCH_3$, $NHCH_3$ or $CH(OCH_3)_2$.
7. Compounds of Preferred 6 where R is H;
$R_1$ is F, Cl, Br, $NO_2$, $CH_3$, $CF_3$ $C_1$-$C_2$ alkoxy, allyloxy, OC(Cl)=CHCl, $CO_2CH_3$, $CO_2C_2H_5$, $CO_2NHCH_3$, $CO_2N(CH_3)_2$, $SO_2NHCH_3$ $SO_2N(CH_3)_2$, $SO_2CH_3$, $SO_2C_2H_5$, $OSO_2CH_3$, $OSO_2C_2H_5$, $R_1$—A, $R_1$—B, $R_1$—C, $R_1$—X, $R_1$—Z or $R_1$—AB; and
$R_X$ is H.

Specifically Preferred for reasons of greatest ease of synthesis and/or greatest herbicidal efficacy are:
2-(cyanomethyl)-6-[[(4,6-dimethoxypyrimidin-2-yl)aminocarbonyl]aminosulfonyl]benzoic acid, ethyl ester, m.p. 201°-204° C.; and
2-(acetoxymethyl)-6-[[(4-methoxy-6-methyl-1,3,5-triazin-2-yl)aminocarbonyl]aminosulfonyl]benzoic acid, ethyl ester, m.p. 175°-176° C.

DETAILED DESCRIPTION OF THE INVENTION

Synthesis

The compounds of Formula I can be prepared from sulfonamides of Formula II and heterocyclic amines of Formula III by one or more methods described in the literature.

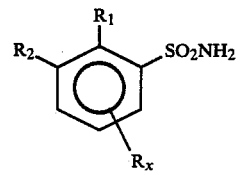

Several representative routes are described below.

U.S. Pat. No. 4,394,506 (issued 7/19/83) teaches the conversion of sulfonamides to sulfonyl isocyanates and sulfonyl isothiocyanates, and their subsequent coupling with heterocyclic amines of Formula III to give sulfonylureas.

U.S. Pat. No. 4,398,939 (issued 8/16/83) teaches the formation of n-butylsulfonylureas from sulfonamides followed by phosgenation to give the sulfonyl isocyanates. Alternatively, the sulfonamides can be treated with thionyl chloride followed by phosgenation to afford the sulfonyl isocyanates. Additionally, methylcarbamate derivatives of compounds of Formula III react with sulfonamides in the presence of trimethylaluminum to give sulfonylureas.

U.S. Pat. No. 4,443,245 (issued 4/17/84) teaches two methods for the synthesis of sulfonylureas. Either a phenyl carbamate of a sulfonamide and a heterocyclic amine, or a sulfonamide and a phenyl carbamate of a heterocyclic amine couple to give a sulfonylurea in an inert solvent with base.

The preparation of sulfonamides from sulfonyl chlorides is widely reported in the literature; for reviews see: F. Hawking and J. S. Lawrence. "The Sulfonamides," H. K. Lewis and Co., London, 1950 and E. H. Northey, "The Sulfonamides and Allied Compounds," Reinhold Publishing Corp., New York, 1948.

Additionally, primary sulfonamides, such as those of Formula II, can be formed by removal of an N-t-butyl protecting group from the corresponding secondary sulfonamide with trifluoroacetic acid (J. D. Catt and W.

L. Matier, *J. Org. Chem.*, 39, 566 (1974)) or polyphosphoric acid (J. G. Lombardino, *J. Org. Chem.*, 36 (1971), 1843).

The requisite sulfonyl chlorides may be synthesized by known methods or with slight modifications thereof, by one skilled in the art. Several representative teachings are listed below.

Aromatic nitro groups may be transformed into sulfonyl chlorides by reduction, diazotization and coupling with sulfur dioxide/cupric chloride as taught in U.S. Pat. No. 4,310,346 (issued 1/12/82).

European Publication No. 94,821 (published 11/23/83) describes the displacement of aromatic halides with thiolate anions and subsequent oxidative chlorination to yield sulfonyl chlorides.

Halogen-metal exchange of aromatic halides or proton-metal exchange of aromatics followed by quenching with sulfur dioxide gives sulfinate salts. These salts yield sulfonyl chlorides upon reaction with N-chlorosuccinimide as taught in U.S. Pat. No. 4,481,029 (issued 11/6/84). Directed proton-metal exchange of aromatic compounds has been reviewed by Gschwend and Rodriguez, *Org. Reactions*, 26 (1979), 1. Directed lithiation of aryl-N-t-butylsulfonamides is described by J. G. Lombardino, *J. Org. Chem.*, 36 (1971), 1843. Also, aryllithiums may be converted directly to arylsulfonyl chlorides with sulfuryl chloride as described in S. N. Bhattacharya, et. al., *J. Chem. Soc. C*, (1968), 1265.

Electrophilic chlorsulfonation of an aromatic ring to give a sulfonyl chloride is well known in the literature. This technique works best for alkyl aryl ethers and alkyl aromatics. Its application is described by E. H. Huntress and F. H. Carten, *J. Am. Chem. Soc.*, 62 (1940), 511-14 and 603-4.

Transformation of phenols to sulfonyl chlorides can be accomplished by the formation of a thiocarbamate, rearrangement, hydrolysis and oxidative chlorination as described by M. S. Newman and H. A. Karnes, *J. Org. Chem.*, 31 (1966), 3980.

Compounds of Formula II can be prepared by a variety of methods known in the literature. The most universal scheme, where benzyl halides of Formula IV are reacted with the appropriate reagent, is shown below.

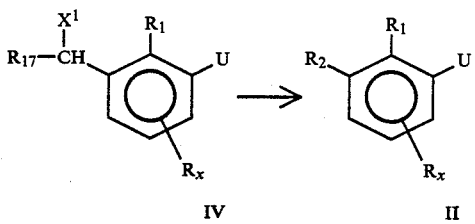

wherein
U is $SO_2NH_2$ or a previously described sulfonamide precursor, and $X^1$ is Cl, Br or I and $R_2$ is of the structure $-CH(R_{17})-$. Some specific methods are listed below.

NITRILES ($R_2=CH(R_{17})CN$)

Nitriles can be prepared by nucleophilic displacement of benzyl halides, usually benzyl chlorides or bromides, with potassium or sodium cyanide. Many solvents are applicable, but frequently dimethylsulfoxide is used. Thus, a benzyl bromide of formula IV can be contacted with potassium cyanide in dimethylsulfoxide for 0.5 h to 24 h at 20° to 140° C. For a review of this reaction, refer to Friedrich and Wallenfels, in Rappoport, "The Chemistry of the Cyano Group", pp. 77-86, Interscience Publishers, New York, 1970.

ISONITRILES ($R_2=CH(R_{17})NC$)

Heavy metal cyanides and benzylhalides react to give isonitriles. The reaction is best carried out in the dark using silver cyanide and a benzyl iodide. Typical procedures are given by A. Gautier, *Ann. Chem.*, 142 (1867), 28 and H. L. Jackson and B. C. McKusick, *Org. Syn.*, Col. Vol. IV, 438.

AZIDES ($R_2=CH(R_{17})N_3$)

Compounds of Formula II may be prepared by reacting an azide anion with a benzyl halide. Typically sodium azide in alcohol or wet acetone is mixed with a benzyl bromide at 20°-100° C. This nucleophilic displacement is reviewed in Biffin, Miller and Paul, in Patai, "The Chemistry of the Azido Group," pp. 57-119, Interscience Pub., New York, 1971.

PHOSPHONATES ($R_2=CH(R_{17})P(O)R_{10}R_{11}$)

Alkyl phosphites are heated with benzylic halides to give phosphonates. The reaction is known as the Arbuzov reaction and it is reviewed by Arbuzov, *Pure Appl. Chem.*, 9 (1964), 307-335.

AMINES ($R_2=CH(R_{17})NR_{12}R_{13}$)

Tertiary amines are prepared by alkylation of a secondary amine with a benzylic halide. The reaction is well documented in the literature.

Primary amines can be prepared by reduction of compounds of Formula II where $R_2$ is azide. Generally lithium aluminum hydride or hydrogen and palladium catalyst are used.

NITRO ($R_2=CH(R_{17})NO_2$)

Nitrites react with benzylic halides to give benzylic nitro compounds. The reaction is usually carried out with sodium nitrite on a benzylic bromide in dimethylformamide or dimethylsulfoxide. When silver nitrite is used, diethyl ether at 0°-25° C. are the preferred reaction conditions. The reaction is exhaustively discussed by N. Kornblum, *Org. Reactions*, 12 (1962), 101.

SELENO ETHERS ($R_2=CH(R_{17})SeR_{14}$)

Alkali alkylselenides can be prepared by in situ combination of an alkali metal t-butoxide with the selenol $HSeR_{14}$ in the solvent to be used for the displacement reaction. The selenols, $HSeR_{14}$, can be prepared by a variety of methods reviewed by D. L. Klayman, "Selenols and their Derivatives" in *Organic Selenium Compounds: Their Chemistry and Biology*, D. L. Klayman, W. H. H. Gunther ed., New York, 1973, and K. J. Irgolic and M. V. Kudchadker, "Organic Chemistry of Selenium" in *Selenium*, R. A. Zingaro, W. C. Cooper ed., Van Nostrand Reinhold, New York, 1974.

Benzyl halides may be formed through a variety of methods described in the literature. Several are listed below.

BENZYLIC CHLORIDES ($X^1=Cl$)

Treatment of alkyl benzene derivatives with N-chlorosuccinimide, NCS, in a suitable solvent, such as carbon tetrachloride or dichloromethane, and catalyzed by light or a free radical initiator, such as azoisobutyronitrile or benzoyl peroxide, gives the benzylic chloride.

Treatment of a benzylic alcohol with thionyl chloride, either neat or in the presence of a base such as pyridine, gives the benzylic chloride. For typical examples, see H. Gilman and J. E. Kirby, *J. Am. Chem.*, Soc., 51, 3475 (1929) and M. S. Newman, *J. Am. Chem. Soc.*, 62, 2295 (1940).

BENZYLIC BROMIDES ($X^1$=Br)

Treatment of alkyl benzene derivatives with N-bromosuccinimide by a method analogous to the case of N-chlorosuccinimide gives the benzylic bromide. Benzylic alcohols in an inert solvent such as benzene or dichloromethane react with phosphorus tribromide to give benzylic bromides.

BENZYLIC IODIDES ($X^1$=I)

Treatment of a benzylic chloride or benzylic bromide with sodium iodide gives the benzylic iodide. The reaction, known as the Finkelstein reaction, works well in refluxing acetone.

Benzylic alcohols may be treated with iodine and phosphorus (red) or phosphorus (red) and phosphorus (yellow) to give the benzylic iodide.

ESTERS ($R_2$=CH($R_{17}$)OCOR$_{22}$

Reaction of a benzyl bromide or iodide with a carboxylic acid salt in a dipolar aprotic solvent, results in good yields of the carboxylic esters. For a leading reference see Parker, *Adv. Org. Chem.*, 5, (1965) 1–46.

METHANESULFONATES ($R_2$=CH($R_{17}$)OSO$_2$CH$_3$)

Primary and secondary alcohols react with methanesulfonyl chloride in dry pyridine at room temperature to give mesylates, usually in good yield. The reaction is well documented in the literature.

Compounds of Formula II, where $R_2$ contains an oxygen functionality, such as an aldehyde or ketone, may be prepared by a variety of methods known to one skilled in the art. Two such routes are shown below.

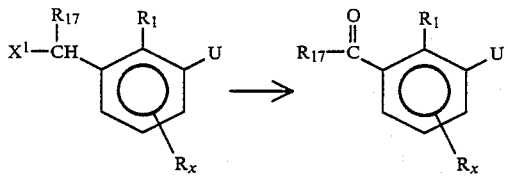

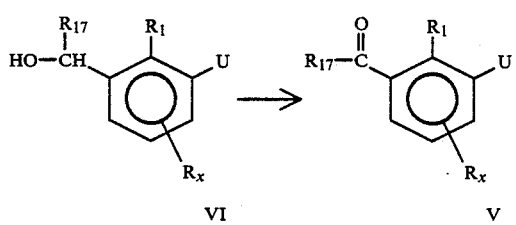

Primary and secondary benzylic halides may be oxidized to aldehydes and ketones, respectively using dimethylsulfoxide. For reviews of this reaction see Durst, *Adv. Org. Chem.*, 285–388 (1969) pp. 343–356 and W. Epstein and F. Sweat, *Chem. Rev.*, 67 (1967), 247–60.

Primary benzylic alcohols may be oxidized to aldehydes and secondary benzylic alcohols may be oxidized to ketones by one skilled in the art. One or more of a variety of methods, such as an oxidizing agent, catalytic dehydrogenation, Oppenauer oxidation or halosuccinimide oxidation may be used.

Acetals, thioacetals, ketals and thioketals are easily prepared by one skilled in the art from compounds of Formula V.

Oximes, and oxime ethers of Formula Va are easily prepared by one skilled in the art from compounds of Formula V and hydroxylamine or o-alkylhydroxylamine with or without an appropriate base.

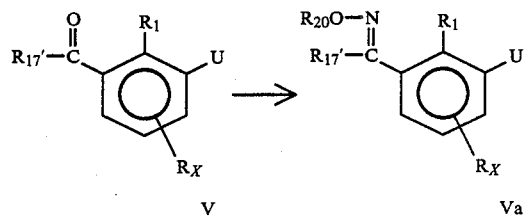

wherein
$R_{17}'$ is H or $C_1$–$C_2$ alkyl.

Additionally, compounds of the Formula Ia can be prepared from VII by treatment with an appropriate salt or amine.

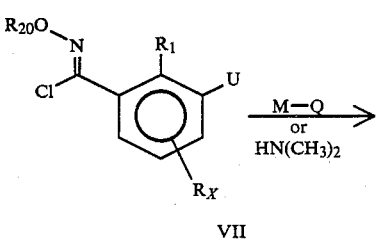

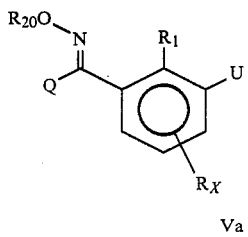

wherein
M is Na$^+$ or K$^+$
Q is CN, OCH$_3$ and SCH$_3$.

The reaction is effected by reacting VII with at least one molar equivalent of M-Q in an inert solvent such as acetone, methyl ethyl ketone, tetrahydrofuran, dimethylformamide or methanol. The reaction is carried out at 0° C. to 80° C. for one to twenty-four hours.

Compounds of the Formula VII are themselves readily prepared from the corresponding carboxylic acids, VIII.

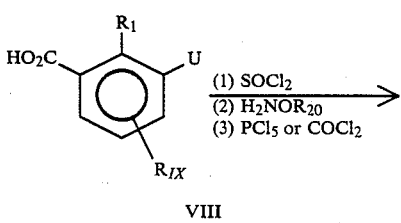

-continued

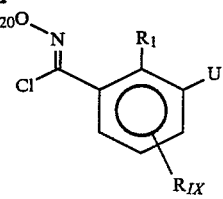

VII

The carboxylic acids are converted to their acid chlorides which are in turn converted to N-alkoxyamides. Subsequent reaction of the amides with a suitable halogenating agent provides compounds of the Formula VII.

Benzylic alcohols and alkyl benzene derivatives are either known or may be prepared by one skilled in the art.

The heterocylic amines A-1 to A-7 are either known, disclosed in this application or can be prepared by methods obvious to one skilled in the art.

For a review of the synthesis and reactions of 2-aminopyrimidines (A-1, Z=CH) see *The Chemistry of Heterocyclic Compounds*, Vol 16, Wiley-Interscience, New York (1962). For a review of the synthesis and reactions of 2-amino-1,3,5-triazines (A-1, Z=N) see *The Chemistry of Heterocyclic Compounds*, Vol. 13, Wiley-Interscience, New York (1959), F. C. Schaefer, U.S. Pat. No. 3,154,537 and F. C. Schaefer and K. R. Huffman *J. Org. Chem.*, 28 (1963), 1812.

The synthesis of bicyclic amines A-2 and A-3 is taught in U.S. Pat. No. 4,339,267.

The synthesis of amino furo[2,3-d]pyrimidines, A-4, is taught in U.S. Pat. No. 4,487,626.

The synthesis of aminotriazoles, A-5, is taught in U.S. Pat. No. 4,421,550.

The synthesis of aminomethylheterocycles, A-6, is taught in U.S. Pat. No. 4,496,392.

The synthesis of aminocyano hetereocycles, A-7, is taught in European Publication No. 125,864 (published 11/21/84).

Agriculturally suitable salts of compounds of Formula I are also useful herbicides and can be prepared in a number of ways known to the art. For example, metal salts can be made by contacting compounds of Formula I with a solution of an alkali or alkaline earth metal salt having a sufficiently basic anion (e.g. hydroxide, alkoxide, carbonate or hydride). Quaternary amine salts can be made by similar techniques.

Salts of compounds of Formula I can also be prepared by exchange of one cation for another. Cationic exchange can be effected by direct contacting of an aqueous solution of a salt of a compound of Formula I (e.g., alkali metal or quaternary amine salt) with a solution containing the cation to be exchanged. This method is most effective when the desired salt containing the exchanged cation is insoluble in water, e.g., a copper salt, and can be separated by filtration.

Exchange may also be effected by passing an aqueous solution of a salt of a compound of Formula I (e.g., an alkali metal or quaternary amine salt) through a column packed with a cation exchange resin containing the cation to be exchanged. In this method, the cation of the resin is exchanged for that of the original salt of the resin is exchanged for that of the original salt and the desired product is eluted from the column. This method is particularly useful when the desired salt is water-soluble, e.g., a potassium, sodium or calcium salt.

Acid addition salts, useful in this invention, can be obtained by reacting a compound of Formula I with a suitable acid, e.g., p-toluenesulfonic acid, trichloroacetic acid or the like.

The preparation of the compounds of this invention is further illustrated by the following examples.

EXAMPLE 1

Ethyl 2-Amino-6-methylbenzoate

A reaction mixture of 185 g of ethyl 6-methyl-2-nitrobenzoate and 176 g of powdered iron in 343 mL of glacial acetic acid and 2200 mL of ethanol was heated at reflux for 5 hours. The reaction mixture was allowed to cool, diluted with excess water and extracted with ethyl acetate. The organic layer was dried over sodium sulfate, filtered and concentrated to an orange oil 148.3 g.

NMR ($CDCl_3$, 90 MHz): 1.32 (t, $CH_3$, 3H); 2.40 (s, $CH_3$, 3H); 4.25 (q, $CH_2$, 2H); 6.25 (br s, $NH_2$, 2H); 6.50 (d, ArH, 2H); and 7.05 (dd, ArH, 1H).

EXAMPLE 2

2-Carboethoxy-N-(1,1-dimethylethyl)-3-methylbenzenesulfonamide

To 31.5 g of ethyl 2-amino-6-methylbenzoate in 65 mL of concentrated hydrochloric acid and 185 mL of glacial acetic acid at 0° C. was added a solution of 13.0 g of sodium nitrite in 28 mL of $H_2O$, keeping the temperature below 5° C. The solution was stirred an additional one-half hour and then poured portionwise into a suspension of 7.8 g of cupric chloride dihydrate, 16.0 mL of anhydrous sulfur dioxide and 140 mL of glacial acetic acid at 15° C. The resulting reaction mixture was warmed to room temperature and stirred an additional 3.5 hours. The reaction mixture was poured into 1 liter of ice/water and the solids filtered to give 35.5 g of a yellow solid. The solids were dissolved in 350 mL of tetrahydrofuran and treated at −50° to −60° C. with 46 mL of tert-butyl amine. The reaction mixture was warmed to 0° C. over 2 hours and then the solids were removed by filtration. Removal of the solvent provided 31.0 g of an orange solid. Recrystallization from ethanol/water provided 30 g of a pale yellow solid, m.p. 89°–91° C.

$^1$HNMR (90 MHz, $CDCl_3$): 1.15 (s, $CH_3$, 9H); 1.34 (t, $CH_3$, 3H); 2.31 (s, $CH_3$, 3H); 4.40 (q, $CH_2$, 2H); 5.22 (br s, NH, 1H); 7.44 (d, ArH, 2H); and 7.85 (dd, ArH, 1H).

EXAMPLE 3

2-Bromomethyl-2-carboethoxy-N-(1,1-dimethylethyl)-benzenesulfonamide

A mixture of 67.0 g of 2-carboethoxy-N-(1,1-dimethylethyl)-3-methylbenzenesulfonamide and 47.6 g of NBS and 0.5 g of azobisisobutyronitrile in 700 mL of carbontetrachloride was heated at reflux for 3 hours. The resulting reaction mixture was allowed to cool and the solids removed by filtration. Concentration provided a waxy yellow solid which was washed with 1:1 hexane/n-butyl chloride to yield 44.36 g of a white solid, m.p. 74°–75° C.

$^1$HNMR (200 MHz, $CDCl_3$): 1.25 (s, $CH_3$, 9H); 1.47 (t, $CH_3$, 3H); 4.50 (q, $CH_2$, 2H); 4.54 (s, $CH_2$, 2H); 5.20 (s, NH, 1H); 7.43–7.65 (m, ArH, 2H); and 8.02 (d, ArH, 1H).

EXAMPLE 4

3-Bromomethyl-2-carboethoxybenzenesulfonamide

A solution of 5.7 g of 3-bromomethyl-2-carboethoxy-N-(1,1-dimethylethyl)benzenesulfonamide in 60 mL of trifluoroacetic acid was stirred at room temperature for 16 hours. Concentration provided a viscous oil which was triturated with n-butyl chloride. The solids were collected to yield 3.91 g of a white solid, m.p. 138°–140° C.

$^1$HNMR (90 MHz, CDCl$_3$): 1.40 (t, CH$_3$, 3H); 4.48 (q, CH$_2$, 2H); 4.62 (s, CH$_2$, 2H); 6.95 (br s, NH$_2$, 2H); and 7.4–8.2 (m, ArH, 3H).

EXAMPLE 5

3-Azidomethyl-2-carboethoxybenzenesulfonamide

A solution of 1.64 g of 3-bromomethyl-2-carboethoxybenzenesulfonamide and 0.43 g of sodium azide in ethanol was heated to reflux for 3 hours. The resulting reaction mixture was cooled to room temperature and the ethanol was removed on the rotovap. The residue was partitioned between water and ethyl acetate. The organic phase was dried over magnesium sulfate, filtered and concentrated to give 1.32 g of a waxy solid.

$^1$HNMR (200 MHz, CDCl$_3$): 1.40 (t, CH$_3$, 3H); 4.46 (q, CH$_2$, 2H); 4.47 (s, CH$_2$, 2H); 5.49 (br s, NH$_2$, 2H); 7.75–7.85 (m, ArH, 2H); and 7.98 (dd, ArH, 1H).

EXAMPLE 6

2-(Azidomethyl)-6-[((4,6-dimethoxypyrimidin-2-yl)aminocarbonyl)aminosulfonyl]benzoic acid, ethyl ester To a suspension of 0.21 g of the compound from Example 5 and 0.23 g of 4,6-dimethoxy-2-pyrimidinylcarbamic acid, phenyl ester in 4.0 mL of dry acetonitrile was added 0.12 mL of 1,8-diazabicyclo[5.4.0]undec-7-ene (DBU). After being stirred at room temperature for 2 hours, the resulting reaction mixture was diluted with 4.0 mL of water, acidified with 1N hydrochloric acid to pH 2 and the solids collected by vacuum filtration. The solids were further washed with ether and then air dried to give 0.21 g of a white solid, m.p. 158°–160° C.

$^1$HNMR (200 MHz, CDCl$_3$): 1.41 (t, CH$_3$, 3H); 3.98 (s, OCH$_3$, 6H); 4.43 (q, CH$_2$, 2H); 4.44 (s, CH$_2$, 2H); 5.78 (s, Het-H, 1H); 7.22 (br s, NH, 1H); 7.60–7.80 (m, ArH, 2H); 8.36 (dd, ArH, 1H); and 12.52 (br s, NH, 1H).

EXAMPLE 7

3-Acetoxymethyl-2-carboethoxy-N-(1,1-dimethylethyl)benzenesulfonamide

A solution of 5.0 g of 3-bromomethyl-2-carboethoxy-N-(1,1-dimethylethyl)benzenesulfonamide and 1.5 g of potassium acetate in 50 mL of dimethylsulfoxide was stirred at room temperature for 6 hours. The resulting reaction mixture was poured onto ice and extracted with ethyl acetate. The organic phase was washed with a solution of saturated sodium chloride and then dried over magnesium sulfate. Removal of the drying agent by filtration and concentration provided a white solid. Chromatography on silica gel with 1:1 ethyl acetate/hexane provided 2.58 g of a white solid, m.p. 81°–82° C.

$^1$HNMR (90 MHz, CDCl$_3$): 1.22 (s, CH$_3$, 9H); 1.40 (t, CH$_3$, 3H); 2.20 (s, CH$_3$, 3H); 4.48 (q, CH$_2$, 2H); 5.23 (br s, NH, CH$_2$, 3H); 7.53–7.70 (m, ArH, 2H); and 8.00–8.16 (m, ArH, 1H).

EXAMPLE 8

3-Acetoxymethyl-2-carboethoxybenzenesulfonamide

A solution of 2.58 g of 3-acetoxymethyl-2-carboethoxy-N-(1,1-dimethylethyl)benzenesulfonamide in 25 mL of trifluoroacetic acid was stirred at room temperature overnight. Removal of the solvent on the rotovap followed by trituration with n-butyl chloride provided 2.0 g of a white solid, m.p. 98°–100° C.

$^1$HNMR (90 MHz, CDCl$_3$): 1.51 (t, CH$_3$, 3H); 2.20 (s, CH$_3$, 3H); 4.48 (q, CH$_2$, 2H); 5.23 (s, NH, CH$_2$, 2H); 5.35 (br s, NH$_2$, 2H); 7.50–7.70 (m, ArH, 2H); and 7.98–8.15 (m, ArH, 1H).

EXAMPLE 9

2-Acetoxymethyl-6-[((4,6-dimethoxypyrimidin-2-yl)aminocarbonyl)aminosulfonyl]benzoic acid, ethyl ester To a suspension of 0.25 g of the compound from Example 8 and 0.23 g of 4,6-dimethoxy-2-pyrimidinylcarbamic acid, phenyl ester in 4.0 mL of dry acetonitrile was added 0.12 mL of 1,8-diazabicyclo[5.4.0]undec-7-ene (DBU). After being stirred at room temperature for 2 hours, the reaction mixture was diluted with 4.0 mL of water and then acidified with 1N hydrochloric acid to pH 2. The solids were collected by vacuum filtration and washed with ether to yield 0.28 g of a white solid, m.p. 162°–163° C.

$^1$HNMR (200 MHz, DMSO-d$_6$): 1.22 (t, CH$_3$, 3H); 2.00 (s, CH$_3$, 3H); 3.90 (s, OCH$_3$, 6H); 4.28 (q, CH$_2$, 2H); 5.08 (s, CH$_2$, 2H); 5.60 (s, Het-H, 1H); 7.70–7.90 (m, ArH, 2H); and 8.03–8.10 (m, ArH, 1H).

EXAMPLE 10

3-Bromomethyl-6-[((4,6-dimethoxypyrimidin-2-yl)aminocarbonyl)aminosulfonyl]benzoic acid, ethyl ester To a suspension of 0.31 g of the compound from Example 4 and 0.28 g of 4,6-dimethoxy-2-pyrimidinylcarbamic acid, phenyl ester in 5.0 ml of dry acetonitrile was added 0.15 ml of DBU. After stirring at room temperature for three hours, the reaction mixture was diluted with 5.0 ml of water and then acidified with 1N hydrochloric acid to pH3. The solids were collected by vacuum filtration and washed with n-butylchloride to yield 0.38 g of a white solid; m.p. 195°–197° C.;

$^1$HNMR (200 mhz, DMSO-d$_6$): 1.28 (t, CH$_3$, 3H); 3.90 (s, OCH$_3$, 6H); 4.35 (q, CH$_2$, 2H); 4.68 (s, CH$_2$, 2H); 6.00 (s, CH, 1H); 7.75 (d, d, ARH, 1H); 7.94 (d, ARH, 1H); 8.15 (d, ARH, 1H); 10.68 (br, s, N—H, 1H); and 12.65 (brs, N—H, 1H).

The invention is further exemplified, but not limited to the compounds in Tables I–VII. The compounds depicted in these tables may be prepared by methods described in Examples 1–10, or by modifications thereof apparent to those skilled in the art.

General Structures

General Formula I

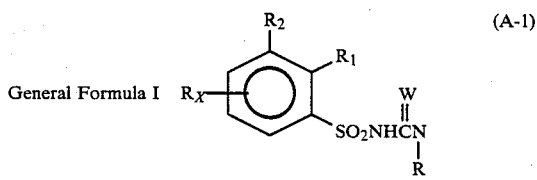

(A-1)

-continued
General Structures
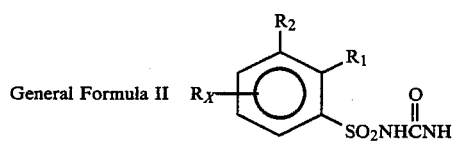
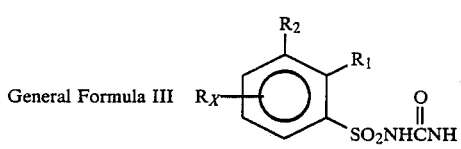
-continued
General Structures
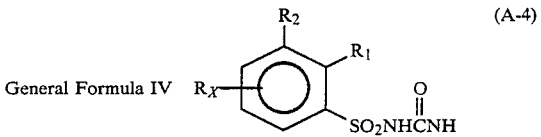
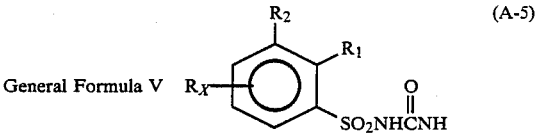
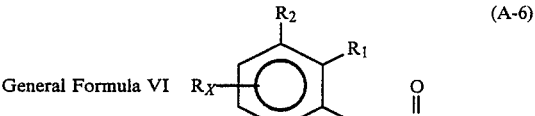
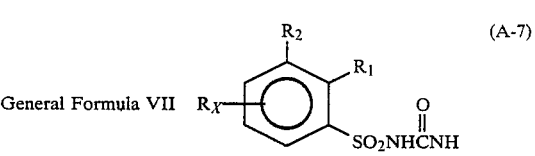

TABLE I

General Formula I

| R₁ | R₂ | Rₓ | W | R | X | Y | Z | m.p. (°C.) |
|---|---|---|---|---|---|---|---|---|
| F | CH₂CN | H | O | H | OCH₃ | H | CH | |
| F | CH₂CN | H | O | CH₃ | OCH₃ | CH₃ | CH | |
| F | CH₂CN | H | O | H | CH₃ | OCH₃ | N | |
| F | CH₂SCN | H | O | H | OCH₃ | OCH₃ | CH | |
| F | CH₂SCN | H | O | H | OCH₃ | CH₂CH₃ | CH | |
| F | CH₂SCN | H | O | H | CH₂CH₃ | OCH₃ | N | |
| F | CH₂P(O)(OCH₃)₂ | H | O | H | OCH₃ | CH₂OCH₃ | CH | |
| F | CH₂P(O)(OCH₃)₂ | H | O | H | OCH₃ | OCH₃ | CH | |
| F | CH₂P(O)(OCH₃)₂ | H | O | H | OCH₂CH₃ | OCH₃ | CH | |
| F | CH₂P(O)(OCH₃)₂ | H | O | H | OCH₃ | CH₃ | CH | |
| Cl | CH₂CN | 6-Cl | O | H | OCH₃ | CH₃ | CH | |
| Cl | CH₂CN | H | O | H | Cl | CH₂CH₂OCH(CH₃)₂ | CH | |
| Cl | CH₂CN | H | O | H | OCH₃ | OCH₃ | N | |
| Cl | CH₂SCN | 6-Cl | O | H | CH₃ | CH(CH₃)(CH₂OCH₃) | CH | |
| Cl | CH₂SCN | H | O | H | OCH₃ | CH₃ | CH | |
| Cl | CH₂SCN | H | O | H | OCH₃ | CH₃ | N | |
| Cl | CH₂SCN | H | O | H | Cl | NH₂ | CH | |
| Cl | CH₂SCN | H | O | H | OCH₃ | OCH₃ | CH | |
| Cl | CH₂SCN | H | O | H | OCH₃ | (CH₂)₄CH₂OCH₂CH₂CH₃ | N | |
| Cl | CH₂P(O)(OCH₃)₂ | H | O | H | OCF₂H | CH₃ | CH | |
| Cl | CH₂P(O)(OCH₃)₂ | H | O | H | OCH₃ | CH₃ | CH | |
| Cl | CH₂P(O)(OCH₃)₂ | H | O | H | OCH₃ | NH₂ | N | |
| Cl | CH₂P(O)(OCH₃)(OCH₂CH₃)₂ | H | O | H | CH₃ | NHCH₃ | CH | |
| Cl | CH₂CN | H | O | H | OCH₃ | NHCH₂CH₃ | CH | |
| Br | CH₂CN | H | S | H | OCH₃ | OCH₃ | N | |
| Br | CH₂CN | H | O | H | CH₂F | CH₃ | CH | |
| Br | CH₂SCN | H | O | H | OCH₃ | OCH₃ | CH | |
| Br | CH₂SCN | H | O | H | OCH₃ | NHCH(CH₃)₂ | CH | |
| Br | CH₂SCN | H | O | H | OCH₃ | CH₃ | N | |
| Br | CH₂P(O)(OCH₃)₂ | H | O | H | OCH₂CH₂F | OCH₃ | CH | |
| Br | CH₂P(O)(OCH₃)₂ | H | O | H | OCH₃ | N(CH₃)₂ | CH | |
| Br | CH₂P(O)(SCH₃)₂ | H | O | H | OCH₃ | OCH₃ | N | |
| NO₂ | CH₂CN | H | O | H | OCH₃ | CH₃ | CH | |
| NO₂ | CH₂CN | H | O | H | CH₃ | OCH₃ | N | |
| NO₂ | CH₂SCN | H | O | H | OCH₃ | CH₂CH₂CH₂CH₃ | CH | |
| NO₂ | CH₂SCN | H | O | H | CH₂CH₃ | OCH₃ | CH | |
| NO₂ | CH₂SCN | H | O | H | CH₃ | OCH₂CH₂Cl | CH | |
| NO₂ | CH₂P(O)(OCH₃)₂ | H | O | H | OCH₃ | OCH₃ | CH | |
| NO₂ | CH₂P(O)(OCH₃)₂ | H | O | H | CH₂CH₂CH₂CH₃ | SCH₂CH₂F | N | |
| NO₂ | CH₂P(O)(SCH₃)₂ | H | O | H | OCH₃ | OCH₃ | CH | |
| CH₃ | CH₂CN | H | O | H | OCH₃ | SCH₃ | CH | |
| CH₃ | CH₂CN | H | O | H | CH₃ | SCH(CH₃)₂ | N | |
| CH₃ | CH₂SCN | H | O | H | OCH₃ | OCH₃ | CH | |
| CH₃ | CH₂SCN | H | O | H | OCH₂(CH₃)₂ | OCH₃ | CH | |
| CH₃ | CH₂P(O)(OCH₃)₂ | H | O | H | Br | OCH₃ | CH | |
| CH₃ | CH₂P(O)(N(CH₃)₂)₂ | H | O | H | OCH₃ | OCH₃ | N | |
| CH₃CH₃ | CH₂CN | H | O | H | CH₃CH₂OCH₂CH₂CH₃ | OCH₃ | CH | |
| CH₃CH₃ | CH₂SCN | H | O | H | OCH₃ | OCH₂CH₂OCH₃ | CH | |
| n-C₄H₉ | CH₂P(O)(OCH₃)₂ | H | O | H | OCH₃ | OCH₃ | N | |

TABLE I-continued

General Formula I

| $R_1$ | $R_2$ | $R_X$ | W | R | X | Y | Z | m.p. (°C.) |
|---|---|---|---|---|---|---|---|---|
| CH=CH$_2$ | CH$_2$CN | H | O | H | F | OCH$_3$ | CH | |
| CH=CHCH$_3$ | CH$_2$CN | H | O | H | OCH$_3$ | OCH$_3$ | CH | |
| CH$_2$CH=CH$_2$ | CH$_2$SCN | H | O | H | CH$_3$ | OCH$_3$ | N | |
| CCl=CCl$_2$ | CH$_2$SCN | H | O | H | OCH$_2$CH$_2$OCH(CH$_3$)$_2$ | OCH$_3$ | CH | |
| C≡CCH$_3$ | CH$_2$P(O)(OCH$_3$)$_2$ | H | O | H | CH$_3$ | CH$_2$CH$_3$ | CH | |
| CH$_2$C≡CH | CH$_2$CN | H | O | H | OCH$_3$ | OCH$_3$ | N | |
| CH$_2$Cl | CH$_2$CN | H | O | H | N(CH$_3$)$_2$ | OCH$_3$ | CH | |
| CH$_2$Cl | CH$_2$SCN | H | O | H | Cl | OCH$_3$ | CH | |
| CH$_2$Br | CH$_2$P(O)(OCH$_3$)$_2$ | H | O | H | OCH$_3$ | OCH$_3$ | N | |
| CH$_2$Br | CH$_2$CN | H | O | H | CH$_3$ | CH$_3$ | CH | |
| CF$_3$ | CH$_2$CN | H | O | H | OCH$_3$ | OCH$_3$ | CH | |
| CF$_3$ | CH$_2$CN | H | O | H | OCH$_3$ | OCH$_3$ | N | |
| CF$_3$ | CH$_2$SCN | H | O | H | Br | OCH$_3$ | CH | |
| CF$_3$ | CH$_2$SCN | H | O | H | OCH$_3$ | CH$_2$CH$_3$ | CH | |
| CF$_3$ | CH$_2$P(O)(OCH$_3$)$_2$ | H | O | H | OCH$_3$ | OCH$_3$ | N | |
| CF$_3$ | CH$_2$P(O)(OCH$_3$)$_2$ | H | O | H | OCH$_2$CH$_3$ | CH$_3$ | CH | |
| CF$_3$ | CH$_2$NH$_2$ | H | O | H | OCH$_3$ | H | CH | |
| CH$_2$CHClCH$_2$Cl | CH$_2$CN | H | O | H | CH$_3$ | OCH$_3$ | N | |
| CH$_2$CF$_3$ | CH$_2$CN | H | O | H | I | OCH$_3$ | CH | |
| OCH$_3$ | CH$_2$CN | H | O | H | OCH$_3$ | CH$_2$OCH$_3$ | CH | |
| OCH$_3$ | CH$_2$CN | H | O | H | CH$_3$ | OCH$_3$ | CH | |
| OCH$_3$ | CH$_2$CN | H | O | H | CH$_3$ | OCH$_3$ | N | |
| OCH$_3$ | CH$_2$CN | H | O | H | OCH$_3$ | NHCH$_3$ | CH | |
| OCH$_3$ | CH$_2$CN | H | O | H | CH$_3$ | OCH$_3$ | CH | |
| OCH$_3$ | CH$_2$CN | H | O | H | OCH$_2$CF$_2$H | OCH$_3$ | CH | |
| OCH$_3$ | CH$_2$CN | H | O | H | OCH$_3$ | OCH$_3$ | N | |
| OCH$_3$ | CH$_2$CN | H | O | H | CH$_3$ | CH$_3$ | CH | |
| OCH$_3$ | CH$_2$CN | H | O | H | CH$_2$Br | OCH$_3$ | CH | |
| OCH$_3$ | CH$_2$SCN | H | O | H | CH$_3$ | OCH$_3$ | N | |
| OCH$_3$ | CH$_2$SCN | H | O | H | OCH$_3$ | N(CH$_3$)$_2$ | CH | |
| OCH$_3$ | CH$_2$SCN | H | O | H | CH$_3$ | OCH$_3$ | CH | |
| OCH$_3$ | CH$_2$SCN | H | O | H | CH$_3$ | SCH$_3$ | CH | |
| OCH$_3$ | CH$_2$SCN | H | O | H | OCH$_3$ | CH$_3$ | N | |
| OCH$_3$ | CH$_2$SCN | H | O | H | OCH$_2$CF$_3$ | CF$_3$ | CH | |
| OCH$_3$ | CH$_2$P(O)(OCH$_3$)$_2$ | H | O | H | OCH$_3$ | OCH$_3$ | CH | |
| OCH$_3$ | CH$_2$P(O)(OCH$_3$)$_2$ | H | O | H | OCH$_3$ | CH$_3$ | N | |
| OCH$_3$ | CH$_2$P(O)(OCH$_3$)$_2$ | H | O | H | CH$_2$Cl | CH$_3$ | CH | |
| OCH$_3$ | CH$_2$P(O)(OCH$_3$)$_2$ | H | O | H | OCH$_3$ | OCH$_3$ | CH | |
| OCH$_3$ | CH$_2$P(O)(OCH$_3$)$_2$ | H | O | H | OCH$_3$ | OCH$_3$ | CH | |
| OCH$_3$ | CH$_2$P(O)(OCH$_3$)$_2$ | H | O | H | Cl | CH$_3$ | CH | |
| OCH$_3$ | CH$_2$N(CH$_3$)$_2$ | H | O | H | OCH$_3$ | OCH$_3$ | CH | |
| OCH$_3$ | CH$_2$N(CH$_3$)$_2$ | H | O | H | OCH$_3$ | CH$_3$ | N | |
| OCH$_3$ | CH$_2$N(CH$_3$)$_2$ | H | O | H | CH$_3$ | CH$_3$ | CH | |
| OCH$_3$ | CH$_2$N(CH$_3$)$_2$ | H | O | H | Cl | OCH$_3$ | CH | |
| OCH$_3$ | CH$_2$N(CH$_3$)$_2$ | H | O | H | OCH$_3$ | OCH$_3$ | N | |
| OCH$_3$ | CH$_2$N(CH$_3$)$_2$ | H | O | H | OCH$_3$ | OCH$_3$ | N | |
| OCH$_3$ | CH$_2$SeCH$_3$ | H | O | H | OCH$_3$ | CH$_3$ | CH | |
| OCH$_3$ | CH$_2$SeCH$_3$ | H | O | H | OCH$_3$ | OCH$_3$ | CH | |
| OCH$_3$ | CH$_2$SeCH$_3$ | H | O | H | Cl | OCH$_3$ | CH | |
| OCH$_3$ | CH$_2$SeCH$_3$ | H | O | H | CH$_3$ | CH$_3$ | CH | |

TABLE I-continued

General Formula I

| R₁ | R₂ | Rₓ | W | R | X | Y | Z | m.p. (°C.) |
|---|---|---|---|---|---|---|---|---|
| OCH₃ | CH₂SeCH₃ | H | O | H | OCH₃ | OCH₃ | N | |
| OCH₃ | CH₂SeCH₃ | H | O | H | OCH₃ | CH₃ | N | |
| OCH₃ | CH₂SeCH₃ | H | O | H | OCH₂CH₃ | NHCH₃ | N | |
| OCH₃ | CH₂N₃ | H | O | H | OCH₃ | OCH₃ | CH | |
| OCH₃ | CH₂N₃ | H | O | H | OCH₃ | CH₃ | CH | |
| OCH₃ | CH₂N₃ | H | O | H | Cl | CH₃ | CH | |
| OCH₃ | CH₂N₃ | H | O | H | CH₃ | OCH₃ | CH | |
| OCH₃ | CH₂N₃ | H | O | H | OCH₃ | OCH₃ | N | |
| OCH₃ | CH₂NO₂ | H | O | H | OCH₃ | CH₃ | N | |
| OCH₃ | CH₂NO₂ | H | O | H | CH₃ | OCH₃ | CH | |
| OCH₃ | CH₂NO₂ | H | O | H | OCH₃ | OCH₃ | CH | |
| OCH₃ | CH₂NO₂ | H | O | H | Cl | OCH₃ | CH | |
| OCH₃ | CH₂NO₂ | H | O | H | OCH₃ | CH₃ | CH | |
| OCH₃ | CH₂NO₂ | H | O | H | CH₃ | CH₃ | CH | |
| OCH₃ | CH₂NC | H | O | H | OCH₃ | OCH₃ | N | |
| OCH₃ | CH₂CN | H | O | H | OCH₃ | OCH₃ | N | |
| OCH₂CH₃ | CH₂CN | H | O | H | OCH₃ | OCH₃ | CH | |
| OCH₂CH₃ | CH₂SCN | H | O | H | OCH₃ | SCH₃ | CH | |
| OCH₂CH₃ | CH₂SCN | H | O | H | OCH₃ | OCH₃ | CH | |
| OCH₂CH₃ | CH₂P(O)(OCH₃)₂ | H | O | H | OCH₃ | OCH₂CH=CH₂ | CH | |
| OCH₂CH₃ | CH₂P(O)(OCH₃)₂ | H | O | H | OCH₃ | OCH₃ | CH | |
| OCH₂CH₃ | CH₂N₃ | H | O | H | CH₃ | CH₃ | N | |
| OCH₂CH₃ | CH₂NO₂ | H | O | H | OCH₃ | OCH₃ | N | |
| OCH₂CH₃ | CH₂N(CH₃)₂ | H | O | H | OCH₃ | OCH₃ | CH | |
| OCH(CH₃)₂ | CH₂CN | H | O | H | CH₃ | CH₃ | N | |
| O-n-D₄H₉ | CH₂CN | H | O | H | OCH₃ | OCH₂C≡CH | CH | |
| OCH₂CH₂OCH₃ | CH₂CN | H | O | H | OCH₃ | CH₃ | N | |
| OCH₂CH₂OCH₃ | CH₂SCN | H | O | H | OCH₃ | OCH₃ | CH | |
| OCH₂CH₂OCH₃ | CH₂P(O)(OCH₃)₂ | H | O | H | OCH₃ | OCH₃ | CH | |
| OCH₂CH₂OCH₃ | CH₂P(O)(OCH₃)₂ | H | O | H | CH₃ | OCH₂CH₂OCH₃ | CH | |
| OCH₂CH₂OCH₃ | CH₂NH(CH₂CH₂CH₃) | H | O | H | OCH₃ | CH₃ | CH | |
| OCH₂CH₂OCH₃ | CH₂CN | H | O | H | OCH₃ | OCH₃ | CH | |
| OCF₂H | CH₂CN | H | O | H | CH₃ | CH₃ | N | |
| OCF₂H | CH₂SCN | H | O | H | OCH₃ | OCH₃ | CN | |
| OCF₂H | CH₂CN | H | O | H | OCH₃ | CH₂SCH₃ | N | |
| OCF₂H | CH₂P(O)(OCH₃)₂ | H | O | H | CH₃ | CH₃ | CH | |
| OCF₂H | CH₂F(O)(OCH₃)₂ | H | O | H | CH₃ | CH₃ | CH | |
| OCF₂H | CH₂N(CH₂CH₃)₂ | H | O | H | OCH₃ | OCH₃ | CH | |
| OCF₂H | CH₂CN | H | O | H | OCH₃ | CH₃ | N | |
| OCH₂CH₂F | CH₂CN | H | O | H | OCH₃ | OCH₃ | CH | |
| OCH₂CH₂F | CH₂CN | H | O | H | OCH₃ | OCH₃ | CH | |
| OCH₂CF₃ | CH₂CN | H | O | H | OCH₃ | CH₃ | N | |
| OCH₂CH₂Cl | CH₂CN | H | O | H | OCH₃ | CH₃ | CH | |
| OCH₂CH₂Cl | CH₂CN | H | O | H | OCH₃ | OCH₃ | CH | |
| OCH₂CH₂Cl | CH₂CN | H | O | H | OCH₃ | CH₃ | CH | |
| OCH₂CH₂Cl | CH₂SCN | H | O | H | OCH₃ | CH₃ | CH | |
| OCH₂CH₂Cl | CH₂SCN | H | O | H | CH₃ | CH₃ | CH | |
| OCH₂CH₂Cl | CH₂SCN | H | O | H | OCH₃ | OCH₃ | CH | |
| OCH₂CH₂Cl | CH₂SCN | H | O | H | OCH₃ | CH₂CH₂OCH₂CH₃ | N | |
| OCH₂CH₂Cl | CH₂SCN | H | O | H | CH₂CH₃ | OCH₃ | CH | |

TABLE I-continued

General Formula I

| $R_1$ | $R_2$ | $R_X$ | W | R | X | Y | Z | m.p. (°C.) |
|---|---|---|---|---|---|---|---|---|
| OCH$_2$CH$_2$Cl | CH$_2$P(O)(OCH$_3$)$_2$ | H | O | H | I | OCH$_3$ | CH | |
| OCH$_2$CH$_2$Cl | CH$_2$P(O)(OCH$_3$)$_2$ | H | O | H | OCH$_3$ | OCH$_3$ | N | |
| OCH$_2$CH$_2$Cl | CH$_2$SeCH$_3$ | H | O | H | CH$_3$ | OCH$_3$ | CH | |
| OCH$_2$CH=CH$_2$ | CH$_2$CN | H | O | H | OCH$_3$ | NH$_2$ | CH | |
| OCH$_2$CH=CH$_2$ | CH$_2$CN | H | O | H | OCH$_3$ | OCH$_3$ | N | |
| OCH$_2$CH=CH$_2$ | CH$_2$CN | H | O | H | CH$_3$ | NHCH$_2$CH$_3$ | CH | |
| OCH$_2$CH=CH$_2$ | CH$_2$CN | H | O | H | OCH$_3$ | OCH$_3$ | CH | |
| OCH$_2$CH=CH$_2$ | CH$_2$CN | H | O | H | OCH$_3$ | OCH$_3$ | N | |
| OCH$_2$CH=CH$_2$ | CH$_2$P(O)(OCH$_3$)$_2$ | H | O | H | CH$_3$ | OCH$_3$ | CH | |
| OCH$_2$CH=CH$_2$ | CH$_2$SeCH$_2$CH$_3$ | H | O | H | OCH$_3$ | OCH$_2$C≡CH | CH | |
| OCH$_2$CH=CH$_2$ | CH$_2$CN | H | O | H | OCH$_3$ | OCH$_3$ | N | |
| OCH$_2$C≡CH | CH$_2$CN | H | O | H | CH$_2$C$_3$ | OCH$_3$ | CH | |
| OCH$_2$C≡CH | CH$_2$CN | H | O | H | OCH$_3$ | OCH$_2$CH$_2$CH=CH$_3$ | CH | |
| OCH$_2$C≡CH | CH$_2$SCN | H | O | H | OCH$_3$ | CH$_2$SCH$_3$ | CH | |
| OCH$_2$C≡CH | CH$_2$SCN | H | O | H | OCH$_3$ | OCH$_3$ | N | |
| OCH$_2$C≡CH | CH$_2$SCN | H | O | H | CH$_3$ | CH$_2$SCH$_2$CH$_2$CH$_2$ | CH | |
| OCH$_2$C≡CH | CH$_2$P(O)(OCH$_3$)$_2$ | H | O | H | OCH$_3$ | OCH$_3$ | N | |
| OCH$_2$C≡CH | CH$_2$P(O)(OCH$_3$)$_2$ | H | O | H | CH$_3$ | CH$_2$CH$_2$F | CH | |
| OCH$_2$C≡CH | CH$_2$CN | H | O | H | OCH$_3$ | OCH$_3$ | CH | |
| OC(Cl)=CHCl | CH$_2$CN | H | O | H | I | OCH$_2$C≡CH | CH | |
| OC(Cl)=CHCl | CH$_2$CN | H | O | H | OCH$_3$ | C≡CH | N | |
| OC(Cl)=CHCl | CH$_2$P(O)(OCH$_3$)$_2$ | H | O | H | OCH$_3$ | OCH$_3$ | CH | |
| OC(Cl)=CHCl | CH$_2$P(O)(OCH$_3$)$_2$ | H | O | H | CH$_3$ | OCH$_3$ | N | |
| CO$_2$CH$_3$ | CH$_2$CN | H | O | H | OCH$_3$ | CH$_3$ | CH | 191–193 |
| CO$_2$CH$_3$ | CH$_2$CN | H | O | H | CH$_2$CH$_3$ | CH$_3$ | CH | 194–195 |
| CO$_2$CH | CH$_2$CN | H | O | H | OCH$_3$ | OCH$_3$ | CH | 197(d) |
| CO$_2$CH$_3$ | CH$_2$CN | H | O | H | CH$_2$CH$_2$ | CH$_3$ | N | |
| CO$_2$CH$_3$ | CH$_2$CN | H | O | H | Cl | OCH$_3$ | CH | 173–176 |
| CO$_2$CH$_3$ | CH$_2$CN | H | O | H | OCH$_3$ | CH$_3$ | CH | |
| CO$_2$CH$_3$ | CH$_2$CN | H | O | H | Cl | OCH$_3$ | N | |
| CO$_2$CH$_3$ | CH$_2$SCN | H | O | H | OCH$_3$ | OCH$_3$ | CH | 202–204 |
| CO$_2$CH$_3$ | CH$_2$SCN | H | O | H | CH$_3$ | CH$_3$ | CH | 184–187 |
| CO$_2$CH$_3$ | CH$_2$SCN | H | O | H | OCH$_3$ | OCH$_3$ | N | |
| CO$_2$CH$_3$ | CH$_2$SCN | H | O | H | CH$_3$ | CH$_3$ | N | |
| CO$_2$CH$_3$ | CH$_2$CN | H | O | H | NHCH$_3$ | OCH$_3$ | CH | |
| CO$_2$CH$_3$ | CH$_2$P(O)(OCH$_3$)$_2$ | H | O | H | OCH$_3$ | CH(OCH$_3$)$_2$ | CH | |
| CO$_2$CH$_3$ | CH$_2$P(O)(OCH$_3$)$_2$ | H | O | H | OCH$_3$ | OCH$_3$ | N | |
| CO$_2$CH$_3$ | CH$_2$P(O)(OCH$_3$)$_2$ | H | O | H | CH$_3$ | CH$_3$ | CH | |
| CO$_2$CH$_3$ | CH$_2$P(O)(OCH$_3$)$_2$ | H | O | H | CH$_3$ | OCH$_2$CF$_3$ | CH | |
| CO$_2$CH$_3$ | CH$_2$P(O)(OCH$_3$)$_2$ | H | O | H | cyclopropyl | OCH$_3$ | CH | |
| CO$_2$CH$_3$ | CH$_2$P(O)(OCH$_3$)$_2$ | H | O | H | OCH$_3$ | CH$_3$ | N | |
| CO$_2$CH$_3$ | CH$_2$P(S)(SCH$_3$)$_2$ | H | O | H | CH$_3$ | CH$_3$ | CH | |
| CO$_2$CH$_3$ | CH$_2$P(O)(SCH$_3$)$_2$ | H | O | H | OCH$_3$ | OCH$_3$ | CH | |
| CO$_2$CH$_3$ | CH$_2$N(CH$_2$CH$_3$)$_2$ | H | O | H | cyclopropyl | OCH$_3$ | CH$_3$ | |

TABLE I-continued

General Formula I

| R₁ | R₂ | R_X | W | R | X | Y | Z | m.p. (°C.) |
|---|---|---|---|---|---|---|---|---|
| CO₂CH₃ | CH₂N(CH₂CH₃)₂ | H | O | H | Cl | OCH₃ | CH | |
| CO₂CH₃ | CH₂N(CH₂CH₃)₂ | H | O | H | OCH₃ | OCH₃ | N | |
| CO₂CH₃ | CH₂N(CH₂CH₃)₂ | H | O | H | CH₃ | OCH₃ | CH | |
| CO₂CH₃ | CH₂N(CH₃)₂ | H | O | H | OCH₃ | OCH₃ | CH | |
| CO₂CH₃ | CH₂N(CH₃)₂ | H | O | H | OCH₃ | CH₃ | N | |
| CO₂CH₃ | CH₂N(CH₃)₂ | H | O | H | CH₃ | OCH₃ | N | |
| CO₂CH₃ | CH₂N(CH₃)₂ | H | O | H | CH₂CH₃ | OCH₃ | CH | |
| CO₂CH₃ | CH₂N(CH₃)₂ | H | O | H | OCH₃ | OCH₃ | N | |
| CO₂CH₃ | CH₂N(CH₃)(CH₂CH₃) | H | O | H | Cl | OCH₃ | CH | |
| CO₂CH₃ | CH₂N(CH₃)(CH₂CH₃) | H | O | H | OCH₃ | OCH₃ | N | |
| CO₂CH₃ | CH₂SeCH₃ | H | O | H | CH₃ | CH₃ | CH | |
| CO₂CH₃ | CH₂SeCH₃ | H | O | H | OCH₃ | OCH₃ | CH | |
| CO₂CH₃ | CH₂SeCH₃ | H | O | H | OCH₃ | CH₃ | N | |
| CO₂CH₃ | CH₂SeCH₃ | H | O | H | Cl | OCH₃ | CH | |
| CO₂CH₃ | CH₂N₃ | H | O | H | OCH₃ | OCH₃ | CH | 175-178 |
| CO₂CH₃ | CH₂N₃ | H | O | H | OCH₃ | OCH₃ | N | 181-183 |
| CO₂CH₃ | CH₂N₃ | H | O | H | Cl | CH₃ | CH | 176-177 |
| CO₂CH₃ | CH₂N₃ | H | O | H | OCH₂CH₃ | NHCH₃ | CH | |
| CO₂CH₃ | CH₂N₃ | H | O | H | OCH₃ | CH₃ | N | 164-165 |
| CO₂CH₃ | CH₂N₃ | H | O | H | CH₃ | CH₃ | CH | 179-181 |
| CO₂CH₃ | CH₂N₃ | H | O | H | CH₃ | OCH₃ | CH | 175-177 |
| CO₂CH₃ | CH₂NO₂ | H | O | H | OCH₃ | OCH₃ | CH | |
| CO₂CH₃ | CH₂NO₂ | H | O | H | CH₃ | OCH₃ | N | |
| CO₂CH₃ | CH₂NO₂ | H | O | H | CH₃ | OCH₃ | CH | 201-204 |
| CO₂CH₃ | CH₂NO₂ | H | O | H | CH₃ | OCH₃ | N | 191-193 |
| CO₂CH₃ | CH₂NC | H | O | H | CH₃ | NHCH₃ | CH | 166-168 |
| CO₂CH₃ | CH₂CN | H | O | H | OCH₃ | N(OCH₃)CH₃ | CH | |
| CO₂CH₃ | CH₂CN | H | O | H | CH₃ | OCH₃ | N | 188-190 |
| CO₂CH₃ | CH₂CN | H | O | H | CH₃ | OCH₃ | CH | 213-214 |
| CO₂CH₃ | CH₂CN | H | O | H | CH₃ | OCH₃ | N | 191-193 |
| CO₂CH₃ | CH₂CN | H | O | H | Cl | OCH₃ | CH | 192-195 |
| CO₂CH₃ | CH₂SCN | H | O | H | CH₃ | OCH₃ | N | 175-177 |
| CO₂CH₃ | CH₂SCN | H | O | H | CH₃ | CH₃ | N | 184-186 |
| CO₂CH₃ | CH₂SCN | H | O | H | Cl | OCH₃ | CH | 187-190 |
| CO₂CH₃ | CH₂SCN | H | O | H | CH₃ | OCH₃ | N | 158-164 |
| CO₂CH₃ | CH₂P(O)(OCH₃)₂ | H | O | H | OCH₃ | OCH₃ | CH | 137-140 |
| CO₂CH₂CH₃ | CH₂P(O)(OCH₃)₂ | H | O | H | OCH₃ | OCH₃ | CH | |
| CO₂CH₂CH₃ | CH₂P(O)(OCH₃)₂ | H | O | H | CH₃ | OCH₃ | N | |
| CO₂CH₃ | CH₂N₃ | H | O | H | OCH₂CH₃ | NHCH₃ | CH | 158-160 |
| CO₂CH₃ | CH₂N₃ | H | O | H | OCH₂CH₃ | OCH₃ | N | >250 |
| CO₂CH₂CH₃ | CH₂N₃ | H | O | H | OCH₃ | CH₃ | N | 150-152 |

TABLE I-continued

General Formula I

| R₁ | R₂ | R_X | W | R | X | Y | Z | m.p. (°C.) |
|---|---|---|---|---|---|---|---|---|
| CO₂CH(CH₃)₂ | CH₂CN | H | O | H | OCH₃ | OCH₃ | CH | |
| CO₂CH(CH₃)₂ | CH₂CN | H | O | H | OCH₃ | CH₃ | CH | |
| CO₂CH₂CH=CH₂ | CH₂CN | H | O | H | OCH₃ | OCH₃ | N | |
| CO₂CH₂CH=CH₂ | CH₂SCN | H | O | H | OCH₃ | OCH₃ | CH | |
| CO₂CH₂CH=CH₂ | CH₂SCN | H | O | H | OCH₃ | CN | N | |
| CO₂CH₂C≡CH | CH₂P(O)(OCH₃)₂ | H | O | H | OCH₃ | OCH₃ | CH | |
| CO₂CH₂CH₂Cl | CH₂P(O)(OCH₃)₂ | H | O | H | CH₃ | OCH₃ | CH | |
| CO₂CH₂CH₂Cl | CH₂CN | H | O | H | OCH₃ | CHO | CH | |
| CO₂CH₂CH₂F | CH₂SCN | H | O | H | CH₃ | OCH₃ | CH | |
| CO₂CH₂CH₂F | CH₂SCN | H | O | H | CH₃ | OCH₃ | N | |
| CO₂CH₂CF₃ | CH₂CN | H | O | H | OCH₃ | OCH₃ | CH | |
| CO₂CH₂CH₂OCH₃ | CH₂P(O)(OCH₃)₂ | H | O | H | OCH₃ | N₃ | CH | |
| CO₂CH₂CH₂SCH₃ | CH₂CN | H | O | H | OCH₃ | CH₃ | N | |
| CO₂CH₂CH₂SCH₃ | CH₂SCN | H | O | H | OCH₃ | OCH₃ | CH | |
| C(O)NHCH₃ | CH₂CN | H | O | H | OCH₃ | OCH₃ | CH | |
| C(O)NHCH₃ | CH₂SCN | H | O | H | OCH₃ | CH₃ | CH | |
| C(O)NHCH₃ | CH₂P(O)(OCH₃)₂ | H | O | H | CH₂CH₃ | OCH₃ | CH | |
| C(O)N(CH₃)₂ | CH₂CN | H | O | H | OCH₃ | OCH₃ | N | |
| C(O)N(CH₃)₂ | CH₂CN | H | O | H | OCH₃ | CH₃ | CH | |
| C(O)N(CH₃)₂ | CH₂SCN | H | O | H | OCH₃ | OCH₃ | CH | |
| C(O)N(CH₃)₂ | CH₂SCN | H | O | H | OCH₃ | CH₃ | N | |
| CO₂CH₂CH₃ | CH₂N₃ | H | O | H | Cl | CH₃ | CH | 183–185 |
| CO₂CH₂CH₃ | CH₂N₃ | H | O | H | OCH₃ | OCH₃ | CH | 158–159 |
| CO₂CH₂CH₃ | CH₂N₃ | H | O | H | Cl | CH₃ | N | 157–159 |
| CO₂CH₂CH₃ | CH₂SCN | H | O | H | OCH₃ | OCH₃ | CH | 165–168 |
| C(O)N(CH₃)₂ | CH₂SCN | H | O | H | CH₃ | OCH₃ | CH | |
| C(O)N(CH₃)₂ | CH₂P(O)(OCH₃)₂ | H | O | H | OCH₃ | OCH₃ | CH | |
| C(O)N(CH₃)₂ | CH₂P(O)(OCH₃)₂ | H | O | H | OCH₃ | OCH₃ | N | |
| C(O)N(CH₃)₂ | CH₂SeCH₂CH₂CH₃ | H | O | H | OCH₃ | OCH₃ | CH | |
| C(O)N(CH₃)₂ | CH₂N(CH₃)₂ | H | O | H | OCH₃ | CH(OCH₃)₂ | CH | |
| SO₂NHCH₃ | CH₂CN | H | O | H | OCH₃ | OCH₃ | CH | |
| SO₂NHCH₃ | CH₂CN | H | O | H | OCH₃ | OCH₃ | N | |
| SO₂NHCH₃ | CH₂CN | H | O | H | CH₃ | CH₃ | CH | |
| SO₂NHCH₃ | CH₂SCN | H | O | H | OCH₃ | OCH₃ | CH | |
| SO₂NHCH₃ | CH₂SCN | H | O | H | OCH₃ | CH₃ | N | |
| SO₂NHCH₃ | CH₂SCN | H | O | H | CH₃ | CH₃ | CH | |
| SO₂NHCH₃ | CH₂P(O)(OCH₃)₂ | H | O | H | OCH₃ | OCH₃ | CH | |
| SO₂NHCH₃ | CH₂P(O)(OCH₃)₂ | H | O | H | Cl | CH₃ | N | |
| SO₂NHCH₂CH₃ | CH₂CN | H | O | H | CH₃ | OCH₃ | CH | |
| SO₂NHCH₂CH₃ | CH₂CN | H | O | H | OCH₃ | CH₃ | N | |
| SO₂NHCH₂CH₃ | CH₂SCN | H | O | H | OCH₃ | OCH₃ | CH | |
| SO₂NHCH₂CH₃ | CH₂SCN | H | O | H | OCH₃ | CH₃ | N | |
| SO₂NHCH₂CH₃ | CH₂P(O)(OCH₃)₂ | H | O | H | OCH₃ | OCH₃ | CH | |
| SO₂N(CH₃)(CH₂CH₃) | CH₂CN | H | O | H | CH₃ | OCH₃ | CH | |
| SO₂NHCH₂CH₂CH₃ | CH₂CN | H | O | H | OCH₃ | CH₃ | N | |
| SO₂N(CH₂CH₃)₂ | CH₂SCN | H | O | H | Cl | OCH₃ | CH | |

TABLE I-continued

General Formula I

| $R_1$ | $R_2$ | W | R | X | Y | Z | m.p. (°C.) |
|---|---|---|---|---|---|---|---|
| $SO_2N(CH_3)(CH(CH_3)_2)$ | $CH_2SCN$ | O | H | $OCH_3$ | $OCH_3$ | N | |
| $SO_2N(CH_3)(OCH_3)$ | $CH_2P(O)(OCH_3)$ | O | H | $OCH_3$ | $OCH_3$ | CH | |
| $SO_2N(CH_3)(OCH_3)$ | $CH_2P(O)(OCH_3)$ | O | H | $OCH_3$ | $CH_3$ | CH | |
| $SO_2N(CH_3)(OCH_3)$ | $CH_2CN$ | O | H | $OCH_3$ | $OCH_3$ | CH | |
| $SO_2N(CH_3)(OCH_3)$ | $CH_2CN$ | O | H | $OCH_3$ | $OCH_3$ | N | |
| $SO_2N(CH_3)_2$ | $CH_2CN$ | O | H | $OCH_3$ | $OCH_3$ | CH | |
| $SO_2N(CH_3)_2$ | $CH_2CN$ | O | H | $OCH_3$ | $OCH_3$ | CH | |
| $SO_2N(CH_3)_2$ | $CH_2CN$ | O | H | $OCH_3$ | $CH_3$ | CH | |
| $SO_2N(CH_3)_2$ | $CH_2CN$ | O | H | $OCH_3$ | $OCH_2CH=CH_2$ | CH | |
| $SO_2N(CH_3)_2$ | $CH_2CN$ | O | H | $OCH_3$ | $CH_3$ | N | |
| $SO_2N(CH_3)_2$ | $CH_2SCN$ | O | H | $CH_2CH_3$ | $OCH_3$ | CH | |
| $SO_2N(CH_3)_2$ | $CH_2SCN$ | O | H | $OCH_3$ | $N(CH_3)(CH(CH_3)_2)$ | CH | |
| $SO_2N(CH_3)_2$ | $CH_2SCN$ | O | H | $OCH_3$ | $OCH_3$ | N | |
| $SO_2N(CH_3)_2$ | $CH_2P(O)(OCH_3)_2$ | O | H | $OCH_3$ | $OCH_3$ | CH | |
| $SO_2N(CH_3)_2$ | $CH_2P(O)(OCH_3)_2$ | O | H | $CH_3$ | $CH_3$ | CH | |
| $SO_2N(CH_3)_2$ | $CH_2P(O)(OCH_3)_2$ | O | H | $OCH_3$ | $OCH_3$ | N | |
| $SO_2N(CH_3)_2$ | $CH_2P(O)(OCH_3)_2$ | O | H | $OCH_3$ | $OCH_2C(CH_3)=CH_2$ | CH | |
| $SO_2N(CH_3)_2$ | $CH_2P(O)(OCH_3)_2$ | O | H | $OCH_3$ | $CH_2S(CH_2)_3CH_3$ | CH | |
| $SO_2N(CH_3)_2$ | $CH_2NO_2$ | O | H | $OCH_3$ | $OCH_3$ | N | |
| $SO_2N(CH_3)_2$ | $CH_2CN$ | O | H | $OCH_3$ | $(CH_2)_4CH_2SCH_2CH_3$ | CH | |
| $SO_2CH_3$ | $CH_2CN$ | O | H | $OCH_3$ | $OCH_3$ | CH | |
| $SO_2CH_3$ | $CH_2CN$ | O | H | $OCH_3$ | $OCH_3$ | N | |
| $SO_2CH_3$ | $CH_2CN$ | O | H | $CH_3$ | $CH_3$ | CH | |
| $SO_2CH_3$ | $CH_2SCN$ | O | H | $OCH_3$ | $OCH_3$ | CH | |
| $SO_2CH_3$ | $C(O)H$ | O | H | $OCH_3$ | $OCH_3$ | CH | |
| $SO_2CH_3$ | $CH_2N_3$ | O | H | $OCH_3$ | $OCH_3$ | N | |
| $SO_2CH_3$ | $CH_2SCN$ | O | H | $OCH_3$ | $OCH_3$ | CH | |
| $SO_2CH_3$ | $CH_2SCN$ | O | H | $CH_3$ | cyclopropyl | CH | |
| $SO_2CH_3$ | $CH_2SCN$ | O | H | $OCH_3$ | $OCH_3$ | CH | |
| $SO_2CH_3$ | $CH_2P(O)(OCH_3)_2$ | O | H | $OCH_3$ | $OCH_3$ | CH | |
| $SO_2CH_3$ | $CH_2P(O)(OCH_3)_2$ | O | H | $CH_3$ | $OCH_3$ | CH | |
| $SO_2CH_3$ | $CH_2P(O)(OCH_3)_2$ | O | H | $CH_3$ | $CH_3$ | CH | |
| $SO_2CH_2CH_3$ | $CH_2CN$ | O | H | $OCH_3$ | 2-methylcyclopropyl | CH | |
| $SO_2CH_2CH_3$ | $CH_2CN$ | O | H | $CH_3$ | $CH_3$ | N | |
| $SO_2CH_2CH_3$ | $CH_2CN$ | O | H | $OCH_3$ | $OCH_3$ | CH | |
| $SO_2CH_2CH_3$ | $CH_2CN$ | O | H | $OCH_3$ | $OCH_3$ | CH | |
| $SO_2CH_2CH_3$ | $CH_2SCN$ | O | H | $OCH_3$ | $OCH_3$ | CH | |
| $SO_2CH_2CH_3$ | $CH_2SCN$ | O | H | $OCH_3$ | $CH_3$ | CH | |
| $SO_2CH_2CH_3$ | $CH_2SCN$ | O | H | $CH_3$ | $C\equiv CH$ | CH | |
| $SO_2CH_2CH_3$ | $CH_2SCN$ | O | H | $CH_2CH_3$ | cyclopentyl | CH | |
| $SO_2CH_2CH_3$ | $CH_2P(O)(OCH_3)_2$ | O | H | $OCH_3$ | $OCH_3$ | N | |
| $SO_2CH_2CH_3$ | $CH_2P(O)(OCH_3)_2$ | O | H | $OCH_3$ | $CH_3$ | CH | |
| $SO_2CH_2CH_3$ | $CH_2P(O)(OCH_3)_2$ | O | H | $OCH_3$ | $OCH_3$ | CH | |
| $SO_2CH_2CH_2CH_3$ | $CH_2CN$ | O | H | $OCH_3$ | $OCH_3$ | CH | |
| $SO_2CH_2CH_2CH_3$ | $CH_2CN$ | O | H | $OCH_3$ | $CH_3$ | CH | |
| $SO_2CH_2CH_2CH_3$ | $CH_2CN$ | O | H | $CH_3$ | $CH_3$ | CH | |
| $SO_2CH_2CH_2CH_3$ | $CH_2CN$ | O | H | $Cl$ | $OCH_3$ | N | |
| $SO_2CH_2CH_2CH_3$ | $CH_2N_3$ | O | H | $OCH_3$ | $OCH_3$ | N | |
| $SO_2CH_2CH_2CH_3$ | $CH_2CN$ | O | H | $OCH_3$ | $CH_3$ | N | |
| $SO_2CH_2CH_2CH_3$ | $CH_2CN$ | O | H | $OCH_3$ | $OCH_3$ | CH | |

TABLE I-continued

General Formula I

| R₁ | R₂ | Rₓ | W | R | X | Y | Z | m.p. (°C.) |
|---|---|---|---|---|---|---|---|---|
| SO₂CH₂CH₂CH₃ | CH₂N₃ | H | O | H | OCH₃ | CH₃ | CH | |
| SO₂CH₂CH₂CH₃ | CH₂N₃ | H | O | H | CH₃ | CH₃ | CH | |
| SO₂CH₂CH₂CH₃ | CH₂N₃ | H | O | H | Cl | OCH₃ | CH | |
| SO₂CH₂CH₂CH₃ | CH₂N₃ | H | O | H | OCH₃ | OCH₃ | N | |
| SO₂CH₂CH₂CH₃ | CH₂CN | H | O | H | OCH₃ | CH₃ | N | |
| SCH₃ | CH₂CN | H | O | H | OCH₃ | OCH₃ | CH | |
| SCH₂CH₂CH₃ | CH₂SCN | H | O | H | OCH₃ | OCH₃ | N | |
| S(O)CH₂CH₃ | CH₂P(O)(OCH₃)₂ | H | O | H | CH₃ | CH₃ | N | |
| S(O)CH₂CH₂CH₃ | CH₂CN | H | O | H | OCH₃ | OCH₃ | N | |
| OSO₂CH₃ | CH₂CN | H | O | H | CH₃ | CH₃ | CH | |
| OSO₂CH₃ | CH₂CN | H | O | H | OCH₃ | OCH₃ | CH | |
| OSO₂CH₃ | CH₂CN | H | O | H | OCH₃ | OCH₃ | N | |
| OSO₂CH₃ | CH₂CN | H | O | H | OCH₃ | CHO | CH | |
| OSO₂CH₃ | CH₂CN | H | O | H | OCH₃ | CHO | CH | |
| OSO₂CH₃ | CH₂CN | H | O | H | OCH₃ | OCH₃ | CH | |
| OSO₂CH₃ | CH₂SCN | H | O | H | OCH₃ | C≡CCH₃ | CH | |
| OSO₂CH₃ | CH₂SCN | H | O | H | OCH₃ | OCH₃ | N | |
| OSO₂CH₃ | CH₂SCN | H | O | H | OCH₃ | OCH₃ | CH | |
| OSO₂CH₃ | CH₂SCN | H | O | H | CH₃ | CH₃ | CH | |
| OSO₂CH₃ | CH₂P(O)(OCH₃)₂ | H | O | H | OCH₃ | OCH₃ | N | |
| OSO₂CH₃ | CH₂P(O)(OCH₃)₂ | H | O | H | OCH₃ | OCH₃ | CH | |
| OSO₂CH₃ | CH₂CN | H | O | H | CH₃ | OCH₃ | CH | |
| OSO₂CH₂CH₃ | CH₂CN | H | O | H | OCH₃ | OCH₃ | N | |
| OSO₂CH₂CH₃ | CH₂CN | H | O | H | OCH₃ | OCH₃ | CH | |
| OSO₂CH₂CH₃ | CH₂CN | H | O | H | CH₃ | CH₃ | CH | |
| OSO₂CH₂CH₃ | CH₂SCN | H | O | H | OCH₃ | CH(OCH₃)₂ | CH | |
| OSO₂CH₂CH₃ | CH₂SCN | H | O | H | CH₃ | CH₃ | N | |
| OSO₂CH₂CH₃ | CH₂SCN | H | O | H | OCH₃ | OCH₃ | CH | |
| OSO₂CH₂CH₃ | CH₂P(O)(OCH₃)₂ | H | O | H | OCH₃ | OCH₃ | CH | |
| OSO₂CH₂CH₃ | CH₂P(O)(OCH₃)₂ | H | O | H | CH₃ | CH₃ | N | |
| OSO₂CH₂CH₃ | CH₂P(O)(OCH₃)₂ | H | O | H | OCH₃ | OCH₃ | N | |
| OSO₂CH₂CH₂CH₃ | CH₂CN | H | O | H | CH₃ | COCH₃ | CH | |
| OSO₂CH₂CH₂CH₃ | CH₂CN | H | O | H | CH₂CH₃ | OCH₃ | CH | |
| OSO₂CH₂CH₂CH₃ | CH₂CN | H | O | H | OCH₃ | CH(SCH₃)(OCH₂CH₃) | CH | |
| OSO₂CH₂CH₂CH₃ | CH₂CN | H | O | H | OCH₃ | OCH₃ | CH | |
| OSO₂CH₂CH₂CH₃ | CH₂CN | H | O | H | OCH₃ | OCH₃ | N | |
| OSO₂CH₂CH₂CH₃ | CH₂CN | H | O | H | CH₃ | CH₃ | CH | |
| CH₂OCH₃ | CH₂P(O)(OCH₃)₂ | H | O | H | OCH₃ | OCH₃ | CH | |
| CH₂SCH₃ | CH₂P(O)(OCH₃)₂ | H | O | H | CH₃ | C(CH₃)(SCH₃)₂ | N | |
| CH₂CH₂OCH₃ | CH₂P(O)(OCH₃)₂ | H | O | H | OCH₃ | OCH₃ | CH | |
| CH₂CH₂OCH₃ | CH₂CN | H | O | H | OCH₃ | OCH₃ | CH | |
| CH₂CH₂SCH₂CH₃ | CH₂CN | H | O | H | CH₃ | CH₃ | N | |
| CH₂CN | CH₂CN | H | O | H | OCH₃ | 1,3-dioxolan-2-yl | CH | |
| C₂H₅ | CH₂CN | H | O | H | OCH₃ | OCH₃ | N | |
| C₂H₅ | CH₂CN | H | O | H | OCH₃ | OCH₃ | CH | |
| C₂H₅ | CH₂SCN | H | O | H | CH₃ | CH₃ | CH | |
| COCH₃ | CH₂SCN | H | O | H | OCH₃ | 2-methyl-1,3-oxathion-2-yl | N | |
| COCH₂OCH₃ | CH₂P(O)(OCH₃)₂ | H | O | H | OCH₃ | OCH₃ | CH | |
| COC≡CCH₃ | CH₂CN | H | O | H | CH₃ | CH₃ | CH | |
| COCH₂CH₂Cl | CH₂CN | H | O | H | CH₃ | OCH₃ | CH | |
| C(O)-cyclo-propyl | CH₂CN | H | O | H | OCH₃ | OCH₃ | N | |

TABLE I-continued

General Formula I

| R₁ | R₂ | Rₓ | W | R | X | Y | Z | m.p. (°C.) |
|---|---|---|---|---|---|---|---|---|
| C(O)-cyclo-propyl | CH₂CN | H | O | H | CH₃ | OCH₃ | CH | |
| C(O)-cyclo-propyl | CH₂SCN | H | O | H | OCH₃ | CH₃ | CH | |
| CH(OCH₃)₂ | CH₂SCN | H | O | H | OCH₃ | OCH₃ | N | |
| CH(OCH₃)₂ | CH₂SCN | H | O | H | OCH₃ | OCH₃ | CH | |
| CH(OCH₂CH₃)₂ | CH₂P(O)(OCH₃)₂ | H | O | H | OCH₃ | OCH₃ | CH | |
| CH(OCH₂CH₃)₂ | CH₂P(O)(OCH₃)₂ | H | O | H | CH₃ | CH₃ | CH | |
| 1,3-dioxyl-2-yl | CH₂CN | H | O | H | CH₃ | OCH₃ | CH | |
| 1,3-dioxyl-2-yl | CH₂CN | H | O | H | OCH₃ | OCH₃ | N | |
| R₁-A | CH₂CN | H | O | H | CH₂CH₃ | OCH₃ | CH | |
| R₁-A | CH₂CN | H | O | H | OCH₃ | 1,3-oxathion-2-yl | CH | |
| R₁-A | CH₂CN | H | O | H | OCH₃ | OCH₃ | N | |
| R₁-A | CH₂CN | H | O | H | OCH₃ | OCH₃ | CH | |
| R₁-A | CH₂CN | H | O | H | OCH₃ | CH₃ | CH | |
| R₁-A | CH₂SCN | H | O | H | CH₃ | OCH₃ | N | |
| R₁-A | CH₂SCN | H | O | H | CH₃ | 2-methyl-1,3-dithian-2-yl | CH | |
| R₁-A | CH₂P(O)(OCH₃)₂ | H | O | H | OCH₃ | OCH₃ | CH | |
| R₁-A | CH₂P(O)(OCH₃)₂ | H | O | H | OCH₃ | OCH₃ | N | |
| R₁-A | CH₂P(O)(OCH₃)₂ | H | O | H | OCH₃ | CH₃ | CH | |
| R₁-B | CH₂CN | H | O | H | OCH₃ | OCH₃ | CH | |
| R₁-B | CH₂CN | H | O | H | OCH₃ | OCH₃ | N | |
| R₁-B | CH₂CN | H | O | H | OCH₃ | 4-methyl-1,3-dioxolan-2-yl | CH | |
| R₁-B | CH₂CN | H | O | H | OCH₃ | OCH₃ | CH | |
| R₁-B | CH₂SCN | H | O | H | Cl | OCH₃ | CH | |
| R₁-B | CH₂SCN | H | O | H | OCH₃ | OCH₃ | N | |
| R₁-B | CH₂SCN | H | O | H | CH₃ | CH₃ | CH | |
| R₁-B | CH₂P(O)(OCH₃)₂ | H | O | H | OCH₃ | OCH₃ | CH | |
| R₁-B | CH₂P(O)(OCH₃)₂ | H | O | H | CH₃ | CH₃ | CH | |
| R₁-C | CH₂CN | H | O | H | OCH₃ | OCH₃ | N | |
| R₁-C | CH₂CN | H | O | H | OCH₃ | OCH₃ | CH | |
| R₁-C | CH₂CN | H | O | H | OCH₃ | 4-methyl-1,3-oxathiolan-2-yl | CH | |
| R₁-C | CH₂CN | H | O | H | CH₃ | CH₃ | CH | |
| R₁-C | CH₂SCN | H | O | H | OCH₃ | OCH₃ | CH | |
| R₁-C | CH₂SCN | H | O | H | OCH₃ | OCH₃ | N | |
| R₁-C | CH₂SCN | H | O | H | CH₃ | CH₃ | CH | |
| R₁-C | CH₂P(O)(OMe)₂ | H | O | H | OCH₃ | OCH₃ | CH | |
| R₁-C | CH₂P(O)(OMe)₂ | H | O | H | OCH₃ | OCH₃ | N | |
| R₁-C | CH₂P(O)(OMe)₂ | H | O | H | CH₂CH₃ | 2,4-dimethyl-1,3-dithiolan-2-yl | CH | |
| R₁-D | CH₂P(O)(OMe)₂ | H | O | H | OCH₃ | OCH₃ | N | |
| R₁-D | CH₂P(O)(OMe)₂ | H | O | H | OCH₃ | OCH₃ | CH | |
| R₁-E | CH₂CN | H | O | H | OCH₃ | OCH₃ | CH | |
| R₁-F | CH₂CN | H | O | H | OCH₃ | N(OCH₃)CH₃ | CH | |
| R₁-G | CH₂CN | H | O | H | OCH₃ | OCH₃ | N | |
| R₁-H | CH₂SCN | H | O | H | CH₃ | CH₃ | CH | |
| R₁-I | CH₂SCN | H | O | H | OCH₃ | OCH₃ | CH | |
| R₁-J | CH₂P(O)(OMe)₂ | H | O | H | OCH₃ | OCH₃ | N | |
| R₁-K | CH₂SCN | H | O | H | OCH₃ | OCH₃ | CH | |
| R₁-L | CH₂SCN | H | O | H | CH₃ | CH₃ | CH | |
| R₁-M | CH₂CN | H | O | H | OCH₃ | OCH₃ | CH | |
| R₁-N | CH₂CN | H | O | H | OCH₃ | OCH₃ | N | |
| R₁-O | CH₂CN | H | O | H | OCH₃ | OCH₃ | CH | |

TABLE I-continued

General Formula I

| R₁ | R₂ | Rₓ | W | R | X | Y | Z | m.p. (°C.) |
|---|---|---|---|---|---|---|---|---|
| R₁-P | CH₂CN | H | O | H | Cl | OCH₃ | CH | |
| R₁-Q | CH₂CN | H | O | H | OCH₃ | OCH₃ | N | |
| R₁-R | CH₂P(O)(OMe)₂ | H | O | H | OCH₃ | OCH₃ | CH | |
| R₁-S | CH₂P(O)(OMe)₂ | H | O | H | OCH₃ | OCH₃ | CH | |
| CO₂CH₂CH₃ | CH₂N₃ | 6-CHF₂ | O | H | CH₃ | CH₃ | CH | |
| CO₂CH₂CH₃ | CH₂N₃ | 6-CHF₂ | O | H | OCH₃ | OCH₃ | CH | |
| CO₂CH₂CH₃ | CH₂N₃ | 6-OCH₃ | O | H | Cl | OCH₃ | CH | |
| CO₂CH₂CH₃ | CH₂CN | 6-CHF₂ | O | H | OCH₃ | OCH₃ | CH | |
| CO₂CH(CH₃)₂ | CH₂N₃ | H | O | H | Cl | OCH₃ | N | |
| CO₂CH(CH₃)₂ | CH₂N₃ | H | O | H | OCH₃ | CH₃ | CH | 157–160 |
| CO₂CH(CH₃)₂ | CH₂N₃ | H | O | H | OCH₃ | OCH₃ | CH | 168–171 |
| CO₂CH(CH₃)₂ | CH₂N₃ | H | O | H | Cl | CH₃ | CH | 165–167 |
| CO₂CH(CH₃)₂ | CH₂N₃ | H | O | H | CH₃ | CH₃ | CH | 181–183 |
| CO₂CH(CH₃)₂ | CH₂N₃ | H | O | H | OCH₃ | OCH₃ | CH | 183–185 |
| CO₂CH(CH₃)₂ | CH₂CN | H | O | H | Cl | CH₃ | CH | 157–158 |
| CO₂CH(CH₃)₂ | CH₂CN | H | O | H | OCH₃ | OCH₃ | N | 208–211 |
| CO₂CH(CH₃)₂ | CH₂CN | H | O | H | Cl | OCH₃ | CH | 207–208 |
| CO₂CH(CH₃)₂ | CH₂CN | H | O | H | CH₃ | CH₃ | CH | 204–205 |
| CO₂CH(CH₃)₂ | CH₂CN | H | O | H | OCH₃ | CH₃ | CH | 196–198 |
| CO₂CH(CH₃)₂ | CH₂CN | H | O | H | OCH₃ | OCH₃ | CH | 173–174 |
| Cl | CH(CH₃)CN | H | O | H | OCH₃ | OCH₃ | N | 192–193 |
| OCH₃ | CHFCN | H | O | H | CH₃ | CH₃ | CH | |
| CO₂CH₃ | CH(CH₂CH₃)SCN | H | O | H | OCH₃ | OCH₃ | CH | |
| NO₂ | CH(CH₃)P(O)(OCH₃)₂ | H | O | H | CH₃ | CH₃ | CH | |
| SO₂N(CH₃)₂ | CH(CH₂CH₃)P(S)(CH₃)₂ | H | O | H | OCH₃ | OCH₃ | CH | |
| CO₂CH(CH₃)₂ | CH(CH₃)N(CH₃)₂ | H | O | H | Cl | OCH₃ | CH | |
| OCH₃ | CH(OC(O)CH₃) | H | O | H | OCH₃ | OCH₃ | CH | |
| OCH₃ | CH(CH₂CH₃)N₃ | H | O | H | OCH₃ | CH₃ | CH | |
| Cl | CH(CH₂CH₃)N₃ | H | O | H | OCH₃ | OCH₃ | N | |
| CO₂CH₂CH₃ | CH₂SeCH₃ | H | O | H | OCH₃ | OCH₃ | CH | |
| OCH₂CH₃ | CH(CH₂CH₃)N₃ | H | O | H | OCH₃ | OCH₃ | CH | |
| OCH₂CH₃ | CH(CH₃)N₃ | H | O | H | OCH₃ | OCH₃ | CH | |
| OCH₂CH₃ | CH(CH₃)N₃ | H | O | H | OCH₃ | OCH₃ | CH | |
| OCH₂CH₃ | CH(CH₃)N₃ | H | O | H | OCH₃ | OCH₃ | CH | |
| OCH₂CH₃ | CH(CH₃)N₃ | H | O | H | OCH₃ | CH₃ | CH | |
| OCH₂CH₃ | CH(CH₃)CN | H | O | H | OCH₃ | CH₃ | CH | |
| OCH₂CH₃ | CH(CH₃)CN | H | O | H | OCH₃ | OCH₃ | CH | |
| OCH₂CH₃ | CH(CH₃)CN | H | O | H | OCH₃ | OCH₃ | CH | |
| CO₂CH₃ | CH(CH₂CH₃)NC | H | O | H | OCH₃ | OCH₃ | CH | |
| Cl | CH(OCH₃)₂ | H | O | H | Cl | OCH₃ | CH | |
| NO₂ | CH(OCH₃)₂ | H | O | H | OCH₃ | OCH₃ | CH | |
| SO₂N(CH₃)₂ | CH(OCH₃)₂ | H | O | H | OCH₃ | OCH₃ | CH | |
| SO₂N(CH₃)₂ | CH(OCH₃)₂ | H | O | H | OCH₃ | OCH₃ | N | |
| OCH₃ | CH(OCH₃)₂ | H | O | H | OCH₃ | CH₃ | CH | |
| OCH₃ | CH(OCH₃)₂ | H | O | H | OCH₃ | OCH₃ | CH | |
| OCH₂CH₃ | CH(OCH₃)₂ | H | O | H | OCH₃ | OCH₃ | CH | |
| CO₂CH₃ | CH(OCH₃)₂ | H | O | H | OCH₃ | OCH₃ | N | |
| CO₂CH₃ | CH(OCH₃)₂ | H | O | H | OCH₃ | CH₃ | CH | |
| CO₂CH₃ | CH(OCH₂CH₃)₂ | H | O | H | OCH₃ | OCH₃ | CH | |

TABLE I-continued

General Formula I

| $R_1$ | $R_2$ | $R_X$ | W | R | X | Y | Z | m.p. (°C.) |
|---|---|---|---|---|---|---|---|---|
| $CO_2CH_3$ | $C(CH_3)(OCH_3)_2$ | H | O | H | $OCH_3$ | $OCH_3$ | CH | |
| $CO_2CH_3$ | $C(CH_3)(OCH_3)_2$ | H | O | H | $OCH_3$ | $CH_3$ | CH | |
| $CO_2CH_3$ | $C(CH_3)(OCH_3)_2$ | H | O | H | $OCH_3$ | $OCH_3$ | N | |
| $CO_2CH_3$ | $C(CH_3)(OCH_3)_2$ | H | O | H | $CH_3$ | $CH_3$ | CH | |
| $CO_2CH_3$ | $C(CH_3)(OCH_3)_2$ | H | O | H | Cl | $OCH_3$ | CH | |
| $OCH_3$ | $C(CH_3)(OCH_3)_2$ | H | O | H | $OCH_3$ | $OCH_3$ | CH | |
| $OCH_2CH_3$ | $C(CH_3)(OCH_3)_2$ | H | O | H | $OCH_3$ | $OCH_3$ | CH | |
| $OCH_2CH_3$ | $C(CH_3)(OCH_3)_2$ | H | O | H | $OCH_3$ | $CH_3$ | CH | |
| $OCH_2CH_3$ | $C(CH_3)(OCH_3)_2$ | H | O | H | $OCH_3$ | $OCH_3$ | N | |
| $OCH_2CH_3$ | $C(CH_3)(OCH_3)_2$ | H | O | H | $CH_3$ | $CH_3$ | CH | |
| $CO_2CH_3$ | $C(CH_2CH_3)(OCH_3)_2$ | H | O | H | $OCH_3$ | $CH_3$ | CH | |
| $CO_2CH_3$ | $CH(SCH_3)_3$ | H | O | H | $OCH_3$ | $OCH_3$ | CH | |
| $CO_2CH_3$ | $C(CH_2CH_3)(SCH_3)_2$ | H | O | H | $OCH_3$ | $OCH_3$ | CH | |
| $CO_2CH_3$ | $CH(O_2CCH_3)_2$ | H | O | H | $OCH_3$ | $OCH_3$ | CH | |
| $OCH_3$ | $CH(OCCH_3)_2$ | H | O | H | $OCH_3$ | $OCH_3$ | CH | |
| $CO_2CH_3$ | $CH(CN)(OSi(CH_3)_3)$ | H | O | H | $OCH_3$ | $OCH_3$ | CH | |
| $CO_2CH_3$ | $CH(CN)(OSi(CH_3)_3)$ | H | O | H | $OCH_3$ | $CH_3$ | CH | |
| $CO_2CH_3$ | $C(CN)OH$ | H | O | H | $OCH_3$ | $OCH_3$ | CH | |
| $CO_2CH_3$ | $C(CH_3)(CN)OH$ | H | O | H | $OCH_3$ | $OCH_3$ | CH | |
| $CO_2CH_3$ | $C(CH_2CH_3)(CN)OCH_3$ | H | O | H | $OCH_3$ | $OCH_3$ | CH | |
| Cl | 1,3-dithiolan-2-yl | H | O | H | Cl | $OCH_3$ | CH | |
| $CO_2CH_3$ | 1,3-dithiolan-2-yl | H | O | H | $OCH_3$ | $OCH_3$ | CH | |
| $CO_2CH_3$ | 1,3-dithiolan-2-yl | H | O | H | $OCH_3$ | $CH_3$ | CH | |
| $CO_2CH_3$ | 1,3-dioxolan-2-yl | H | O | H | $OCH_3$ | $OCH_3$ | N | |
| $NO_2$ | 1,3-dioxolan-2-yl | H | O | H | $OCH_3$ | $OCH_3$ | CH | |
| $CO_2CH_3$ | 2-methyl-1,3-dioxolan-2-yl | H | O | H | $OCH_3$ | $OCH_3$ | CH | |
| $CO_2CH_3$ | 1,3-dioxolan-2-yl | H | O | H | $OCH_3$ | $OCH_3$ | CH | |
| $CO_2CH_3$ | 1,3-dioxolan-2-yl | H | O | H | $OCH_3$ | $CH_3$ | CH | |
| $CO_2CH_3$ | 1,3-dioxolan-2-yl | H | O | H | Cl | $OCH_3$ | CH | |
| $SO_2N(CH_3)_2$ | 1,3-dithian-2-yl | H | O | H | $OCH_3$ | $OCH_3$ | CH | |
| $CO_2CH_3$ | 2-methyl-1,3-dioxan-2-yl | H | O | H | $OCH_3$ | $OCH_3$ | CH | |
| $C_6H_5$ | $CH_2CN$ | H | O | H | $OCH_3$ | $OCH_3$ | CH | |
| Cl | $\overset{O}{\underset{\|}{C}}H$ | H | O | H | $OCH_3$ | $OCH_3$ | CH | |
| $NO_2$ | $\overset{O}{\underset{\|}{C}}CH_3$ | H | O | H | $OCH_3$ | $OCH_3$ | CH | |
| $OCH_3$ | $\overset{O}{\underset{\|}{C}}H$ | H | O | H | $OCH_3$ | $OCH_3$ | CH | |

TABLE I-continued

General Formula I

| R₁ | R₂ | R_X | W | R | X | Y | Z | m.p. (°C.) |
|---|---|---|---|---|---|---|---|---|
| OCH₃ | O=CH | H | O | H | OCH₃ | CH₃ | CH | |
| OCH₃ | O=CCH₃ | H | O | H | OCH₃ | OCH₃ | CH | |
| OCH₂CH₃ | O=CH | H | O | H | OCH₃ | OCH₃ | CH | |
| OCH₂CH₃ | O=CCH₃ | H | O | H | OCH₃ | OCH₃ | CH | |
| OCH₂CH₃ | O=CCH₃ | H | O | H | OCH₃ | CH₃ | N | |
| OCH₂CH₃ | O=CCH₃ | H | O | H | OCH₃ | CH₃ | CH | |
| OCH₂CH₃ | O=CCH₃ | H | O | H | CH₃ | CH₃ | CH | |
| OCH₂CH₃ | O=CCH₃ | H | O | H | OCH₃ | OCH₃ | CH | |
| OCH₂CH₃ | O=CCH₃ | H | O | H | Cl | OCH₃ | N | |
| OCH₂CH₃ | O=CCH₃ | H | O | H | OCH₃ | OCH₃ | CH | |
| OCH₂CH₃ | O=CCH₂CH₃ | H | O | H | OCH₃ | OCH₃ | CH | |
| OCH₂CH₃ | O=CCH₂CH₃ | H | O | H | OCH₃ | OCH₃ | N | |
| OCH₂CH₃ | O=CCH₂CH₃ | H | O | H | Cl | OCH₃ | CH | |
| CO₂CH₃ | O=CH | H | O | H | OCH₃ | OCH₃ | CH | |

TABLE I-continued

General Formula I

| $R_1$ | $R_2$ | $R_X$ | W | R | X | Y | Z | m.p. (°C.) |
|---|---|---|---|---|---|---|---|---|
| $CO_2CH_3$ | O=CH | H | O | H | $OCH_3$ | $CH_3$ | CH | |
| $CO_2CH_3$ | O=CH | H | O | H | Cl | $OCH_3$ | CH | |
| $CO_2CH_3$ | O=CH | H | O | H | $OCH_3$ | $OCH_3$ | N | |
| $CO_2CH_3$ | O=CH | H | O | H | $OCH_3$ | $CH_3$ | N | |
| $CO_2CH_3$ | O=CH | H | O | H | $CH_3$ | $CH_3$ | CH | |
| $CO_2CH_3$ | O=CCH_3 | H | O | H | $OCH_3$ | $OCH_3$ | CH | |
| $CO_2CH_3$ | O=CCH_3 | H | O | H | $OCH_3$ | $CH_3$ | CH | |
| $CO_2CH_3$ | O=CCH_3 | H | O | H | $OCH_3$ | $OCH_3$ | N | |
| $CO_2CH_3$ | O=CCH_3 | H | O | H | $OCH_3$ | $CH_3$ | N | |
| $CO_2CH_2CH_3$ | O=CCH_3 | H | O | H | $OCH_3$ | $OCH_3$ | CH | |
| $CO_2CH_2CH_3$ | O=CCH_3 | H | O | H | $OCH_3$ | $CH_3$ | CH | |
| $CO_2CH_2CH_3$ | O=CH | H | O | H | Cl | $OCH_3$ | CH | |
| $OSO_2CH_3$ | O=CH | H | O | H | $OCH_3$ | $CH_3$ | CH | |

TABLE I-continued

General Formula I

| R₁ | R₂ | Rₓ | W | R | X | Y | Z | m.p. (°C) |
|---|---|---|---|---|---|---|---|---|
| SO₂CH₂CH₃ | O=CH | H | O | H | OCH₃ | OCH₂CH₃ | CH | |
| C(O)N(CH₂CH₃)₂ | Cl | H | O | H | CH₃ | CH₃ | CH | |
| Cl | CH₂N₃ | H | O | H | OCH₃ | OCH₃ | CH | |
| Cl | CH₂N₃ | H | O | H | OCH₃ | CH₃ | CH | |
| Cl | CH₂N₃ | H | O | H | CH₃ | CH₃ | CH | |
| Cl | CH₂N₃ | H | O | H | Cl | CH₃ | CH | |
| Cl | CH₂N₃ | H | O | H | OCH₃ | OCH₃ | N | |
| Cl | CH₂N₃ | H | O | H | OCH₃ | CH₃ | N | |
| CO₂CH₂CH₃ | O=CH | H | O | H | OCH₃ | OCH₃ | CH | |
| CO₂CH₂CH₃ | O=CH | H | O | H | CH₃ | CH₃ | CH | |
| CO₂CH₂CH₃ | O=CH | H | O | H | OCH₃ | OCH₃ | N | |
| CO₂CH₂CH₃ | O=CH | H | O | H | OCH₃ | CH₃ | N | |
| CO₂CH₂CH₃ | CH₂N₃ | H | O | H | OCH₃ | OCH₃ | CH | |
| CO₂CH₂CH₃ | CH₂N₃ | H | O | H | OCH₃ | CH₃ | CH | |
| CO₂CH₂CH₃ | CH₂N₃ | H | O | H | CH₃ | CH₃ | CH | |
| CO₂CH₂CH₃ | CH₂N₃ | H | O | H | Cl | OCH₃ | CH | |
| CO₂CH₂CH₃ | CH₂N₃ | H | O | H | OCH₃ | OCH₃ | N | |
| CO₂CH₂CH₃ | CH₂N₃ | H | O | H | OCH₃ | CH₃ | N | |
| CO₂CH₂CH₃ | CH₂CN | H | O | H | OCH₃ | OCH₃ | CH | |
| CO₂CH₂CH₃ | CH₂CN | H | O | H | OCH₃ | CH₃ | CH | |
| CO₂CH₂CH₃ | CH₂CN | H | O | H | CH₃ | CH₃ | CH | |
| CO₂CH₂CH₃ | CH₂CN | H | O | H | Cl | OCH₃ | CH | |
| CO₂CH₂CH₃ | CH₂CN | H | O | H | OCH₃ | OCH₃ | N | |
| CO₂CH₂CH₃ | CH₂CN | H | O | H | OCH₃ | CH₃ | N | |
| CO₂CH₂CH₃ | CH=NOCH₃ | H | O | H | OCH₃ | OCH₃ | CH | |
| CO₂CH₂CH₃ | CH=NOCH₃ | H | O | H | OCH₃ | CH₃ | CH | |
| CO₂CH₂CH₃ | CH=NOCH₃ | H | O | H | CH₃ | CH₃ | CH | |
| CO₂CH₂CH₃ | CH=NOCH₃ | H | O | H | Cl | OCH₃ | CH | |
| CO₂CH₂CH₃ | CH=NOCH₃ | H | O | H | OCH₃ | OCH₃ | N | |
| CO₂CH₂CH₃ | CH=NOCH₃ | H | O | H | OCH₃ | CH₃ | N | |
| CO₂CH₃ | C(CH₃)=NOH | H | O | H | OCH₃ | OCH₃ | CH | |
| CO₂CH₃ | C(CH₃)=NOH | H | O | H | OCH₃ | CH₃ | CH | |
| CO₂CH₃ | C(CH₃)=NOH | H | O | H | CH₃ | CH₃ | CH | |
| CO₂CH₃ | C(CH₃)=NOH | H | O | H | Cl | OCH₃ | CH | |
| CO₂CH₃ | C(CH₃)=NOH | H | O | H | OCH₃ | OCH₃ | N | |
| CO₂CH₃ | C(CH₃)=NOH | H | O | H | OCH₃ | CH₃ | N | |
| OCH₂CH₃ | C(CH₃)=NOH | H | O | H | OCH₃ | OCH₃ | CH | |
| OCH₂CH₃ | C(CH₃)=NOH | H | O | H | OCH₃ | CH₃ | CH | |
| OCH₂CH₃ | C(CH₃)=NOH | H | O | H | CH₃ | CH₃ | CH | |
| OCH₂CH₃ | C(CH₃)=NOH | H | O | H | Cl | OCH₃ | CH | |
| OCH₂CH₃ | C(CH₃)=NOH | H | O | H | OCH₃ | OCH₃ | N | |
| OCH₂CH₃ | C(CH₃)=NOH | H | O | H | OCH₃ | CH₃ | N | |

TABLE I-continued

General Formula I

| R$_1$ | R$_2$ | R$_X$ | W | R | X | Y | Z | m.p. (°C.) |
|---|---|---|---|---|---|---|---|---|
| OCH$_2$CH$_3$ | C(CH$_3$)=NOCH$_3$ | H | O | H | OCH$_3$ | OCH$_3$ | CH | |
| OCH$_2$CH$_3$ | C(CH$_3$)=NOCH$_3$ | H | O | H | OCH$_3$ | CH$_3$ | CH | |
| OCH$_2$CH$_3$ | C(CH$_3$)=NOCH$_3$ | H | O | H | OCH$_3$ | OCH$_3$ | N | |
| OCH$_2$CH$_3$ | C(CH$_3$)=NOCH$_3$ | H | O | H | OCH$_3$ | CH$_3$ | N | |
| F | CH=NOH | H | O | H | OCH$_3$ | OCH$_3$ | CH | |
| F | CH=NOCH$_3$ | H | O | H | OCH$_3$ | OCH$_3$ | CH | |
| F | C(CH$_3$)=NOH | H | O | H | OCH$_3$ | OCH$_3$ | CH | |
| F | C(CH$_3$)=NOCH$_3$ | H | O | H | OCH$_3$ | OCH$_3$ | CH | |
| Cl | CH=NOH | H | O | H | OCH$_3$ | OCH$_3$ | CH | |
| Cl | CH=NOCH$_3$ | H | O | H | OCH$_3$ | OCH$_3$ | CH | |
| Cl | C(CH$_3$)=NOH | H | O | H | OCH$_3$ | OCH$_3$ | CH | |
| Cl | C(CH$_3$)=NOCH$_3$ | H | O | H | OCH$_3$ | OCH$_3$ | CH | |
| NO$_2$ | CH=NOH | H | O | H | OCH$_3$ | OCH$_3$ | CH | |
| NO$_2$ | CH=NOCH$_3$ | H | O | H | OCH$_3$ | OCH$_3$ | CH | |
| NO$_2$ | C(CH$_3$)=NOH | H | O | H | OCH$_3$ | OCH$_3$ | CH | |
| NO$_2$ | C(CH$_3$)=NOCH$_3$ | H | O | H | OCH$_3$ | OCH$_3$ | CH | |
| CH$_3$ | CH=NOH | H | O | H | OCH$_3$ | OCH$_3$ | CH | |
| CH$_3$ | CH=NOCH$_3$ | H | O | H | OCH$_3$ | OCH$_3$ | CH | |
| CH$_3$ | C(CH$_3$)=NOH | H | O | H | OCH$_3$ | OCH$_3$ | CH | |
| CH$_3$ | C(CH$_3$)=NOCH$_3$ | H | O | H | OCH$_3$ | OCH$_3$ | CH | |
| C(O)N(CH$_3$)$_2$ | CH=NOH | H | O | H | OCH$_3$ | OCH$_3$ | CH | |
| C(O)N(CH$_3$)$_2$ | CH=NOCH$_3$ | H | O | H | OCH$_3$ | OCH$_3$ | CH | |
| C(O)N(CH$_3$)$_2$ | C(CH$_3$)=NOH | H | O | H | OCH$_3$ | OCH$_3$ | CH | |
| C(O)N(CH$_3$)$_2$ | C(CH$_3$)=NOCH$_3$ | H | O | H | OCH$_3$ | OCH$_3$ | CH | |
| SO$_2$N(CH$_3$)$_2$ | CH=NOH | H | O | H | OCH$_3$ | OCH$_3$ | CH | |
| SO$_2$N(CH$_3$)$_2$ | CH=NOCH$_3$ | H | O | H | OCH$_3$ | OCH$_3$ | CH | |
| SO$_2$N(CH$_3$)$_2$ | C(CH$_3$)=NOH | H | O | H | OCH$_3$ | OCH$_3$ | CH | |
| SO$_2$N(CH$_3$)$_2$ | C(CH$_3$)=NOCH$_3$ | H | O | H | OCH$_3$ | OCH$_3$ | CH | |
| SO$_2$CH$_3$ | CH=NOH | H | O | H | OCH$_3$ | OCH$_3$ | CH | |
| SO$_2$CH$_3$ | CH=NOCH$_3$ | H | O | H | OCH$_3$ | OCH$_3$ | CH | |
| SO$_2$CH$_3$ | C(CH$_3$)=NOH | H | O | H | OCH$_3$ | OCH$_3$ | CH | |
| SO$_2$CH$_3$ | CH(CH$_3$)=NOCH$_3$ | H | O | H | OCH$_3$ | OCH$_3$ | CH | |
| OSO$_2$CH$_3$ | CH=NOH | H | O | H | OCH$_3$ | OCH$_3$ | CH | |
| OSO$_2$CH$_3$ | CH=NOCH$_3$ | H | O | H | OCH$_3$ | OCH$_3$ | CH | |
| OSO$_2$CH$_3$ | C(CH$_3$)=NOH | H | O | H | OCH$_3$ | OCH$_3$ | CH | |
| OSO$_2$CH$_3$ | C(CH$_3$)=NOCH$_3$ | H | O | H | OCH$_3$ | OCH$_3$ | CH | |
| CH$_2$OCH$_3$ | CH=NOH | H | O | H | OCH$_3$ | OCH$_3$ | CH | |
| CH$_2$OCH$_3$ | CH=NOCH$_3$ | H | O | H | OCH$_3$ | OCH$_3$ | CH | |
| CH$_2$OCH$_3$ | C(CH$_3$)=NOH | H | O | H | OCH$_3$ | OCH$_3$ | CH | |
| CH$_2$OCH$_3$ | C(CH$_3$)=NOCH$_3$ | H | O | H | OCH$_3$ | OCH$_3$ | CH | |
| CH$_2$SCH$_3$ | CH=NOH | H | O | H | OCH$_3$ | OCH$_3$ | CH | |
| CH$_2$SCH$_3$ | CH=NOCH$_3$ | H | O | H | OCH$_3$ | OCH$_3$ | CH | |
| CH$_2$SCH$_3$ | C(CH$_3$)=NOH | H | O | H | OCH$_3$ | OCH$_3$ | CH | |
| CH$_2$SCH$_3$ | C(CH$_3$)=NOCH$_3$ | H | O | H | OCH$_3$ | OCH$_3$ | CH | |
| CH$_2$CN | CH=NOH | H | O | H | OCH$_3$ | OCH$_3$ | CH | |
| CH$_2$CN | CH=NOCH$_3$ | H | O | H | OCH$_3$ | OCH$_3$ | CH | |
| CH$_2$CN | C(CH$_3$)=NOH | H | O | H | OCH$_3$ | OCH$_3$ | CH | |
| CH$_2$CN | C(CH$_3$)=NOCH$_3$ | H | O | H | OCH$_3$ | OCH$_3$ | CH | |
| CH(OCH$_3$)$_2$ | CH=NOH | H | O | H | OCH$_3$ | OCH$_3$ | CH | |
| CH(OCH$_3$)$_2$ | C(CH$_3$)=NOH | H | O | H | OCH$_3$ | OCH$_3$ | CH | |
| CH(OCH$_3$)$_2$ | C(CH$_3$)=NOH | H | O | H | OCH$_3$ | OCH$_3$ | CH | |

TABLE I-continued

General Formula I

| $R_1$ | $R_2$ | $R_X$ | W | R | X | Y | Z | m.p. (°C.) |
|---|---|---|---|---|---|---|---|---|
| CH(OCH$_3$)$_2$ | C(CH$_3$)=NOCH$_3$ | H | O | H | OCH$_3$ | OCH$_3$ | CH | |
| R$_1$-A | CH=NOH | H | O | H | OCH$_3$ | OCH$_3$ | CH | |
| R$_1$-B | CH=NOH | H | O | H | OCH$_3$ | OCH$_3$ | CH | |
| R$_1$-C | CH=NOH | H | O | H | OCH$_3$ | OCH$_3$ | CH | |
| R$_1$-D | CH=NOH | H | O | H | OCH$_3$ | OCH$_3$ | CH | |
| R$_1$-E | CH=NOH | H | O | H | OCH$_3$ | OCH$_3$ | CH | |
| R$_1$-F | CH=NOH | H | O | H | OCH$_3$ | OCH$_3$ | CH | |
| R$_1$-G | CH=NOH | H | O | H | OCH$_3$ | OCH$_3$ | CH | |
| R$_1$-H | CH=NOH | H | O | H | OCH$_3$ | OCH$_3$ | CH | |
| R$_1$-I | CH=NOH | H | O | H | OCH$_3$ | OCH$_3$ | CH | |
| R$_1$-J | CH=NOH | H | O | H | OCH$_3$ | OCH$_3$ | CH | |
| R$_1$-K | CH=NOH | H | O | H | OCH$_3$ | OCH$_3$ | CH | |
| R$_1$-L | CH=NOH | H | O | H | OCH$_3$ | OCH$_3$ | CH | |
| R$_1$-M | CH=NOH | H | O | H | OCH$_3$ | OCH$_3$ | CH | |
| R$_1$-N | CH=NOH | H | O | H | OCH$_3$ | OCH$_3$ | CH | |
| R$_1$-O | CH=NOH | H | O | H | OCH$_3$ | OCH$_3$ | CH | |
| R$_1$-P | CH=NOH | H | O | H | OCH$_3$ | OCH$_3$ | CH | |
| R$_1$-Q | CH=NOH | H | O | H | OCH$_3$ | OCH$_3$ | CH | |
| R$_1$-R | CH=NOH | H | O | H | OCH$_3$ | OCH$_3$ | CH | |
| R$_1$-S | CH=NOH | H | O | H | OCH$_3$ | OCH$_3$ | CH | |
| NO$_2$ | CH$_2$CN | 6-Cl | O | H | CH$_3$ | CH$_3$ | CH | |
| NO$_2$ | CH$_2$CN | 6-Cl | O | H | CH$_3$ | CH$_3$ | CH | |
| NO$_2$ | CH$_2$CN | 6-Cl | O | H | OCH$_3$ | OCH$_3$ | CH | |
| NO$_2$ | CH$_2$CN | 6-Cl | O | H | Cl | CH$_3$ | CH | |
| NO$_2$ | CH$_2$CN | 6-Cl | O | H | OCH$_3$ | OCH$_3$ | N | |
| NO$_2$ | CH$_2$CN | 6-Cl | O | H | OCH$_3$ | OCH$_3$ | N | |
| CF$_3$ | CH$_2$CN | 6-F | O | H | OCH$_3$ | OCH$_3$ | CH | |
| OCH$_3$ | CH$_2$CN | 6-F | O | H | CH$_3$ | CH$_3$ | CH | |
| OCH$_3$ | CH$_2$CN | 6-Cl | O | H | OCH$_3$ | OCH$_3$ | CH | |
| OCH$_3$ | CH$_2$O(CO)CH$_3$ | 6-Cl | O | H | OCH$_3$ | OCH$_3$ | CH | |
| OCH$_3$ | CH$_2$O(CO)CH$_3$ | 6-OCH$_3$ | O | H | OCH$_3$ | OCH$_3$ | CH | |
| OCH$_3$ | CH$_2$N$_3$ | 6 OCH$_3$ | O | H | OCH$_3$ | OCH$_3$ | CH | |
| OCH$_3$ | CH$_2$N$_3$ | H | O | H | CH$_3$ | CH$_3$ | CH | |
| OCH$_3$ | CH$_2$NO$_2$ | H | O | H | OCH$_3$ | OCH$_3$ | CH | |
| OCH$_3$ | CH$_2$N$_3$ | H | O | H | OCH$_3$ | OCH$_3$ | N | |
| OCH$_2$CH$_2$Cl | CH$_2$O(CO)CH$_3$ | H | O | H | CH$_3$ | CH$_3$ | CH | |
| OCH$_2$CH$_2$Cl | CH$_2$O(CO)CH$_3$ | H | O | H | OCH$_3$ | OCH$_3$ | CH | |
| Cl | CH$_2$O(CO)CH$_3$ | H | O | H | OCH$_3$ | OCH$_3$ | CH | |
| Cl | CH$_2$O(CO)CH$_3$ | H | O | H | CH$_3$ | CH$_3$ | CH | |
| Cl | CH$_2$O(CO)CH$_3$ | H | O | H | OCH$_3$ | OCH$_3$ | CH | |
| OCH$_3$ | CH$_2$O(CO)CH$_3$ | H | O | H | CH$_3$ | CH$_3$ | CH | |
| OCH$_3$ | CH$_2$O(CO)CH$_3$ | H | O | H | CH$_3$ | CH$_3$ | CH | |
| OCH$_3$ | CH$_2$O(CO)CH$_3$ | H | O | H | CH$_3$ | CH$_3$ | N | |
| OCH$_3$ | CH$_2$O(CO)CH$_3$ | H | O | H | OCH$_3$ | OCH$_3$ | CH | |
| OCH$_2$CH$_2$Cl | CH$_2$O(CO)CH$_3$ | H | O | H | OCH$_3$ | OCH$_3$ | CH | |
| OCH$_2$CH$_2$Cl | CH$_2$O(CO)CH$_3$ | H | O | H | CH$_3$ | CH$_3$ | CH | |
| C(O)N(CH$_3$)$_2$ | CH$_2$O(CO)CH$_3$ | H | O | H | OCH$_3$ | OCH$_3$ | CH | |

TABLE I-continued

General Formula I

| R₁ | R₂ | R_X | W | R | X | Y | Z | m.p. (°C.) |
|---|---|---|---|---|---|---|---|---|
| C(O)N(CH₃)₂ | CH₂O(CO)CH₃ | H | O | H | OCH₃ | OCH₃ | N | |
| C(O)N(CH₃)₂ | CH₂O(CO)CH₃ | 6-Cl | O | H | OCH₃ | OCH₃ | CH | |
| SO₂N(CH₃)₂ | CH₂O(CO)CH₃ | 6-Cl | O | H | OCH₃ | OCH₃ | N | |
| SO₂N(CH₃)₂ | CH₂O(CO)CH₃ | H | O | H | OCH₃ | OCH₃ | CH | |
| SO₂N(CH₃)₂ | CH₂OSO₂CH₃ | H | O | H | OCH₃ | OCH₃ | CH | |
| SO₂N(CH₃)₂ | CH₂CN | 6-Cl | O | H | OCH₃ | OCH₃ | CH | |
| SO₂CH₃ | CH₂CN | 6-Cl | O | H | OCH₃ | OCH₃ | CH | |
| SO₂CH₃ | CH₂O(CO)CH₃ | H | O | H | OCH₃ | CH₃ | CH | |
| SO₂CH₃ | CH₂O(CO)CH₃ | 6-Cl | O | H | OCH₃ | OCH₃ | N | |
| SO₂CH₃ | CH₂N₃ | H | O | H | OCH₃ | OCH₃ | CH | |
| SO₂CH₃ | CH₂N₃ | 6-Cl | O | H | OCH₃ | CH₃ | CH | |
| SO₂CH₃ | CH₂OSO₂CH₃ | 6-Cl | O | H | OCH₃ | OCH₃ | CH | |
| SO₂CH₃ | CH₂OSO₂CH₃ | H | O | H | CH₃ | OCH₃ | CH | |
| SO₂CH₂CH₂CH₃ | CH₂N₃ | 6-Cl | O | H | OCH₃ | OCH₃ | N | |
| SO₂CH₂CH₂CH₃ | CH₂N₃ | 6-Cl | O | H | OCH₃ | OCH₃ | CH | |
| SO₂CH₂CH₂CH₃ | CH₂N₃ | H | O | H | CH₃ | OCH₃ | CH | |
| SO₂CH₂CH₂CH₃ | CH₂O(CO)CH₃ | H | O | H | OCH₃ | OCH₃ | N | |
| SO₂CH₂CH₂CH₃ | CH₂O(CO)CH₃ | 6-Cl | O | H | OCH₃ | OCH₃ | CH | |
| SO₂CH₂CH₂CH₃ | CH₂OSO₂CH₃ | H | O | H | OCH₃ | OCH₃ | N | |
| SO₂CH₂CH₂CH₃ | CH₂OSO₂CH₃ | 6-Cl | O | H | OCH₃ | OCH₃ | CH | |
| 1,3-dioxyl-2-yl | CH₂O(CO)CH₃ | 6-Cl | O | H | OCH₃ | OCH₃ | CH | |
| 1,3-dioxyl-2-yl | CH₂O(CO)CH₃ | H | O | H | OCH₃ | CH₃ | CH | |
| R₁-A | CH₂O(CO)CH₃ | H | O | H | OCH₃ | OCH₃ | N | |
| R₁-A | CH₂O(CO)CH₃ | H | O | H | OCH₃ | OCH₃ | CH | |
| R₁-A | CH₂O(CO)CH₃ | 6-Cl | O | H | OCH₃ | OCH₃ | CH | |
| R₁-A | CH₂N₃ | H | O | H | CH₃ | OCH₃ | CH | 180-181 |
| CO₂CH₃ | CH₂O(CO)CH₃ | H | O | H | OCH₃ | OCH₃ | CH | 182-184 |
| CO₂CH₃ | CH₂O(CO)CH₃ | 6-Cl | O | H | CH₃ | OCH₃ | CH | 188-190 |
| CO₂CH₃ | CH₂CN | 6-Cl | O | H | Cl | CH₃ | CH | 172-173 |
| CO₂CH₃ | CH₂CN | 6-Cl | O | H | OCH₃ | OCH₃ | CH | 181-183 |
| CO₂CH₃ | CH₂CN | 6-Cl | O | H | OCH₃ | CH₃ | CH | |
| CO₂CH₃ | CH₂N₃ | H | O | H | OCH₃ | OCH₃ | CH | |
| CO₂CH₃ | CH₂O(CO)CH₃ | H | O | H | CH₃ | OCH₃ | CH | 179-180 |
| CO₂CH₃ | CH₂O(CO)CH₃ | 6-F | O | H | OCH₂CH₃ | NHCH₃ | N | >250 |
| CO₂CH₃ | CH₂N₃ | 6-OCF₂H | O | H | OCH₃ | OCH₃ | CH | |
| CO₂CH₃ | CH₂SCN | 6-Cl | O | H | OCH₃ | OCH₃ | CH | |
| CO₂CH₂CH₃ | CH₂SCN | 6-Cl | O | H | OCH₃ | OCH₃ | N | |
| CO₂CH₂CH₃ | CH₂CN | 6-Cl | O | H | OCH₃ | OCH₃ | CH | 172-173 |
| CO₂CH₂CH₃ | CH₂CN | 6-Cl | O | H | OCH₃ | CH₃ | CH | 162-163 |
| CO₂CH₂CH₃ | CH₂O(CO)CH₃ | H | O | H | OCH₃ | OCH₃ | CH | 160-162 |
| CO₂CH₂CH₂ | CH₂O(CO)CH₃ | H | O | H | Cl | OCH₃ | CH | 166-168 |

TABLE I-continued

General Formula I

| $R_1$ | $R_2$ | $R_Y$ | W | R | X | Y | Z | m.p. (°C.) |
|---|---|---|---|---|---|---|---|---|
| $CO_2CH_2CH_3$ | $CH_2O(CO)CH_3$ | H | O | H | $OCH_3$ | $CH_3$ | N | 175-176 |
| $CO_2CH_2CH_3$ | $CH_2O(CO)CH_3$ | H | O | H | $OCH_3$ | $OCH_3$ | N | 180-182 |
| $CO_2CH_2CH_3$ | $CH_2CN$ | 6-Cl | O | H | $OCH_3$ | $OCH_3$ | CH | |
| $CO_2CH_2CH_3$ | $CH_2NO_2$ | H | O | H | $CH_3$ | $OCH_3$ | CH | 148-150 |
| $CO_2CH_2CH_3$ | $CH_2NO_2$ | H | O | H | $OCH_3$ | $OCH_3$ | CH | 156-159 |
| $CO_2CH_2CH_3$ | $CH_2NO_2$ | H | O | H | $OCH_3$ | $CH_3$ | N | 152-153 |
| $CO_2CH_2CH_3$ | $CH_2NO_2$ | H | O | H | $OCH_3$ | $OCH_3$ | N | 138-140 |
| $CO_2CH_2CH_3$ | $CH_2NO_2$ | 6-Cl | O | H | Cl | $CH_3$ | CH | 155-157 |
| $CO_2CH_2CH_3$ | $CH_2NO_2$ | 6-Cl | O | H | $OCH_3$ | $OCH_3$ | CH | |
| $CO_2CH_2CH_3$ | $CH_2N_3$ | 6-Cl | O | H | $OCH_3$ | $OCH_3$ | N | |
| $R_1$-B | $CH_2N_3$ | 6-Cl | O | H | $OCH_3$ | $OCH_3$ | CH | |
| $R_1$-B | $CH_2OSO_2CH_3$ | H | O | H | $OCH_3$ | $CH_3$ | CH | |
| $R_1$-B | $CH_2OSO_2CH_3$ | H | O | H | $OCH_3$ | $OCH_3$ | CH | |
| $R_1$-C | $CH_2O(CO)CH_3$ | H | O | H | $OCH_3$ | $CH_3$ | CH | |
| $R_1$-C | $CH_2O(CO)CH_3$ | H | O | H | $OCH_3$ | $OCH_3$ | CH | |
| $R_1$-D | $CH_2N_3$ | H | O | H | $OCH_3$ | $CH_3$ | CH | |
| $R_1$-O | $CH_2N_3$ | 6-Cl | O | H | $OCH_3$ | $CH_3$ | CH | |
| $R_1$-O | $CH_2N_3$ | 6-Cl | O | H | $OCH_3$ | $OCH_3$ | CH | |
| $R_1$-X | $CH_2N_3$ | 6-Cl | O | H | $CH_3$ | $CH_3$ | CH | |
| $R_1$-X | $CH_2N_3$ | 6-Cl | O | H | $OCH_3$ | $OCH_3$ | CH | |
| $R_1$-X | $CH_2N_3$ | H | O | H | $OCH_3$ | $CH_3$ | N | |
| $R_1$-Y | $CH_2N_3$ | H | O | H | $CH_3$ | $CH_3$ | CH | |
| $R_1$-Y | $CH_2N_3$ | H | O | H | $CH_3$ | $OCH_3$ | CH | |
| $R_1$-Y | $CH_2N_3$ | H | O | H | $OCH_3$ | $CH_3$ | CH | |
| $R_1$-X | $CH_2O(CO)CH_3$ | H | O | H | $OCH_3$ | $OCH_3$ | CH | |
| $R_1$-X | $CH_2O(CO)CH_3$ | H | O | H | $CH_3$ | $CH_3$ | CH | |
| $R_1$-X | $CH_2O(CO)CH_3$ | H | O | H | $OCH_3$ | $OCH_3$ | CH | |
| $R_1$-Y | $CH_2O(CO)CH_3$ | H | O | H | $OCH_3$ | $CH_3$ | CH | |
| $R_1$-Y | $CH_2O(CO)CH_3$ | H | O | H | $OCH_3$ | $OCH_3$ | CH | |
| $R_1$-X | $CH_2N_3$ | 6-Cl | O | $CH_3$ | $OCH_3$ | $CH_3$ | CH | |
| $R_1$-X | $CH_2N_3$ | 6-Cl | O | $CH_3$ | $OCH_3$ | $OCH_3$ | CH | |
| $R_1$-Z | $CH_2O(CO)CH_3$ | 6-Cl | O | H | $OCH_3$ | $CH_3$ | CH | |
| $R_1$-Z | $CH_2O(CO)CH_3$ | 6-Cl | O | H | $OCH_3$ | $OCH_3$ | CH | |
| $R_1$-Z | $CH_2N_3$ | H | O | H | $OCH_3$ | $CH_3$ | CH | |
| $R_1$-Z | $CH_2N_3$ | H | O | H | $OCH_3$ | $OCH_3$ | CH | |
| $R_1$-AA | $CH_2O(CO)CH_3$ | H | O | H | $OCH_3$ | $CH_3$ | CH | |
| $R_1$-AA | $CH_2O(CO)CH_3$ | H | O | H | $OCH_3$ | $OCH_3$ | CH | |
| $R_1$-AA | $CH_2NO_2$ | H | O | H | $OCH_3$ | $CH_3$ | CH | |
| $R_1$-AA | $CH_2NO_2$ | H | O | H | $OCH_3$ | $OCH_3$ | CH | |
| $R_1$-AA | $CH_2N_3$ | H | O | H | $OCH_3$ | $CH_3$ | CH | |
| $R_1$-AB | $CH_2O(CO)CH_3$ | H | O | H | $OCH_3$ | $CH_3$ | CH | |
| $R_1$-AB | $CH_2O(CO)CH_3$ | H | O | H | $OCH_3$ | $OCH_3$ | CH | |
| $R_1$-AC | $CH_2O(CO)CH_3$ | H | O | H | $OCH_3$ | $CH_3$ | CH | |
| $R_1$-AC | $CH_2O(CO)CH_3$ | H | O | H | $OCH_3$ | $OCH_3$ | CH | |
| $R_1$-AC | $CH_2N_3$ | H | O | H | $OCH_3$ | $CH_3$ | CH | |
| $R_1$-AC | $CH_2N_3$ | H | O | H | $OCH_3$ | $OCH_3$ | CH | |
| $R_1$-AD | $CH_2O(CO)CH_3$ | 6-Cl | O | H | $OCH_3$ | $CH_3$ | CH | |
| $R_1$-AD | $CH_2N_3$ | H | O | H | $OCH_3$ | $OCH_3$ | CH | |
| $CO_2CH_2CH_3$ | $CH_2O(CO)CH_3$ | H | O | $CH_3$ | $OCH_3$ | $CH_3$ | CH | |
| $CO_2CH_2CH_3$ | $CH_2O(CO)CH_3$ | H | O | $CH_3$ | $OCH_3$ | $OCH_3$ | CH | |
| $CO_2CH_2CH_3$ | $CH_2O(CO)CH_3$ | H | O | $CH_3$ | $OCH_3$ | $CH_3$ | N | |

TABLE I-continued

General Formula I

| R₁ | R₂ | R_X | W | R | X | Y | Z | m.p. (°C.) |
|---|---|---|---|---|---|---|---|---|
| OCH₂CH₃ | CH(CH₃)N₃ | H | O | CH₃ | OCH₃ | CH₃ | N | |
| OCH₂CH₃ | CH(CH₃)N₃ | 6-Cl | O | H | CH₃ | OCH₃ | CH | |
| NO₂ | CH₂O(O)CH₃ | 6-Cl | O | H | OCH₃ | OCH₃ | CH | |
| CO₂CH₃ | CH₂O(O)CH₃ | H | O | CH₃ | OCH₃ | CH₃ | N | |
| CO₂CH₃ | CH(CH₃)O(CO)CH₃ | H | O | H | OCH₃ | OCH₃ | CH | |
| NO₂ | O=CH | 6-Cl | O | H | OCH₃ | OCH₃ | CH | |
| OCH₃ | O=C—CH₃ | 6-Cl | O | H | OCH₃ | OCH₃ | CH | |
| OCH₃ | O=C—CH₃ | H | O | CH₃ | OCH₃ | CH₃ | N | |
| SO₂CH₂CH₃ | O=CH | 6-Cl | O | CH₃ | OCH₃ | CH₃ | N | |
| SO₂CH₂CH₃ | O=CH | 6-CF₂H | O | H | OCH₃ | OCH₃ | CH | |
| CO₂CH₂CH₃ | CH₂N₃ | 6-Cl | O | H | OCH₃ | OCH₃ | CH | |
| CO₂CH₂CH₂CH₃ | CH₂N₃ | H | O | CH₃ | OCH₃ | CH₃ | N | |
| CO₂CH₃ | CH=NOCH₃ | 6-Cl | O | CH₃ | OCH₃ | CH₃ | CH | |
| F | CH=NOH | 6-F | O | H | OCH₃ | OCH₃ | CH | |
| F | CH=NOH | H | O | CH₃ | OCH₃ | CH₃ | N | |
| NO₂ | CH=NOCH₃ | 6-Cl | O | H | OCH₃ | OCH₃ | CH | |
| CH₂OCH₃ | CH=NOH | H | O | CH₃ | OCH₃ | CH₃ | CH | |
| CH₂OCH₃ | CH=4NOH | 6-Cl | O | H | OCH₃ | OCH₃ | CH | |
| R₁-A | CH=NOH | H | O | H | OCH₃ | OCH₃ | N | |
| R₁-A | CH=NOH | 6-Cl | O | H | OCH₃ | OCH₃ | CH | |
| R₁-B | CH=NOH | 6-Cl | O | CH₃ | OCH₃ | CH₃ | CH | |
| R₁-C | CH=NOH | 6-Cl | O | H | OCH₃ | OCH₃ | N | |
| R₁-D | CH=NOH | 6-Cl | O | H | OCH₃ | OCH₃ | CH | |
| R₁-E | CH=NOH | H | O | CH₃ | OCH₃ | CH₃ | CH | |
| R₁-O | CH=NOH | 6-Cl | O | H | OCH₃ | OCH₃ | N | |
| R₁-O | CH=NOH | 6-Cl | O | H | OCH₃ | OCH₃ | CH | |
| R₁-W | CH=NOH | H | O | H | OCH₃ | CH₃ | N | |
| R₁-W | CH=NOH | H | O | H | OCH₃ | OCH₃ | CH | |
| R₁-X | CH=NOH | 6-Cl | O | H | OCH₃ | OCH₃ | N | |
| R₁-X | CH=NOCH₃ | 6-Cl | O | H | OCH₃ | OCH₃ | CH | |
| R₁-Y | CH=NOCH₃ | 6-Cl | O | H | OCH₃ | OCH₃ | CH | |
| R₁-Y | CH=NOH | H | O | CH₃ | CH₃ | CH₃ | N | |
| R₁-Z | CH=NOH | 6-Cl | O | CH₃ | OCH₃ | CH₃ | N | |
| R₁-Z | CH=NOH | H | O | H | OCH₃ | OCH₃ | CH | |
| R₁-AA | CH=NOH | 6-Cl | O | H | OCH₃ | OCH₃ | CH | |

TABLE I-continued

General Formula I

| R₁ | R₂ | Rₓ | W | R | X | Y | Z | m.p. (°C.) |
|---|---|---|---|---|---|---|---|---|
| R₁-AA | CH=NOH | H | O | H | OCH₃ | OCH₃ | CH | |
| R₁-AA | CH=NOH | H | O | CH₃ | OCH₃ | CH₃ | N | |
| R₁-AB | CH=NOH | H | O | H | OCH₃ | OCH₃ | CH | |
| R₁-AC | CH=NOH | 6-Cl | O | H | OCH₃ | OCH₃ | CH | |
| R₁-AC | CH=NOH | 6-Cl | O | H | OCH₃ | OCH₃ | CH | |
| R₁-AD | CH=NOH | H | O | H | OCH₃ | OCH₃ | CH | |
| R₁-AD | CH=NOH | 6-F | O | H | OCH₃ | OCH₃ | CH | |
| F | CH₂Br | H | O | H | OCH₃ | CH₃ | CH | |
| F | CH₂Br | H | O | H | OCH₃ | OCH₃ | CH | |
| F | CH₂Cl | H | O | H | OCH₃ | OCH₃ | N | |
| F | CH₂Cl | H | O | H | OCH₃ | CH₃ | CH | |
| Cl | CH₂Br | H | O | H | OCH₃ | CH₃ | CH | |
| Cl | CH₂Cl | H | O | H | OCH₃ | OCH₃ | CH | |
| Cl | CH₂Cl | H | O | H | OCH₃ | OCH₃ | N | |
| Br | CH₂Br | H | O | H | OCH₃ | CH₃ | CH | |
| Br | CH₂Br | H | O | H | OCH₃ | OCH₃ | N | |
| Br | CH₂Cl | H | O | H | OCH₃ | OCH₃ | CH | |
| Br | CH₂Cl | H | O | H | OCH₃ | CH₃ | N | |
| NO₂ | CH₂Br | H | O | H | OCH₃ | OCH₃ | CH | 191-194 (D) |
| NO₂ | CH₂Br | H | O | H | CH₃ | CH₃ | CH | 200-201 |
| NO₂ | CH₂Br | H | O | H | OCH₃ | OCH₃ | CH | 194-195 |
| NO₂ | CH₂Br | H | O | H | Cl | OCH₃ | CH | 184-186 |
| NO₂ | CH₂Cl | H | O | H | OCH₃ | OCH₃ | CH | 180-183 |
| NO₂ | CH₂Cl | H | O | H | OCH₃ | CH₃ | CH | 154-157 |
| NO₂ | CH₂Cl | H | O | H | OCH₃ | OCH₃ | N | |
| CO₂CH₃ | C(Cl)=NOCH₃ | H | O | H | OCH₃ | OCH₃ | CH | |
| CO₂CH₃ | C(Cl)=NOCH₃ | H | O | H | OCH₃ | OCH₃ | CH | |
| CO₂CH₂CH₃ | C(Cl)=NOCH₃ | H | O | H | OCH₃ | OCH₃ | N | |
| CO₂CH₂CH₃ | C(CN)=NOCH₃ | H | O | H | OCH₃ | OCH₃ | CH | |
| CO₂CH₃ | C(CN)=NOCH₃ | H | O | H | OCH₃ | OCH₃ | N | |
| Br | C(Cl)=NOCH₃ | H | O | H | OCH₃ | OCH₃ | CH | |
| Br | C(CN)=NOCH₃ | H | O | H | OCH₃ | OCH₃ | CH | |
| CO₂CH₃ | C(CN)=NOCH₃ | H | O | H | OCH₃ | OCH₃ | N | |
| NO₂ | C(Cl)=NOCH₃ | H | O | H | OCH₃ | OCH₃ | CH | |
| NO₂ | C(CN)=NOCH₃ | H | O | H | OCH₃ | OCH₃ | CH | |
| NO₂ | C(CN)=NOCH₃ | H | O | H | OCH₃ | OCH₃ | N | |
| OCH₃ | C(Cl)=NOCH₃ | H | O | H | OCH₃ | OCH₃ | CH | |
| SO₂CH₃ | C(CN)=NOCH₃ | H | O | H | OCH₃ | OCH₃ | CH | |
| SO₂CH₃ | C(SCH₃)=NOCH₃ | H | O | H | OCH₃ | OCH₃ | CH | |
| SO₂CH₃ | C(Cl)=NOCH₃ | H | O | H | OCH₃ | OCH₃ | N | |
| F | C(Cl)=NOCH₃ | H | O | H | OCH₃ | OCH₃ | CH | |
| CF₃ | C(CN)=NOCH₃ | H | O | H | OCH₃ | OCH₃ | CH | |
| CF₃ | C(CN)=NOCH₃ | H | O | H | OCH₃ | OCH₃ | N | |
| CF₃ | C(CN)=NOCH₃ | H | O | H | OCH₃ | CH₃ | CH | |

TABLE I-continued

General Formula I

| R₁ | R₂ | Rₓ | W | R | X | Y | Z | m.p. (°C) |
|---|---|---|---|---|---|---|---|---|
| SO₂CH₃ | CH₂Br | H | O | H | OCH₃ | OCH₃ | CH | 176–178 |
| SO₂CH₃ | CH₂Br | H | O | H | OCH₃ | OCH₃ | N | 174–176 |
| SO₂CH₃ | CH₂Cl | H | O | H | OCH₃ | OCH₃ | CH | 173–176 |
| SO₂CH₃ | CH₂Cl | H | O | H | OCH₃ | OCH₃ | N | 190–191 |
| SO₂N(CH₃)₂ | CH₂Cl | H | O | H | OCH₃ | OCH₃ | CH+ | 171–173 |
| SO₂N(CH₃)₂ | CH₂Cl | H | O | H | OCH₃ | OCH₃ | CH | 180–182 |
| OSO₂CH₃ | CH₂Br | H | O | H | OCH₃ | OCH₃ | CH | |
| OSO₂CH₃ | CH₂Cl | H | O | H | OCH₃ | OCH₃ | CH | |
| CO₂CH₃ | CH₂Br | H | O | H | CH₃ | CH₃ | CH | 203–204 |
| CO₂CH₃ | CH₂Br | H | O | H | OCH₃ | CH₃ | CH | 181–182 |
| CO₂CH₃ | CH₂Br | H | O | H | OCH₃ | OCH₃ | CH | 195–197 |
| CO₂CH₃ | CH₂Br | H | O | H | Cl | OCH₃ | CH | 177–178 |
| CO₂CH₃ | CH₂Cl | H | O | H | OCH₃ | CH₃ | CH | 157–159 |
| CO₂CH₃ | CH₂Cl | H | O | H | OCH₃ | OCH₃ | CH | 179–181 |
| CO₂CH₃ | CH₂Cl | H | O | H | OCH₃ | OCH₃ | N | 190–195 |
| CO₂CH₂CH₃ | CH₂Br | H | O | H | CH₃ | CH₃ | N | 193–194 |
| CO₂CH₂CH₃ | CH₂Br | H | O | H | OCH₃ | CH₃ | N | 177–178 |
| CO₂CH₂CH₃ | CH₂Br | H | O | H | OCH₃ | CH₃ | CH | 184 |
| CO₂CH₂CH₃ | CH₂Br | H | O | H | Cl | OCH₃ | CH | 188 |
| CO₂CH₂CH₃ | CH₂Br | H | O | H | OCH₃ | OCH₃ | CH | 209–210 |
| CO₂CH₂CH₃ | CH₂Br | H | O | H | OCH₂CH₃ | NHCH₃ | N | 157–159 |
| C(O)N(CH₃)₂ | CH₂Br | H | O | H | CH₃ | CH₃ | N | 179–181 |
| C(O)N(CH₃)₂ | CH₂Br | H | O | H | OCH₃ | CH₃ | N | 190–195 |
| C(O)C(CH₃) | CH₂Br | H | O | H | Cl | OCH₃ | CH | 193–194 |
| C(O)N(CH₃)₂ | CH₂Br | H | O | H | OCH₃ | OCH₃ | CH | 177–178 |
| C(O)N(CH₃)₂ | CH₂Br | H | O | H | OCH₃ | OCH₃ | N | 146–148 |
| NO₂ | CH₂N | | O | H | CH₃ | CH₃ | CH | 190 |
| NO₂ | CH₂N | | O | H | OCH₃ | CH₃ | CH | 182–183 |

TABLE II

General Formula II

| $R_1$ | $R_2$ | $R_x$ | $X_1$ | $Y_1$ | m.p. (°C.) |
|---|---|---|---|---|---|
| F | $CH_2CN$ | H | $CH_3$ | O | |
| Cl | $CH_2SCN$ | H | $OCH_3$ | O | |
| $CF_3$ | $CH_2P(O)(OCH_2CH_3)_2$ | H | $OCH_3$ | $CH_2$ | |
| $NO_2$ | $CH_2CN$ | H | $OCH_3$ | O | |
| $OCH_3$ | $CH_2CN$ | H | $OCH_3$ | O | |
| $OCH_3$ | $CH_2SCN$ | H | $OCH_3$ | $CH_2$ | |
| $OCH_2CH_3$ | $CH_2SCN$ | H | $OCH_3$ | O | |
| $OCH_2CH_3$ | $CH_2CN$ | H | $OCH_3$ | $CH_2$ | |
| $CO_2CH_3$ | $CH_2CN$ | H | $OCF_2H$ | O | |
| $CO_2CH_3$ | $CH_2CN$ | H | $OCH_3$ | $CH_2$ | |
| $CO_2CH_3$ | $CH_2SCN$ | H | $OCH_3$ | O | |
| $CO_2CH_3$ | $CH_2P(O)(OCH_3)_2$ | H | $OCH_3$ | O | |
| $CO_2CH_2CH_3$ | $CH_2P(O)(OCH_3)_2$ | H | $OCH_3$ | O | |
| $CO_2CH_2CH_3$ | $CH_2CN$ | H | $OCH_3$ | $CH_3$ | |
| $CO_2N(CH_3)_2$ | $CH_2CN$ | H | $CH_3$ | O | |
| $SO_2NHCH_3$ | $CH_2CN$ | H | $OCH_3$ | O | |
| $SO_2N(CH_3)_2$ | $CH_2CN$ | H | $OCH_3$ | $CH_2$ | |
| $SO_2N(CH_3)_2$ | $CH_2SCN$ | H | $OCH_3$ | O | |
| $SO_2CH_3$ | $CH_2SCN$ | H | $OCH_3$ | O | |
| $SO_2CH_3$ | $CH_2CN$ | H | $OCF_2H$ | $CH_2$ | |
| $SO_2CH_2CH_3$ | $CH_2CN$ | H | $OCH_3$ | O | |
| $SO_2CH_2CH_3$ | $CH_2P(O)(OCH_3)_2$ | H | $OCH_3$ | O | |
| $OSO_2CH_3$ | $CH_2P(O)(OCH_3)_2$ | H | $OCH_3$ | $CH_2$ | |
| $OSO_2CH_3$ | $CH_2CN$ | H | $OCH_2C$ | O | |
| $OSO_2CH_2CH_3$ | $CH_2SCN$ | H | $OCH_3$ | O | |
| $R_1$-A | $CH_2CN$ | H | $CH_3$ | O | |
| $R_1$-A | $CH_2SCN$ | H | $OCH_3$ | $CH_2$ | |
| $R_1$-B | $CH_2P(O)(OCH_3)_2$ | H | $OCH_3$ | O | |
| $R_1$-C | $CH_2CN$ | H | $OCH_3$ | O | |
| F | CH=NOH | H | $CH_3$ | O | |
| $OCH_3$ | $CH=NOH_3$ | H | $OCH_3$ | O | |
| $COOCH_3$ | $C(CH_3)=NOH$ | H | $OCF_2H$ | $CH_2$ | |
| $CO_2N(CH_3)_2$ | $C(CH_3)=NOCH_3$ | H | $CH_3$ | O | |
| $SO_2N(CH_3)_2$ | CH=NOH | H | $OCH_3$ | O | |
| $SO_2CH_3$ | $CH=NOCH_3$ | H | $OCH_3$ | $CH_2$ | |
| $OSO_2CH_2CH_3$ | $C(CH_3)=NOH$ | H | $OCF_2H$ | O | |
| $R_1$-A | $C(CH_3)=NOCH_3$ | H | $CH_3$ | O | |
| $R_1$-B | CH=NOH | H | $CH_3$ | $CH_2$ | |
| $R_1$-C | $CH=NOCH_3$ | H | $OCH_3$ | O | |
| F | $CH_2O(CO)CH_3$ | H | $OCH_3$ | O | |
| F | $CH_2CN$ | 6-Cl | $OCH_3$ | O | |
| F | $CH_2OSO_2CH_3$ | H | $OCH_3$ | O | |
| $CF_3$ | $CH_2O(CO)CH_3$ | H | $OCH_3$ | O | |
| $OCH_3$ | $CH_2O(CO)CH_3$ | H | $OCH_3$ | O | |
| $OCH_3$ | $CH_2CN$ | 6-Cl | $OCH_3$ | O | |
| $OCH_3$ | $CH_2N_3$ | 6-Cl | $OCH_3$ | O | |
| $CO_2CH_3$ | $CH_2OSO_2CH_3$ | H | $OCH_3$ | O | |
| $CO_2CH_3$ | $CH_2O(CO)CH_3$ | H | $OCH_3$ | O | |
| $CO_2CH_3$ | $CH_2O(CO)CH_3$ | H | $OCH_3$ | $CH_2$ | |
| $CO_2CH_3$ | $CH_2N_3$ | H | $OCH_3$ | O | |
| $CO_2CH_2CH_3$ | $CH_2O(CO)CH_3$ | H | $OCH_3$ | O | |
| $CO_2CH_2CH_3$ | $CH_2OSO_2CH_3$ | H | $OCH_3$ | O | |
| $SO_2CH_2CH_3$ | $CH_2O(CO)CH_3$ | H | $OCH_3$ | O | |
| $R_1$-A | $CH_2O(CO)CH_3$ | H | $OCH_3$ | O | |
| $R_1$-A | $CH_2OSO_2CH_3$ | H | $OCH_3$ | O | |
| $R_1$-W | $CH_2O(CO)CH_3$ | H | $OCH_3$ | O | |
| $R_1$-X | $CH_2N_3$ | H | $OCH_3$ | O | |
| $R_1$-X | $CH_2NO_2$ | H | $OCH_3$ | $CH_2$ | |
| $R_1$-X | $CH_2O(CO)CH_3$ | H | $OCH_3$ | $CH_2$ | |
| $R_1$-Y | $CH_2O(CO)CH_3$ | H | $OCH_3$ | O | |
| $R_1$-Y | $CH_2N_3$ | H | $OCH_3$ | O | |
| $R_1$-AB | $CH_2N_3$ | H | $OCH_3$ | $CH_2$ | |
| $R_1$-AB | $CH_2N_3$ | 6-Cl | $OCH_3$ | O | |
| $R_1$-AC | $CH_2N_3$ | H | $OCH_3$ | O | |
| $R_1$-AC | $CH_2O(CO)CH_3$ | H | $OCH_3$ | O | |
| F | CH Br | H | $OCH_3$ | O | |
| $NO_2$ | $CH_2Br$ | H | $OCH_3$ | O | |
| $CH_2CH_3$ | $CH_2Br$ | H | $OCH_3$ | O | |
| $CO_2N(CH_3)_2$ | $CH_2Br$ | H | $OCH_3$ | O | |
| $SO_2N(CH_3)_2$ | $CH_2Br$ | H | $OCH_3$ | O | |
| $OCH_3$ | $CH_2Br$ | H | $OCH_3$ | O | |
| $CO_2CH_3$ | $C(CN)=NOCH_3$ | H | $OCH_3$ | O | |
| $NO_2$ | $C(Cl)=NOCH_3$ | H | $OCH_3$ | O | |

TABLE III

General Formula III

| R₁ | R₂ | Rₓ | X₁ | m.p. (°C.) |
|---|---|---|---|---|
| F | CH₂CN | H | CH₃ | |
| Cl | CH₂SCN | H | OCH₃ | |
| CF₃ | CH₂P(O)(OCH₂CH₃)₂ | H | OCH₃ | |
| NO₂ | CH₂CN | H | OCH₃ | |
| OCH₃ | CH₂CN | H | OCH₃ | |
| OCH₃ | CH₂SCN | H | OCH₃ | |
| OCH₂CH₃ | CH₂SCN | H | OCH₃ | |
| OCH₂CH₃ | CH₂CN | H | OCH₃ | |
| CO₂CH₃ | CH₂CN | H | OCF₂H | |
| CO₂CH₃ | CH₂CN | H | OCH₃ | |
| CO₂CH₃ | CH₂SCN | H | OCH₃ | |
| CO₂CH₃ | CH₂P(O)(OCH₃)₂ | H | OCH₃ | |
| CO₂CH₂CH₃ | CH₂P(O)(OCH₃)₂ | H | OCH₃ | |
| CO₂CH₂CH₃ | CH₂CN | H | OCH₃ | |
| CO₂N(CH₃)₂ | CH₂CN | H | CH₃ | |
| SO₂NHCH₃ | CH₂CN | H | OCH₃ | |
| SO₂N(CH₃)₂ | CH₂CN | H | OCH₃ | |
| SO₂N(CH₃)₂ | CH₂SCN | H | OCH₃ | |
| SO₂CH₃ | CH₂SCN | H | OCH₃ | |
| SO₂CH₃ | CH₂CN | H | OCF₂H | |
| SO₂CH₂CH₃ | CH₂CN | H | OCH₃ | |
| SO₂CH₂CH₃ | CH₂P(O)(OCH₃)₂ | H | OCH₃ | |
| OSO₂CH₃ | CH₂P(O)(OCH₃)₂ | H | OCH₃ | |
| OSO₂CH₃ | CH₂CN | H | OCH₂CH₃ | |
| OSO₂CH₂CH₃ | CH₂SCN | H | OCH₃ | |
| R₁-A | CH₂CN | H | CH₃ | |
| R₁-A | CH₂SCN | H | OCH₃ | |
| R₁-B | CH₂P(O)(OCH₃)₂ | H | OCH₃ | |
| R₁-C | CH₂CN | H | OCH₃ | |
| F | CH=NOH | H | CH₃ | |
| OCH₃ | CH=NOCH₃ | H | OCH₃ | |
| COOCH₃ | C(CH₃)=NOH | H | OCH₃ | |
| CO₂N(CH₃)₂ | C(CH₃)=NOCH₃ | H | OCF₂H | |
| SO₂N(CH₃)₂ | CH=NOH | H | CH₃ | |
| SO₂CH₃ | CH=NOCH₃ | H | OCH₃ | |
| OSO₂CH₂CH₃ | C(CH₃)=NOH | H | CH₃ | |
| R₁-A | C(CH₃)=NOCH₃ | H | OCH₃ | |
| R₁-B | CH=NOH | H | OCF₂H | |
| R₁-C | CH=NOCH₃ | H | OCH₃ | |
| F | CH₂CN | 6-Cl | CH₃ | |
| F | CH₂O(CO)CH₃ | H | OCH₃ | |
| CO₂CH₃ | CH₂N₃ | H | OCH₃ | |
| CO₂CH₃ | CH₂N₃ | 6-Cl | OCH₃ | |
| CO₂CH₂CH₃ | CH₂O(CO)CH₃ | H | OCH₃ | |
| CO₂CH₂CH₃ | CH₂OSO₂CH₃ | H | OCH₃ | |
| SO₂NHCH₃ | CH₂CN | 6-Cl | OCH₃ | |
| SO₂CH₂CH₃ | CH₂O(CO)CH₃ | H | OCH₃ | |
| R₁-A | CH₂O(CO)CH₃ | H | OCH₃ | |
| R₁-A | CH₂CN | 6-Cl | OCH₃ | |
| R₁-C | CH₂CN | 6-OCHF₂ | OCH₃ | |
| R₁-X | CH₂N₃ | H | OCH₃ | |
| R₁-X | CH₂O(CO)CH₃ | H | OCH₃ | |
| R₁-Y | CH₂N₃ | H | OCH₃ | |
| R₁-Y | CH₂O(CO)CH₃ | H | OCH₃ | |
| R₁-Z | CH₂O(CO)CH₃ | H | OCH₃ | |
| R₁-Z | CH₂N₃ | H | OCH₃ | |
| R₁-Z | CH(CH₃)N₃ | H | OCH₃ | |
| R₁-AB | CH₂N₃ | H | OCH₃ | |
| R₁-AC | CH₂O(CO)CH₃ | H | OCH₃ | |
| F | CH₂=NOH | 6-Cl | OCH₃ | |
| R₁-X | CH=NOH | H | OCH₃ | |
| F | CH₂Br | H | OCH₃ | |
| F | CH₂Cl | H | OCH₃ | |
| F | C(CN)=NOCH₃ | H | OCH₃ | |
| NO₂ | CH₂Br | H | OCH₃ | |
| OCH₃ | CH₂Br | H | OCH₃ | |
| CO₂CH₃ | CH₂Br | H | OCH₃ | |
| CO₂CH₃ | CH₂Cl | H | OCH₃ | |
| CO₂CH₃ | C(CN)=NOCH₃ | H | OCH₃ | |
| SO₂CH₃ | CH₂Br | H | OCH₃ | |
| SO₂CH₃ | CH₂Cl | H | OCH₃ | |

TABLE IV

General Formula IV

| R₁ | R₂ | Rₓ | X₁ | Y₃ | m.p. (°C.) |
|---|---|---|---|---|---|
| F | CH₂CN | H | CH₃ | H | |
| Cl | CH₂SCN | H | OCH₃ | H | |

TABLE IV-continued

General Formula IV

| $R_1$ | $R_2$ | $R_x$ | $X_1$ | $Y_3$ | m.p. (°C.) |
|---|---|---|---|---|---|
| $CF_3$ | $CH_2P(O)(OCH_2CH_3)_2$ | H | $OCH_3$ | $CH_3$ | |
| $NO_2$ | $CH_2CN$ | H | $OCH_3$ | H | |
| $OCH_3$ | $CH_2CN$ | H | $OCH_3$ | H | |
| $OCH_3$ | $CH_2SCN$ | H | $OCH_3$ | $CH_3$ | |
| $OCH_2CH_3$ | $CH_2SCN$ | H | $OCH_3$ | H | |
| $OCH_2CH_3$ | $CH_2CN$ | H | $OCH_3$ | $CH_3$ | |
| $CO_2CH_3$ | $CH_2CN$ | H | $OCF_2H$ | H | |
| $CO_2CH_3$ | $CH_2CN$ | H | $OCH_3$ | $CH_3$ | |
| $CO_2CH_3$ | $CH_2SCN$ | H | $OCH_3$ | H | |
| $CO_2CH_3$ | $CH_2P(O)(OCH_3)_2$ | H | $OCH_3$ | H | |
| $CO_2CH_2CH_3$ | $CH_2P(O)(OCH_3)_2$ | H | $OCH_3$ | H | |
| $CO_2CH_2CH_3$ | $CH_2CN$ | H | $OCH_3$ | $CH_3$ | |
| $CO_2N(CH_3)_2$ | $CH_2CN$ | H | $CH_3$ | H | |
| $SO_2NHCH_3$ | $CH_2CN$ | H | $OCH_3$ | H | |
| $SO_2N(CH_3)_2$ | $CH_2CN$ | H | $OCH_3$ | H | |
| $SO_2N(CH_3)_2$ | $CH_2SCN$ | H | $OCH_3$ | H | |
| $SO_2CH_3$ | $CH_2SCN$ | H | $OCH_3$ | H | |
| $SO_2CH_3$ | $CH_2CN$ | H | $OCF_2H$ | $CH_3$ | |
| $SO_2CH_2CH_3$ | $CH_2CN$ | H | $OCH_3$ | H | |
| $SO_2CH_2CH_3$ | $CH_2P(O)(OCH_3)_2$ | H | $OCH_3$ | H | |
| $OSO_2CH_3$ | $CH_2P(O)(OCH_3)_2$ | H | $OCH_3$ | $CH_3$ | |
| $OSO_2CH_3$ | $CH_2CN$ | H | $OCH_2CH_3$ | H | |
| $OSO_2CH_2CH_3$ | $CH_2SCN$ | H | $OCH_3$ | H | |
| $R_1$-A | $CH_2CN$ | H | $CH_3$ | H | |
| $R_1$-A | $CH_2SCN$ | H | $OCH_3$ | $CH_3$ | |
| $R_1$-B | $CH_2P(O)(OCH_3)_2$ | H | $OCH_3$ | H | |
| $R_1$-C | $CH_2CN$ | H | $OCH_3$ | H | |
| F | CH=NOH | H | $CH_3$ | H | |
| $OCH_3$ | $CH=NOH_3$ | H | $CH_3$ | $CH_3$ | |
| $COOCH_3$ | $C(CH_3)=NOH$ | H | $OCH_3$ | H | |
| $CO_2N(CH_3)_2$ | $C(CH_3)=NOCH_3$ | H | $OCH_3$ | H | |
| $SO_2N(CH_3)_2$ | CH=NOH | H | $CH_3$ | H | |
| $SO_2CH_3$ | $CH=NOCH_3$ | H | $CH_3$ | $CH_3$ | |
| $OSO_2CH_2CH_3$ | $C(CH_3)=NOH$ | H | $CH_3$ | H | |
| $R_1$-A | $C(CH_3)=NOCH_3$ | H | $OCH_3$ | H | |
| $R_1$-B | CH=NOH | H | $CH_3$ | $CH_3$ | |
| $R_1$-C | $CH=NOCH_3$ | H | $OCH_3$ | H | |
| F | $CH_2CN$ | 6-Cl | $OCH_3$ | H | |
| F | $CH_2O(CO)CH_3$ | H | $OCH_3$ | H | |
| F | $CH_2OSO_2CH_3$ | H | $OCH_3$ | H | |
| $NO_2$ | $CH_2CN$ | 6-Cl | $OCH_3$ | H | |
| $CO_2CH_3$ | $CH_2O(CO)CH_3$ | H | $OCH_3$ | H | |
| $CO_2CH_2CH_3$ | $CH_2O(CO)CH_3$ | H | $OCH_3$ | H | |
| $CO_2CH_2CH_3$ | $CH_2CN$ | 6-Cl | $OCH_3$ | H | |
| $CO_2CH_2CH_3$ | $CH_2N_3$ | 6-F | $OCH_3$ | H | |
| $SO_2CH_3$ | $CH_2O(CO)CH_3$ | H | $OCH_3$ | H | |
| $SO_2CH_2CH_3$ | $CH_2O(CO)CH_3$ | H | $OCH_3$ | H | |
| $SO_2CH_2CH_3$ | $CH_2N_3$ | 6-Cl | $OCH_3$ | H | |
| $R_1$-A | $CH_2O(CO)CH_3$ | H | $OCH_3$ | H | |
| $R_1$-A | $CH_2CN$ | 6-Cl | $OCH_3$ | $CH_3$ | |
| $R_1$-B | $CH_2CN$ | 6-Cl | $OCH_3$ | H | |
| $R_1$-X | $CH_2N_3$ | H | $OCH_3$ | H | |
| $R_1$-Y | $CH_2N_3$ | H | $OCH_3$ | H | |
| $R_1$-Z | $CH_2O(CO)CH_3$ | H | $OCH_3$ | H | |
| $R_1$-AC | $CH_2N_3$ | H | $OCH_3$ | H | |
| $R_1$-AD | $CH_2N_3$ | H | $OCH_3$ | H | |
| $OCH_3$ | CH=NOH | 6-Cl | $OCH_3$ | H | |
| $CO_2CH_3$ | CH=NOH | 6-Cl | $OCH_3$ | H | |
| F | $CH_2Br$ | H | $OCH_3$ | H | |
| F | $CH_2Cl$ | H | $OCH_3$ | H | |
| $CF_3$ | $CH_2Br$ | H | $OCH_3$ | H | |
| $CF_3$ | $CH_2Cl$ | H | $OCH_3$ | H | |
| $CO_2CH_3$ | $CH_2Br$ | H | $OCH_3$ | H | |
| $CO_2CH_3$ | $CH_2Cl$ | H | $OCH_3$ | H | |
| $CO_2CH_3$ | $C(CN)=NOCH_3$ | H | $OCH_3$ | H | |
| $SO_2CH_3$ | $CH_2Br$ | H | $OCH_3$ | H | |
| $SO_2CH_3$ | $CH_2Cl$ | H | $OCH_3$ | H | |
| $R_1$-A | $CH_2Br$ | H | $OCH_3$ | H | |
| $R_1$-B | $CH_2Cl$ | H | $OCH_3$ | H | |
| $OCH_3$ | $CH_2Br$ | H | $OCH_3$ | H | |
| $NO_2$ | $CH_2Br$ | H | $OCH_3$ | H | |
| $NO_2$ | $C(CN)=NOCH_3$ | H | $OCH_3$ | H | |

TABLE V

General Formula V

| $R_1$ | $R_2$ | $R_X$ | $X_2$ | $Y_2$ | m.p. (°C.) |
|---|---|---|---|---|---|
| F | $CH_2CN$ | H | $CH_3$ | $OCH_3$ | |
| Cl | $CH_2SCN$ | H | $CH_3$ | $OCH_2CH_3$ | |
| $CF_3$ | $CH_2P(O)(OCH_2CH_3)_2$ | H | $CH_3$ | $OCH_3$ | |
| $NO_2$ | $CH_2CN$ | H | $CH_3$ | $SCH_3$ | |
| $OCH_3$ | $CH_2CN$ | H | $CH_2CH_3$ | $OCH_3$ | |
| $OCH_3$ | $CH_2SCN$ | H | $CH_3$ | $SCH_2CH_3$ | |
| $OCH_2CH_3$ | $CH_2SCN$ | H | $CH_3$ | $OCH_3$ | |
| $OCH_2CH_3$ | $CH_2CN$ | H | $CH_2CF_3$ | $OCH_3$ | |
| $CO_2CH_3$ | $CH_2CN$ | H | $CH_3$ | $CH_3$ | |
| $CO_2CH_3$ | $CH_2CN$ | H | $CH_3$ | $OCH_3$ | |
| $CO_2CH_3$ | $CH_2SCN$ | H | $CH_3$ | $CH_2CH_3$ | |
| $CO_2CH_3$ | $CH_2P(O)(OCH_3)_2$ | H | $CH_2CH_3$ | $OCH_3$ | |
| $CO_2CH_2CH_3$ | $CH_2P(O)(OCH_3)_2$ | H | $CH_3$ | $OCH_3$ | |
| $CO_2CH_2CH_3$ | $CH_2CN$ | H | $CH_3$ | $OCH_2CH_3$ | |
| $CO_2N(CH_3)_2$ | $CH_2CN$ | H | $CH_2CF_3$ | $OCH_3$ | |
| $SO_2NHCH_3$ | $CH_2CN$ | H | $CH_3$ | $OCH_3$ | |
| $SO_2N(CH_3)_2$ | $CH_2CN$ | H | $CH_3$ | $SCH_3$ | |
| $SO_2N(CH_3)_2$ | $CH_2SCN$ | H | $CH_2CH_3$ | $OCH_3$ | |
| $SO_2CH_3$ | $CH_2SCN$ | H | $CH_3$ | $OCH_3$ | |
| $SO_2CH_3$ | $CH_2CN$ | H | $CH_3$ | $SCH_2CH_3$ | |
| $SO_2CH_2CH_3$ | $CH_2CN$ | H | $CH_3$ | $OCH_3$ | |
| $SO_2CH_2CH_3$ | $CH_2P(O)(OCH_3)_2$ | H | $CH_2CF_3$ | $OCH_3$ | |
| $OSO_2CH$ | $CH_2P(O)(OCH_3)_2$ | H | $CH_3$ | $CH_3$ | |
| $OSO_2CH_3$ | $CH_2CN$ | H | $CH_3$ | $OCH_3$ | |
| $OSO_2CH_2CH_3$ | $CH_2SCN$ | H | $CH_2CH_3$ | $OCH_3$ | |
| $R_1$-A | $CH_2CN$ | H | $CH_3$ | $OCH_3$ | |
| $R_1$-A | $CH_2SCN$ | H | $CH_3$ | $CH_2CH_3$ | |
| $R_1$-B | $CH_2P(O)(OCH_3)_2$ | H | $CH_3$ | $OCH_3$ | |
| $R_1$-C | $CH_2CN$ | H | $CH_3$ | $OCH_3$ | |
| F | $CH=NOH$ | H | $CH_3$ | $OCH_3$ | |
| $OCH_3$ | $CH=NOHCH_3$ | H | $CH_3$ | $CH_3$ | |
| $COOCH_3$ | $C(CH_3)=NOH$ | H | $CH_2CH_3$ | $OCH_3$ | |
| $CO_2N(CH_3)_2$ | $C(CH_3)=NOCH_3$ | H | $CH_2CF_3$ | $CH_3$ | |
| $SO_2N(CH_3)_2$ | $CH=NOH$ | H | $CH_3$ | $OCH_2CH_3$ | |
| $SO_2CH_3$ | $CH=NOCH_3$ | H | $CH_3$ | $OCH_3$ | |
| $OSO_2CH_2CH_3$ | $C(CH_3)=NOH$ | H | $CH_2CF_3$ | $OCH_3$ | |
| $R_1$-A | $C(CH_3)=NOCH_3$ | H | $CH_2CH_3$ | $CH_3$ | |
| $R_1$-B | $CH=NOH$ | H | $CH_3$ | $OCH_3$ | |
| $R_1$-C | $CH=NOCH_3$ | H | $CH_3$ | $CH_3$ | |
| F | $CH_2CN$ | 6-Cl | $CH_3$ | $OCH$ | |
| F | $CH_2O(CO)CH_3$ | H | $CH_3$ | $OCH_3$ | |
| $NO_2$ | $CH_2O(CO)CH_3$ | H | $CH_3$ | $OCH_3$ | |
| $NO_2$ | $CH_2N_3$ | H | $CH_3$ | $OCH_3$ | |
| $OCH_2CH_3$ | $CH_2O(CO)CH_3$ | H | $CH_3$ | $OCH_3$ | |
| $CO_2CH_3$ | $CH_2N_3$ | H | $CH_3$ | $OCH_3$ | |
| $CO_2CH_3$ | $CH_2CN$ | 6-Cl | $CH_3$ | $OCH_3$ | |
| $CO_2CH_2CH_3$ | $CH_2O(CO)CH_3$ | H | $CH_3$ | $OCH_3$ | |
| $SO_2CH_2CH_3$ | $CH_2CN$ | 6-Cl | $CH_3$ | $OCH_3$ | |
| $R_1$-A | $CH_2O(CO)CH_3$ | H | $CH_3$ | $OCH_3$ | |
| $R_1$-B | $CH_2O(CO)CH_3$ | H | $CH_3$ | $OCH_3$ | |
| $R_1$-X | $CH_2N_3$ | H | $CH_3$ | $OCH_3$ | |
| $R_1$-X | $CH_2O(CO)CH_3$ | H | $CH_3$ | $OCH_3$ | |
| $R_1$-AC | $CH_2O(CO)CH_3$ | H | $CH_3$ | $OCH_3$ | |
| $R_1$-AC | $CH_2N_3$ | H | $CH_3$ | $OCH_3$ | |
| $R_1$-AD | $CH_2CN$ | H | $CH_3$ | $OCH_3$ | |
| $R_1$-AD | $CH_2N_3$ | H | $CH_3$ | $OCH_3$ | |
| F | $CH=NOH$ | 6-Cl | $CH_3$ | $OCH_3$ | |
| $CO_2CH_3$ | $CH=NOH$ | 6-$OCF_2H$ | $CH_3$ | $OCH_3$ | |
| $R_1$-X | $CH=NOH$ | H | $CH_3$ | $OCH_3$ | |
| $R_1$-Y | $CH=NOH$ | H | $CH_3$ | $OCH_3$ | |
| F | $CH_2Br$ | H | $CH_3$ | $OCH_3$ | |
| $CF_3$ | $CH_2Br$ | H | $CH_3$ | $OCH_3$ | |
| $NO_2$ | $CH_2Br$ | H | $CH_3$ | $OCH_3$ | |
| $NO_2$ | $CH_2Cl$ | H | $CH_3$ | $OCH_3$ | |
| $CO_2CH_3$ | $CH_2Br$ | H | $CH_3$ | $OCH_3$ | |
| $CO_2CH_3$ | $CH_2Cl$ | H | $CH_3$ | $OCH_3$ | |
| $CO_2CH_3$ | $C(CN)=NOCH_3$ | H | $CH_3$ | $OCH_3$ | |
| $SO_2N(CH_3)_2$ | $CH_2Br$ | H | $CH_3$ | $OCH_3$ | |
| $SO_2N(CH_3)_2$ | $CH_2Cl$ | H | $CH_3$ | $OCH_3$ | |
| $R_1$-A | $CH_2Br$ | H | $CH_3$ | $OCH_3$ | |
| $R_1$-A | $CH_2Cl$ | H | $CH_3$ | $OCH_3$ | |
| $R_1$-AD | $CH_2Br$ | H | $CH_3$ | $OCH_3$ | |
| $R_1$-B | $CH_2Br$ | H | $CH_3$ | $OCH_3$ | |

TABLE VI

General Formula VII

| $R_1$ | $R_2$ | $R_X$ | $X_3$ | m.p. (°C.) |
|---|---|---|---|---|
| F | $CH_2CN$ | H | $OCH_3$ | |
| Cl | $CH_2SCN$ | H | $OCH_3$ | |
| $CF_3$ | $CH_2P(O)(OCH_2CH_3)_2$ | H | $OCH_3$ | |
| $NO_2$ | $CH_2CN$ | H | $CH_3$ | |
| $OCH_3$ | $CH_2CN$ | H | $OCH_3$ | |
| $OCH_3$ | $CH_2SCN$ | H | $CH_3$ | |
| $OCH_2CH_3$ | $CH_2SCN$ | H | $OCH_3$ | |
| $OCH_2CH_3$ | $CH_2CN$ | H | $CH_3$ | |
| $CO_2CH_3$ | $CH_2CN$ | H | $OCH_3$ | |
| $CO_2CH_3$ | $CH_2CN$ | H | $CH_3$ | |
| $CO_2CH_3$ | $CH_2SCN$ | H | $OCH_3$ | |
| $CO_2CH_3$ | $CH_2P(O)(OCH_3)_2$ | H | $CH_3$ | |
| $CO_2CH_2CH_3$ | $CH_2P(O)(OCH_3)_2$ | H | $OCH_3$ | |
| $CO_2CH_2CH_3$ | $CH_2CN$ | H | $CH_3$ | |
| $CO_2N(CH_3)_2$ | $CH_2CN$ | H | $OCH_3$ | |
| $SO_2NHCH_3$ | $CH_2CN$ | H | $CH_3$ | |
| $SO_2N(CH_3)_2$ | $CH_2CN$ | H | $OCH_3$ | |
| $SO_2N(CH_3)_2$ | $CH_2SCN$ | H | $CH_3$ | |
| $SO_2CH_3$ | $CH_2SCN$ | H | $OCH_3$ | |
| $SO_2CH_3$ | $CH_2CN$ | H | $OCH_3$ | |
| $SO_2CH_2CH_3$ | $CH_2CN$ | H | $CH_3$ | |
| $SO_2CH_2CH_3$ | $CH_2P(O)(OCH)_2$ | H | $CH_3$ | |
| $OSO_2CH_3$ | $CH_2P(O)(OCH_3)_2$ | H | $CH_3$ | |
| $OSO_2CH_3$ | $CH_2CN$ | H | $OCH_3$ | |
| $OSO_2CH_2CH_3$ | $CH_2SCN$ | H | $OCH_3$ | |
| $R_1$-A | $CH_2CN$ | H | $CH_3$ | |
| $R_1$-A | $CH_2SCN$ | H | $OCH_3$ | |
| $R_1$-B | $CH_2P(O)(OCH_3)_2$ | H | $CH_3$ | |
| $R_1$-C | $CH_2CN$ | H | $OCH_3$ | |
| F | CH=NOH | H | $OCH_3$ | |
| $OCH_3$ | CH=NOCH$_3$ | H | $OCH_3$ | |
| $COOCH_3$ | $C(CH_3)$=NOH | H | $CH_3$ | |
| $CO_2N(CH_3)_2$ | $C(CH_3)$=NOCH$_3$ | H | $CH_3$ | |
| $SO_2CH_3$ | CH=NOH | H | $OCH_3$ | |
| $OSO_2CH_2CH_3$ | $C(CH_3)$=NOCH$_3$ | H | $OCH_3$ | |
| $R_1$-A | $C(CH_3)$=NOH | H | $OCH_3$ | |
| $R_1$-B | $C(CH_3)$=NOCH | H | $CH_3$ | |
| $R_1$-C | CH=NOH | H | $OCH_3$ | |

TABLE VI-continued

General Formula VII

| $R_1$ | $R_2$ | $R_X$ | $X_3$ | m.p. (°C.) |
|---|---|---|---|---|
| F | $CH_2CN$ | 6-OCF$_2$H | $OCH_3$ | |
| F | $CH_2O(CO)CH_3$ | H | $OCH_3$ | |
| $NO_2$ | $CH_2CN$ | 6-Cl | $OCH_3$ | |
| $NO_2$ | $CH_2O(CO)CH_3$ | H | $OCH_3$ | |
| $CO_2CH_3$ | $CH_2O(CO)CH_3$ | H | $OCH_3$ | |
| $CO_2CH_3$ | $CH_2OSO_2CH_3$ | H | $OCH_3$ | |
| $CO_2CH_2CH_3$ | $CH_2OSO_2CH_3$ | H | $OCH_3$ | |
| $CO_2CH_2CH_3$ | $CH_2O(CO)CH_3$ | H | $OCH_3$ | |
| $SO_2CH_2CH_3$ | $CH_2O(CO)CH_3$ | H | $OCH_3$ | |
| $SO_2CH_2CH_3$ | $CH_2CN$ | 6-Cl | $OCH_3$ | |
| $R_1$-A | $CH_2O(CO)CH_3$ | H | $OCH_3$ | |
| $R_1$-A | $CH_2OSO_2CH_3$ | H | $OCH_3$ | |
| $R_1$-A | $CH_2CN$ | 6-Cl | $OCH_3$ | |
| $R_1$-X | $CH_2CN$ | H | $OCH_3$ | |
| $R_1$-X | $CH_2O(CO)CH_3$ | H | $OCH_3$ | |
| $R_1$-Y | $CH_2CN$ | H | $OCH_3$ | |
| $R_1$-Y | $CH_2N_3$ | H | $OCH_3$ | |
| $R_1$-AC | $CH_2N_3$ | H | $OCH_3$ | |
| $R_1$-AC | $CH_2CN$ | H | $OCH_3$ | |
| F | CH=NOH | 6-Cl | $OCH_3$ | |
| $CO_2CH_3$ | CH=NOCH$_3$ | 6-Cl | $OCH_3$ | |
| $R_1$-A | CH=NOH | 6-Cl | $OCH_3$ | |
| $R_1$-X | CH=NOCH$_3$ | H | $OCH_3$ | |
| $R_1$-Y | CH=NOCH$_3$ | H | $OCH_3$ | |
| F | $CH_2Br$ | H | $OCH_3$ | |
| F | C(Cl)=NOCH$_3$ | H | $OCH_3$ | |
| $NO_2$ | $CH_2Br$ | H | $OCH_3$ | |
| $NO_2$ | $CH_2Cl$ | H | $OCH_3$ | |
| $CO_2CH_3$ | $CH_2Br$ | H | $OCH_3$ | |
| $CO_2CH_3$ | $CH_2Cl$ | H | $OCH_3$ | |
| $CO_2CH_3$ | C(CN)=NOCH$_3$ | H | $OCH_3$ | |
| $SO_2CH_3$ | $CH_2Br$ | H | $OCH_3$ | |
| $SO_2CH_3$ | C(CN)=NOCH$_3$ | H | $OCH_3$ | |
| $SO_2N(CH_3)_2$ | $CH_2Br$ | H | $OCH_3$ | |
| $SO_2N(CH_3)_2$ | $CH_2Cl$ | H | $OCH_3$ | |
| $R_1$-A | $CH_2(CN)$=NOCH$_3$ | H | $OCH_3$ | |
| $OCH_3$ | C(CN)=NOCH$_3$ | H | $OCH_3$ | |

TABLE VII

General Formula VII

| $R_1$ | $R_2$ | $R_X$ | $X_4$ | $Y_4$ | m.p. (°C.) |
|---|---|---|---|---|---|
| F | $CH_2CN$ | H | $CH_3$ | $OCH_3$ | |
| Cl | $CH_2SCN$ | H | $OCH_3$ | $CH_3$ | |
| $CF_3$ | $CH_2P(O)(OCH_2CH_3)_2$ | H | $OCH_2CH_3$ | $OCH_3$ | |
| $NO_2$ | $CH_2CN$ | H | $CH_2OCH_3$ | $OCH_3$ | |
| $OCH_3$ | $CH_2CN$ | H | Cl | $OCH_3$ | |
| $OCH_3$ | $CH_2SCN$ | H | $CH_3$ | $OCH_2CH_3$ | |
| $OCH_2CH_3$ | $CH_2SCN$ | H | $OCH_3$ | $OCH_3$ | |
| $OCH_2CH_3$ | $CH_2CN$ | H | $CH_3$ | Cl | |
| $CO_2CH_3$ | $CH_2CN$ | H | $CH_3$ | $OCH_3$ | |
| $CO_2CH_3$ | $CH_2CN$ | H | $OCH_3$ | $OCH_3$ | |
| $CO_2CH_3$ | $CH_2SCN$ | H | $OCH_3$ | $CH_3$ | |
| $CO_2CH_3$ | $CH_2P(O)(OCH_3)_2$ | H | $OCH_2CH_3$ | $OCH_3$ | |
| $CO_2CH_2CH_3$ | $CH_2P(O)(OCH_3)_2$ | H | $OCH_3$ | $OCH_3$ | |
| $CO_2CH_2CH_3$ | $CH_2CN$ | H | $OCH_3$ | $OCH_2CH_3$ | |
| $CO_2N(CH_3)_2$ | $CH_2CN$ | H | $CH_2OCH_3$ | $OCH_3$ | |
| $SO_2NHCH_3$ | $CH_2CN$ | H | $OCH_3$ | $CH_3$ | |
| $SO_2N(CH_3)_2$ | $CH_2CN$ | H | $OCH_3$ | $OCH_3$ | |
| $SO_2N(CH_3)_2$ | $CH_2SCN$ | H | Cl | $OCH_3$ | |
| $SO_2CH_3$ | $CH_2SCN$ | H | $OCH_3$ | $CH_3$ | |
| $SO_2CH_3$ | $CH_2CN$ | H | $OCH_3$ | $OCH_3$ | |
| $SO_2CH_2CH_3$ | $CH_2CN$ | H | $OCH_3$ | $OCH_3$ | |
| $SO_2CH_2CH_3$ | $CH_2P(O)(OCH_3)_2$ | H | $CH_3$ | $OCH_3$ | |
| $OSO_2CH_3$ | $CH_2P(O)(OCH_3)_2$ | H | $OCH_3$ | $OCH_2CH_3$ | |
| $OSO_2CH_3$ | $CH_2CN$ | H | $OCH_3$ | $OCH_3$ | |
| $OSO_2CH_2CH_3$ | $CH_2SCN$ | H | $OCH_2CH_3$ | $OCH_3$ | |
| $R_1$-A | $CH_2CN$ | H | $OCH_3$ | $OCH_3$ | |
| $R_1$-A | $CH_2SCN$ | H | $OCH_3$ | $CH_3$ | |
| $R_1$-B | $CH_2P(O)(OCH_3)_2$ | H | $CH_2OCH_3$ | $OCH_3$ | |
| $R_1$-C | $CH_2CN$ | H | $OCH_3$ | $OCH_3$ | |
| F | CH=NOH | H | $CH_3$ | $OCH_3$ | |
| $OCH_3$ | CH=NOCH$_3$ | H | $OCH_3$ | $CH_3$ | |
| $COOCH_3$ | $C(CH_3)$=NOH | H | $OCH_2CH_3$ | $OCH_3$ | |
| $CO_2N(CH_3)_2$ | $C(CH_3)$=NOCH$_3$ | H | $CH_2OCH_3$ | $OCH_3$ | |
| $SO_2CH_3$ | CH=NOH$_3$ | H | Cl | $OCH_3$ | |

TABLE VII-continued

General Formula VII

| $R_1$ | $R_2$ | $R_X$ | $X_4$ | $Y_4$ | m.p. (°C.) |
|---|---|---|---|---|---|
| $OSO_2CH_2CH_3$ | $C(CH_3)=NOCH_3$ | H | $CH_3$ | $OCH_2CH_3$ | |
| $R_1$-A | $C(CH_3)=NOH$ | H | $OCH_3$ | $OCH_3$ | |
| $R_1$-B | $CH(CH_3)=NOCH_3$ | H | $OCH_3$ | Cl | |
| $R_1$-C | $CH=NOH$ | H | $CH_3$ | $OCH_3$ | |
| F | $CH_2CN$ | 6-Cl | $CH_3$ | $OCH_3$ | |
| F | $CH_2O(CO)CH_3$ | H | $OCH_3$ | $OCH_3$ | |
| $NO_2$ | $CH_2O(CO)CH_3$ | H | $OCH_3$ | $OCH_3$ | |
| $CO_2CH_3$ | $CH_2O(CO)CH_3$ | H | $OCH_3$ | $OCH_3$ | |
| $CO_2CH_3$ | $CH_2O(CO)CH_3$ | 6-Cl | $CH_3$ | $OCH_3$ | |
| $CO_2CH_3$ | $CH_2OSO_2CH_3$ | H | $OCH_3$ | $OCH_3$ | |
| $CO_2CH_2CH_3$ | $CH_2OSO_2CH_3$ | H | $OCH_3$ | $OCH_3$ | |
| $CO_2CH_2CH_3$ | $CH_2N_3$ | H | $OCH_3$ | $OCH_3$ | |
| $CO_2CH_2CH_3$ | $CH_2CN$ | 6-Cl | $OCH_3$ | $OCH_3$ | |
| $SO_2CH_2CH_3$ | $CH_2O(CO)CH_3$ | H | $CH_3$ | $OCH_3$ | |
| $SO_2CH_2CH_3$ | $CH_2OSO_2CH_3$ | H | $OCH_3$ | $OCH_3$ | |
| $R_1$-A | $CH_2CN$ | 6-Cl | $OCH_3$ | $OCH_3$ | |
| $R_1$-A | $CH_2O(CO)CH_3$ | H | $OCH_3$ | $CH_3$ | |
| $R_1$-B | $CH_2O(CO)CH_3$ | H | $OCH_3$ | $CH_3$ | |
| $R_1$-C | $CH_2N_3$ | H | $OCH_3$ | $OCH_3$ | |
| $R_1$-X | $CH_2O(CO)CH_3$ | H | $OCH_3$ | $OCH_3$ | |
| $R_1$-Y | $CH_2O(CO)CH_3$ | H | $OCH_3$ | $OCH_3$ | |
| $R_1$-AC | $CH_2N_3$ | H | $OCH_3$ | $OCH_3$ | |
| $R_1$-AD | $CH_2O(CO)CH_3$ | H | $OCH_3$ | $OCH_3$ | |
| $R_1$-AD | $CH_2OSO_2CH_3$ | H | $OCH_3$ | $OCH_3$ | |
| F | $CH_2Br$ | H | $OCH_3$ | $OCH_3$ | |
| F | $CH_2Cl$ | H | $CH_3$ | $OCH_3$ | |
| $CO_2CH_3$ | $CH_2Br$ | H | $CH_3$ | $OCH_3$ | |
| $CO_2CH_3$ | $CH_2Cl$ | H | $OCH_3$ | $OCH_3$ | |
| $SO_2CH_3$ | $CH_2Br$ | H | $OCH_3$ | $OCH_3$ | |
| $SO_2N(CH_3)_2$ | $CH_2Br$ | H | $CH_3$ | $OCH_3$ | |
| F | $C(CN)=NOCH_3$ | H | $OCH_3$ | $OCH_3$ | |

Formulations

Useful formulations of the compounds of Formula I can be prepared in conventional ways. They include dusts, granules, pellets, solutions, suspensions, emulsions, wettable powders, emulsifiable concentrates and the like. Many of these may be applied directly. Sprayable formulations can be extended in suitable media and used at spray volumes of from a few liters to several hundred liters per hectare. High strength compositions are primarily used as intermediates for further formulation. The formulations, broadly, contain about 0.1% to 99% by weight of active ingredient(s) and at least one of (a) about 0.1% to 20% surfactant(s) and (b) about 1% to 99.9% solid or liquid inert diluent(s). More specifically, they will contain these ingredients in the following approximate proportions:

| | Weight Percent* | | |
|---|---|---|---|
| | Active Ingredient | Diluent(s) | Surfactant(s) |
| Wettable Powders | 20–90 | 0–74 | 1–10 |
| Oil Suspensions, Emulsions, Solutions, (including Emulsifiable Concentrates) | 3–50 | 40–95 | 0–15 |
| Aqueous Suspension | 10–50 | 40–84 | 1–20 |
| Dusts | 1–25 | 70–99 | 0–5 |
| Granules and Pellets | 0.1–95 | 5–99.9 | 0–15 |
| High Strength Compositions | 90–99 | 0–10 | 0–2 |

*Active ingredient plus at least one of a Surfactant or a Diluent equals 100 weight percent.

Lower or higher levels of active ingredient can, of course, be present depending on the intended use and the physical properties of the compound. Higher ratios of surfactant to active ingredient are sometimes desirable, and are achieved by incorporation into the formulation or by tank mixing.

Typical solid diluents are described in Watkins, et al., "Handbook of Insecticide Dust Diluents and Carriers", 2nd Ed., Dorland Books, Caldwell, N.J., but other solids, either mined or manufactured, may be used. The more absorptive diluents are preferred for wettable powders and the denser ones for dusts. Typical liquid diluents and solvents are described in Marsden, "Solvents Guide," 2nd Ed., Interscience, New York, 1950. Solubility under 0.1% is preferred for suspension concentrates: solution concentrates are preferably stable against phase separation at 0° C. "McCutcheon's Detergents and Emulsifiers Annual", MC Publishing Corp., Ridgewood, N.J., as well as Sisely and Wood, "Encyclopedia of Surface Active Agents", Chemical Publishing Co., Inc., New York, 1964, list surfactants and recommended uses. All formulations can contain minor amounts of additives to reduce foaming, caking, corrosion, microbiological growth, etc.

The methods of making such compositions are well known. Solutions are prepared by simply mixing the ingredients. Fine solid compositions are made by blending and, usually, grinding as in a hammer or fluid energy mill. Suspensions are prepared by wet milling (see, for example, Littler, U.S. Pat. No. 3,060,084). Granules and pellets may be made by spraying the active material upon preformed granular carriers or by agglomeration techniques. See J. E. Browning, "Agglomeration", *Chemical Engineering*, Dec. 4, 1967, pp. 147ff. and "Perry's Chemical Engineer's Handbook", 5th Ed., McGraw-Hill, New York, 1963, pp. 8–57ff.

For further information regarding the art of formulation, see for example:

H. M. Loux, U.S. Pat. No. 3,235,361, Feb. 15, 1966, Col. 6, line 16 through Col. 7, line 19 and Examples 10 through 41;

R. W. Luckenbaugh, U.S. Pat. No. 3,309,192, Mar. 14, 1967, Col. 5, line 43 through Col. 7, line 62 and Examples 8, 12, 15, 39, 41, 52, 53, 58, 132, 138–140, 162–164, 166, 167 and 169–182;

H. Gysin and E. Knusli, U.S. Pat. No. 2,891,855, Jun. 23, 1959, Col. 3, line 66 through Col. 5, line 17 and Examples 1–4;

G. C. Klingman, "Weed Control as a Science", John Wiley and Sons, Inc., New York, 1961, pp. 81–96; and J. D. Fryer and S. A. Evans, "Weed Control Handbook", 5th Ed., Blackwell Scientific Publications, Oxford, 1968, pp. 101–103.

In the following examples, all parts are by weight unless otherwise indicated.

EXAMPLE 11

High Strength Concentrate

| | |
|---|---|
| 2-(cyanomethyl)-6-[[(4,6-dimethoxypyrimidin-2-yl)-aminocarbonyl]aminosulfonyl]benzoic acid, ethyl ester | 99% |
| trimethylnonyl polyethylene glycol ether | 1% |

The surfactant is sprayed upon the active ingredient in a blender and the mixture sifted through a U.S. Ser. No. 40 sieve (0.42 mm openings) prior to packaging. The concentrate may be formulated further for practical use.

EXAMPLE 12

Wettable Powder

| | |
|---|---|
| 2-(acetoxymethyl)-6-[[(4-methoxy-6-methyl-1,3,5-triazin-2-yl)aminocarbonyl]aminosulfonyl]benzoic acid, ethyl ester | 65% |
| dodecylphenol polyethylene glycol ether | 2% |
| sodium ligninsulfonate | 4% |
| sodium silicoaluminate | 6% |
| montmorillonite (calcined) | 23% |

The ingredients are thoroughly blended. The liquid surfactant is added by spraying upon the solid ingredients in the blender. After grinding in a hammer mill to produce particles essentially all below 100 microns, the material is reblended and sifted through a U.S. Ser. No. 50 sieve (0.3 mm opening) and packaged.

EXAMPLE 13

Aqueous Suspension

| | |
|---|---|
| 2-(cyanomethyl)-6-[[(4,6-dimethoxypyrimidin-2-yl)-aminocarbonyl]aminosulfonyl]benzoic acid, ethyl ester | 50.0% |
| polyacrylic acid thickener | 0.3% |
| dodecylphenol polyethylene glycol ether | 0.5% |
| disodium phosphate | 1% |
| monosodium phosphate | 0.5% |
| polyvinyl alcohol | 1.0% |
| water | 56.7% |

The ingredients are blended and ground together in a sand mill to produce particles essentially all under 5 microns in size.

EXAMPLE 14

Oil Suspension

| | |
|---|---|
| 2-(acetoxymethyl)-6-[[(4-methoxy-6-methyl-1,3,5-triazin-2-yl)aminocarbonyl]aminosulfonyl]benzoic acid, ethyl ester | 35% |
| blend of polyalcohol carboxylic esters and oil soluble petroleum sulfonates | 6% |
| xylene | 59% |

The ingredients are combined and ground together in a sand mill to produce particles essentially all below 3 microns. The product can be used directly, extended with oils, or emulsified in water.

EXAMPLE 15

Oil Suspension

| | |
|---|---|
| 2-(cyanomethyl)-6-[[(4,6-dimethoxypyrimidin-2-yl)-aminocarbonyl]aminosulfonyl]benzoic acid, ethyl ester | 25% |
| polyoxyethylene sorbitol hexaoleate | 5% |
| highly aliphatic hydrocarbon oil | 70% |

The ingredients are ground together in a sand mill until the solid particles have been reduced to under about 5 microns. The resulting thick suspension may be applied directly, but preferably after being extended with oils or emulsified in water.

EXAMPLE 16

Aqueous Suspension

| | |
|---|---|
| 2-(acetoxymethyl)-6-[[(4-methoxy-6-methyl-1,3,5-triazin-2-yl)aminocarbonyl]aminosulfonyl]benzoic acid, ethyl ester | 25% |
| hydrated attapulgite | 3% |
| crude calcium ligninsulfonate | 10% |
| sodium dihydrogen phosphate | 0.5% |
| water | 61.5% |

The ingredients are ground together in a ball or roller mill until the solid particles have been reduced to diameters under 10 microns.

EXAMPLE 17

Wettable Powder

| | |
|---|---|
| 2-(cyanomethyl)-6-[[(4,6-dimethoxypyrimidin-2-yl)-aminocarbonyl]aminosulfonyl]benzoic acid, ethyl ester | 40% |
| dioctyl sodium sulfonsuccinate | 1.5% |
| sodium ligninsulfonate | 3% |
| low viscosity methyl cellulose | 1.5% |
| attapulgite | 54% |

The ingredients are thoroughly blended, passed through an air mill, to produce an average particle size under 15 microns, reblended, and sifted through a U.S. Ser. No. 50 sieve (0.3 mm opening) before packaging.

All compounds of the invention may be formulated in the same manner.

EXAMPLE 18

Granule

| | |
|---|---|
| wettable powder of Example 17 | 15% |
| gypsum | 69% |
| potassium sulfate | 16% |

The ingredients are blended in a rotating mixer and water sprayed on to accomplish granulation. When most of the material has reached the desired range of 1.0 to 0.42 cm (U.S. Ser. No. 18 to 40 sieves), the granules are removed, dried, and screened. Oversized material is crushed to produce additional material in the desired range. These granules contain % active ingredient.

EXAMPLE 19

Wettable Powder

| | |
|---|---|
| 2-(acetoxymethyl)-6-[[(4-methoxy-6-methyl-1,3,5-triazin-2-yl)aminocarbonyl]aminosulfonyl]benzoic acid, ethyl ester | 50% |
| sodium alkylnaphthalenesulfonate | 2% |
| low viscosity methyl cellulose | 2% |
| diatomaceous earth | 46% |

The ingredients are blended, coarsely hammer-milled and the air milled to produce particles of active essentially all below 10 microns in diameter. The product is reblended before packaging.

EXAMPLE 20

Extruded Pellet

| | |
|---|---|
| 2-(cyanomethyl)-6-[[(4,6-dimethoxypyrimidin-2-yl)aminocarbonyl]aminosulfonyl]benzoic acid, ethyl ester | 40% |
| anhydrous sodium sulfate | 10% |
| crude calcium ligninsulfonate | 5% |
| sodium alkylnaphthalenesulfonate | 1% |
| calcium/magnesium bentonite | 59% |

The ingredients are blended, hammer-milled and then moistened with about 12% water. The mixture is extruded as cylinders about 3 mm diameter which are cut to produce pellets about 3 mm long. These may be used directly after drying, or the dried pellets may be crushed to pass a U.S. Ser. No. 20 sieve (0.84 mm openings). The granules held on a U.S. Ser. No. 40 sieve (0.42 mm openings) may be packaged for use and the fines recycled.

EXAMPLE 21

Wettable Powder

| | |
|---|---|
| 2-(acetoxymethyl)-6-[[(4-methoxy-6-methyl-1,3,5-triazin-2-yl)aminocarbonyl]aminosulfonyl]benzoic acid, ethyl ester | 80% |
| sodium alkylnaphthalenesulfonate | 2% |
| sodium ligninsulfonate | 2% |
| synthetic amorphous silica | 3% |

-continued

| | |
|---|---|
| kaolinite | 13% |

The ingredients are blended and then ground in a hammer-mill to produce particles with an average particle size less than 25 microns in diameter. The material is reblended and sifted through a U.S. Ser. No. 50 sieve (0.3 mm opening) before being packaged.

EXAMPLE 22

High Strength Concentrate

| | |
|---|---|
| 2-(cyanomethyl)-6-[[(4,6-dimethoxypyrimidin-2-yl)aminocarbonyl]aminosulfonyl]benzoic acid, ethyl ester | 98.5% |
| silica aerogel | 0.5% |
| synthetic amorphous fine silica | 1.0% |

The ingredients are blended and ground in a hammer-mill to produce a high strength concentrate essentially all passing a U.S. Ser. No. 50 sieve (0.3 mm openings). This material may then be formulated in a variety of ways.

Utility

Test results indicate that the compounds of the present invention are highly active preemergent or postemergent herbicides or plant growth regulants. Many of them have utility for broad-spectrum pre- and/or post-emergence weed control in areas where complete control of all vegetation is desired, such as around fuel storage tanks, industrial storage areas, parking lots, drive-in theaters, around billboards, highway and railroad structures. Some of the compounds have utility for selective weed control in crops such as wheat barley, corn, soybeans, sugarbeets and cotton. Alternatively, the subject compounds are useful to modify plant growth.

The rates of application for the compounds of the invention are determined by a number of factors, including their use as plant growth modifiers or as herbicides, the crop species involved, the types of weeds to be controlled, weather and climate, formulations selected, mode of application, amount of foliage present, etc. In general terms, the subject compounds should be applied at levels of around 0.010 to 20 kg/ha, the lower rates being suggested for use on lighter soils and/or those having a low organic matter content, for plant growth modification or for situations where only short-term persistence is required such as herbicide for fallow land.

The compounds of the invention may be used in combination with any other commercial herbicide; non-limiting examples of which are those of the sulfonylurea, triazine, triazole, uracil, urea, amide, diphenyl ether, carbamate and imidazolinone, cineole and bipyridylium types.

The herbicidal properties of the subject compounds were discovered in a number of greenhouse tests. The test procedures and results follow.

Compounds

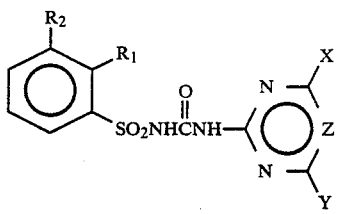

| Compound | R₁ | R₂ | X | Y | Z |
|---|---|---|---|---|---|
| 1 | COOCH$_2$CH$_3$ | CH$_2$CN | CH$_3$ | CH$_3$ | CH |
| 2 | COOCH$_2$CH$_3$ | CH$_2$CN | CH$_3$ | OCH$_3$ | CH |
| 3 | COOCH$_2$CH$_3$ | CH$_2$CN | OCH$_3$ | OCH$_3$ | CH |
| 4 | COOCH$_2$CH$_3$ | CH$_2$CN | Cl | OCH$_3$ | CH |
| 5 | COOCH$_2$CH$_3$ | CH$_2$CN | CH$_3$ | OCH$_3$ | N |
| 6 | COOCH$_2$CH$_3$ | CH$_2$CN | OCH$_3$ | OCH$_3$ | N |
| 7 | COOCH$_2$CH$_3$ | CH$_2$SCN | CH$_3$ | CH$_3$ | CH |
| 8 | COOCH$_2$CH$_3$ | CH$_2$SCN | CH$_3$ | OCH$_3$ | CH |
| 9 | COOCH$_2$CH$_3$ | CH$_2$SCN | OCH$_3$ | OCH$_3$ | CH |
| 10 | COOCH$_2$CH$_3$ | CH$_2$SCN | Cl | OCH$_3$ | CH |
| 11 | COOCH$_2$CH$_3$ | CH$_2$SCN | CH$_3$ | OCH$_3$ | N |
| 12 | COOCH$_2$CH$_3$ | CH$_2$SCN | OCH$_3$ | OCH$_3$ | N |
| 13 | COOCH$_2$CH$_3$ | CH$_2$OC(O)CH$_3$ | CH$_3$ | CH$_3$ | CH |
| 14 | COOCH$_2$CH$_3$ | CH$_2$OC(O)CH$_3$ | CH$_3$ | OCH$_3$ | CH |
| 15 | COOCH$_2$CH$_3$ | CH$_2$OC(O)CH$_3$ | OCH$_3$ | OCH$_3$ | CH |
| 16 | COOCH$_2$CH$_3$ | CH$_2$OC(O)CH$_3$ | Cl | OCH$_3$ | CH |
| 17 | COOCH$_2$CH$_3$ | CH$_2$OC(O)CH$_3$ | CH$_3$ | OCH$_3$ | N |
| 18 | COOCH$_2$CH$_3$ | CH$_2$OC(O)CH$_3$ | OCH$_3$ | OCH$_3$ | N |
| 19 | CO$_2$CH$_2$CH$_3$ | CH$_2$N$_3$ | CH$_3$ | CH$_3$ | CH |
| 20 | CO$_2$CH$_2$CH$_3$ | CH$_2$N$_3$ | CH$_3$ | OCH$_3$ | CH |
| 21 | CO$_2$CH$_2$CH$_3$ | CH$_2$N$_3$ | OCH$_3$ | OCH$_3$ | CH |
| 22 | CO$_2$CH$_2$CH$_3$ | CH$_2$N$_3$ | Cl | OCH$_3$ | CH |
| 23 | CO$_2$CH$_2$CH$_3$ | CH$_2$N$_3$ | CH$_3$ | OCH$_3$ | N |
| 24 | CO$_2$CH$_2$CH$_3$ | CH$_2$N$_3$ | OCH$_3$ | OCH$_3$ | N |
| 25 | CO$_2$CH$_2$CH$_3$ | CH$_2$NO$_2$ | CH$_3$ | OCH$_3$ | CH |
| 26 | CO$_2$CH$_2$CH$_3$ | CH$_2$NO$_2$ | OCH$_3$ | OCH$_3$ | CH |
| 27 | CO$_2$CH$_2$CH$_3$ | CH$_2$NO$_2$ | Cl | OCH$_3$ | CH |
| 28 | CO$_2$CH$_2$CH$_3$ | CH$_2$NO$_2$ | CH$_3$ | OCH$_3$ | N |
| 29 | CO$_2$CH$_2$CH$_3$ | CH$_2$NO$_2$ | OCH$_3$ | OCH$_3$ | N |
| 30 | CO$_2$CH(CH$_3$)$_2$ | CH$_2$CN | CH$_3$ | CH$_3$ | CH |
| 31 | CO$_2$CH(CH$_3$)$_2$ | CH$_2$CN | CH$_3$ | OCH$_3$ | CH |
| 32 | CO$_2$CH(CH$_3$)$_2$ | CH$_2$CN | OCH$_3$ | OCH$_3$ | CH |
| 33 | CO$_2$CH(CH$_3$)$_2$ | CH$_2$CN | Cl | OCH$_3$ | CH |
| 34 | CO$_2$CH(CH$_3$)$_2$ | CH$_2$CN | CH$_3$ | OCH$_3$ | N |
| 35 | CO$_2$CH(CH$_3$)$_2$ | CH$_2$CN | OCH$_3$ | OCH$_3$ | N |
| 36 | CO$_2$CH(CH$_3$)$_2$ | CH$_2$N$_3$ | CH$_3$ | CH$_3$ | CH |
| 37 | CO$_2$CH(CH$_3$)$_2$ | CH$_2$N$_3$ | CH$_3$ | OCH$_3$ | CH |
| 38 | CO$_2$CH(CH$_3$)$_2$ | CH$_2$N$_3$ | OCH$_3$ | OCH$_3$ | CH |
| 39 | CO$_2$CH(CH$_3$)$_2$ | CH$_2$N$_3$ | Cl | OCH$_3$ | CH |
| 40 | CO$_2$CH(CH$_3$)$_2$ | CH$_2$N$_3$ | CH$_3$ | OCH$_3$ | N |
| 41 | CO$_2$CH(CH$_3$)$_2$ | CH$_2$N$_3$ | OCH$_3$ | OCH$_3$ | N |
| 42 | CO$_2$CH$_3$ | CH$_2$OC(O)CH$_3$ | CH$_3$ | CH$_3$ | CH |
| 43 | CO$_2$CH$_3$ | CH$_2$OC(O)CH$_3$ | CH$_3$ | OCH$_3$ | CH |
| 44 | CO$_2$CH$_3$ | CH$_2$OC(O)CH$_3$ | OCH$_3$ | OCH$_3$ | CH |
| 45 | CO$_2$CH$_3$ | CH$_2$OC(O)CH$_3$ | Cl | OCH$_3$ | CH |
| 46 | CO$_2$CH$_3$ | CH$_2$OC(O)CH$_3$ | CH$_3$ | OCH$_3$ | N |
| 47 | CO$_2$CH$_3$ | CH$_2$OC(O)CH$_3$ | OCH$_3$ | OCH$_3$ | N |
| 48 | CO$_2$CH$_3$ | CH$_2$OC(O)CH$_3$ | NHCH$_3$ | OC$_2$H$_5$ | N |
| 49 | CO$_2$CH$_3$ | CH$_2$N$_3$ | CH$_3$ | CH$_3$ | CH |
| 50 | CO$_2$CH$_3$ | CH$_2$N$_3$ | CH$_3$ | OCH$_3$ | CH |
| 51 | CO$_2$CH$_3$ | CH$_2$N$_3$ | OCH$_3$ | OCH$_3$ | CH |
| 52 | CO$_2$CH$_3$ | CH$_2$N$_3$ | Cl | OCH$_3$ | CH |
| 53 | CO$_2$CH$_3$ | CH$_2$N$_3$ | CH$_3$ | OCH$_3$ | N |
| 54 | CO$_2$CH$_3$ | CH$_2$N$_3$ | OCH$_3$ | OCH$_3$ | N |
| 55 | CO$_2$CH$_3$ | CH$_2$N$_3$ | NHCH$_3$ | OC$_2$H$_5$ | N |
| 56 | CO$_2$CH$_3$ | CH$_2$CN | CH$_3$ | CH$_3$ | CH |
| 57 | CO$_2$CH$_3$ | CH$_2$CN | CH$_3$ | OCH$_3$ | CH |
| 58 | CO$_2$CH$_3$ | CH$_2$CN | OCH$_3$ | OCH$_3$ | CH |
| 59 | CO$_2$CH$_3$ | CH$_2$CN | Cl | OCH$_3$ | CH |
| 60 | CO$_2$CH$_3$ | CH$_2$CN | CH$_3$ | OCH$_3$ | N |
| 61 | CO$_2$CH$_3$ | CH$_2$CN | OCH$_3$ | OCH$_3$ | N |
| 62 | CO$_2$CH$_3$ | CH$_2$Br | CH$_3$ | CH$_3$ | CH |
| 63 | CO$_2$CH$_3$ | CH$_2$Br | CH$_3$ | OCH$_3$ | CH |
| 64 | CO$_2$CH$_3$ | CH$_2$Br | OCH$_3$ | OCH$_3$ | CH |
| 65 | CO$_2$CH$_3$ | CH$_2$Br | Cl | OCH$_3$ | CH |
| 66 | CO$_2$CH$_3$ | CH$_2$Br | CH$_3$ | OCH$_3$ | N |
| 67 | CO$_2$CH$_3$ | CH$_2$Br | OCH$_3$ | OCH$_3$ | N |
| 68 | CO$_2$CH$_2$CH$_3$ | CH$_2$Br | CH$_3$ | CH$_3$ | CH |

-continued
Compounds

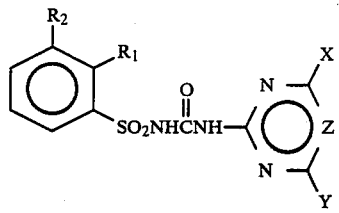

| Compound | $R_1$ | $R_2$ | X | Y | Z |
|---|---|---|---|---|---|
| 69 | $CO_2CH_2CH_3$ | $CH_2Br$ | $CH_3$ | $OCH_3$ | CH |
| 70 | $CO_2CH_2CH_3$ | $CH_2Br$ | $OCH_3$ | $OCH_3$ | CH |
| 71 | $CO_2CH_2CH_3$ | $CH_2Br$ | Cl | $OCH_3$ | CH |
| 72 | $CO_2CH_2CH_3$ | $CH_2Br$ | $CH_3$ | $OCH_3$ | N |
| 73 | $CO_2CH_2CH_3$ | $CH_2Br$ | $OCH_3$ | $OCH_3$ | N |
| 74 | $C(O)N(CH_3)_2$ | $CH_2Br$ | $CH_3$ | $CH_3$ | CH |
| 75 | $C(O)N(CH_3)_2$ | $CH_2Br$ | $CH_3$ | $OCH_3$ | CH |
| 76 | $C(O)N(CH_3)_2$ | $CH_2Br$ | $OCH_3$ | $OCH_3$ | CH |
| 77 | $C(O)N(CH_3)_2$ | $CH_2Br$ | Cl | $OCH_3$ | CH |
| 78 | $C(O)N(CH_3)_2$ | $CH_2Br$ | $CH_3$ | $OCH_3$ | N |
| 79 | $C(O)N(CH_3)_2$ | $CH_2Br$ | $OCH_3$ | $OCH_3$ | N |
| 80 | $NO_2$ | $CH_2Br$ | $CH_3$ | $CH_3$ | CH |
| 81 | $NO_2$ | $CH_2Br$ | $CH_3$ | $OCH_3$ | CH |
| 82 | $NO_2$ | $CH_2Br$ | $OCH_3$ | $OCH_3$ | CH |
| 83 | $NO_2$ | $CH_2Br$ | Cl | $OCH_3$ | CH |
| 84 | $NO_2$ | $CH_2Br$ | $CH_3$ | $OCH_3$ | N |
| 85 | $NO_2$ | $CH_2Br$ | $OCH_3$ | $OCH_3$ | N |
| 86 | $NO_2$ | $CH_2OC(O)CH_3$ | $CH_3$ | $CH_3$ | CH |
| 87 | $NO_2$ | $CH_2OC(O)CH_3$ | $CH_3$ | $OCH_3$ | CH |
| 88 | $NO_2$ | $CH_2OC(O)CH_3$ | $OCH_3$ | $OCH_3$ | CH |
| 89 | $NO_2$ | $CH_2OC(O)CH_3$ | Cl | $OCH_3$ | CH |
| 90 | $NO_2$ | $CH_2OC(O)CH_3$ | $CH_3$ | $OCH_3$ | N |
| 91 | $NO_2$ | $CH_2OC(O)CH_3$ | $OCH_3$ | $OCH_3$ | N |
| 92 | $NO_2$ | $CH_2N_3$ | $CH_3$ | $CH_3$ | CH |
| 93 | $NO_2$ | $CH_2N_3$ | $CH_3$ | $OCH_3$ | CH |
| 94 | $NO_2$ | $CH_2N_3$ | $OCH_3$ | $OCH_3$ | CH |
| 95 | $NO_2$ | $CH_2N_3$ | Cl | $OCH_3$ | CH |
| 96 | $NO_2$ | $CH_2N_3$ | $CH_3$ | $OCH_3$ | N |
| 97 | $NO_2$ | $CH_2N_3$ | $OCH_3$ | $OCH_3$ | N |

TEST A

Seeds of crabgrass (Digitaria spp.), barnyard-grass (Echinochloa crusqualli), cheatgrass (Bromus Secalinus), giant foxtail (Setaria faberii), wild oats (Avena fatua), velvetleaf (Abutilon theophrasti), morningglory (Ipomoea spp., cocklebur (Xanthium pensylvanicum), sorghum, corn, barley, soybean, sugar-beet, cotton, rice, wheat and purple nutsedge (Cyperus rotundus) tubers were planted and treated preemergence with the test chemicals dissolved in a non-phytotoxic solvent. At the same time, these crop and weed species were treated with a soil/foliage application. At the time of treatment, the plants ranged in height from 2 to 18 cm. Treated plants and controls were maintained in a greenhouse for sixteen days, after which all species were compared to controls and visually rated for response to treatment. The ratings, summarized in Table A, are based on a numerical scale extending from 0=no injury, to 10=complete kill. The accompanying descriptive symbols have the following meanings:

B=burn;
C=chlorosis/necrosis;
D=defoliation;
E=emergence inhibition;
G=growth retardation;
H=formative effect;
U=unusual pigmentation;
X=axillary stimulation;
S=albinism; and
6Y=abscised buds or flowers.

| (TEST A) | | | | | | | | | | | | |
|---|---|---|---|---|---|---|---|---|---|---|---|---|
| | CMPD 1 | | CMPD 2 | | CMPD 3 | | CMPD 4 | | CMPD 5 | | CMPD 6 | |
| RATE RATE = KG/HA | 0.05 | 0.01 | 0.05 | 0.01 | 0.05 | 0.01 | 0.05 | 0.01 | 0.05 | 0.01 | 0.05 | 0.01 |
| POSTEMERGENCE | | | | | | | | | | | | |
| COTTON | 9C | 9G | 9C | 3C,8G | 10C | 9C | 9C | 7H | 3C,9G | 3C,8H | 3C,9G | 2C,5G |
| MORNING GLORY | 3C,9G | 7G | 10C | 5C,9G | 10C | 10C | 8G | 7G | 4C,8H | 6G | 3C,8H | 5G |
| COCKLEBUR | 10C | 7G | 10C | 3C,9H | 10C | 10C | 10C | 10C | 10C | 4G | 4C,8H | 3H |
| NUTSEDGE | 3C,9G | 2C,8G | 5C,9G | 9G | 10C | 10C | 10C | 2C,9G | 3C,8G | 0 | 3C,8G | 3G |
| CRABGRASS | 3C,9H | 3C,6G | 5C,9H | 3G | 2C,8G | 2C,7G | 7G | 0 | 4C,9G | 2C,9G | 3C,9G | 6G |
| BARNYARD GRASS | 9C | 9H | 10C | 9H | 10C | 9C | 10C | 9C | 10C | 6C,9G | 4C,9H | 3C,8G |
| WILD OATS | 3C,7G | 3G | 3C,9G | 2G | 2C,9G | 3C,6G | 3C,4G | 0 | 2C,5G | 2C,4G | 2C,6G | 0 |
| WHEAT | 10C | 9G | 2C,9G | 4C,9G | 2C,9G | 2C,9G | 2C,6G | 3G | 2C,9G | 9C | 2C,9G | 2G |
| CORN | 10C | 9C | 10C | 9C | 6U,9C | 10C | 6U,9C | 4U,9G | 4U,9C | 6U,9C | 9C | 3C,8G |
| SOYBEAN | 6C,9G | 4C,9G | 9C | 5C,9G | 9C | 6C,9G | 2C,7H | 7H | 5C,9G | 3C,7H | 5C,9G | 3C,7H |

-continued (TEST A)

| | | | | | | | | | | | | |
|---|---|---|---|---|---|---|---|---|---|---|---|---|
| RICE | 9C | 9C | 9C | 5C,9G | 9C | 9C | 4C,9G | 3C,9G | 4C,9G | 4C,9G | 5C,9G | 3C,9G |
| SORGHUM | 9G | 3C,9G | 9C | 3C,9G | 9C | 6C,9G | 4C,9G | 2C,9G | 9C | 3C,9G | 6C,9G | 1C,9G |
| CHEATGRASS | 9G | 5G | 8G | 5G | 2C,8G | 6G | 2C,6G | 2G | 2C,7G | 5G | 6G | 2G |
| SUGAR BEETS | 10C | 9C | 10C | 9C | 10C | 10C | 10C | 6G | 9C | 2G | 2C,4G | 0 |
| VELVETLEAF | 3C,7H | 4G | 9C | 7G | 10C | 10C | 2C,9G | 7G | 6C,9G | 3C,6G | 4C,8H | 2C,6G |
| GIANT FOXTAIL | 6C,9H | 3C,7G | 9C | 5C,9G | 10C | 9C | 3C,8G | 7G | 9C | 3C,7G | 3C,9G | 2C,7G |
| BARLEY | 9G | 3C,9G | 5C,9G | 2C,9G | 6C,9G | 5C,9G | 6C,9G | 2C,7G | 2C,9G | 2C,6G | 2C,6G | 2C,4G |
| PREEMERGENCE | | | | | | | | | | | | |
| COTTON | 2G | 0 | 5G | 0 | 2C,8G | 3G | 7H | 0 | 4G | 0 | 0 | 0 |
| MORNING GLORY | 0 | 0 | 7H | 0 | 9G | 2G | 7H | 5G | 2G | 0 | 0 | 0 |
| COCKLEBUR | — | 0 | 8H | 1C | 3C,8G | 3C,7H | 7H | — | — | 3G | — | 0 |
| NUTSEDGE | 7G | 0 | 9G | 0 | 9G | 4G | 3C,9G | 0 | 2G | 0 | 0 | 0 |
| CRABGRASS | 0 | 3G | 6G | 0 | 2C,5G | 4G | 2G | 0 | 2G | 2G | 0 | 0 |
| BARNYARD GRASS | 2G | 0 | 9H | 0 | 2C,9H | 2G | 3C,9H | 0 | 3C,9H | 0 | 5G | 0 |
| WILD OATS | 5G | 0 | 3G | 0 | 2C,7G | 3G | 2C,5G | 0 | 0 | 0 | 2G | 0 |
| WHEAT | 9G | 7G | 9H | 5G | 1C,8G | 2C,7G | 2C,7G | 0 | 2C,8G | 2G | 2C,5G | 0 |
| CORN | 9G | 2C,8G | 9H | 9H | 9H | 2C,8H | 9H | 7G | 3C,9G | 3C,6G | 3C,7G | 3C,5G |
| SOYBEAN | 2C,6G | 3G | 9H | 3C,5G | 3C,8H | 5G | 2C,6G | 2C,6H | 2C,6G | 4G | 2C,4G | 4G |
| RICE | 9H | 0 | 9H | 0 | 2C,9H | 3G | 2C,9H | 2C,7G | 3C,9H | 2G | 2C,8H | 0 |
| SORGHUM | 9H | 3C,5G | 9H | 3C,3G | 3C,9H | 2C,7H | 3C,9H | 2C,7H | 3C,8H | 3C,8G | 3C,8H | 3C,7G |
| CHEATGRASS | 7G | 0 | 4G | 0 | 8H | 5G | 6G | 0 | 4G | 0 | 7G | 0 |
| SUGAR BEETS | 8H | 2H | 8H | 3G | 2C,9G | 2C,5H | 6G | 3G | 3H | 2H | 0 | 2H |
| VELVETLEAF | 0 | 0 | 2H | 5G | 5H | 2H | 3H | 0 | 3H | 2G | 0 | 0 |
| GIANT FOXTAIL | 0 | 0 | 7G | 0 | 2C,8H | 5G | 7G | 0 | 3G | 3G | 0 | 0 |
| BARLEY | 9G | 8G | 9H | 7G | 2C,8G | 2C,9G | 9G | 7G | 9G | 8G | 8G | 2C,7G |

| | CMPD 7 | | CMPD 8 | | CMPD 9 | | CMPD 10 | | CMPD 11 | | CMPD 12 | |
|---|---|---|---|---|---|---|---|---|---|---|---|---|
| RATE RATE = KG/HA | 0.05 | 0.01 | 0.05 | 0.01 | 0.05 | 0.01 | 0.05 | 0.01 | 0.05 | 0.01 | 0.05 | 0.01 |
| POSTEMERGENCE | | | | | | | | | | | | |
| COTTON | 1C,7G | 4G | 3C,8G | 6G | 10C | 7G | 10C | 5G | 2C,8G | 6G | 7G | 6G |
| MORNING GLORY | 2C,9G | 7G | 10C | 3C,9G | 10C | 2C,9G | 2C,7G | 4G | 9C | 3C,8G | 4C,8H | 7G |
| COCKLEBUR | 10C | 7G | 3C,9H | 2C,8H | 10C | 10C | 10C | — | 10C | 10C | 3C,9G | 3G |
| NUTSEDGE | 3C,9G | 2G | 9C | 2C,6G | 3C,7G | 2C,5G | 7G | 0 | 0 | 0 | 2G | 0 |
| CRABGRASS | 2C,8G | 0 | 7G | 0 | 2C,7G | 0 | 4G | 0 | 2C,8G | 0 | 0 | 0 |
| BARNYARD GRASS | 2C,8H | 2C,6G | 9C | 2C,8H | 6C,9G | 2C,8H | 4C,8G | 2C,7H | 3C,9G | 2C,6H | 2C,7G | 2G |
| WILD OATS | 2C,6G | 0 | 3C,8G | 0 | 2C,7G | 0 | 2C,5G | 0 | 0 | 0 | 0 | 0 |
| WHEAT | 9C | 0 | 2C,9G | 2C,9G | 2C,9G | 4G | 4G | 3G | 8G | 0 | 0 | 0 |
| CORN | 3C,8G | 2C,8G | 10C | 3U,8G | 3C,8G | 3C,8G | 2C,8G | 2C,7H | 3U,9G | 3C,6H | 2C,8G | 3C,4G |
| SOYBEAN | 3C,7G | 2C,6G | 3C,9G | 2C,7H | 5C,9G | 4C,9G | 3C,7H | 2C,6G | 6C,9G | 5C,9G | 3C,9G | 3C,9H |
| RICE | 6C,9G | 2C,9G | 5C,9G | 3C,8G | 4C,9G | 3C,8G | 2C,9G | 2C,8G | 3C,9G | 3C,8G | 3C,9G | 3G |
| SORGHUM | 3C,8G | 2C,6G | 2C,9G | 3C,8G | 2C,8H | 2H,4G | 2C,9G | 3G | 2C,9G | 2C,6G | 3C,8G | 2G |
| CHEATGRASS | 9G | 0 | 2C,8G | 2G | 2C,7G | 3G | 5G | 0 | 4G | 0 | 0 | 0 |
| SUGAR BEETS | 3C,8G | 4G | 3C,9G | 2C,8G | 10C | 7G | 2C,7G | 2C,7G | 3C,9G | 2C,7G | 2G | 0 |
| VELVETLEAF | 3C,9H | 1C,7G | 3C,9G | 3C,9G | 4C,9G | 4C,9G | 4C,9G | 8G | 4C,9H | 2C,7H | 4C,9H | 2C,7H |
| GIANT FOXTAIL | 2C,8G | 0 | 3C,9G | 7G | 6C,9G | 6G | 7G | 3G | 7G | 0 | 4G | 2G |
| BARLEY | 2C,5G | 5G | 2C,7G | 5G | 3C,9G | 3C,6G | 3C,7G | 2C,5G | 4G | 0 | 3G | 4C,5G |
| PREEMERGENCE | | | | | | | | | | | | |
| COTTON | 1C,7G | 4G | 8G | 7G | 8G | 7G | 7G | 6G | 7G | 6G | 7G | 3G |
| MORNING GLORY | 9H | 3G | 2C,9H | 7G | 9G | 7G | 9G | 6G | 9G | 7G | 9G | 0 |
| COCKLEBUR | 2C,3H | 0 | 7H | 0 | 3C,7H | 3G | 0 | — | — | 0 | 0 | 0 |
| NUTSEDGE | 3C,9G | 0 | 9G | 0 | 8G | 0 | 7G | 0 | 0 | 0 | 0 | 0 |
| CRABGRASS | 5G | 0 | 3C,9G | 0 | 2C,6G | 0 | 2C | 0 | 3C,5G | 0 | 2C,7G | 0 |
| BARNYARD GRASS | 0 | 0 | 2C,9H | 0 | 7H | 0 | 7H | 0 | 2C,9H | 0 | 0 | 0 |
| WILD OATS | 2C,7G | 3C,5G | 4C,8G | 3C,5G | 3C,6G | 2C,3G | 3C,6G | 0 | 2C,5G | 0 | 0 | 0 |
| WHEAT | 7H | 8G | 2C,9G | 7G | 7G | 2C,5G | 2C,8G | 3G | 9G | 0 | 2C,7G | 0 |
| CORN | 7G | 2G | 1C,8G | 2C,7H | 2C,7G | 2C | 7G | 0 | 2C,7G | 2G | 2C,7G | 0 |
| SOYBEAN | 2C,7H | 5G | 4C,8H | 2C,6H | 4C,8H | 2C,6G | 2C,7G | 2C,6G | 2C,7G | 4G | 6G | 2G |
| RICE | 3C,9H | 3C,9H | 4C,9H | 3C,9H | 3C,9H | 2C,7G | 10H | 2C,9H | 2C,9H | 3C,9H | 2C,8G | 7G |
| SORGHUM | 1C,8H | 2C,6H | 2C,8G | 2C,8H | 8G | 2C,6G | 2C,8G | 7G | 3C,8G | 2C,8G | 3C,8G | 6G |
| CHEATGRASS | 9G | 9G | 2C,9H | 8G | 8G | 7G | 8G | 4G | 3C,9H | 0 | 2G | 0 |
| SUGAR BEETS | 7G | 2G | 9G | 7G | 2C,7G | 2C,6H | 3C,9G | 2G | 9C | 2C,9G | 2G | 0 |
| VELVETLEAF | 7H | 0 | 7H | 6G | 1C,8G | 2G | 7G | 0 | 2C,7G | 5H | 7G | 0 |
| GIANT FOXTAIL | 2C,7G | 0 | 3C,9G | 0 | 9H | 2G | 2C,6G | 0 | 2G | 0 | 2G | 0 |
| BARLEY | 3G | 0 | 8G | 5G | 4G | 2G | 5G | 0 | 8G | 5G | 7G | 0 |

| | CMPD 13 | | CMPD 14 | | CMPD 15 | | CMPD 16 | | CMPD 17 | | CMPD 18 | |
|---|---|---|---|---|---|---|---|---|---|---|---|---|
| RATE RATE = KG/HA | 0.05 | 0.01 | 0.05 | 0.01 | 0.05 | 0.01 | 0.05 | 0.01 | 0.05 | 0.01 | 0.05 | 0.01 |
| POSTEMERGENCE | | | | | | | | | | | | |
| COTTON | 10C | 3C,8G | 10C | 10C | 9C | 10C | 9C | 4C,9H | 9C | 4C,9H | 4C,9G | 5C,9G |
| MORNING GLORY | 10C | 10C | 10C | 9C | 10C | 10C | 10C | 9C | 9C | 5C,9G | 6C,9G | 5C,9G |
| COCKLEBUR | 10C | 10C | 10C | 10C | 9C | 10C | 10C | 10C | 10C | 10C | 10C | 10C |
| NUTSEDGE | 10C | 8C | 9C | 5C,9G | 10C | 9C | 10C | 9C | 5C,9G | 5G | 9C | 7G |
| CRABGRASS | 10C | 6C,9G | 9C | 3C,7G | 10C | 5G | 3C,8G | 4G | 10C | 5C,9G | 5C,9G | 4C,8G |
| BARNYARD GRASS | 9C | 9C | 9C | 9C | 9C | 9C | 10C | 9C | 9C | 9C | 10C | 4C,9H |
| WILD OATS | 9C | 2C,7G | 5C,9G | 4C,9G | 5C,9G | 4C,9G | 3C,5G | 2G | 5C,9G | 2G | 3C,9G | 3C |
| WHEAT | 10C | 10C | 10C | 9C | 5C,9G | 3C,9G | 4C,9G | 2G | 10C | 5C,9G | 9G | 5C,9G |
| CORN | 10C | 10C | 9C | 10C | 10C | 9C | 6C,9G | 5C,9G | 10C | 10C | 9C | 5C,9G |
| SOYBEAN | 4C,9G | 3C,8H | 5C,9G | 5C,9G | 9C | 9C | 5C,9G | 8G | 9C | 5C,9G | 4C,9G | 5C,9G |
| RICE | 9C | 6C,9G | 9C | 9C | 9C | 9C | 9C | 5C,9G | 9C | 9C | 9C | 6C,9G |

|  | (TEST A) | | | | | | | | | | | |
|---|---|---|---|---|---|---|---|---|---|---|---|---|
| SORGHUM | 6C,9G | 5C,9G | 9C | 5C,9G | 9C | 5C,9G | 9C | 3C,9G | 10C | 9C | 5C,9G | 3C,9G |
| CHEATGRASS | 9C | 2C,7G | 9C | 5C,9G | 9C | 9C | 3C,7G | 3C,5G | 5C,9G | 6G | 6G | 3G |
| SUGAR BEETS | 10C | 10C | 10C | 10C | 10C | 10C | 10C | 5C,9G | 10C | 10C | 10C | 2G |
| VELVETLEAF | 10C | 4C,8G | 9C | 10C | 10C | 10C | 9C | 6C,9G | 10C | 9C | 9C | 4C,8G |
| GIANT FOXTAIL | 10C | 4C,9G | 10C | 9C | 10C | 10C | 10C | 4C,8H | 10C | 5C,9G | 9C | 4C,9G |
| BARLEY | 3C,9G | 2C,6G | 5C,9G | 5G | 9C | 6C,9G | 9G | 2G | 3C,8G | 6G | 5G | 0 |
| PREEMERGENCE | | | | | | | | | | | | |
| COTTON | 2C,8G | 7G | 2C,9G | 8G | 9G | 8G | 9G | 7G | 9G | 7G | 8G | 5G |
| MORNING GLORY | 9H | 8G | 9G | 6G | 9H | 7G | 9G | 9G | 9G | 9G | 9G | 8G |
| COCKLEBUR | 2C,8H | 2G | 9H | 7G | 9G | 3G | 8H | 0 | 9G | — | 2G | 2G |
| NUTSEDGE | 10E | 5G | 10E | 9G | 9G | 9G | 10C | 3G | 4C,8G | 0 | 9G | 0 |
| CRABGRASS | 3C,8G | 3C,9G | 3C,9G | 3C,9G | 7G | 5G | 3C,7G | 2G | 4C,9G | 5C,9G | 4C,8G | 2C |
| BARNYARD GRASS | 2C,9H | 3C,8H | 4C,9H | 8H | 9H | 5H | 9H | 9H | 9H | 5C,9H | 9H | 4H |
| WILD OATS | 3C,8G | 3C,7G | 5C,8G | 3C,9G | 3C,8G | 8G | 3C,7G | 3C,4G | 4C,9G | 3C,7G | 4C,9H | 3C,6G |
| WHEAT | 2C,9G | 2C,8G | 4C,9G | 9G | 9H | 8G | 9G | 7G | 4C,9H | 3C,9H | 3C,8H | 3G |
| CORN | 3C,9G | 4C,8H | 5C,9G | 9G | 4C,9H | 8H | 9G | 3C,9G | 4U,9H | 3C,9G | 3C,9G | 4G |
| SOYBEAN | 2C,8H | 2C,7G | 4C,9H | 3C,7G | 9H | 3C,7H | 3C,8G | 2C,3G | 4C,9H | 5G | 3C,7H | 3G |
| RICE | 10E | 2C,9H | 5C,9H | 3C,9H | 9H | 9H | 10E | 9H | 10E | 10E | 10E | 9H |
| SORGHUM | 10H | 3C,9H | 4C,9H | 2C,9H | 4C,9H | 9H | 6C,9H | 9H | 10H | 5C,9H | 9H | 9H |
| CHEATGRASS | 2C,9h | 2C,9H | 9H | 3C,9G | 3C,9G | 8G | 9G | 5G | 4C,9H | 9H | 7G | 3G |
| SUGAR BEETS | 2C,9G | 2C,5G | 9C | 9G | 9C | 3C,9H | 9C | 9G | 9C | 9C | 7G | 0 |
| VELVETLEAF | 3C,9H | 6H | 3C,9G | 7G | 5C,9G | 3G | 4C,9G | 7G | 4C,9G | 4H | 4C,8G | 3H |
| GIANT FOXTAIL | 2C,9H | 3G | 4C,9H | 3C,9G | 3C,9H | 8H | 9H | 2H | 9H | 3H | 9H | 2C,5G |
| BARLEY | 8G | 9G | 3C,9G | 7G | 8G | 7G | 8G | 4G | 9H | 9G | 9H | 5G |

|  | CMPD 19 | | CMPD 20 | | CMPD 21 | | CMPD 22 | | CMPD 23 | | CMPD 24 | |
|---|---|---|---|---|---|---|---|---|---|---|---|---|
| RATE = KG/HA | 0.01 | 0.05 | 0.01 | 0.05 | 0.01 | 0.05 | 0.01 | 0.05 | 0.01 | 0.05 | 0.01 | 0.05 |
| POSOL | | | | | | | | | | | | |
| COTTON | 3C,8G | 3C,9G | 4C,9G | 10C | 3C,9G | 9C | 4C,8G | 9C | 4C,9H | 3C,9G | 4C,8H | 4C,9H |
| MORNING GLORY | 3C,8H | 3C,8H | 10C | 10C | 10C | 10C | 3C,8H | 5C,9G | 10C | 5C,9G | 10C | 10C |
| COCKLEBUR | 10C | 10C | 10C | 10C | 10C | 10C | 10C | 10C | 10C | 10C | 10C | 10C |
| NUTSEDGE | 2C,7G | 2C,7G | 4C,9G | 9C | 3C,8G | 10C | 2C,8G | 5C,9G | 9G | 9C | 8G | 5C,9G |
| CRABGRASS | 5G | 3C,8G | 5G | 2C,8G | 7G | 4C,9G | 2G | 2C,4G | 3C,7G | 9C | 2C,5G | 6C,9G |
| BARNYARD GRASS | 4C,9H | 9C | 9C | 9C | 9C | 10C | 4C,9H | 9C | 9C | 9C | 3C,9H | 9C |
| WILD OATS | 4G | 9G | 2C,6G | 3C,9G | 2C,5G | 4C,9G | 0 | 2G | 2G | 3C,8G | 0 | 2C,5G |
| WHEAT | 8G | 9G | 4C,9G | 4C,9G | 8G | 4C,9G | 0 | 5G | 8G | 5C,9G | 0 | 7G |
| CORN | 9C | 9C | 9C | 10C | 10C | 10C | 9C | 5C,9G | 10C | 10C | 10C | 5C,9G |
| SOYBEAN | 4C,8H | 5C,9G | 4C,9G | 9C | 9C | 9C | 2C,4H | 4C,9G | 4C,9G | 9C | 4C,9G | 5C,9G |
| RICE | 4C,9G | 9C | 9C | 9C | 9C | 9C | 4C,9G | 5C,9G | 9C | 9C | 9C | 9C |
| SORGHUM | 9G | 3C,9G | 9C | 9C | 9C | 10C | 3C,9G | 3C,9G | 9C | 9C | 3C,9H | 9C |
| CHEATGRASS | 7G | 5C,9G | 3C,8G | 9C | 3C,9G | 9C | 4G | 3C,8G | 3C,6G | 5C,9G | 0 | 3C,5G |
| SUGAR BEETS | 9C | 9C | 5C,9G | 10C | 5C,9G | 10C | 2C,5G | 10C | 9C | 10C | 9C | 9C |
| VELVETLEAF | 3C,8G | 9C | 9C | 10C | 9C | 10C | 4C,8G | 10C | 9C | 10C | 3C,7H | 9C |
| GIANT FOXTAIL | 9G | 5C,9G | 5C,9G | 9C | 10C | 10C | 3C,6G | 5C,9G | 9C | 10C | 3C,8G | 9C |
| BARLEY | 8G | 9G | 2C,9G | 5C,9G | 5C,9G | 9C | 2C,2G | 8G | 2G | 2C,8G | 0 | 2C,6G |
| PRSOL | | | | | | | | | | | | |
| COTTON | 4G | 8G | 0 | 7G | 5G | 6G | 2G | 6G | 1C | 8G | | 2G |
| MORNING GLORY | 0 | 0 | 2G | 3G | 0 | 5G | 0 | 5G | 2C | 9H | 0 | 8H |
| COCKLEBUR | 0 | 0 | | 8H | 3G | 9H | 2H | 6H | 2G | 9H | 0 | 9H |
| NUTSEDGE | 0 | 8G | 0 | 10E | 2G | 9G | 0 | 8G | 2G | 9G | 0 | 10E |
| CRABGRASS | 2G | 9H | 0 | 3C,6G | 2G | 2C,5G | 2G | 2G | 2G | 3C,6G | 0 | 3C,8G |
| BARNYARD GRASS | 3G | 4C,9H | 5G | 3C,9H | 2C,8H | 9H | 7G | 9H | 3C,8H | 9H | 0 | 3C,8H |
| WILD OATS | 0 | 0 | 2G | 3C,6G | 2G | 2C,2G | 0 | 4G | 1C | 3G | 0 | 0 |
| WHEAT | 3G | 5G | 2G | 8G | 2G | 3G | 0 | 0 | 4G | 9H | 0 | 2G |
| CORN | 0 | 9G | 2C,5G | 3C,9G | 2C,3G | 3C,8H | 3C,5G | 3C,9H | 4C,8H | 3C,9H | 2C,5G | 4C,8G |
| SOYBEAN | 0 | 0 | 2G | 3C,7H | 0 | 3G | 0 | 2C,2G | 3C,3H | 4C,7G | 2H | 3C,6G |
| RICE | 2C,8H | 3C,9H | 3G | 3C,9H | 2G | 9H | 4G | 8G | 3C,5G | 9G | 3C,6G | 9H |
| SORGHUM | 2C,7H | 3C,9H | 3C,9H | 3C,9H | 9G | 9H | 8G | 9G | 2C,9G | 5C,9G | 2C,8G | 4C,9H |
| CHEATGRASS | 3G | 3C,7G | 4G | 8G | 5G | 9G | 0 | 7G | 0 | 8G | 0 | 5G |
| SUGAR BEETS | 8G | 4G | 5H | 4C,8G | 4G | 6G | 0 | 5G | 5H | 4C,9G | 3C,5H | 4C,9G |
| VELVETLEAF | 0 | 0 | 2G | 3C,8G | 2G | 8G | 2H | 4G | 0 | 6H | 0 | 1H |
| GIANT FOXTAIL | 3G | 7G | 5G | 4C,9H | 2C,7G | 9H | 5G | 7G | 2C,5G | 9H | 0 | 3C,8H |
| BARLEY | 0 | 6G | 4G | 8G | 2G | 3C,8G | 2G | 6G | 3C,8G | 8G | 0 | 2D,8G |

|  | CMPD 25 | | CMPD 26 | | CMPD 27 | | CMPD 28 | | CMPD 29 | | CMPD 30 | |
|---|---|---|---|---|---|---|---|---|---|---|---|---|
| RATE = KG/HA | 0.01 | 0.05 | 0.01 | 0.05 | 0.01 | 0.05 | 0.01 | 0.05 | 0.01 | 0.05 | 0.01 | 0.05 |
| POSOL | | | | | | | | | | | | |
| COTTON | 5G | 3C,9G | 7G | 5C,9G | 3G | 9H | 2G | 4C,9G | 0 | 2C,8G | 0 | 0 |
| MORNING GLORY | 9C | 10C | 10C | 10C | 2C,5H | 9C | 4C,8G | 5C,9G | 4C,9G | 9C | 2H | 4H |
| COCKLEBUR | 4C,9G | 10C | 10C | 10C | 3C,8G | 10C | 10C | 10C | 4C,9H | 10C | 2C | 3C,8H |
| NUTSEDGE | 3C,8G | 5C,9G | 10C | 9C | 5C,9G | 5C,9G | 3C,7G | 4C,8G | 3C,5G | 4C,8G | 5G | 3C,9G |
| CRABGRASS | 2C,5G | 6C,9G | 3C,6G | 5C,9G | 0 | 2C,8G | 7G | 5C,9G | 7G | 5C,9G | 0 | 0 |
| BARNYARD GRASS | 3C,9H | 9C | 9C | 9C | 5C,9H | 9C | 9C | 9C | 3C,7H | 5C,9H | 8H | 3C,9H |
| WILD OATS | 5G | 4C,8G | 2C,4G | 4C,8G | 0 | 2G | 0 | 3G | 0 | 0 | 0 | 1C |
| WHEAT | 9G | 4C,9G | 3C,8G | 2C,9G | 3G | 2G | 9G | 9C | 0 | 5G | 0 | 2G |
| CORN | 9C | 10C | 10C | 10C | 3C,9G | 5U,9G | 9C | 10C | 3C,9G | 10C | 3C,9G | 9C |
| SOYBEAN | 9C | 5C,9G | 4C,9G | 9C | 2C,5H | 3C,8G | 4C,9G | 5C,9G | 3C,8G | 4C,9G | 3C,7H | 2C,7G |
| RICE | 9C | 9C | 9C | 9C | 4C,9G | 5C,9G | 5C,9G | 9C | 3C,9G | 5C,9G | 8G | 2C,9G |
| SORGHUM | 4C,9G | 10C | 5C,9G | 10C | 3C,9G | 9C | 5C,9G | 10C | 5C,9H | 4C,9G | 1C,4G | 2C,5G |

-continued (TEST A)

| | | | | | | | | | | | | |
|---|---|---|---|---|---|---|---|---|---|---|---|---|
| CHEATGRASS | 6G | 6C,9G | 3C,6G | 9C | 2G | 7G | 3G | 6G | 0 | 2G | 0 | 3G |
| SUGAR BEETS | 4C,8G | 9C | 9C | 10C | 3G | 9G | 6C,9G | 9C | 3C,5G | 5C,9G | 1C,2G | 3C,8G |
| VELVETLEAF | 8G | 9C | 10C | 10C | 7G | 4C,9G | 3C,8H | 5C,9G | 3C,4H | 4C,9G | 0 | 1C,4G |
| GIANT FOXTAIL | 4C,9G | 9C | 9C | 10C | 3C,5G | 4C,9G | 3C,8G | 9C | 3C,7G | 5C,9H | 4G | 7G |
| BARLEY | 2C,5G | 4C,9G | 3C,7H | 5C,9G | 0 | 6G | 2G | 5G | 0 | 2G | 3G | 8G |
| PRSOL | | | | | | | | | | | | |
| COTTON | 4G | 8G | 5G | 7G | 5G | 8G | 0 | 8G | 0 | 5G | 0 | 0 |
| MORNING GLORY | 7G | 9G | 8G | 9G | 7G | 9G | 0 | 9G | 0 | 8H | 0 | 0 |
| COCKLEBUR | 0 | 3C,3H | 0 | 8G | 5G | 4H | 8H | | 0 | 5H | 0 | 0 |
| NUTSEDGE | 0 | 9G | 7G | 10E | 0 | 9G | 0 | 10E | 0 | 0 | 0 | 8G |
| CRABGRASS | 5G | 3C,7G | 2G | 3C,9G | 0 | 5G | 0 | 3C,8G | 0 | 2G | 0 | 10E |
| BARNYARD GRASS | 4G | 9H | 0 | 9H | 5G | 9H | 0 | 9H | 0 | 3G | 0 | 3G |
| WILD OATS | 2G | 3C,6G | 2G | 3C,5G | 0 | 4G | 0 | 2C,4G | 0 | 3G | 0 | 0 |
| WHEAT | 2G | 8G | 2G | 7G | 0 | 5G | 0 | 3C,9G | 0 | 0 | 0 | 0 |
| CORN | 2C,8H | 3C,9H | 0 | 3C,9G | 3C,5H | 3C,9G | 3C,5H | 3C,9G | 0 | 3C,3G | 2C,3G | 2C,7G |
| SOYBEAN | 2C,2H | 3C,7H | 2H | 3C,7G | 2C | 2C,3H | 1C,1H | 3C,8G | 0 | 3C,5G | 0 | 2C,7H |
| RICE | 9C | 10H | 3C,5G | 3C,9G | 9H | 9H | 3C,9G | 10H | 6G | 9H | 0 | 6G |
| SORGHUM | 3C,9H | 5C,9H | 3C,7G | 3C,9G | 9G | 9H | 4C,9G | 4C,9H | 2G | 9H | 0 | 6G |
| CHEATGRASS | 2G | 4C,9G | 5G | 3C,9G | 0 | 4G | 0 | 3C,9H | 0 | 3G | 0 | 2G |
| SUGAR BEETS | 2H | 3G | 5G | 8G | 4G | 8G | 7G | 4C,9G | 2G | 8G | 0 | 6G |
| VELVETLEAF | 2G | 8H | 5G | 8G | 3G | 4C,9H | 1H | 2C,8G | 0 | 2H | 0 | 2G |
| GIANT FOXTAIL | 3G | 9H | 2H | 9H | 0 | 8G | 0 | 3C,7G | 0 | 2G | 0 | 9G |
| BARLEY | 2C,7G | 3C,9G | 0 | 8G | 2C | 2C,9G | 4G | 3C,8G | 0 | 2C,6G | 0 | 7G |

| | CMPD 31 | | CMPD 32 | | CMPD 33 | | CMPD 34 | | CMPD 35 | | CMPD 36 | |
|---|---|---|---|---|---|---|---|---|---|---|---|---|
| RATE = KG/HA | 0.01 | 0.05 | 0.01 | 0.05 | 0.01 | 0.05 | 0.01 | 0.05 | 0.01 | 0.05 | 0.01 | 0.05 |
| POSOL | | | | | | | | | | | | |
| COTTON | 1C,5G | 4C,8G | 2C,8H | 3C,9G | 0 | 3C,8G | 0 | 2C,9H | 0 | 3C,8H | 3C,8G | 3C,8G |
| MORNING GLORY | 1C,5H | 3C,9H | 5G | 9G | 0 | 1C,2G | 1C | 3C,8H | 2C | 3C,7H | 2C,8G | 3C,7H |
| COCKLEBUR | 4C,9H | 4C,9H | 10C | 9C | 3C,9H | 9C | 2C,3G | 4C,9H | 1C | 4C,9H | 3C,8H | 4C,9H |
| NUTSEDGE | 8G | 8G | 6G | 8G | 3G | 3C,9G | 0 | 3C,8G | 0 | 4G | 5G | 3C,9G |
| CRABGRASS | 0 | 3G | 2G | 6G | 0 | 2G | 2G | 5G | 0 | 3G | 0 | 2G |
| BARNYARDGRASS | 8H | 2C,9H | 9H | 4C,9G | 6G | 2C,9H | 3C,8H | 5C,9H | 0 | 3C,8H | 8H | 9G |
| WILD OATS | 0 | 0 | 0 | 5G | 0 | 0 | 0 | 0 | 0 | 0 | 5G | 2C,9G |
| WHEAT | 0 | 4G | 0 | 5G | 0 | 0 | 0 | 0 | 0 | 0 | 5G | 9G |
| CORN | 9C | 6U,9C | 4C,9G | 5C,9G | 9G | 3C,9G | 2C,8H | 6U,9C | 9G | 3C,9G | 4C,9G | 4C,9G |
| SOYBEAN | 3C,8H | 4C,9H | 3C,9H | 3C,9H | 1H | 4H | 2C,8G | 2C,9G | 2C,6H | 3C,8G | 3C,9G | 3C,8G |
| RICE | 7G | 2C,9G | 9G | 9G | 5G | 9G | 0 | 3C,9G | 3G | 2C,7G | 9G | 9C |
| SORGHUM | 1C,5G | 3C,8H | 6G | 2C,8H | 4G | 7G | 2G | 6G | 3G | 3C,9H | 2C,7H | 2C,9G |
| CHEATGRASS | 6G | 8G | 5G | 6G | 3G | 5G | 0 | 3G | 0 | 5G | 6G | 9G |
| SUGAR BEETS | 2C,6G | 4C,9G | 3C,7H | 3C,8G | 0 | 10C | 2C,7H | 9G | 2C,5G | 3C,8H | 2C,6G | 3C,8G |
| VELVETLEAF | 2C,7G | 3C,8G | 9G | 10C | 0 | 8G | 4G | 4C,9H | 1C,4G | 7G | 3C,8H | 4C,9H |
| GIANT FOXTAIL | 6G | 8G | 7G | 4C,9G | 2G | 7G | 7G | 2C,9G | 6G | 8G | 5G | 8G |
| BARLEY | 3G | 9G | 9G | 9G | 3G | 7G | 0 | 0 | 0 | 0 | 5G | 9G |
| PRSOL | | | | | | | | | | | | |
| COTTON | 0 | 0 | 2G | 2G | 0 | 0 | 0 | 2G | 0 | 2G | 0 | 0 |
| MORNING GLORY | 0 | 3C | 0 | 1C | 0 | 2G | 0 | 2G | 0 | 0 | 2G | 3G |
| COCKLEBUR | | 2C | 2C | 8H | 3G | 3C,6H | 0 | 2C | 0 | 0 | 6H | 7G |
| NUTSEDGE | 2G | 0 | 0 | 9G | 0 | 6G | 0 | 2G | 0 | 0 | 0 | 8G |
| CRABGRASS | 0 | 10E | 3G | 4G | 0 | 0 | 2G | 4G | 0 | 0 | 0 | 2G |
| BARNYARD GRASS | 6G | 8H | 6G | 8H | 5G | 5G | 4G | 5G | 0 | 4G | 4G | 6H |
| WILD OATS | 0 | 2G | 0 | 0 | 0 | 0 | 0 | 0 | 0 | 0 | 2G | 6G |
| WHEAT | 0 | 2G | 0 | 2G | 0 | 0 | 0 | 0 | 0 | 0 | 0 | 6G |
| CORN | 2C,4G | 3C,7G | 0 | 1C,3G | 2C,3G | 2C,7G | 2C,5G | 2C,8G | 0 | 8G | 2C | 8G |
| SOYBEAN | 1C | 2C,3G | 0 | 1C,2G | 0 | 0 | 3G | 2C,4G | 0 | 0 | 4G | 2C,4G |
| RICE | 0 | 4G | 0 | 3G | 0 | 2G | 0 | 0 | 0 | 2C,6G | 2G | 8H |
| SORGHUM | 1C,4G | 2C,7G | 1C,6G | 2C,7H | 5G | 2C,6H | 2G | 3C,9H | 0 | 3C,9H | 6G | 9G |
| CHEATGRASS | 2G | 0 | 2G | 5G | 0 | 0 | 2G | 0 | 0 | 0 | 3G | 7G |
| SUGAR BEETS | 7G | 2C,8G | 7G | 2C,6G | 0 | 3G | 3G | 2C,4G | 0 | 6G | 6G | 6G |
| VELVETLEAF | 0 | 2C,6G | 0 | 3G | 2G | 3G | 0 | 2C,4G | 0 | 0 | 0 | 6G |
| GIANT FOXTAIL | 3G | 9H | 4G | 4G | 3G | 4G | 3G | 4G | 0 | 0 | 3G | 5G |
| BARLEY | 5G | 6G | 4G | 7G | 6G | 7G | 3G | 7G | 0 | 7G | 2G | 7G |

| | CMPD 37 | | CMPD 38 | | CMPD 39 | | CMPD 40 | | CMPD 41 | | CMPD 42 | |
|---|---|---|---|---|---|---|---|---|---|---|---|---|
| RATE = KG/HA | 0.01 | 0.05 | 0.01 | 0.05 | 0.01 | 0.05 | 0.01 | 0.05 | 0.01 | 0.05 | 0.01 | 0.05 |
| POSOL | | | | | | | | | | | | |
| COTTON | 5C,9G | 9C | 9C | 9C | 7G | 4C,9G | 3C,9G | 10C | 2C,8G | 2C,9H | 4C,9G | 10C |
| MORNING GLORY | 3C,8H | 10C | 10C | 10C | 2C,8G | 10C | 3C,9G | 10C | 3C,8G | 10C | 10C | 10C |
| COCKLEBUR | 3C,9G | 10C | 10C | 10C | 8H | 10C | 10C | 10C | 9C | 10C | 10C | 10C |
| NUTSEDGE | 2C,8G | 9G | 8G | 2C,9G | 3G | 2C,8G | 8G | 8G | 3C,7G | 2C,8G | 9C | 10C |
| CRABGRASS | 0 | 2G | 2G | 5G | 0 | 2G | 0 | 4G | 0 | 5G | 4C,9G | 9C |
| BARNYARD GRASS | 3C,9H | 9C | 2C,9H | 9C | 2C,5H | 3C,9H | 3C,7H | 9C | 3H | 3C,7H | 6C,9G | 9C |
| WILD OATS | 3G | 2C,8G | 2G | 2C,8G | 0 | 2G | 0 | 6G | 0 | 2G | 9G | 3C,9G |
| WHEAT | 3G | 9G | 5G | 9G | 0 | 0 | 2G | 5G | 0 | 0 | 3C,9G | 4C,9G |
| CORN | 9C | 10C | 5C,9G | 10C | 9G | 9C | 3C,9G | 9C | 8H | 5C,9G | 9C | 6U,9C |
| SOYBEAN | 4C,9G | 3C,9G | 4C,9G | 5C,9G | 2H | 2C,7G | 3C,9G | 5C,9G | 4C,9G | 9C | 5C,9G | 9C |
| RICE | 3C,9G | 9C | 4C,9G | 9C | 3C,9G | 7G | 5C,9G | 5C,9G | 2C,5G | 5C,9G | 9C | 9C |
| SORGHUM | 2C,7G | 3C,9G | 2C,9H | 3C,9G | 3G | 2C,9G | 2C,9G | 5C,9G | 3C,9H | 2C,9G | 3C,9G | 10C |
| CHEATGRASS | 7G | 2C,8G | 7G | 4C,9G | 0 | 5G | 0 | 3G | 0 | 3G | 9G | 9C |

-continued

| (TEST A) | | | | | | | | | | | | |
|---|---|---|---|---|---|---|---|---|---|---|---|---|
| SUGAR BEETS | 3C,8G | 5C,9G | 4C,9G | 5C,9G | 1H | 2C,5G | 9C | 9C | 5C,9H | 10C | 5C,9G | 5C,9H |
| VELVETLEAF | 3C,8G | 9C | 9C | 10C | 7G | 2C,9G | 9C | 10C | 2G | 6H | 10C | 10C |
| GIANT FOXTAIL | 5G | 8G | 6G | 4C,9G | 2G | 4G | 3G | 6G | 2G | 3C,7G | 4C,9G | 10C |
| BARLEY | 3G | 2C,9G | 7G | 2C,9G | 0 | 3G | 0 | 3G | 0 | 0 | 9G | 6C,9G |
| PRSOL | | | | | | | | | | | | |
| COTTON | 2G | 7G | 2G | 2G | 0 | 0 | 0 | 4G | 5G | 4G | 9G | 9G |
| MORNING GLORY | 2G | 6G | 0 | 0 | 2G | 6G | 2C,2H | 8G | 7H | 7H | 8G | 9G |
| COCKLEBUR | 2C,3H | 2C,5H | 1C | 8G | 1C | 2C,3H | 3C,3G | | 7G | 6G | 7G | 9H |
| NUTSEDGE | 0 | 8G | 4G | 9G | 0 | 8G | 7G | 8G | 0 | 8G | 9C | 10E |
| CRABGRASS | 0 | 5G | | 2G | 0 | 0 | 0 | 0 | 0 | 0 | 7H | 5C,9H |
| BARNYARD GRASS | 2C,8G | 9H | 5G | 7H | 0 | 6H | 0 | 4G | 0 | 0 | 7G | 9H |
| WILD OATS | 3G | 2C,7G | 0 | 3G | 2G | 3G | 0 | 2G | 0 | 0 | 3G | 2C,7G |
| WHEAT | 2G | 8G | 0 | 0 | 0 | 0 | 0 | 0 | 0 | 0 | 8H | 9H |
| CORN | 3C,6G | 9G | 1C,2G | 2C,4G | 0 | 3C,5G | 2C,4G | 2C,8G | 2C,5G | 2C,5G | 2C,8H | 2C,9H |
| SOYBEAN | 2H | 2C,5G | 0 | 0 | 0 | 2G | 2C,2H | 3C,8H | 0 | 2G | 3C,7H | 9H |
| RICE | 7G | 8G | 4G | 8G | 0 | 8G | 2G | 8G | 3G | 6G | 5C,9H | 10E |
| SORGHUM | 2C,9H | 2C,9G | 2C,8G | 2C,9G | 3G | 4C,9G | 3C,7G | 9H | 2C,6G | 2C,8G | 9H | 10E |
| CHEATGRASS | 7G | 7G | 7G | 8G | 2G | 6G | 0 | 5G | 0 | 0 | 8G | 9H |
| SUGAR BEETS | 3H | 8G | 2G | 7G | 2C,8G | 0 | 5G | 8G | 7G | 4C,9G | 3C,8G | 3C,8G |
| VELVETLEAF | 2G | 6G | 0 | 3H | 0 | 2H | 2C,5G | 5G | 0 | 0 | 6G | 3C,8G |
| GIANT FOXTAIL | 2G | 7G | 0 | 3H | 0 | 0 | 0 | 2G | 0 | 0 | 5G | 9H |
| BARLEY | 3G | 7G | 0 | 0 | 1C | 3G | 0 | 5G | 0 | 2G | 8G | 8G |

| | CMPD 43 | | CMPD 44 | | CMPD 45 | | CMPD 46 | | CMPD 47 | | CMPD 48 | |
|---|---|---|---|---|---|---|---|---|---|---|---|---|
| RATE = KG/HA | 0.01 | 0.05 | 0.01 | 0.05 | 0.01 | 0.05 | 0.01 | 0.05 | 0.01 | 0.05 | 0.01 | 0.05 |
| POSOL | | | | | | | | | | | | |
| COTTON | 9C | 10C | 10C | 10C | 9C | 10C | 9C | 9C | 3C,8H | 10C | 3C,3G | 3C,8G |
| MORNING GLORY | 10C | 10C | 10C | 10C | 10C | 10C | 10C | 10C | 9C | 10C | 3C,7G | 3C,8G |
| COCKLEBUR | 10C | 10C | 10C | 10C | 10C | 10C | 10C | 10C | 10C | 10C | 3G | 2H |
| NUTSEDGE | 3C,9G | 10C | 9C | 10C | 3C,9G | 10C | 2C,5G | 5C,9G | 8G | 2C,8G | 0 | |
| CRABGRASS | 5C,9G | 9C | 9G | 9C | 8G | 5C,9G | 9C | 9C | 5C,9G | 9C | 2C,8G | 3C,8G |
| BARNYARD GRASS | 5C,9G | 10C | 10C | 10C | 10C | 10C | 9C | 9C | 3C,9G | 9C | 1H | 3G |
| WILD OATS | 3C,9G | 4C,9G | 3C,9G | 4C,9G | 5G | 8G | 2C,7G | 9G | 2C,7G | 3C,9G | 6G | 9G |
| WHEAT | 9G | 3C,9G | 9C | 5C,9G | 5G | 8G | 9G | 9C | 9G | 2C,9G | 3G | 3G |
| CORN | 5C,9G | 9C | 9C | 9C | 4C,9G | 9C | 9C | 5U,9C | 9G | 6U,9G | 9H | 3C,9H |
| SOYBEAN | 6C,9G | 9C | 5C,9G | 9C | 3C,9H | 3C,9G | 4C,9G | 9C | 5C,9G | 9C | 3G | 2C,5G |
| RICE | 9C | 9C | 9C | 10C | 9C | 10C | 9C | 9C | 9C | 9C | 3C,5G | 3C,7G |
| SORGHUN | 9C | 9C | 10C | 10C | 9C | 10C | 9C | 10C | 9G | 9C | 3G | 2C,5G |
| CHEATGRASS | 5C,9G | 9C | 10C | 10C | 6G | 9G | 2C,7G | 4C,9G | 5G | 8G | 0 | 2G |
| SUGAR BEETS | 9C | 10C | 10C | 10C | 9C | 9C | 10C | 9C | 7G | 6C,9G | 0 | 0 |
| VELVETLEAF | 10C | 10C | 10C | 10C | 10C | 10C | 5C,9G | 5C,9G | 5C,9G | 10C | 3C,7G | 3C,9H |
| GIANT FOXTAIL | 9C | 10C | 10C | 10C | 3C,9G | 10C | 5C,9G | 9C | 4C,9G | 10C | 3C,8G | 3C,9G |
| BARLEY | 3C,9G | 9C | 6C,9G | 6C,9G | 4C,8H | 7G | 2C,6G | 2C,8G | 3G | 6G | 2G | 0 |
| PRSOL | | | | | | | | | | | | |
| COTTON | 9G | 9G | 9G | 9G | 8G | 9G | 9G | 9G | 7G | 7G | 0 | 2G |
| MORNING GLORY | 9G | 9G | 9H | 9H | 8G | 9H | 9G | 9G | 8G | 9G | 0 | 5G |
| COCKLEBUR | 4G | | | | 7G | 4G | 6G | 9H | 0 | 2G | 0 | 5G |
| NUTSEDGE | 9G | 10E | 9G | 9G | 9G | 10E | 6G | 5C,9G | 0 | 5G | 0 | 0 |
| CRABGRASS | 3C,9H | 4C,9H | 7G | 2C,8G | 7G | 2C,8H | 8G | 9H | 5G | | 0 | 8G |
| BARNYARD GRASS | 7G | 6H | 6G | 9H | 8G | 9H | 9H | 9H | 3G | 9H | 0 | 4G |
| WILD OATS | 2C,6G | 6G | 4G | 5G | 0 | 3G | 3G | 2C,6G | 0 | 2C,5G | 0 | 2C,5G |
| WHEAT | 2C,8G | 3C,8G | 2G | 4G | 0 | 5G | 8G | 9H | 0 | 2C,8G | 0 | 0 |
| CORN | 8G | 3C,9H | 3C,7G | 3C,9H | 9G | 9H | 2U,9G | 9H | 3C,5G | 3C,8H | 0 | 3C,6G |
| SOYBEAN | 4C,6G | 9H | 8H | 3C,8H | 2G | 2C,8H | 2C,7H | 9H | 2C,2G | 3C,7H | 0 | 2H |
| RICE | 10H | 10H | 5G | 10H | 10H | 10H | 9H | 10E | 8G | 10E | 0 | 5G |
| SORGHUM | 10H | 10H | 6G | 9H | 9H | 10H | 9H | 10H | 2C,8H | 9H | 0 | 2C,5G |
| CHEATGRASS | 9H | 10H | 5G | 9H | 3G | 4G | 6G | 9H | 0 | 8G | 0 | 2G |
| SUGAR BEETS | 2C,5G | 5C,9G | 8G | 3C,8G | 8G | 3C,9H | 8G | 2C,9G | 8G | 9G | 0 | 5G |
| VELVETLEAF | 7G | 8H | 8G | 5C,9H | 7G | 3C,8G | 7G | 3C,9G | 0 | 7H | 0 | 2C,5G |
| GIANT FOXTAIL | 8G | 4C,9H | 6G | 9H | 4G | 3C,7G | 3G | 2C,5G | 0 | 7G | 0 | 3C,8G |
| BARLEY | 8G | 8G | 4G | 8G | 7G | 8G | 9G | 2C,9H | 2C,2G | 2C,8G | 0 | 5G |

| | CMPD 49 | | CMPD 50 | | CMPD 51 | | CMPD 52 | | CMPD 53 | | CMPD 54 | |
|---|---|---|---|---|---|---|---|---|---|---|---|---|
| RATE = KG/HA | 0.01 | 0.05 | 0.01 | 0.05 | 0.01 | 0.05 | 0.01 | 0.05 | 0.01 | 0.05 | 0.01 | 0.05 |
| POSOL | | | | | | | | | | | | |
| COTTON | 3C,8G | 9C | 9C | 9C | 10C | 9C | 9C | 10C | 4C,9G | 10C | 4C,8G | 10C |
| MORNING GLORY | 9C | 10C | 10C | 10C | 10C | 10C | 10C | 10C | 5C,9G | 10C | 9C | 10C |
| COCKLEBUR | 7H | 10C | 10C | 10C | 10C | 10C | 10C | 10C | 10C | 10C | 7H | 10C |
| NUTSEDGE | 5G | 8G | 9G | 4C,9G | 5C,9G | 9C | 7G | 9G | 3G | 8G | 6G | 8G |
| CRABGRASS | 8G | 6C,9G | 4C,9G | 9C | 8G | 5C,9G | 5G | 8G | 6C,9G | 9C | 8G | 9C |
| BARNYARD GRASS | 3C,8H | 2C,9H | 9H | 9C | 9C | 9C | 9C | 9C | 9C | 10C | 3C,8H | 9C |
| WILD OATS | 8G | 3C,9G | 9G | 6C,9G | 5C,9G | 5C,9G | 2G | 2C,8G | 2C,5G | 4C,9G | 8G | 9G |
| WHEAT | 3C,9G | 2C,9G | 9C | 4C,9G | 2C,9G | 9C | 4G | 3C,9G | 4C,9G | 9C | 7G | 5C,9G |
| CORN | 5U,9C | 3U,9G | 9C | 4U,9G | 10C | 10C | 10C | 5U,9G | 5U,9C | 10C | 9C | 9C |
| SOYBEAN | 3C,8H | 4C,9G | 5C,9G | 9C | 9C | 9C | 3C,7G | 4C,9G | 4C,9G | 9C | 4C,9G | 5C,9G |
| RICE | 9C | 9C | 9C | 9C | 9C | 9C | 9C | 9C | 9C | 9C | 9C | 9C |
| SORGHUM | 3C,9G | 3C,9G | 9C | 5C,9G | 9C | 9C | 4C,9G | 9C | 5C,9G | 10C | 5C,9G | 9C |
| CHEATGRASS | 8G | 3C,9G | 2C,9G | 5C,9G | 6C,9G | 9C | 7G | 3C,8G | 3C,8G | 9C | 7G | 3C,9G |
| SUGAR BEETS | 3C,8H | 10C | 9C | 10C | 10C | 10C | 10C | | 9C | 9C | 4C,9H | 10C |

-continued (TEST A)

| | | | | | | | | | | | |
|---|---|---|---|---|---|---|---|---|---|---|---|
| VELVETLEAF | 9C | 10C | 10C | 10C | 10C | 10C | 10C | 10C | 4C,9H | 10C | 4C,9H | 10C |
| GIANT FOXTAIL | 3C,8G | 9C | 9C | 10C | 9C | 10C | 3C,8G | 9C | 4C,8H | 10C | 3C,8G | 9C |
| BARLEY | 8G | 3C,9G | 4C,9G | 5C,9G | 9C | 9C | 6G | 9G | 7G | 3C,9G | 5G | 8G |
| PRSOL | | | | | | | | | | | | |
| COTTON | 2G | 8G | 5G | 8G | 6G | 8G | 2G | 7G | 6G | 8G | 2G | 6G |
| MORNING GLORY | 0 | 4G | 0 | 9G | | 8G | 0 | 5G | 3H | 9G | 0 | 7H |
| COCKLEBUR | 0 | 0 | | 3C,6H | 1H | | 0 | 6G | 2H | 3C,7H | | 5G |
| NUTSEDGE | 0 | 10E | 0 | 9G | 3G | 8G | 0 | 5G | 0 | 3G | 0 | 0 |
| CRABGRASS | 5G | 3C,8H | 4G | 3C,8G | 2G | 7G | 0 | 3G | 3G | | 3G | 3C,8G |
| BARNYARD GRASS | 2H | 9H | 7G | 9H | 2C,4G | 9H | 6G | 8H | 8H | 9H | 4G | 7G |
| WILD OATS | 5G | 6G | 6G | 3C,6G | 0 | 5G | 2G | 3G | 4G | 6G | 0 | 3G |
| WHEAT | 5G | 8G | 6G | 7G | 0 | 8G | 0 | 6G | 7G | 8H | 0 | 8G |
| CORN | 5G | 3C,9H | 2C,4G | 3C,9H | 3G | 2U,9H | 2C,4G | 3U,9H | 3C,7G | 4U,9H | 2C,7G | 4C,8G |
| SOYBEAN | 2G | 3C,6H | 2H | 9H | 1H | 3C,6H | 0 | 1C | 2C,2H | 4C,9H | 2C,2H | 2C,4G |
| RICE | 9H | 9H | 6G | 10H | 4G | 9H | 6G | 10E | 9H | 10H | 7G | 10H |
| SORGHUM | 3C,9H | 9H | 3C,7G | 10H | 3C,7G | 10E | 8G | 10H | 9H | 10H | 9G | 10H |
| CHEATGRASS | 5G | 9H | 7G | 9H | 6G | 8G | 2G | 6G | 5G | 6H | 0 | 3G |
| SUGAR BEETS | 7H | 9G | 6G | 4C,9G | 9G | 9C | 6H | 8H | 9G | 9G | 5H | 8G |
| VELVETLEAF | 0 | 5G | 4G | 5G | 2H | 7G | 0 | 2G | 2G | 7G | 0 | 7G |
| GIANT FOXTAIL | 2G | 9H | 7G | 8H | 4G | 9H | 0 | 6G | 3G | 9H | 0 | 8G |
| BARLEY | 7G | 6G | 3G | 8G | 2G | 6G | 0 | 7G | 7G | 9G | 5G | 8G |

| | CMPD 55 | | CMPD 56 | | CMPD 57 | | CMPD 58 | | CMPD 59 | | CMPD 60 | |
|---|---|---|---|---|---|---|---|---|---|---|---|---|
| RATE = KG/HA | 0.01 | 0.05 | 0.01 | 0.05 | 0.01 | 0.05 | 0.01 | 0.05 | 0.01 | 0.05 | 0.01 | 0.05 |
| POSOL | | | | | | | | | | | | |
| COTTON | 2C,3G | 4C,8H | 4C,9H | 2C,9H | 3C,9G | 10C | 9C | 10C | 8G | 6C,9G | 3C,6G | 4C,9G |
| MORNING GLORY | 2C,7G | 6G | 3C,8H | 10C | 5C,9G | 10C | 9C | 10C | 3C,8G | 10C | 2C,5G | 4C,8H |
| COCKLEBUR | 5H | 3H | 7H | 10C | 9C | 10C | 10C | 10C | 10C | 10C | 3C,7G | 10C |
| NUTSEDGE | 2G | 3G | 9G | 2C,9G | 9G | 4C,9G | 9G | 6C,9G | 9G | 4C,9G | 4G | 3C,8G |
| CRABGRASS | 4C,7G | 2C,8G | 4C,9G | 9C | 8G | 4C,9G | 7G | 6C,9G | 5G | 8G | 4C,9G | 5C,9G |
| BARNYARD GRASS | 2G | 3H | 4C,8H | 9C | 4C,9H | 9C | 6C,9H | 10C | 9C | 10C | 9C | 10C |
| WILD OATS | 3G | 4G | 4C,8G | 4C,9G | 3C,8G | 6C,9G | 2C,9G | 4C,9G | 4G | 9G | 9G | 9G |
| WHEAT | 2G | 2G | 9C | 9C | 8G | 6C,9G | 9G | 4C,9G | 5G | 3C,9G | 5C,9G | 3C,9G |
| CORN | 3C,9H | 2C,8H | 10C | 10C | 4U,9C | 10C | 4U,9C | 10C | 5U,9G | 10C | 5C,9G | 10C |
| SOYBEAN | 1H | 4G | 4C,9G | 9C | 3C,9G | 9C | 9C | 9C | 2C,8G | 6C,9G | 4C,8G | 5C,9G |
| RICE | 4C,8G | 7G | 5C,9G | 5C,9G | 9C | 9C | 5C,9G | 6C,9G | 4C,9G | 6C,9G | 5C,9G | 6C,9G |
| SORGHUM | 4C,8G | 2C,8G | 2C,9G | 3C,9G | 3C,9G | 10C | 3C,7G | 10C | 3C,9G | 9C | 4C,9G | 9C |
| CHEATGRASS | 3G | 3G | 8G | 5C,9G | 4C,8G | 6C,9G | 3C,9G | 9C | 5G | 8G | 2C,8G | 9C |
| SUGAR BEETS | 4G | 5G | 9C | 10C | 9C | 9C | 9C | 9C | 5C,9G | 6C,9G | 3C,7H | 9C |
| VELVETLEAF | 3C,8H | 3C,8H | 4C,8H | 5C,9G | 5C,9H | 10C | 9C | 10C | 7G | 9C | 3C,7G | 4C,8H |
| GIANT FOXTAIL | 4C,8G | 2C,8G | 5C,9H | 9C | 5C,9G | 9C | 9C | 9C | 9C | 9C | 5C,9G | 9C |
| BARLEY | 0 | 3G | 9G | 5C,9G | 2C,8G | 9C | 5C,9G | 9C | 2C,9G | 2C,9G | 8G | 5C,9G |
| PRSOL | | | | | | | | | | | | |
| COTTON | 4G | 0 | 5G | 6G | 1C | 8G | 3G | 8G | 2G | 7G | 2G | 7G |
| MORNING GLORY | 0 | 0 | 0 | 7H | 0 | 9G | 3G | 9G | 2G | 9G | 2G | 2C,4G |
| COCKLEBUR | 0 | 0 | 2H | | 0 | 8H | 0 | 8H | | 8H | 0 | 2C,2G |
| NUTSEDGE | 0 | 0 | 9G | 10E | 8G | 10E | 5G | 10E | 10E | 10E | 2G | 9G |
| CRABGRASS | 0 | 8G | 0 | 3C,8G | 3C,6G | 4C,8H | 4G | 8H | 3G | 9G | 2G | 9H |
| BARNYARD GRASS | 0 | 2G | 0 | 2C,3G | 2C | 4C,9H | 3G | 9H | 5G | 9H | 2C,7G | 9H |
| WILD OATS | 0 | 2G | 0 | 4G | 4G | 2C,6G | 3G | 2C,6G | 2G | 3C,7G | 4G | 7G |
| WHEAT | 0 | 0 | 0 | 7G | 5G | 8G | 5G | 7G | 7G | 8G | 8H | 4C,9H |
| CORN | 0 | 3C,3G | 3C,6G | 3C,9G | 3C,5G | 4C,9G | 2C,5G | 3C,8H | 3C,7G | 9H | 2C,8G | 3C,8G |
| SOYBEAN | 0 | 4H | 3G | 2C,5G | 2G | 3C,7H | 3G | 3C,7H | 3G | 3C,8H | 3G | 3C,3H |
| RICE | 0 | 0 | 0 | 8G | 3C,4G | 3C,9H | 3G | 9H | 8H | 10H | 6G | 9H |
| SORGHUM | 0 | 4G | 3C,7G | 9H | 3C,8H | 5C,9H | 3C,8H | 4C,9H | 3C,8H | 10E | 2C,8H | 3C,9H |
| CHEATGRASS | 0 | 2G | 0 | 7G | 6G | 4C,8G | 2G | 9G | 5G | 7G | 6G | 9H |
| SUGAR BEETS | 5G | 6H | 5G | 6G | 6G | 8G | 3H | 7G | 2C | 7G | 2G | 4C,9G |
| VELVETLEAF | 0 | 2H | 1H | 2C,4H | 0 | 7G | 0 | 9G | 0 | 5G | 2G | 2C,5H |
| GIANT FOXTAIL | 0 | 5G | 0 | 2C,9G | 3C,6G | 4C,9H | 2C,7G | 9H | 2G | 9H | 5G | 9H |
| BARLEY | 0 | 0 | 2G | 2C,8G | 4G | 4C,8G | 4G | 3C,7G | 8G | 9H | 8G | 3C,9H |

| | CMPD 61 | | CMPD 62 | | CMPD 63 | | CMPD 64 | | CMPD 65 | | CMPD 66 | |
|---|---|---|---|---|---|---|---|---|---|---|---|---|
| RATE = KG/HA | 0.01 | 0.05 | 0.01 | 0.05 | 0.01 | 0.05 | 0.01 | 0.05 | 0.01 | 0.05 | 0.01 | 0.05 |
| POSOL | | | | | | | | | | | | |
| COTTON | 4C,9H | 4C,9G | 7G | 3C,9G | 4C,9G | 9G | 9G | 10C | 7G | 9C | 8H | 3C,9G |
| MORNING GLORY | 4C,8H | 4C,9G | 6H | 2C,9G | 4C,9G | 9C | 4C,9G | 10C | 2C,6G | 9C | 4C,9H | 5C,9G |
| COCKLEBUR | 2C,5G | 9C | 5H | 5C,9G | 8H | 10C | 2C,8G | 10C | 2C,7G | 10C | 3C,9G | 10C |
| NUTSEDGE | 5G | 2C,9G | | 9G | 2C,8G | 10C | 9G | | 5C,9G | 8G | 0 | 3C,6G |
| CRABGRASS | 4C,9G | 6C,9G | | 8G | | | | 8G | 0 | 6G | 6G | |
| BARNYARD GRASS | 3C,9H | 10C | 6H | 3C,9H | 9H | 5C,9H | 9H | 9C | 8H | 4C,9H | 3C,9H | 9C |
| WILD OATS | 7G | 3C,9G | 3G | 9G | 5G | 9G | 6G | 5C,9G | 0 | 2G | 2G | 2C,5G |
| WHEAT | 7G | 9C | 6G | 9G | 9G | 9G | 8G | 2C,9G | 3G | 5G | 2G | 3C,9G |
| CORN | 5U,9G | 10C | 2C,9H | 2C,9G | 9G | 9H | 9H | 3U,9C | 8H | 9H | 3C,9H | 3U,9C |
| SOYBEAN | 3C,8G | 5C,9G | 5G | 3C,8G | 3C,6G | 9C | 5C,9G | 9C | 0 | 3G | 3C,8G | 9C |
| RICE | 5C,9G | 5C,9G | 4C,9G | 5C,9G | 5C,9G | 5C,9G | | 6C,9G | 9G | 9C | 5C,9G | 5C,9G |
| SORGHUM | 5C,9G | 9C | 3C,7H | 4C,9G | 3C,7G | 4C,9G | 8H | 9C | 5G | 2C,9H | 3C,8G | 9C |
| CHEATGRASS | 3C,7G | 9C | 9G | 2C,8G | 8G | 3C,9G | 4C,9G | 5C,9G | 0 | 3G | 0 | 2C,7G |
| SUGAR BEETS | 2C,4G | 9C | 9C | 5C,9G | | 10C | 10C | 9C | 10C | 10C | 10C | 9C |
| VELVETLEAF | 3C,7G | 4C,8H | 5G | 3C,9G | 9G | 9C | 5C,9G | | 7G | 5C,9G | 3C,7H | 4C,9H |

-continued
(TEST A)

| | | | | | | | | | | | | |
|---|---|---|---|---|---|---|---|---|---|---|---|---|
| GIANT FOXTAIL | 5C,9G | 9C | 3C,7G | 7G | 7G | 4C,9G | | 5C,9G | 2G | 8G | 2C,2G | 3C,8G |
| BARLEY | 7G | 3C,9G | 2G | 9G | 5G | 9G | 2C,9G | 4C,9G | 2G | 7G | 3C,5G | 3C,7G |
| PRSOL | | | | | | | | | | | | |
| COTTON | 0 | 7G | 0 | 7G | 3G | 9G | 3G | 8G | 0 | 6G | 6G | 8G |
| MORNING GLORY | 0 | 3C,4G | 2G | 8H | 0 | 8G | 5G | 7G | 0 | 8G | 7H | 8G |
| COCKLEBUR | 0 | 3C,4G | 0 | 6H | 0 | 0 | 0 | 0 | 0 | 9H | 0 | 0 |
| NUTSEDGE | 5G | 10E | 5G | 10E | 0 | 9G | 0 | 9G | 0 | 4G | 0 | 0 |
| CRABGRASS | 5G | 10E | 4G | 2C,8G | 3G | 7G | 0 | 0 | 0 | 3G | 0 | 3C,8G |
| BARNYARD GRASS | 0 | 9H | 0 | 9H | 5G | 9H | 2G | 9H | 3G | 8H | 5G | 9H |
| WILD OATS | 2G | 3C,7G | 0 | 6G | 0 | 3C,7G | 2G | 7G | 0 | 0 | 2G | 3C,3G |
| WHEAT | 0 | 2C,8G | 5G | 7G | 4G | 8G | 2G | 7G | 0 | 2G | 2G | 8G |
| CORN | 2C,2G | 3C,8G | 2C,2G | 2C,8G | 4C,8G | 8H | 0 | 2C,7G | 1C | 3C,7G | 3C,7G | 3C,8G |
| SOYBEAN | 1H | 2C,7G | 1H | 3C,7H | 2C,4H | 3C,6G | 1H | 3C,6H | 0 | 3H | 3G | 3C,8H |
| RICE | 3G | 10H | 9H | 10H | 9H | 9H | 5G | 10H | 8G | 10E | 9H | 10H |
| SORGHUM | 3C,8H | 5C,9H | 3C,5G | 9H | 3C,8H | 4C,9H | 0 | 9H | 3C,3G | 9H | 2C,9G | 2C,9G |
| CHEATGRASS | 0 | 4C,9H | 9H | 9H | 8G | 3C,8G | 0 | 9H | 0 | 5G | 2G | 2C,7G |
| SUGAR BEETS | 0 | 7G | 0 | 8G | 7G | 9G | 3G | 9G | 0 | 8G | 3G | 9G |
| VELVETLEAF | 0 | 1C | 0 | 8G | 2H | 8G | 1H | 7G | 0 | 7G | 0 | 8H |
| GIANT FOXTAIL | 5G | 9H | 0 | 6G | 0 | 2C,8H | 2G | 8H | 0 | 3G | 0 | 3G |
| BARLEY | 2G | 3C,9G | 3G | 7G | 0 | 5G | 0 | 3G | 0 | 4G | 2G | 8G |

| | CMPD 67 | | CMPD 68 | | CMPD 69 | | CMPD 70 | | CMPD 71 | | CMPD 72 | |
|---|---|---|---|---|---|---|---|---|---|---|---|---|
| RATE = KG/HA | 0.01 | 0.05 | 0.01 | 0.05 | 0.01 | 0.05 | 0.01 | 0.05 | 0.01 | 0.05 | 0.01 | 0.05 |
| POSOL | | | | | | | | | | | | |
| COTTON | 5G | 9G | 2C,5G | 5C,9G | 7G | 9C | 7G | 4C,8G | 4C,9G | 5C,9G | 3C,7G | 4C,9G |
| MORNING GLORY | 4C,9H | 4C,9G | 3C,8G | 10C | 3C,7G | 10C | 3C,7H | 10C | 3C,7G | 9C | 3C,8G | 4C,9H |
| COCKLEBUR | 2H | 4C,8H | 2H,6G | 10C | 3C,8H | 10C | 2C,8G | 10C | 10C | 10C | 6C,9G | 10C |
| NUTSEDGE | 0 | 0 | 2C,8G | 4C,8G | 3C,5G | 5C,9G | 3C,5G | 10C | 5G | 5C,9G | 10C | 3C,8G |
| CRABGRASS | 0 | 0 | 2G | 3C,7G | 2C | 3C,7G | 0 | 2C,6G | 0 | 3C,8G | 0 | 2C,5G |
| BARNYARD GRASS | 2H | 4C,9H | 8H | 5C,9H | 4C,9H | 9C | 3C,9H | 5C,9H | 9H | 9C | 0 | 4C,9H |
| WILD OATS | 0 | 3G | 2C,9G | 4C,9H | 3C,6G | 3C,7G | 0 | 2C,2G | 0 | 2C | 0 | 3C,3G |
| WHEAT | 0 | 3G | 6G | 9G | 3G | 8G | 3G | 5G | 0 | 6G | 0 | 5G |
| CORN | 0 | 3C,9H | 2C,9H | 4C,9H | 3C,9H | 9C | 3C,8H | 9C | 2C,8H | 9C | 1C,3H | 9C |
| SOYBEAN | 3C,8H | 5C,9G | 2C,4H | 3C,8H | 3H,7G | 4C,9G | 4G | 3C,5G | 4C,9G | 5C,9G | 3C,8G | 5C,9G |
| RICE | 3C,7G | 5C,9G | 5C,9G | 9C | 4C,8G | 9C | 4C,9G | 9C | 4C,9G | 9C | 7G | 9C |
| SORGHUM | 0 | 3C,5G | 2C,6G | 9G | 3C,9G | 3C,9G | 3C,9H | 9C | 9G | 3C,9G | 3C,8H | 4C,9G |
| CHEATGRASS | 0 | 2G | 6G | 4C,9G | 7G | 3C,8G | 2C,2G | 7G | 0 | 2C,5G | 0 | 1C |
| SUGAR BEETS | 10C | 10C | 3C,8G | 9C | 3C,7G | 10C | 3C,6G | 9C | 9C | 9C | 9C | 10C |
| VELVETLEAF | 2G | 3C,6G | 6G | 4C,9H | 3C,8G | 9C | 7G | 5C,9G | 3C,8H | 9C | 2H | 3C,8G |
| GIANT FOXTAIL | 0 | 4G | 3G | 4C,8H | 2C,5G | 4C,9G | 3G | 3C,7H | 2G | 3C,7H | 2C,3G | 3C,5G |
| BARLEY | 0 | 2C,5G | 2C,8G | 8G | 2C,5G | 2C,8G | 2C,6G | 2C,9G | 0 | 2C,4G | 0 | 3C,5G |
| PRSOL | | | | | | | | | | | | |
| COTTON | 2G | 5G | 9G | 9G | 2C,8G | 9G | 8G | 9G | 0 | 0 | 8G | 2C,8G |
| MORNING GLORY | 5G | 7G | 8G | 8G | 9G | 9G | 9G | 9G | 3G | 0 | 9G | 9C |
| COCKLEBUR | 0 | 0 | 8H | 8H | 8H | 9H | | 8H | 0 | 0 | 3C,7H | 9H |
| NUTSEDGE | 0 | 0 | 8G | 10E | 8G | 10E | 5G | 10E | 0 | 0 | 5G | 7G |
| CRABGRASS | 0 | 0 | 0 | 9C | 2C,5G | 3C,7G | 0 | 2G | 0 | 0 | 3C,6G | 3C,6G |
| BARNYARD GRASS | 0 | 2G | 2C,4G | 3C,9H | 9H | 3C,9H | 2C,8G | 9H | 0 | 0 | 4C,9H | 6C,9H |
| WILD OATS | 0 | 2G | 2C,8G | 3C,9G | 5C,9G | 9C | 3C,8G | 8G | 0 | 0 | 2C,5G | 3C,8G |
| WHEAT | 0 | 0 | 3C,9H | 5C,9H | 5C,9G | 9C | 2C,7H | 2C,8H | 0 | 2G | 3C,9H | 9C |
| CORN | 2G | 2C,5G | 3C,9H | 10H | 3U,9G | 3C,9G | 3C,8G | 3C,9G | 0 | 2C,5G | 2C,9G | 4C,9G |
| SOYBEAN | 1C | 2C,4G | 3C,7G | 4C,8H | 4C,8G | 3C,9H | 3C,4G | 2C,8H | 0 | 0 | 3C,5G | 3C,8G |
| RICE | 3G | 9H | 9H | 10E | 10E | 10E | 9H | 10E | 0 | 3G | 4C,9G | 10E |
| SORGHUM | 0 | 8G | 3C,9G | 9H | 9H | 4C,9H | 9G | 9H | 0 | 3C,3G | 4C,9G | 4C,9G |
| CHEATGRASS | 0 | 2G | 8G | 9H | 4C,9H | 5C,9H | 5G | 8H | 0 | 5G | 3C,7G | 7C,9H |
| SUGAR BEETS | 4G | 8G | 3C,8G | 9G | 4C,9G | 5C,9G | 7G | 9G | 0 | 2H | 9C | 5C,9G |
| VELVETLEAF | 0 | 0 | 8G | 9G | 9G | 9G | 9G | 9G | 0 | 0 | 3C,7G | 3C,9G |
| GIANT FOXTAIL | 0 | 0 | 0 | 3C,7G | 3C,8G | 3C,9H | 2C | 2C,6G | 0 | 0 | 2C,3G | 3C,7G |
| BARLEY | 0 | 0 | 9G | 2C,9G | 4C,9G | 4C,9G | 9G | 3C,9G | 0 | 2G | 9G | 3C,9G |

| | CMPD 73 | | CMPD 74 | | CMPD 75 | | CMPD 76 | | CMPD 77 | | CMPD 78 | |
|---|---|---|---|---|---|---|---|---|---|---|---|---|
| RATE = KG/HA | 0.01 | 0.05 | 0.01 | 0.05 | 0.01 | 0.05 | 0.01 | 0.05 | 0.01 | 0.05 | 0.01 | 0.05 |
| POSOL | | | | | | | | | | | | |
| COTTON | 0 | 3C,7G | 0 | 0 | 0 | 3G | 0 | 0 | 0 | 0 | 0 | 0 |
| MORNING GLORY | 0 | 2C | 0 | 2C,4G | 0 | 3C,7G | 0 | 0 | 0 | 0 | 0 | 0 |
| COCKLEBUR | 0 | 1H | 0 | 0 | 0 | 0 | 0 | 0 | 0 | 0 | 0 | 0 |
| NUTSEDGE | 0 | 0 | 0 | 0 | 0 | 0 | 0 | 0 | 0 | 0 | 0 | 0 |
| CRABGRASS | 0 | 2G | 0 | 0 | 0 | 0 | 0 | 0 | 0 | 0 | 0 | 0 |
| BARNYARD GRASS | 0 | 3H | 0 | 2H | 0 | 0 | 0 | 0 | 0 | 0 | 0 | 0 |
| WILD OATS | 0 | 2C | 0 | 6G | 0 | 0 | 0 | 0 | 0 | 0 | 0 | 0 |
| WHEAT | 0 | 2G | 0 | 5G | 0 | 0 | 0 | 0 | 0 | 0 | 0 | 0 |
| CORN | 0 | 3C,4G | 0 | 4G | 0 | 0 | 0 | 0 | 0 | 0 | 0 | 0 |
| SOYBEAN | 0 | 0 | 0 | 4G | 0 | 0 | 0 | 0 | 0 | 0 | 2H | 0 |
| RICE | 0 | 3C,8G | 0 | 0 | 0 | 0 | 0 | 0 | 0 | 0 | 0 | 0 |
| SORGHUM | 0 | 2C,4G | 0 | 2G | 0 | 0 | 0 | 0 | 0 | 0 | 0 | 0 |
| CHEATGRASS | 0 | 3C,5G | 0 | 0 | 0 | 0 | 0 | 0 | 0 | 0 | 0 | 0 |
| SUGAR BEETS | 0 | 3C,5G | 0 | 0 | 0 | 3C,7G | 0 | 0 | 0 | 0 | 0 | 0 |
| VELVETLEAF | 0 | 2G | 0 | 0 | 0 | 0 | 0 | 0 | 0 | 0 | 0 | 0 |
| GIANT FOXTAIL | 0 | 2C,5G | 0 | 2G | 0 | 0 | 0 | 0 | 0 | 0 | 0 | 0 |

-continued

(TEST A)

| | | | | | | | | | | | | |
|---|---|---|---|---|---|---|---|---|---|---|---|---|
| BARLEY | 0 | 0 | 0 | 0 | 0 | 0 | 0 | 0 | 0 | 0 | 0 | 0 |
| PRSOL | | | | | | | | | | | | |
| COTTON | 7G | 9G | 0 | 6G | 0 | 0 | 0 | 0 | 0 | 0 | 0 | 0 |
| MORNING GLORY | 8G | 9C | 0 | 7G | 0 | 0 | 0 | 0 | 0 | 0 | 0 | 0 |
| COCKLEBUR | 2C,4G | 3C,7H | 0 | 9H | 0 | 0 | 0 | 0 | 0 | 0 | 0 | 0 |
| NUTSEDGE | 7G | 3G | 0 | 0 | 0 | 0 | 0 | 0 | 0 | 0 | 0 | 0 |
| CRABGRASS | 2G | 2C,3G | 0 | | 0 | 0 | 0 | 0 | 0 | 0 | 0 | 0 |
| BARNYARD GRASS | 3C,7G | 9H | 0 | 2C,6G | 0 | 0 | 0 | 0 | 0 | 0 | 0 | 0 |
| WILD OATS | 0 | 3C,8G | 0 | 3C,8G | 0 | 0 | 0 | 0 | 0 | 0 | 0 | 0 |
| WHEAT | 0 | 8H | 0 | 5G | 0 | 0 | 0 | 0 | 0 | 0 | 0 | 0 |
| CORN | 3C,6G | 3C,9G | 2G | 3C,9H | 0 | 0 | 0 | 0 | 0 | 0 | 0 | 0 |
| SOYBEAN | 3C,4G | 3C,7G | 0 | 2C,2H | 0 | 0 | 0 | 0 | 0 | 0 | 0 | 0 |
| RICE | 4C,9H | 9H | 6G | 9H | 0 | 0 | 0 | 0 | 0 | 0 | 0 | 0 |
| SORGHUM | 4C,8G | 4C,8G | 5G | 3C,9G | 0 | 0 | 0 | 0 | 0 | 0 | 0 | 0 |
| CHEATGRASS | 2G | 7G | 3G | 8G | 0 | 0 | 0 | 0 | 0 | 0 | 0 | 0 |
| SUGAR BEETS | 8G | 5C,9G | 2H | 5G | 0 | 0 | 0 | 0 | 0 | 0 | 0 | 0 |
| VELVETLEAF | 2G | 8G | 0 | 7G | 0 | 0 | 0 | 0 | 0 | 0 | 0 | 0 |
| GIANT FOXTAIL | 5G | 6G | 0 | 3C,7G | 0 | 0 | 0 | 0 | 0 | 0 | 0 | 0 |
| BARLEY | 9G | 9G | 2G | 8G | 0 | 0 | 0 | 0 | 0 | 0 | 0 | 0 |

| | CMPD 79 | | CMPD 80 | | CMPD 81 | | CMPD 82 | | CMPD 83 | | CMPD 84 | |
|---|---|---|---|---|---|---|---|---|---|---|---|---|
| RATE = KG/HA | 0.01 | 0.05 | 0.01 | 0.05 | 0.01 | 0.05 | 0.01 | 0.05 | 0.01 | 0.05 | 0.01 | 0.05 |
| POSOL | | | | | | | | | | | | |
| COTTON | 0 | 0 | 2C,5G | 4C,8G | 2C,7G | 10C | 5C,9G | 10C | 2C,3G | 4C,9G | 10C | 5C,9G |
| MORNING GLORY | 0 | 0 | 2C,2G | 3C,8G | 5C,9G | 10C | 4C,8G | 10C | 10C | 10C | 4C,8H | 10C |
| COCKLEBUR | 0 | 0 | 4C,9H | 9C | 10C | 9C | 10C | 10C | 3H | 10C | 9C | 10C |
| NUTSEDGE | 0 | 0 | | 9C | 3C,8G | 10C | 9C | | 0 | 9C | 6G | 7G |
| CRABGRASS | 0 | 0 | 7G | 5C,9G | 3C,7G | 9C | 5C,9G | 5C,9G | 3G | 7G | 7G | 9C |
| BARNYARD GRASS | 0 | 0 | 9C | 10C | 9C | 10C | 9C | 10C | 5C,9G | 10C | 9C | 10C |
| WILD OATS | 0 | 0 | 2C,3G | 5C,9G | 5C,9G | 5C,9G | 3C,7G | 9C | 0 | 2C,3G | 0 | 2C,3G |
| WHEAT | 0 | 0 | 8G | 2C,9G | 9G | 5C,9G | 8G | 9G | 2G | 5G | 4G | 3C,9G |
| CORN | 0 | 0 | 9C | 9C | 9C | 10C | 10C | 10C | 9C | 9C | 9C | 10C |
| SOYBEAN | 0 | 0 | 3C,6G | 5C,9G | 3C,8H | 9C | 5C,9G | 9C | 2C,3H | 4C,9G | 5C,9G | 5C,9G |
| RICE | 0 | 0 | 9C | 9C | 9C | 9C | 9C | 9C | 9C | 9C | 9C | 9C |
| SORGHUM | 0 | 0 | 9G | 9C | 9C | 10C | 9C | 9C | 9C | 9C | 9C | 9C |
| CHEATGRASS | 0 | 0 | 3C,7G | 4C,9G | 5C,9G | 10C | 9C | 9C | 2G | 6G | 0 | 3C,9G |
| SUGAR BEETS | 0 | 0 | 9C | 10C | 10C | 10C | 10C | 10C | 9C | 9C | 10C | 10C |
| VELVETLEAF | 0 | 0 | 3C,7G | 9C | 3C,8G | 9C | 10C | 10C | 5C,9G | 10C | 3C,7H | 4C,8H |
| GIANT FOXTAIL | 0 | 0 | 5G | 3C,8G | 3C,9H | 9C | 9C | 10C | 3C,6G | 3C,7G | 3C,6G | 9C |
| BARLEY | 0 | 0 | 2C,3G | 3C,6G | 3C,6G | 9G | 7G | 5C,9G | 0 | 3C,8G | 2G | 5G |
| PRSOL | | | | | | | | | | | | |
| COTTON | 0 | 0 | 0 | 7G | 5G | 8G | 8G | 8G | 3G | 3G | 3G | 4G |
| MORNING GLORY | 0 | 0 | 0 | 2C,3G | 1C | 5G | 6G | 8G | 2C | 8G | 3G | 9H |
| COCKLEBUR | | 0 | 0 | 2G | 1C | 1C | 0 | 2G | 0 | 0 | 0 | 3H |
| NUTSEDGE | 0 | 0 | 0 | 10E | 0 | 10E | 0 | 4C,9G | 5G | 0 | 0 | 0 |
| CRABGRASS | 0 | 0 | 0 | 4G | 0 | 5G | 0 | 5C,9G | 2G | 0 | 0 | 5G |
| BARNYARD GRASS | 0 | 0 | 0 | 2G | 0 | 3C,6G | 0 | 3C,7H | 0 | 5H | 0 | 1C |
| WILD OATS | 0 | 0 | 0 | 0 | 0 | 3G | 0 | 2C,4G | 0 | 0 | 0 | 0 |
| WHEAT | 0 | 0 | 0 | 0 | 0 | 6G | 0 | 0 | 0 | 0 | 0 | 0 |
| CORN | 0 | 0 | 0 | 2C,8G | 5G | 3C,9G | 0 | 3C,7G | 2G | 2G | 0 | 3C,7G |
| SOYBEAN | 0 | 0 | 0 | 1H | 2G | 3C,6G | 3C,3G | 4C,8H | 2G | 3G | 2G | 3C,8G |
| RICE | 0 | 0 | 2C,5G | 9H | 5G | 9H | 3C,3G | 8G | 5G | 8G | 2G | 3C,7G |
| SORGHUM | 0 | 0 | 0 | 3C,7G | 2G | 3C,9G | 3G | 3C,7G | 2G | 7G | 3G | 3C,9G |
| CHEATGRASS | 0 | 0 | 0 | 5G | 0 | 7G | 0 | 3G | 2G | 0 | 0 | 0 |
| SUGAR BEETS | 0 | 0 | 7G | 9G | 7G | 9G | 8G | 9G | 7G | 8G | 7G | 8G |
| VELVETLEAF | 0 | 0 | 0 | 8G | 0 | 5H | 5G | 4C,8G | 0 | 3H | 2H | 3C,6H |
| GIANT FOXTAIL | 0 | 0 | 0 | 3G | 0 | 3C,7G | 3G | 3C,8G | 0 | 0 | 0 | 3G |
| BARLEY | 0 | 0 | 0 | 1C | 2G | 2C,4G | 0 | 3C,5G | 0 | 0 | 0 | 0 |

| | CMPD 85 | | CMPD 86 | | CMPD 87 | | CMPD 88 | | CMPD 89 | | CMPD 90 | |
|---|---|---|---|---|---|---|---|---|---|---|---|---|
| RATE = KG/HA | 0.01 | 0.05 | 0.01 | 0.05 | 0.01 | 0.05 | 0.01 | 0.05 | 0.01 | 0.05 | 0.01 | 0.05 |
| POSOL | | | | | | | | | | | | |
| COTTON | 2H,5G | 3C,8G | 0 | 4C,9H | 3C,7G | 5C,9G | 6G | 3C,7G | 0 | 8G | 0 | 3C,8G |
| MORNING GLORY | 5C,9G | 9C | 1H | 2C,5G | 3C,8H | 4C,9G | 4G | 9C | 3C,4G | 4C,9G | 3G | 4C,8H |
| COCKLEBUR | 1H | 6G | 5G | 5C,9G | 3C,8H | 9C | 4C,9G | 10C | 2C,4H | 3C,7G | 4C,9G | 5C,9G |
| NUTSEDGE | 3G | 0 | 6G | 9C | 0 | 4C,9G | 5G | 10C | 0 | 4G | 0 | 0 |
| CRABGRASS | 3G | 7G | 0 | 2C,5G | 5G | 3C,7G | 5G | 9C | 0 | 3C,7G | 0 | 4C,9G |
| BARNYARD GRASS | 4C,8H | 9C | 2C,5H | 3C,8H | 4C,9G | 9C | 4C,9G | 5C,9H | 4C,9H | 10C | 4C,9H | 9C |
| WILD OATS | 0 | 2C,5G | 0 | 2G | 2C,5G | 3C,8G | 0 | 2C,5G | 0 | 0 | 0 | 0 |
| WHEAT | 0 | 2G | 0 | 3G | 2G | 3C,7G | 2G | 2C,8G | 0 | 2G | 2G | 3G |
| CORN | 4C,9H | 9C | 3C,9G | 4C,9G | 9C | 9C | 10C | 10C | 3C,9G | 10C | 9C | 10C |
| SOYBEAN | 3C,8H | 5C,9G | 3C,3G | 3C,9H | 4C,8G | 5C,9G | 4C,9G | 9C | 3C,6H | 4C,9G | 3C,7H | 3C,9G |
| RICE | 5G | 9C | 4C,9G | 5C,9G | 5C,9G | 5C,9G | 4C,9G | 9C | 3C,9G | 5C,9G | 4C,9G | 9C |
| SORGHUM | 8G | 3C,9G | 3C,8G | 5C,9G | 4C,9G | 9C | 3C,9H | 10C | 9G | 9C | 5C,9G | 9C |
| CHEATGRASS | 0 | 0 | | | | | | | | | | |
| SUGAR BEETS | 9C | 10C | 3C,6H | 5C,9G | 5C,9G | 10C | 10C | 10C | 3C,5G | 10C | 3G | 9C |
| VELVETLEAF | 1C,1H | 9C | 0 | 3G | 6G | 9C | 3C,7G | 10C | 3C,7G | 3C,7H | 0 | 3H |
| GIANT FOXTAIL | 2G | 3C,6G | 0 | 4G | 3C,6G | 9C | 3G | 9C | 0 | 3G | 2G | 4C,9G |
| BARLEY | 0 | 0 | 0 | 3G | 2C,5G | 4C,9G | 3G | 4C,9G | 0 | 3G | 0 | 2G |

-continued (TEST A)

| | | | | | | | | | | | |
|---|---|---|---|---|---|---|---|---|---|---|---|
| DOWNY BROME | | 0 | 3C,7G | 3C,8G | 9C | 5C,9G | 9C | 0 | 0 | 0 | 3C,5G |
| PRSOL | | | | | | | | | | | |
| COTTON | 0 | 6G | 0 | 0 | 0 | 3G | 7G | 8G | 0 | 3G | 0 | 0 |
| MORNING GLORY | 0 | 5G | 0 | 0 | 0 | 0 | 2G | 8G | 2C,2H | 3G | 0 | 0 |
| COCKLEBUR | 0 | 0 | 0 | 0 | 0 | 0 | 0 | 3C,6G | 0 | 0 | 0 | 7G |
| NUTSEDGE | 0 | 0 | 0 | 0 | 0 | 0 | 0 | 0 | 0 | 0 | 0 | 0 |
| CRABGRASS | 0 | 0 | 0 | 0 | 0 | 2C,5G | 0 | 3C,8G | 0 | 0 | 0 | 0 |
| BARNYARD GRASS | 0 | 2C | 0 | 0 | 0 | 0 | 0 | 5G | 0 | 3G | 0 | 0 |
| WILD OATS | 0 | 0 | 0 | 0 | 0 | 0 | 0 | 0 | 0 | 0 | 0 | 0 |
| WHEAT | 0 | 0 | 0 | 2G | 0 | 0 | 0 | 5G | 0 | 5G | 0 | 0 |
| CORN | 0 | 2G | 0 | 0 | 0 | 3G | 2G | 2C,5G | 0 | 2C,6G | 0 | 0 |
| SOYBEAN | 2G | 3C,6G | 0 | 2G | 2C,7H | 3C,8H | 2C,7G | 9H | 2G | 3G | 0 | 0 |
| RICE | 0 | 0 | 0 | 0 | 0 | 5G | 2G | 8G | 2G | 6G | 0 | 3G |
| SORGHUM | 0 | 0 | 0 | 0 | 0 | 3G | 0 | 3C,7G | 3G | 6G | 0 | 0 |
| CHEATGRASS | 0 | 0 | | | | | | | | | | |
| SUGAR BEETS | 5G | 9G | 0 | 0 | 0 | 8G | 6G | 8G | 0 | 5G | 0 | 2H |
| VELVETLEAF | 0 | 2G | 0 | 0 | 0 | 0 | 3H | 5H | 0 | 1H | 0 | 0 |
| GIANT FOXTAIL | 0 | 0 | 0 | 0 | 0 | 3G | 0 | 3H | 0 | 0 | 0 | 0 |
| BARLEY | 0 | 0 | 0 | 2G | 0 | 3G | 0 | 4G | 0 | 3G | 0 | 0 |
| DOWNY BROME | | | 0 | 0 | 0 | 3G | 2G | 5G | 0 | 0 | 0 | 0 |

| | CMPD 91 | | CMPD 92 | | CMPD 93 | | CMPD 94 | | CMPD 95 | | CMPD 96 | |
|---|---|---|---|---|---|---|---|---|---|---|---|---|
| RATE = KG/HA | 0.01 | 0.05 | 0.01 | 0.05 | 0.01 | 0.05 | 0.01 | 0.05 | 0.01 | 0.05 | 0.01 | 0.05 |
| POSOL | | | | | | | | | | | | |
| COTTON | 0 | 3C,7G | 5G | 4C,9G | 3C,9G | 5C,9G | 3C,9G | 2C,9G | 2C,7G | 3C,8G | 5C,9G | 9C |
| MORNING GLORY | 0 | 0 | 2C,3H | 3C,8G | 9C | 9C | 10C | 9C | 10C | 10C | 9C | 9C |
| COCKLEBUR | 0 | 4H | 5C,9G | 10C | 10C | 9C | 10C | 10C | 10C | 10C | 10C | 10C |
| NUTSEDGE | 0 | 0 | 3G | 5C,9G | 2C,5G | 3C,7G | 9C | 4C,8G | 3C,3G | 3C,7G | 0 | 2G |
| CRABGRASS | 0 | 3G | 3G | 2C,5G | 3C,6G | 9C | 2C,5G | 4C,8G | 2G | 3C,7G | 2C | 9C |
| BARNYARD GRASS | 3H | 4C,9H | 2C,3G | 4C,9H | 10C | 9C | 3C,8G | 4C,9G | 3C,8H | 9C | 4C,9H | 9C |
| WILD OATS | 0 | 2G | 2G | 2C,8G | 3C,5G | 4C,9G | 2C,5G | 2C,9G | 0 | 2C,3G | 0 | 2C,2G |
| WHEAT | 0 | 2G | 2G | 3G | 5G | 3C,9G | 5G | 8G | 0 | 3C,5G | 0 | 2C,4G |
| CORN | 3C,9H | 5C,9G | 4U,9G | 5C,9G | 9C | 10C | 5C,9G | 9C | 4C,9G | 3C,9G | 4C,9G | 10C |
| SOYBEAN | 0 | 4C,8H | 3C,8G | 4C,9G | 9C | 9C | 5C,9G | 9C | 3C,7G | 4C,9G | 3C,8G | 4C,9G |
| RICE | 2G | 4C,9G | 3C,9G | 4C,9G | 5C,9G | 9C | 3C,9G | 5C,9G | 8G | 5C,9G | 5C,9G | 9C |
| SORGHUM | 7H | 3C,9G | 3C,8G | 3C,9G | 5C,9G | 9C | 3C,8G | 9C | 3C,6G | 3C,9G | 2C,9G | 9C |
| SUGAR BEETS | 2G | 3C,7G | 9C | 9C | 9C | 9C | 9C | 10C | 10C | 10C | 9C | 10C |
| VELVETLEAF | 0 | 3G | 5C,9G | 9C | 3C,9G | 4C,9G | 3C,9H | 9C | 1C,5G | 9C | 4C,8G | 9C |
| GIANT FOXTAIL | 0 | 3C,7G | 0 | 2C,5G | 3C,6G | 9C | 2C,5G | 5C,9G | 0 | 5C,6G | 2C,2G | 9C |
| BARLEY | 0 | 0 | 3G | 6G | 3C,5G | 2C,8G | 4G | 2C,8G | 0 | 4G | 0 | 2G |
| DOWNY BROME | 4G | 4G | 4C,9G | 9C | 3C,9G | 5C,9G | 3C,8G | 9C | 0 | 5G | 0 | 8G |
| PRSOL | | | | | | | | | | | | |
| COTTON | 0 | 0 | 5G | 6G | 3G | 8G | 6G | 9C | 4G | 2G | 7G | 8G |
| MORNING GLORY | 0 | 0 | 0 | 5G | 3G | 9G | 0 | 5G | 4G | 9G | 3C,5G | 8G |
| COCKLEBUR | 0 | 0 | 2C,2H | 3C,5H | 2G | 3C,5H | 2C,3G | 3C,6H | 1H | 2C,3H | 4C,9G | 3C,8H |
| NUTSEDGE | 0 | 0 | 5G | 5G | 0 | 10E | 0 | 9G | 0 | 8G | 0 | 3G |
| CRABGRASS | 0 | 0 | 3C,5G | 3C,6G | 2C,5G | 3C,8G | 0 | 3C,8G | 3G | 3C,7G | 0 | 4C,9G |
| BARNYARD GRASS | 0 | 0 | 0 | 2H | 3G | 3C,8H | 2G | 2G,2H | 0 | 3G | 1C | 2C,8H |
| WILD OATS | 0 | 0 | 4G | 2C,7G | 2G | 3C,6G | 0 | 5G | 0 | 0 | 0 | 2G |
| WHEAT | 0 | 0 | 3G | 6G | 2G | 5G | 0 | 6G | 0 | 4G | 0 | 6G |
| CORN | 0 | 0 | 2C,6G | 3C,7G | 2C,5G | 3C,8H | 3G | 3C,7G | 2C,4G | 3C,8G | 2C,5G | 3C,7H |
| SOYBEAN | 0 | 3G | 3C,6G | 3C,8H | 3C,7G | 4C,9H | 6G | 3C,8H | 3C,6G | 3C,7G | 3C,7H | 4C,8G |
| RICE | 0 | 0 | 8G | 9H | 7G | 9H | 8G | 5G | 6G | 3C,7G | 9H |
| SORGHUM | 0 | 0 | 3C,4G | 3C,6G | 3C,6G | 9H | 2C | 3C,7H | 5G | 3C,9H | 3C,8G | 4C,9H |
| SUGAR BEETS | 0 | 3H | 7H | 7G | 8H | 5C,9G | 10C | 9C | 2C,5G | 9G | 9C | 5C,9G |
| VELVETLEAF | 0 | 2G | 2H | 6H | 2G | 4C,9G | 3G | 2C,8G | 2G | 5H | 1H | 3C,8G |
| GIANT FOXTAIL | 0 | 0 | 0 | 2G | 2G | 3C,7G | 3G | 3C,5G | 0 | 3C,3G | 0 | 3C,3G |
| BARLEY | 0 | 0 | 5G | 5G | 2G | 8G | 3G | 6G | 0 | 4G | 0 | 3C,7G |
| DOWNY BROME | 0 | 0 | 3G | 7G | 2G | 3C,8G | | 3C,8G | 0 | 3G | 0 | 5G |

| | CMPD 97 | |
|---|---|---|
| RATE = KG/HA | 0.01 | 0.05 |
| POSOL | | |
| COTTON | 3C,8G | 5C,9G |
| MORNING GLORY | 4C,9G | 10C |
| COCKLEBUR | 3G | 9C |
| NUTSEDGE | 0 | 0 |
| CRABGRASS | 0 | 2G |
| BARNYARD GRASS | 2C,5H | 3C,8H |
| WILD OATS | 0 | 2G |
| WHEAT | 2G | 2G |
| CORN | 4C,9G | 10C |
| SOYBEAN | 4C,9G | 4C,9G |
| RICE | 0 | 3C,7G |
| SORGHUM | 2G | 3C,5G |
| SUGAR BEETS | 9C | 9C |
| VELVETLEAF | 4C,9G | 5C,9G |
| GIANT FOXTAIL | 2C,5G | 2C,5G |
| BARLEY | 0 | 0 |

-continued
(TEST A)

| | | | |
|---|---|---|---|
| | DOWNY BROME | 2G | 2C,5G |
| | PRSOL | | |
| | COTTON | | 2C,6G |
| | MORNING GLORY | 3C,3H | 8G |
| | COCKLEBUR | 0 | 2C,2G |
| | NUTSEDGE | 0 | 0 |
| | CRABGRASS | 0 | 0 |
| | BARNYARD GRASS | 0 | 0 |
| | WILD OATS | 0 | 0 |
| | WHEAT | 0 | 0 |
| | CORN | 0 | 3G |
| | SOYBEAN | 3C,7G | 3C,7G |
| | RICE | 2G | 5G |
| | SORGHUM | 0 | 4G |
| | SUGAR BEETS | 5G | 9C |
| | VELVETLEAF | 2G | 3C,5H |
| | GIANT FOXTAIL | 0 | 0 |
| | BARLEY | 0 | 0 |
| | DOWNY BROME | 0 | 0 |

It is noted that certain compounds (i.e., 77, 78, etc.) do not show activity at the rate tested. It is thought that these compounds would show activity at higher rates.

TEST B

Postemergence

Three round pans (25 cm diameter by 12.5 cm deep) were filled with Sassafras sandy loam soil. One pan was planted with nutsedge (*Cyperus rotundus*) tubers, crabgrass (*Digitaria sanguinalis*), sicklepod (*Cassia obtusifolia*), jimsonweed (*Datura stramonium*), velvetleaf (*Abutilon theophrasti*), lambsquartes (*Chenopodium album*), rice (*Oryza sativa*) and teaweed (*Sida spinosa*). The second pot was planted with green foxtail (*Setaria viridis*), cocklebur (*Xantium pensylvanicum*), morningglory (*Ipomoea hederacea*), cotton (*Gossypium hirsutum*), johnsongrass (*Sorghum halepense*), barnyardgrass (*Echiochloa crusgalli*), corn (*Zea mays*), soybean (*Glycine max*) and giant foxtail (*Setaria faberi*). The third pot was planted with wheat (*Triticum aestivum*), barley (*Hordeum vulgare*), wild buckwheat (*Polgonum convolvulus* L.), cheatgrass (*Bromus secalinus* L.), sugarbeet (*Beta vulgaris*), wild oats (*Avena fatua*), viola (*Viola arvensis*), blackgrass (*Alopecurus myosuroides*), and rape (*Brassica napus*). The plants were grown for approximately fourteen days, then sprayed postemergence with the chemicals dissolved in a non-phytotoxic solvent.

Preemergence

Three round pans (25 cm diameter by 12.5 cm deep) were filled with Sassafras sandy loam soil. One pan was planted with nutsedge tubers, crabgrass, sicklepod, jimsonweed, velvetleaf, lambsquartes, rice and teaweed. The second pot was planted with green foxtail, cocklebur, morningglory, cotton, johnsongrass, barnyardgrass, corn, soybean and giant foxtail. The third pot was planted with wheat, barley, wild buckwheat, cheatgrass, sugarbeet, wild oat, viola, blackgrass and rape. The three pans were sprayed preemergence with the chemicals dissolved in a non-phytotoxic solvent.

Treated plants and controls were maintained in the greenhouse for 24 days, then all rated plants were compared to controls and visually rated for plant response.

Response ratings are based on a scale of 0 to 100 where 0=no effect and 100=complete control. A dash (—) response means no test.

Response ratings are contained in Table B.

(TEST B)

| | CMPD 3 | | | | |
|---|---|---|---|---|---|
| RATE RATE = G/HA | 0001 | 0004 | 0016 | 0062 | 0250 |
| POSTEMERGENCE | | | | | |
| GIANT FOXTAIL | 90 | 100 | 100 | 100 | — |
| VELVETLEAF | 70 | 100 | 100 | 100 | — |
| SUGAR BEETS | 70 | 100 | 100 | 100 | — |
| CRABGRASS | 0 | 30 | 50 | 70 | — |
| TEAWEED | 30 | 50 | 70 | 100 | — |
| JIMSONWEED | 30 | 60 | 100 | 100 | — |
| RICE | 60 | 90 | 100 | 100 | — |
| COCKLEBUR | 70 | 80 | 90 | 100 | — |
| COTTON | 30 | 100 | 100 | 100 | — |
| SOYBEAN | 90 | 100 | 100 | 100 | — |
| BARNYARD GRASS | 70 | 100 | 100 | 100 | — |
| WILD OATS | 0 | 30 | 50 | 80 | — |
| MORNINGGLORY | 30 | 50 | 70 | 90 | — |
| WHEAT | 30 | 50 | 70 | 100 | — |
| CASSIA | 30 | 50 | 70 | 90 | — |
| JOHNSONGRASS | 30 | 60 | 100 | 100 | — |
| NUTSEDGE | 100 | 100 | 100 | 100 | — |
| CORN | 90 | 100 | 100 | 100 | — |
| WILD BUCKWHEAT | 30 | 60 | 90 | 100 | — |
| PREEMERGENCE | | | | | |
| GIANT FOXTAIL | — | 30 | 60 | 100 | — |
| VELVETLEAF | — | 0 | 30 | 50 | — |
| SUGAR BEETS | — | 50 | 70 | 90 | — |
| CRABGRASS | — | 0 | 30 | 70 | — |
| TEAWEED | — | 0 | 0 | 0 | — |
| JIMSONWEED | — | 0 | 0 | 30 | — |
| RICE | — | 0 | 30 | 80 | — |
| COCKLEBUR | — | 30 | 60 | 90 | — |
| COTTON | — | 0 | 0 | 30 | — |
| SOYBEAN | — | 0 | 20 | 40 | — |
| BARNYARD GRASS | — | 30 | 50 | 80 | — |
| WILD OATS | — | 20 | 40 | 60 | — |
| MORNINGGLORY | — | 0 | 0 | 30 | — |
| WHEAT | — | 0 | 30 | 70 | — |
| CASSIA | — | 0 | 0 | 0 | — |
| JOHNSONGRASS | — | 0 | 30 | 80 | — |
| NUTSEDGE | — | 0 | 30 | 70 | — |
| CORN | — | 0 | 30 | 60 | — |
| WILD BUCKWHEAT | — | 50 | 70 | 90 | — |

| | CMPD 4 | | | | |
|---|---|---|---|---|---|
| RATE RATE = G/HA | 0001 | 0004 | 0016 | 0062 | 0250 |
| POSTEMERGENCE | | | | | |
| GIANT FOXTAIL | 0 | 30 | 50 | — | — |
| VELVETLEAF | 0 | 30 | 50 | — | — |
| SUGAR BEETS | 0 | 30 | 60 | — | — |
| CRABGRASS | 0 | 30 | 50 | — | — |
| TEAWEED | 0 | 30 | 50 | — | — |
| JIMSONWEED | 0 | 0 | 30 | — | — |
| RICE | 0 | 30 | 60 | — | — |
| COCKLEBUR | 0 | 30 | 60 | — | — |
| COTTON | 0 | 20 | 40 | — | — |
| SOYBEAN | 0 | 0 | 20 | — | — |

(TEST B)-continued

| | | | | | |
|---|---|---|---|---|---|
| BARNYARD GRASS | 40 | 60 | 80 | — | — |
| WILD OATS | 0 | 0 | 0 | — | — |
| MORNINGGLORY | 0 | 0 | 30 | — | — |
| WHEAT | 0 | 0 | 0 | — | — |
| CASSIA | 0 | 0 | 30 | — | — |
| JOHNSONGRASS | 0 | 30 | 90 | — | — |
| NUTSEDGE | 0 | 30 | 70 | — | — |
| CORN | 30 | 60 | 80 | — | — |
| WILD BUCKWHEAT | 0 | 30 | 50 | — | — |
| PREEMERGENCE | | | | | |
| GIANT FOXTAIL | — | 30 | 50 | 70 | 90 |
| VELVETLEAF | — | 0 | 20 | 40 | 60 |
| SUGAR BEETS | — | 0 | 30 | 60 | 90 |
| CRABGRASS | — | 0 | 30 | 50 | 70 |
| TEAWEED | — | 0 | 30 | 60 | 90 |
| JIMSONWEED | — | 50 | 70 | 90 | 100 |
| RICE | — | 30 | 50 | 80 | 100 |
| COCKLEBUR | — | 20 | 40 | 60 | 80 |
| COTTON | — | 0 | 0 | 0 | 60 |
| SOYBEAN | — | 0 | 0 | 20 | 30 |
| BARNYARD GRASS | — | 30 | 50 | 80 | 90 |
| WILD OATS | — | 0 | 0 | 30 | 50 |
| MORNINGGLORY | — | 0 | 0 | 20 | 30 |
| WHEAT | — | 0 | 0 | 0 | 30 |
| CASSIA | — | 0 | 0 | 30 | 60 |
| JOHSONGRASS | — | 30 | 50 | 70 | 90 |
| NUTSEDGE | — | 0 | 30 | 60 | 90 |
| CORN | — | 0 | 20 | 50 | 90 |
| WILD BUCKWHEAT | — | 30 | 50 | 70 | 90 |

CMPD 5

| RATE RATE = G/HA | 0001 | 0004 | 0016 | 0062 | 0250 |
|---|---|---|---|---|---|
| POSTEMERGENCE | | | | | |
| GIANT FOXTAIL | 30 | 50 | 70 | — | — |
| VELVETLEAF | 30 | 50 | 70 | 90 | — |
| SUGAR BEETS | 0 | 0 | 30 | — | — |
| CRABGRASS | 30 | 50 | 70 | 90 | — |
| TEAWEED | 0 | 30 | 50 | 70 | — |
| JIMSONWEED | 30 | 50 | 70 | 100 | — |
| RICE | 30 | 50 | 100 | 100 | — |
| COCKLEBUR | 0 | 30 | 60 | 100 | — |
| COTTON | 0 | 0 | 30 | 50 | — |
| SOYBEAN | 0 | 30 | 60 | — | — |
| BARNYARD GRASS | 50 | 70 | 100 | 100 | — |
| WILD OATS | 0 | 0 | 30 | — | — |
| MORNINGGLORY | 0 | 0 | 30 | 50 | — |
| WHEAT | 0 | 0 | 30 | — | — |
| CASSIA | 30 | 50 | 70 | 90 | — |
| JOHNSONGRASS | 30 | 50 | 70 | 90 | — |
| NUTSEDGE | 0 | 30 | 60 | 100 | — |
| CORN | 70 | 100 | 100 | — | — |
| WILD BUCKWHEAT | 0 | 0 | 30 | — | — |
| PREEMERGENCE | | | | | |
| GIANT FOXTAIL | — | 30 | 50 | 70 | 100 |
| VELVETLEAF | — | 0 | 0 | 30 | 60 |
| SUGAR BEETS | — | 0 | 0 | 40 | 90 |
| CRABGRASS | — | 30 | 50 | 70 | 90 |
| TEAWEED | — | 0 | 30 | 50 | 70 |
| JIMSONWEED | — | 0 | 30 | 50 | 70 |
| RICE | — | 0 | 30 | 50 | 80 |
| COCKLEBUR | — | 0 | 0 | 30 | 50 |
| COTTON | — | 0 | 0 | 30 | 60 |
| SOYBEAN | — | 0 | 0 | 0 | 60 |
| BARNYARD GRASS | — | 0 | 30 | 60 | 90 |
| WILD OATS | — | 0 | 0 | 30 | 70 |
| MORNINGGLORY | — | 0 | 0 | 0 | 40 |
| WHEAT | — | 0 | 0 | 30 | 80 |
| CASSIA | — | 30 | 50 | 70 | 100 |
| JOHNSONGRASS | — | 30 | 50 | 70 | 100 |
| NUTSEDGE | — | 0 | 0 | 30 | 80 |
| CORN | — | 0 | 0 | 40 | 90 |
| WILD BUCKWHEAT | — | 50 | 70 | 80 | 90 |

CMPD 6

| RATE RATE = G/HA | 0001 | 0004 | 0016 | 0062 | 0250 |
|---|---|---|---|---|---|
| POSTEMERGENCE | | | | | |
| GIANT FOXTAIL | 0 | 30 | 60 | — | — |
| VELVETLEAF | 0 | 0 | 0 | 60 | — |
| SUGAR BEETS | 0 | 0 | 30 | — | — |
| CRABGRASS | 30 | 50 | 70 | 90 | — |
| TEAWEED | 0 | 0 | 30 | 50 | — |
| JIMSONWEED | 0 | 30 | 60 | 90 | — |
| RICE | 0 | 30 | 60 | 90 | — |
| COCKLEBUR | 0 | 0 | 30 | 70 | — |
| COTTON | 0 | 0 | 0 | 50 | — |
| SOYBEAN | 0 | 40 | 60 | — | — |
| BARNYARD GRASS | 0 | 30 | 100 | 100 | — |
| WILD OATS | 0 | 0 | 0 | — | — |
| MORNINGGLORY | 0 | 0 | 30 | 50 | — |
| WHEAT | 0 | 0 | 0 | — | — |
| CASSIA | 0 | 0 | 30 | 70 | — |
| JOHNSONGRASS | 0 | 30 | 50 | 100 | — |
| NUTSEDGE | 0 | 0 | 30 | 90 | — |
| CORN | 30 | 60 | 90 | — | — |
| WILD BUCKWHEAT | 0 | 0 | 30 | — | — |
| PREEMERGENCE | | | | | |
| GIANT FOXTAIL | — | 30 | 50 | 70 | 90 |
| VELVETLEAF | — | 0 | 0 | 30 | 60 |
| SUGAR BEETS | — | 0 | 0 | 0 | 30 |
| CRABGRASS | — | 0 | 30 | 50 | 70 |
| TEAWEED | — | 0 | 0 | 30 | 60 |
| JIMSONWEED | — | 0 | 30 | 50 | 70 |
| RICE | — | 0 | 30 | 60 | 90 |
| COCKLEBUR | — | 0 | 0 | 0 | 30 |
| COTTON | — | 0 | 0 | 0 | 20 |
| SOYBEAN | — | 0 | 0 | 0 | 40 |
| BARNYARD GRASS | — | 0 | 30 | 50 | 80 |
| WILD OATS | — | 0 | 0 | 30 | 50 |
| MORNINGGLORY | — | 0 | 0 | 0 | 30 |
| WHEAT | — | 0 | 0 | 30 | 60 |
| CASSIA | — | 0 | 0 | 30 | 50 |
| JOHNSONGRASS | — | 30 | 60 | 90 | 100 |
| NUTSEDGE | — | 0 | 0 | 30 | 70 |
| CORN | — | 20 | 40 | 60 | 90 |
| WILD BUCKWHEAT | — | 0 | 30 | 60 | 90 |

CMPD 6

| RATE RATE = G/HA | 0001 | 0004 | 0016 | 0062 | 0250 |
|---|---|---|---|---|---|
| POSTEMERGENCE | | | | | |
| GIANT FOXTAIL | 30 | 50 | 70 | 100 | — |
| VELVETLEAF | 30 | 50 | 70 | 100 | — |
| SUGAR BEETS | 30 | 50 | 70 | 100 | — |
| CRABGRASS | 0 | 30 | 50 | 80 | — |
| TEAWEED | 0 | 30 | 50 | 80 | — |
| JIMSONWEED | 30 | 50 | 70 | 100 | — |
| RICE | 0 | 50 | 70 | 90 | — |
| COCKLEBUR | 30 | 50 | 70 | 80 | — |
| COTTON | 0 | 0 | 60 | 90 | — |
| SOYBEAN | 0 | 30 | 50 | 80 | — |
| BARNYARD GRASS | 30 | 50 | 70 | 100 | — |
| WILD OATS | 0 | 30 | 50 | 80 | — |
| MORNINGGLORY | 0 | 0 | 30 | 80 | — |
| WHEAT | 0 | 30 | 50 | 80 | — |
| CASSIA | 0 | 30 | 60 | 80 | — |
| JOHNSONGRASS | 30 | 50 | 70 | 100 | — |
| NUTSEDGE | 0 | 30 | 50 | 100 | — |
| CORN | 0 | 50 | 70 | 90 | — |
| WILD BUCKWHEAT | 30 | 50 | 70 | 90 | — |
| PREEMERGENCE | | | | | |
| GIANT FOXTAIL | — | 30 | — | 70 | 90 |
| VELVETLEAF | — | 30 | — | 60 | 80 |
| SUGAR BEETS | — | 60 | — | 90 | 100 |
| CRABGRASS | — | 30 | — | 70 | 100 |
| TEAWEED | — | 30 | — | 70 | 90 |
| JIMSONWEED | — | 50 | — | 90 | 100 |
| RICE | — | 30 | — | 70 | 100 |
| COCKLEBUR | — | 0 | — | 50 | 100 |
| COTTON | — | 20 | — | 60 | 80 |
| SOYBEAN | — | 30 | — | 70 | 80 |
| BARNYARD GRASS | — | 30 | — | 70 | 90 |
| WILD OATS | — | 30 | — | 70 | 90 |
| MORNINGGLORY | — | 0 | — | 60 | 90 |
| WHEAT | — | 30 | — | 70 | 90 |
| CASSIA | — | 0 | — | 50 | 70 |
| JOHNSONGRASS | — | 30 | — | 70 | 100 |
| NUTSEDGE | — | 30 | — | 70 | 100 |
| CORN | — | 20 | — | 60 | 80 |
| WILD BUCKWHEAT | — | 60 | — | 80 | 100 |

CMPD 9

| RATE RATE = G/HA | 0001 | 0004 | 0016 | 0062 | 0250 |
|---|---|---|---|---|---|
| POSTEMERGENCE | | | | | |

(TEST B)-continued

| | | | | | |
|---|---|---|---|---|---|
| GIANT FOXTAIL | 30 | 50 | — | 90 | — |
| VELVETLEAF | 50 | 70 | — | 100 | — |
| SUGAR BEETS | 70 | 100 | — | 100 | — |
| CRABGRASS | 0 | 30 | — | 70 | — |
| TEAWEED | 0 | 30 | — | 70 | — |
| JIMSONWEED | 0 | 30 | — | 70 | — |
| RICE | 30 | 70 | — | 100 | — |
| COCKLEBUR | 50 | 70 | — | 100 | — |
| COTTON | 0 | 0 | — | 70 | — |
| SOYBEAN | 70 | 90 | — | 100 | — |
| BARNYARD GRASS | 30 | 50 | — | 90 | — |
| WILD OATS | 0 | 30 | — | 70 | — |
| MORNINGGLORY | 0 | 0 | — | 50 | — |
| WHEAT | 0 | 0 | — | 70 | — |
| CASSIA | 0 | 30 | — | 70 | — |
| JOHNSONGRASS | 0 | 30 | — | 80 | — |
| NUTSEDGE | 0 | 0 | — | 50 | — |
| CORN | 30 | 50 | — | 70 | — |
| WILD BUCKWHEAT | 20 | 40 | — | 80 | — |
| PREEMERGENCE | | | | | |
| GIANT FOXTAIL | — | 30 | — | 70 | 100 |
| VELVETLEAF | — | 30 | — | 80 | 100 |
| SUGAR BEETS | — | 60 | — | 80 | 90 |
| CRABGRASS | — | 30 | — | 70 | 90 |
| TEAWEED | — | 30 | — | 70 | 90 |
| JIMSONWEED | — | 30 | — | 70 | 100 |
| RICE | — | 50 | — | 70 | 90 |
| COCKLEBUR | — | 30 | — | 70 | 90 |
| COTTON | — | 0 | — | 30 | 60 |
| SOYBEAN | — | 30 | — | 60 | 80 |
| BARNYARD GRASS | — | 30 | — | 70 | 90 |
| WILD OATS | — | 30 | — | 50 | 70 |
| MORNINGGLORY | — | 0 | — | 50 | 70 |
| WHEAT | — | 30 | — | 50 | 70 |
| CASSIA | — | 0 | — | 50 | 70 |
| JOHNSONGRASS | — | 50 | — | 90 | 100 |
| NUTSEDGE | — | 0 | — | 50 | 90 |
| CORN | — | 0 | — | 50 | 80 |
| WILD BUCKWHEAT | — | 30 | — | 70 | 100 |

| | CMPD 10 | | | | |
|---|---|---|---|---|---|
| RATE RATE = G/HA | 0001 | 0004 | 0016 | 0062 | 0250 |
| POSTEMERGENCE | | | | | |
| GIANT FOXTAIL | 0 | 0 | 30 | — | — |
| VELVETLEAF | 0 | 30 | 60 | 90 | — |
| SUGAR BEETS | 30 | 50 | 70 | — | — |
| CRABGRASS | 0 | 0 | 30 | 50 | — |
| TEAWEED | 0 | 30 | 50 | 70 | — |
| JIMSONWEED | 0 | 0 | 30 | 50 | — |
| RICE | 0 | 30 | 50 | 70 | — |
| COCKLEBUR | 0 | 0 | 30 | 50 | — |
| COTTON | 0 | 0 | 0 | 20 | — |
| SOYBEAN | 0 | 0 | 0 | — | — |
| BARNYARD GRASS | 30 | 50 | 70 | 90 | — |
| WILD OATS | 0 | 0 | 0 | — | — |
| MORNINGGLORY | 0 | 0 | 0 | 30 | — |
| WHEAT | 0 | 0 | 0 | — | — |
| CASSIA | 0 | 30 | 50 | 80 | — |
| JOHNSONGRASS | 0 | 30 | 60 | 90 | — |
| NUTSEDGE | 0 | 0 | 0 | 0 | — |
| CORN | 0 | 0 | 40 | — | — |
| WILD BUCKWHEAT | 0 | 30 | 50 | — | — |
| PREEMERGENCE | | | | | |
| GIANT FOXTAIL | — | 30 | 50 | 70 | 90 |
| VELVETLEAF | — | 30 | 50 | 70 | 90 |
| SUGAR BEETS | — | 60 | 80 | 90 | 100 |
| CRABGRASS | — | 0 | 30 | 60 | 100 |
| TEAWEED | — | 30 | 50 | 70 | 90 |
| JIMSONWEED | — | 30 | 50 | 80 | 100 |
| RICE | — | 30 | 60 | 90 | 100 |
| COCKLEBUR | — | 0 | 30 | 50 | 70 |
| COTTON | — | 0 | 0 | 30 | 60 |
| SOYBEAN | — | 0 | 0 | 30 | 60 |
| BARNYARD GRASS | — | 30 | 50 | 70 | 90 |
| WILD OATS | — | 0 | 0 | 30 | 60 |
| MORNINGGLORY | — | 30 | 50 | 70 | 90 |
| WHEAT | — | 0 | 0 | 30 | 50 |
| CASSIA | — | 0 | 30 | 50 | 70 |
| JOHNSONGRASS | — | 30 | 60 | 100 | 100 |
| NUTSEDGE | — | 0 | 30 | 60 | 90 |
| CORN | — | 20 | 40 | 60 | 80 |
| WILD BUCKWHEAT | — | 50 | 70 | 90 | 100 |

| | CMPD 11 | | | | |
|---|---|---|---|---|---|
| RATE RATE = G/HA | 0001 | 0004 | 0016 | 0062 | 0250 |
| POSTEMERGENCE | | | | | |
| GIANT FOXTAIL | 0 | 0 | 30 | — | — |
| VELVETLEAF | 0 | 30 | 60 | 100 | — |
| SUGAR BEETS | 0 | 30 | 60 | — | — |
| CRABGRASS | 0 | 30 | 60 | 90 | — |
| TEAWEED | 0 | 0 | 30 | 50 | — |
| JIMSONWEED | 30 | 50 | 70 | 100 | — |
| RICE | 0 | 30 | 60 | 100 | — |
| COCKLEBUR | 30 | 50 | 70 | 90 | — |
| COTTON | 0 | 0 | 30 | 60 | — |
| SOYBEAN | 30 | 60 | 90 | — | — |
| BARNYARD GRASS | 0 | 30 | 60 | 100 | — |
| WILD OATS | 0 | 0 | 0 | — | — |
| MORNINGGLORY | 0 | 0 | 30 | 90 | — |
| WHEAT | 0 | 0 | 0 | — | — |
| CASSIA | 0 | 30 | 60 | 100 | — |
| JOHNSONGRASS | 0 | 0 | 30 | 50 | — |
| NUTSEDGE | 0 | 0 | 0 | 0 | — |
| CORN | 0 | 0 | 30 | — | — |
| WILD BUCKWHEAT | 0 | 30 | 50 | — | — |
| PREEMERGENCE | | | | | |
| GIANT FOXTAIL | — | 30 | 50 | 70 | 90 |
| VELVETLEAF | — | 0 | 30 | 60 | 90 |
| SUGAR BEETS | — | 50 | 70 | 90 | 100 |
| CRABGRASS | — | 70 | 80 | 90 | 100 |
| TEAWEED | — | 30 | 50 | 70 | 90 |
| JIMSONWEED | — | 30 | 60 | 90 | 100 |
| RICE | — | 40 | 80 | 90 | 100 |
| COCKLEBUR | — | 0 | 30 | 60 | 90 |
| COTTON | — | 0 | 30 | 50 | 70 |
| SOYBEAN | — | 0 | 0 | 30 | 70 |
| BARNYARD GRASS | — | 30 | 60 | 90 | 100 |
| WILD OATS | — | 0 | 30 | 50 | 70 |
| MORNINGGLORY | — | 0 | 30 | 60 | 90 |
| WHEAT | — | 0 | 30 | 60 | 90 |
| CASSIA | — | 30 | 50 | 70 | 100 |
| JOHNSONGRASS | — | 50 | 70 | 100 | 100 |
| NUTSEDGE | — | 0 | 0 | 0 | 0 |
| CORN | — | 0 | 30 | 50 | 70 |
| WILD BUCKWHEAT | — | 50 | 70 | 80 | 90 |

| | CMPD 12 | | | | |
|---|---|---|---|---|---|
| RATE RATE = G/HA | 0001 | 0004 | 0016 | 0062 | 0250 |
| POSTEMERGENCE | | | | | |
| GIANT FOXTAIL | — | 0 | 30 | 60 | — |
| VELVETLEAF | — | 30 | 50 | 70 | 100 |
| SUGAR BEETS | — | 0 | 0 | 30 | — |
| CRABGRASS | — | 0 | 30 | 60 | 90 |
| TEAWEED | — | 0 | 30 | 50 | 80 |
| JIMSONWEED | — | 30 | 50 | 70 | 100 |
| RICE | — | 0 | 30 | 60 | 100 |
| COCKLEBUR | — | 30 | 60 | 90 | 90 |
| COTTON | — | 0 | 30 | 50 | 70 |
| SOYBEAN | — | 60 | 80 | 100 | — |
| BARNYARD GRASS | — | 0 | 30 | 60 | 100 |
| WILD OATS | — | 0 | 0 | 0 | — |
| MORNINGGLORY | — | 0 | 30 | 50 | 70 |
| WHEAT | — | 0 | 0 | 0 | — |
| CASSIA | — | 30 | 50 | 70 | 100 |
| JOHNSONGRASS | — | 0 | 0 | 30 | 90 |
| NUTSEDGE | — | 0 | 0 | 30 | 80 |
| CORN | — | 0 | 30 | 70 | — |
| WILD BUCKWHEAT | — | 0 | 0 | 30 | — |
| PREEMERGENCE | | | | | |
| GIANT FOXTAIL | — | 30 | 70 | 90 | |
| VELVETLEAF | — | 0 | 30 | 50 | 70 |
| SUGAR BEETS | — | 0 | 50 | 70 | 90 |
| CRABGRASS | — | 0 | 30 | 60 | 90 |
| TEAWEED | — | 0 | 30 | 50 | 80 |
| JIMSONWEED | — | 30 | 50 | 70 | 90 |
| RICE | — | 30 | 50 | 70 | 90 |
| COCKLEBUR | — | 0 | 30 | 60 | 100 |
| COTTON | — | 0 | 0 | 30 | 50 |
| SOYBEAN | — | 0 | 0 | 30 | 60 |
| BARNYARD GRASS | — | 0 | 30 | 60 | 90 |
| WILD OATS | — | 0 | 0 | 30 | 60 |
| MORNINGGLORY | — | 0 | 30 | 60 | 90 |

(TEST B)-continued

| | | | | | |
|---|---|---|---|---|---|
| WHEAT | — | 0 | 0 | 30 | 50 |
| CASSIA | — | 0 | 30 | 60 | 100 |
| JOHNSONGRASS | — | 30 | 50 | 70 | 90 |
| NUTSEDGE | — | 0 | 30 | 50 | 80 |
| CORN | — | 0 | 0 | 20 | 50 |
| WILD BUCKWHEAT | — | 30 | 50 | 70 | 90 |

| | CMPD 13 | | | | |
|---|---|---|---|---|---|
| RATE RATE = G/HA | 0001 | 0004 | 0016 | 0062 | 0250 |
| POSTEMERGENCE | | | | | |
| GIANT FOXTAIL | 0 | 30 | 50 | — | — |
| VELVETLEAF | 30 | 60 | 100 | 100 | — |
| SUGAR BEETS | 70 | 90 | 100 | — | — |
| CRABGRASS | 0 | 30 | 60 | 90 | — |
| TEAWEED | 30 | 50 | 70 | 90 | — |
| JIMSONWEED | 0 | 30 | 60 | 100 | — |
| RICE | 30 | 60 | 90 | 100 | — |
| COCKLEBUR | 30 | 50 | 70 | 100 | — |
| COTTON | 0 | 0 | 30 | 60 | — |
| SOYBEAN | 30 | 50 | 80 | — | — |
| BARNYARD GRASS | 30 | 50 | 100 | 100 | — |
| WILD OATS | 0 | 0 | 50 | — | — |
| MORNINGGLORY | 0 | 30 | 60 | 90 | — |
| WHEAT | 0 | 30 | 50 | — | — |
| CASSIA | 30 | 50 | 70 | 100 | — |
| JOHNSONGRASS | 30 | 50 | 70 | 90 | — |
| NUTSEDGE | 0 | 0 | 30 | 70 | — |
| CORN | 70 | 90 | 100 | — | — |
| WILD BUCKWHEAT | 0 | 30 | 50 | — | — |
| PREEMERGENCE | | | | | |
| GIANT FOXTAIL | — | 30 | 60 | 90 | 100 |
| VELVETLEAF | — | 30 | 60 | 80 | 90 |
| SUGAR BEETS | — | 30 | 50 | 80 | 90 |
| CRABGRASS | — | 30 | 50 | 70 | 100 |
| TEAWEED | — | 30 | 50 | 70 | 90 |
| JIMSONWEED | — | 30 | 50 | 70 | 90 |
| RICE | — | 70 | 90 | 100 | 100 |
| COCKLEBUR | — | 0 | 30 | 60 | 90 |
| COTTON | — | 30 | 50 | 70 | 90 |
| SOYBEAN | — | 0 | 20 | 60 | 80 |
| BARNYARD GRASS | — | 30 | 60 | 90 | 100 |
| WILD OATS | — | 0 | 30 | 50 | 70 |
| MORNINGGLORY | — | 0 | 30 | 60 | 90 |
| WHEAT | — | 0 | 30 | 50 | 70 |
| CASSIA | — | 30 | 50 | 70 | 90 |
| JOHNSONGRASS | — | 70 | 90 | 100 | 100 |
| NUTSEDGE | — | 0 | 70 | 90 | 100 |
| CORN | — | 0 | 30 | 60 | 100 |
| WILD BUCKWHEAT | — | 30 | 50 | 70 | 90 |

| | CMPD 14 | | | | |
|---|---|---|---|---|---|
| RATE RATE = G/HA | 0001 | 0004 | 0016 | 0062 | 0250 |
| POSTEMERGENCE | | | | | |
| GIANT FOXTAIL | 30 | 50 | 70 | — | — |
| VELVETLEAF | 50 | 90 | 100 | 100 | — |
| SUGAR BEETS | 50 | 70 | 100 | — | — |
| CRABGRASS | 30 | 50 | 70 | 100 | — |
| TEAWEED | 30 | 50 | 70 | 90 | — |
| JIMSONWEED | 30 | 60 | 100 | 100 | — |
| RICE | 30 | 60 | 100 | 100 | — |
| COCKLEBUR | 30 | 60 | 90 | 100 | — |
| COTTON | 0 | 30 | 60 | 90 | — |
| SOYBEAN | 70 | 80 | 90 | — | — |
| BARNYARD GRASS | 30 | 60 | 100 | 100 | — |
| WILD OATS | 0 | 30 | 60 | — | — |
| MORNINGGLORY | 50 | 70 | 90 | 100 | — |
| WHEAT | 30 | 50 | 70 | — | — |
| CASSIA | 30 | 60 | 90 | 100 | — |
| JOHNSONGRASS | 30 | 60 | 100 | 100 | — |
| NUTSEDGE | 0 | 30 | 60 | 90 | — |
| CORN | 70 | 100 | 100 | — | — |
| WILD BUCKWHEAT | 30 | 50 | 70 | — | — |
| PREEMERGENCE | | | | | |
| GIANT FOXTAIL | — | 80 | 90 | 100 | 100 |
| VELVETLEAF | — | 30 | 60 | 90 | 100 |
| SUGAR BEETS | — | 70 | 90 | 100 | 100 |
| CRABGRASS | — | 30 | 60 | 80 | 90 |
| TEAWEED | — | 40 | 60 | 80 | 90 |
| JIMSONWEED | — | 50 | 70 | 80 | 90 |
| RICE | — | 50 | 70 | 90 | 100 |
| COCKLEBUR | — | 30 | 50 | 70 | 90 |

(TEST B)-continued

| | | | | | |
|---|---|---|---|---|---|
| COTTON | — | 30 | 50 | 80 | 90 |
| SOYBEAN | — | 20 | 50 | 70 | 90 |
| BARNYARD GRASS | — | 50 | 70 | 90 | 100 |
| WILD OATS | — | 20 | 30 | 60 | 80 |
| MORNINGGLORY | — | 30 | 50 | 70 | 90 |
| WHEAT | — | 0 | 30 | 50 | 70 |
| CASSIA | — | 50 | 70 | 90 | 100 |
| JOHNSONGRASS | — | 70 | 80 | 90 | 100 |
| NUTSEDGE | — | 0 | 50 | 90 | 100 |
| CORN | — | 60 | 80 | 100 | 100 |
| WILD BUCKWHEAT | — | 70 | 80 | 90 | 90 |

| | CMPD 15 | | | | |
|---|---|---|---|---|---|
| RATE RATE = G/HA | 0001 | 0004 | 0016 | 0062 | 0250 |
| POSTEMERGENCE | | | | | |
| GIANT FOXTAIL | 50 | 80 | 100 | — | — |
| VELVETLEAF | 60 | 100 | 100 | 100 | — |
| SUGAR BEETS | 100 | 100 | 100 | — | — |
| CRABGRASS | 0 | 30 | 50 | 80 | — |
| TEAWEED | 30 | 60 | 90 | 100 | — |
| JIMSONWEED | 30 | 50 | 70 | 90 | — |
| RICE | 50 | 70 | 100 | 100 | — |
| COCKLEBUR | 60 | 80 | 100 | 100 | — |
| COTTON | 30 | 50 | 70 | 100 | — |
| SOYBEAN | 70 | 90 | 100 | — | — |
| BARNYARD GRASS | 60 | 90 | 100 | 100 | — |
| WILD OATS | 0 | 0 | 50 | — | — |
| MORNINGGLORY | 70 | 90 | 100 | 100 | — |
| WHEAT | 30 | 50 | 70 | — | — |
| CASSIA | 50 | 70 | 90 | 100 | — |
| JOHNSONGRASS | 60 | 90 | 100 | 100 | — |
| NUTSEDGE | 50 | 70 | 80 | 90 | — |
| CORN | 70 | 100 | 100 | — | — |
| WILD BUCKWHEAT | 30 | 50 | 70 | — | — |
| PREEMERGENCE | | | | | |
| GIANT FOXTAIL | — | 60 | 100 | 100 | 100 |
| VELVETLEAF | — | 50 | 70 | 90 | 100 |
| SUGAR BEETS | — | 70 | 80 | 90 | 100 |
| CRABGRASS | — | 30 | 50 | 70 | 90 |
| TEAWEED | — | 50 | 70 | 80 | 90 |
| JIMSONWEED | — | 60 | 80 | 90 | 100 |
| RICE | — | 50 | 80 | 90 | 100 |
| COCKLEBUR | — | 70 | 80 | 90 | 100 |
| COTTON | — | 40 | 60 | 80 | 90 |
| SOYBEAN | — | 30 | 50 | 80 | 90 |
| BARNYARD GRASS | — | 50 | 80 | 90 | 100 |
| WILD OATS | — | 0 | 30 | 50 | 80 |
| MORNINGGLORY | — | 50 | 70 | 90 | 100 |
| WHEAT | — | 0 | 30 | 50 | 90 |
| CASSIA | — | 30 | 50 | 70 | 90 |
| JOHNSONGRASS | — | 60 | 100 | 100 | 100 |
| NUTSEDGE | — | 0 | 60 | 90 | 100 |
| CORN | — | 0 | 0 | 60 | 90 |
| WILD BUCKWHEAT | — | 60 | 70 | 80 | 90 |

| | CMPD 16 | | | | |
|---|---|---|---|---|---|
| RATE RATE = G/HA | 0001 | 0004 | 0016 | 0062 | 0250 |
| POSTEMERGENCE | | | | | |
| GIANT FOXTAIL | 0 | 0 | 30 | — | — |
| VELVETLEAF | 30 | 60 | 100 | 100 | — |
| SUGAR BEETS | 70 | 90 | 100 | — | — |
| CRABGRASS | 0 | 30 | 50 | 80 | — |
| TEAWEED | 30 | 50 | 70 | 80 | — |
| JIMSONWEED | 30 | 60 | 90 | 100 | — |
| RICE | 30 | 60 | 100 | 100 | — |
| COCKLEBUR | 30 | 50 | 70 | 100 | — |
| COTTON | 0 | 0 | 0 | 60 | — |
| SOTBEAN | 40 | 30 | 60 | — | — |
| BARNYARD GRASS | 30 | 60 | 90 | 100 | — |
| WILD OATS | 0 | 0 | 0 | — | — |
| MORNINGGLORY | 30 | 50 | 70 | 90 | — |
| WHEAT | 0 | 0 | 0 | — | — |
| CASSIA | 0 | 30 | 50 | 80 | — |
| JOHNSONGRASS | 30 | 60 | 100 | 100 | — |
| NUTSEDGE | 30 | 50 | 70 | 90 | — |
| CORN | 70 | 100 | 100 | — | — |
| WILD BUCKWHEAT | 0 | 30 | 50 | — | — |
| PREEMERGENCE | | | | | |
| GIANT FOXTAIL | — | 30 | 50 | 80 | 100 |
| VELVETLEAF | — | 30 | 50 | 80 | 90 |
| SUGAR BEETS | — | 70 | 80 | 90 | 100 |

(TEST B)-continued

| | CMPD 17 | | | | |
|---|---|---|---|---|---|
| RATE RATE = G/HA | 0001 | 0004 | 0016 | 0062 | 0250 |
| POSTEMERGENCE | | | | | |
| CRABGRASS | — | 0 | 30 | 60 | 90 |
| TEAWEED | — | 60 | 80 | 100 | 100 |
| JIMSONWEED | — | 50 | 70 | 80 | 90 |
| RICE | — | 70 | 80 | 90 | 100 |
| COCKLEBUR | — | 0 | 30 | 60 | 80 |
| COTTON | — | 30 | 50 | 70 | 90 |
| SOYBEAN | — | 0 | 30 | 60 | 80 |
| BARNYARD GRASS | — | 30 | 60 | 90 | 100 |
| WILD OATS | — | 0 | 0 | 30 | 70 |
| MORNINGGLORY | — | 30 | 50 | 80 | 90 |
| WHEAT | — | 0 | 0 | 30 | 50 |
| CASSIA | — | 30 | 50 | 80 | 90 |
| JOHNSONGRASS | — | 60 | 90 | 100 | 100 |
| NUTSEDGE | — | 0 | 50 | 80 | 100 |
| CORN | — | 30 | 50 | 70 | 90 |
| WILD BUCKWHEAT | — | 50 | 70 | 80 | 90 |

| | CMPD 17 | | | | |
|---|---|---|---|---|---|
| RATE RATE = G/HA | 0001 | 0004 | 0016 | 0062 | 0250 |
| POSTEMERGENCE | | | | | |
| GIANT FOXTAIL | 0 | 0 | 40 | — | — |
| VELVETLEAF | 30 | 70 | 100 | 100 | — |
| SUGAR BEETS | 90 | 100 | 100 | — | — |
| CRABGRASS | 30 | 50 | 70 | 90 | — |
| TEAWEED | 0 | 30 | 50 | 80 | — |
| JIMSONWEED | 50 | 70 | 90 | 100 | — |
| RICE | 30 | 90 | 100 | 100 | — |
| COCKLEBUR | 50 | 70 | 90 | 100 | — |
| COTTON | 0 | 0 | 40 | 70 | — |
| SOTBEAN | 40 | 80 | 90 | — | — |
| BARNYARD GRASS | 30 | 60 | 100 | 100 | — |
| WILD OATS | 0 | 0 | 30 | — | — |
| MORNINGGLORY | 30 | 60 | 70 | 90 | — |
| WHEAT | 40 | 80 | 100 | — | — |
| CASSIA | 30 | 50 | 90 | 100 | — |
| JOHNSONGRASS | 30 | 60 | 100 | 100 | — |
| NUTSEDGE | 0 | 30 | 50 | 70 | — |
| CORN | 70 | 100 | 100 | — | — |
| WILD BUCKWHEAT | 0 | 30 | 50 | — | — |
| PREEMERGENCE | | | | | |
| GIANT FOXTAIL | — | 30 | 60 | 90 | 100 |
| VELVETLEAF | — | 50 | 70 | 90 | 100 |
| SUGAR BEETS | — | 70 | 90 | 100 | 100 |
| CRABGRASS | — | 30 | 60 | 90 | 100 |
| TEAWEED | — | 30 | 50 | 70 | 90 |
| JIMSONWEED | — | 70 | 90 | 90 | 100 |
| RICE | — | 80 | 90 | 100 | 100 |
| COCKLEBUR | — | 50 | 70 | 90 | 100 |
| COTTON | — | 0 | 30 | 60 | 90 |
| SOYBEAN | — | 30 | 50 | 80 | 90 |
| BARNYARD GRASS | — | 70 | 90 | 100 | 100 |
| WILD OATS | — | 0 | 30 | 50 | 80 |
| MORNINGGLORY | — | 50 | 70 | 80 | 90 |
| WHEAT | — | 0 | 30 | 60 | 90 |
| CASSIA | — | 50 | 70 | 100 | 100 |
| JOHNSONGRASS | — | 70 | 90 | 100 | 100 |
| NUTSEDGE | — | 0 | 30 | 50 | 70 |
| CORN | — | 0 | 0 | 70 | 90 |
| WILD BUCKWHEAT | — | 50 | 70 | 80 | 90 |

| | CMPD 18 | | | | |
|---|---|---|---|---|---|
| RATE RATE = G/HA | 0001 | 0004 | 0016 | 0062 | 0250 |
| POSTEMERGENCE | | | | | |
| GIANT FOXTAIL | 0 | 30 | 50 | — | — |
| VELVETLEAF | 30 | 50 | 70 | 90 | — |
| SUGAR BEETS | 30 | 50 | 70 | — | — |
| CRABGRASS | 30 | 50 | 70 | 90 | — |
| TEAWEED | 30 | 50 | 70 | 90 | — |
| JIMSONWEED | 30 | 50 | 70 | 90 | — |
| RICE | 30 | 60 | 90 | 100 | — |
| COCKLEBUR | 30 | 50 | 70 | 100 | — |
| COTTON | 0 | 30 | 50 | 70 | — |
| SOYBEAN | 30 | 70 | 90 | — | — |
| BARNYARD GRASS | 30 | 50 | 70 | 100 | — |
| WILD OATS | 0 | 0 | 30 | — | — |
| MORNINGGLORY | 30 | 50 | 70 | 90 | — |
| WHEAT | 0 | 0 | 0 | — | — |
| CASSIA | 30 | 60 | 90 | 100 | — |
| JOHNSONGRASS | 30 | 60 | 90 | 100 | — |
| NUTSEDGE | 0 | 30 | 50 | 70 | — |
| CORN | 50 | 70 | 100 | — | — |
| WILD BUCKWHEAT | 0 | 0 | 30 | — | — |
| PREEMERGENCE | | | | | |
| GIANT FOXTAIL | — | 30 | 50 | 70 | 100 |
| VELVETLEAF | — | 30 | 50 | 70 | 90 |
| SUGAR BEETS | — | 30 | 50 | 70 | 90 |
| CRABGRASS | — | 0 | 30 | 60 | 90 |
| TEAWEED | — | 30 | 50 | 70 | 90 |
| JIMSONWEED | — | 30 | 50 | 80 | 90 |
| RICE | — | 50 | 70 | 90 | 100 |
| COCKLEBUR | — | 0 | 0 | 30 | 80 |
| COTTON | — | 0 | 30 | 50 | 80 |
| SOYBEAN | — | 0 | 30 | 60 | 90 |
| BARNYARD GRASS | — | 30 | 50 | 70 | 100 |
| WILD OATS | — | 0 | 0 | 30 | 70 |
| MORNINGGLORY | — | 30 | 50 | 70 | 90 |
| WHEAT | — | 0 | 0 | 30 | 50 |
| CASSIA | — | 30 | 50 | 70 | 100 |
| JOHNSONGRASS | — | 50 | 70 | 100 | 100* |
| NUTSEDGE | — | 0 | 0 | 30 | 80 |
| CORN | — | 0 | 30 | 60 | 100 |
| WILD BUCKWHEAT | — | 30 | 50 | 70 | 90 |

What is claimed is:
1. A compound selected from

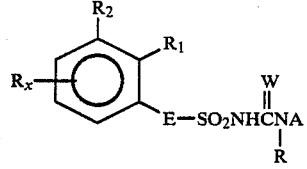

wherein
E is $CH_2$ or a single bond;
W is O or S;
R is H or $CH_3$;
$R_X$ is H, F, Cl, $CH_3$, $OCH_3$, $N(CH_3)_2$ or $OCHF_2$;
$R_1$ is F, Cl, Br, $NO_2$, $C_1$-$C_4$ alkyl, $C_2$-$C_4$ alkenyl, $C_2$-$C_4$ alkynyl, $C_2$-$C_4$ haloalkenyl, $C_2$-$C_4$ alkynyl, $C_1$-$C_4$ haloalkyl, $C_1$-$C_4$ akloxy, $OCH_2CH_2OCH_3$, $C_1$-$C_4$ haloalkoxy, $C_3$-$C_4$ alkenyloxy, $C_2$-$C_4$ haloalkenyloxy, $C_3$-$C_4$ alkynyloxy, $CO_2R_3$, $CONR_4R_5$, $SO_2NR_4'R_5'$, $S(O)_nR_6$, $OSO_2R_7$, $C_1$-$C_2$ alkyl substituted with $C_1$-$C_2$ alkoxy, OH or $C_1$-$C_2$ alkylthio, $CH_2CN$, $C_6H_5$,

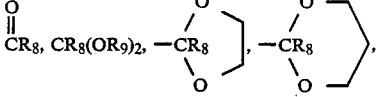

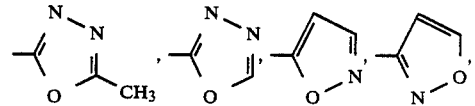

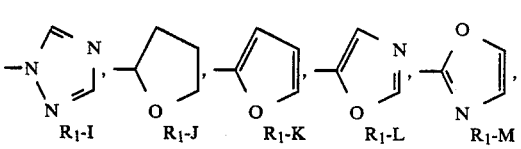

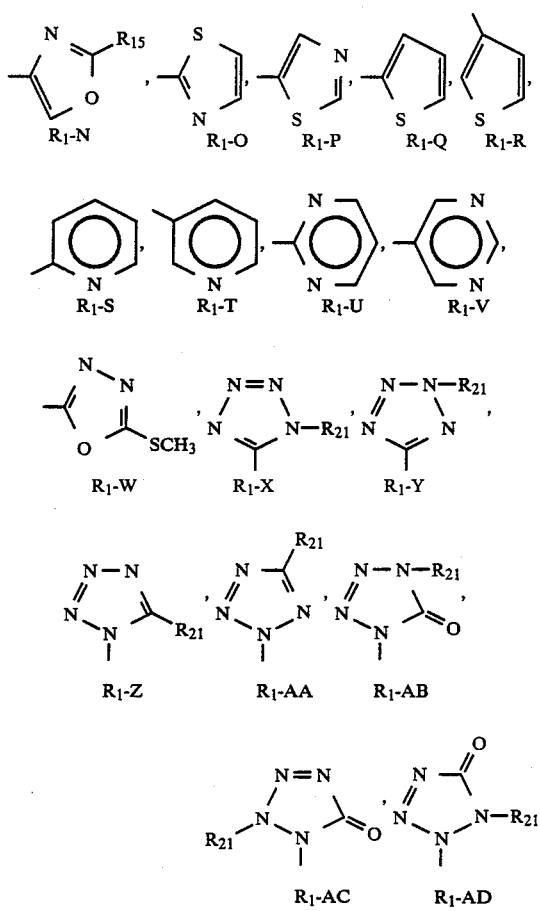

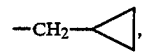

CH₂CH₂Cl, CH₂CH₂F, C₁–C₂ alkyl substituted with OCH₃, SCH₃ or CN;

R₄ is C₁–C₃ alkyl or C₁–C₂ alkoxy;
R₄' is C₁–C₃ alkyl or C₁–C₂ alkoxy;
R₅ is H or C₁–C₃ alkyl;
R₅' is H or C₁–C₃ alkyl;
R₄ and R₅ may be taken together to form —(CH₂)₃— or —(CH₂)₄—;
R₄' and R₅' may be taken together to form —(CH₂)₃— or —(CH₂)₄—;
R₆ is C₁–C₃ alkyl, —CH₂CH=CH₂ or CH₂C≡CH;
R₇ is C₁–C₃ alkyl or N(CH₃)₂;
R₈ is H, C₁–C₄ alkyl, C₃–C₄ alkenyl, C₃–C₄ alkynyl, CH₂CH₂Cl, CH₂CH₂F, C₁–C₂ alkyl substituted with OCH₃ or SCH₃ or C₃–C₆ cycloalkyl;
R₉ is C₁–C₂ alkyl;
R₁₀ and R₁₁ are independently C₁–C₂ alkyl, C₁–C₂ alkoxy, C₁–C₂ alkylthio, NHCH₃ or N(CH₃)₂;
R₁₂ and R₁₃ are independently H or C₁–C₂ alkyl;
R₁₄ is C₁–C₃ alkyl;
R₁₅ is H or CH₃;
R₁₆ is H, C₁–C₂ alkyl or F;
R₁₇ is H or C₁–C₂ alkyl;
R₁₇' is H, C₁–C₂ alkyl, CN, Cl, OCH₃, SCH₃ or N(CH₃)₂;
R₁₈ is C₁–C₂ alkyl;
R₁₉ is H, Si(CH₃)₃ or C₁–C₂ alkyl;
R₂₀ is H or C₁–C₂ alkyl;
R₂₁ is H, C₁–C₃ alkyl or allyl;
R₂₂ is C₁–C₂ alkyl or C₁–C₂ haloalkyl;
R₂₃ is H, CH₃, Cl or Br;
R₂₄ is H or CH₃;
p is 1 or 2;
n is 0, 1 or 2;
A is

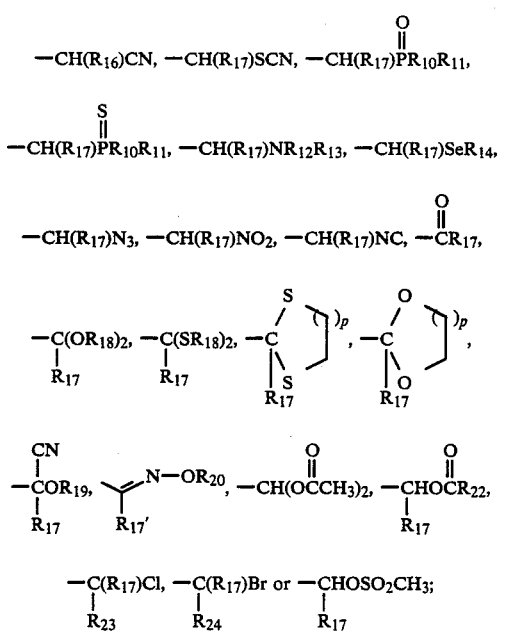

R₃ is C₁–C₄ alkyl, C₃–C₄ alkenyl, C₃–C₄ or alkynyl,

X is H, C₁–C₄ alkyl, C₁–C₄ alkoxy, C₁–C₄ haloalkoxy, C₁–C₄ haloalkyl, C₁–C₄ haloalkylthio, C₁–C₄ alkylthio, halogen, C₂–C₅ alkoxyalkyl, C₂–C₅ alkoxyalkoxy, amino, C₁–C₃ alkylamino or di(C₁–C₃ alkyl)amino;

Y is H, C₁–C₄ alkyl, C₁–C₄ alkoxy, C₁–C₄ haloalkoxy, C₁–C₄ haloalkylthio, C₁–C₄ alkylthio, C₂–C₅ alkoxyalkyl, C₂–C₅ alkoxyalkoxy, amino, C₁–C₃ alkylamino, di(C₁–C₃ alkyl)amino, C₃–C₄ alkenyloxy, C₃–C₄ alkynyloxy, C₂–C₅ alkylthioalkyl, C₂–C₅ alkylsulfinylalkyl, C₂–C₅ alkylsulfonylalkyl, C₁–C₄ haloalkyl, C₂–C₄ alkynyl, C₃–C₅ cycloalkyl, azido, cyano,

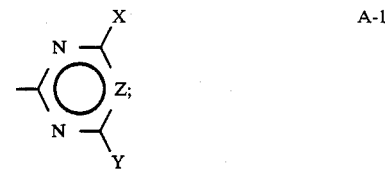

-continued

N(OCH$_3$)CH$_3$;

m is 2 or 3;
Q$_1$ and Q$_2$ are independently O or S;
R$_a$ is H or C$_1$-C$_3$ alkyl;
R$_b$ and R$_c$ are independently C$_1$-C$_3$ alkyl; and
Z is CH, CCH$_3$, CC$_2$H$_5$, CCl or CBr;
and their agriculturally suitable salts; provided that
(1) when X is halogen, then Z is CH and Y is OCH$_3$, OC$_2$H$_5$, NH$_2$, NHCH$_3$, N(CH$_3$)$_2$, OCF$_2$H, OCF$_2$Br or N(OCH$_3$)CH$_3$;
(2) when X or Y is C$_1$ haloalkoxy, then Z is CH;
(3) when W is S, then R is H, Z is CH and Y is CH$_3$, OCH$_3$, OC$_2$H$_5$, CH$_2$OCH$_3$, C$_2$H$_5$, CF$_3$, SCH$_3$, OCH$_2$CH=CH$_2$, OCH$_2$C≡CH, OCH$_2$CH$_2$OCH$_3$, CH(OCH$_3$)$_2$ or

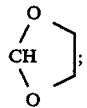

(4) when the total number of carbon atoms of X and Y is greater than four, then the combined number of carbons of R$_1$ and R$_2$ is less than or equal to six;
(5) when R$_2$ is —C(O)R$_{17}$, —C(R$_{23}$)(R$_{17}$)Cl or —C(R$_{24}$)(R$_{17}$)Br then Y is other than cyclopropyl;
(6) when Y is C$_2$-C$_5$ alkylthioalkyl, C$_2$-C$_5$ alkylsulfinylalkyl or C$_2$-C$_5$ alkylsulfonylalkyl, then R$_2$ is other than —CH(R$_{17}$)NO$_2$,

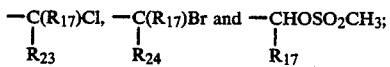

(7) when R$_4'$ is C$_1$-C$_2$ alkoxy and R$_5'$ is H, then R$_2$ is other than CH(R$_{17}$)CN, C(R$_{23}$)(R$_{17}$)Cl and C(R$_{24}$)(R$_{17}$)Br;
(8) when R$_2$ is C(O)R$_{17}$, C(R$_{23}$)(R$_{17}$)Cl or C(R$_{24}$)(R$_{17}$)Br, then R$_1$ is other than C$_1$-C$_4$ haloalkyl or C$_2$ alkyl substituted with C$_1$-C$_2$ alkoxy, OH or C$_1$-C$_2$ alkylthio;
(9) when R$_2$ is C(R$_{23}$)(R$_{17}$)Cl or C(R$_{24}$)(R$_{17}$)Br, then X and Y are other than C$_1$-C$_4$ haloalkoxy or C$_1$-C$_4$ haloalkylthio;
(10) when R$_2$ is C(R$_{23}$)(R$_{17}$)Cl or C(R$_{24}$)(R$_{17}$)Br, then R$_1$ is other than C$_1$-C$_4$ haloalkoxy, C$_3$-C$_4$ alkenyloxy, C$_2$-C$_4$ haloalkenyloxy, C$_2$-C$_4$ alkynyl, C$_3$-C$_4$ alkynyloxy, C$_2$-C$_4$ haloalkenyl and R$_1$—A through R$_1$—W;
(11) when R$_1$ is R$_1$—X, R$_1$—Y, R$_1$—Z, R$_1$—AA, R$_1$—AB, R$_1$—AC or R$_1$—AD, then R$_2$ is other than CH(R$_{16}$)CN, C(R$_{23}$)—(R$_{17}$)Cl and C(R$_{24}$)(R$_{17}$)Br;
(12) when R$_2$ is C(O)R$_{17}$, then R$_1$ is other than SO$_2$NR$_4'$R$_5'$; and
(13) when R$_2$ is CO$_2$R$_3$, then both R$_{12}$ and R$_{13}$ are other than H.

2. A compound of claim 1 where
W is O.

3. A compound of claim 2 where
E is a single bond;
X is C$_1$-C$_2$ alkyl, C$_1$-C$_2$ alkoxy, Cl, F, Br, I, OCF$_2$H, CH$_2$F, CF$_3$, OCH$_2$CH$_2$F, OCH$_2$CHF$_2$, OCH$_2$CF$_3$, CH$_2$Cl or CH$_2$Br; and Y is H, C$_1$-C$_2$ alkyl, C$_1$-C$_2$ alkoxy, CH$_2$OCH$_3$, CH$_2$OCH$_2$CH$_3$, NHCH$_3$, N(OCH$_3$)CH$_3$, N(CH$_3$)$_2$, CF$_3$, SCH$_3$, OCH$_2$CH=CH$_2$, OCH$_2$C≡CH, OCH$_2$CH$_2$OCH$_3$, CH$_2$SCH$_3$,

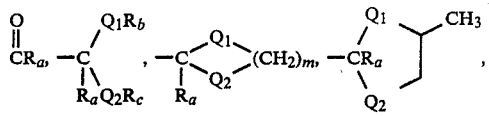

OCF$_2$H, SCF$_2$H, OCF$_2$Br, cyclopropyl, C≡CH or C≡CCH$_3$;
Z is CH;
R$_a$ is H or CH$_3$;
R$_{23}$ is H; and
R$_{24}$ is H.

4. A compound of claim 3 where
R$_2$ is —CH$_2$CN, —CH$_2$N$_3$,

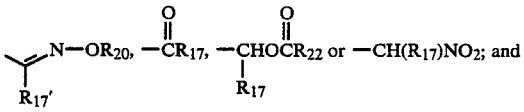

R$_{17}'$ is H, C$_1$-C$_2$ alkyl, Cl or CN.

5. A compound of claim 4 where
R$_1$ is F, Cl, Br, NO$_2$, C$_1$-C$_3$ alkyl, C$_1$-C$_2$ alkyl substituted with 1-3 F or Cl or 1 Br, C$_2$-C$_3$ alkenyl, C$_2$-C$_3$ alkenyl substituted with 1-3 F or Cl, C$_1$-C$_2$ alkoxy, C$_1$-C$_2$ alkoxy substituted with 1-3 F or Cl or 1-Br, allyloxy, propargyloxy, OC(Cl)=CHCl, CO$_2$CH$_3$, CO$_2$C$_2$H$_5$, CO$_2$CH$_2$CH=CH$_2$, CO$_2$CH$_2$CH$_2$Cl, CO$_2$CH$_2$CH$_2$OCH$_3$, CONH(-C$_1$-C$_2$ alkyl), CONCH$_3$(C$_1$-C$_2$ alkyl), SO$_2$N-(OCH$_3$)CH$_3$, SO$_2$NH(C$_1$-C$_2$ alkyl), SO$_2$N(C$_1$-C$_2$ alkyl)$_2$, S(O)$_n$C$_1$-C$_3$ alkyl, OSO$_2$C$_1$-C$_3$ alkyl, C$_1$-C$_2$ alkyl substituted with OCH$_3$ or SCH$_3$, C$_6$H$_5$ and R$_1$—A, R$_1$—B, R$_1$—C, R$_1$—D, R$_1$—E, R$_1$—F, R$_1$—G, R$_1$—H, R$_1$—I, R$_1$—J, R$_1$—K, R$_1$—L, R$_1$—M, R$_1$—N, R$_1$—O, R$_1$—P, R$_1$—Q, R$_1$—R, R$_1$—S, R$_1$—T, R$_1$—U, R$_1$—V, R$_1$—W, R$_1$—X, R$_1$—Y, R$_1$—Z, R$_1$—AA, R$_1$—AB, R$_1$—AC or R$_1$—AD.

6. A compound of claim 5 where
X is CH$_3$, OCH$_3$, OCH$_2$CH$_3$, Cl, OCF$_2$H or OCH$_2$CF$_3$; and
Y is CH$_3$, OCH$_3$, C$_2$H$_5$, CH$_2$OCH$_3$, NHCH$_3$ or CH(OCH$_3$)$_2$.

7. A compound of claim 6 where
R is H;
R$_1$ is F, Cl, Br, NO$_2$, CH$_3$, CF$_3$ C$_1$-C$_2$ alkoxy, allyloxy, OC(Cl)=CHCl, CO$_2$CH$_3$, CO$_2$C$_2$H$_5$, CO$_2$NHCH$_3$, CO$_2$N(CH$_3$)$_2$, SO$_2$NHCH$_3$ SO$_2$N(CH$_3$)$_2$, SO$_2$CH$_3$, SO$_2$C$_2$H$_5$, OSO$_2$CH$_3$, OSO$_2$C$_2$H$_5$, R$_1$—A, R$_1$—B, R$_1$—C, R$_1$—X, R$_1$—Z or R$_1$—AB; and R$_X$ is H.

8. The compound of claim 1 that is 2-(cyanomethyl)-6-[[(4,6-dimethoxypyrimidin-2-yl)aminocarbonyl]aminosulfonyl]benzoic acid, ethyl ester.

9. A composition suitable for controlling the growth of undesired vegetation which comprises an effective amount of a compound of claim 1 and at least one of the following: surfactant, solid inert diluent or liquid inert diluent and mixtures of the foregoing.

10. A composition suitable for controlling the growth of undesired vegetation which comprises an effective amount of a compound of claim 2 and at least one of the following: surfactant, solid inert diluent or liquid inert diluent and mixtures of the foregoing.

11. A composition suitable for controlling the growth of undesired vegetation which comprises an effective amount of a compound of claim 3 and at least one of the following: surfactant, solid inert diluent or liquid inert diluent and mixtures of the foregoing.

12. A composition suitable for controlling the growth of undesired vegetation which comprises an effective amount of a compound of claim 4 and at least one of the following: surfactant, solid inert diluent or liquid inert diluent and mixtures of the foregoing.

13. A composition suitable for controlling the growth of undesired vegetation which comprises an effective amount of a compound of claim 5 and at least one of the following: surfactant, solid inert diluent or liquid inert diluent and mixtures of the foregoing.

14. A composition suitable for controlling the growth of undesired vegetation which comprises an effective amount of a compound of claim 6 and at least one of the following: surfactant, solid inert diluent or liquid inert diluent and mixtures of the foregoing.

15. A composition suitable for controlling the growth of undesired vegetation which comprises an effective amount of a compound of claim 7 and at least one of the following: surfactant, solid inert diluent or liquid inert diluent and mixtures of the foregoing.

16. A composition suitable for controlling the growth of undesired vegetation which comprises an effective amount of the compound of claim 8 and at least one of the following: surfactant, solid inert diluent or liquid inert diluent and mixtures of the foregoing.

17. A method for controlling the growth of undesired vegetation which comprises applying to the locus to be protected an effective amount of a compound of claim 1.

18. A method for controlling the growth of undesired vegetation which comprises applying to the locus to be protected an effective amount of a compound of claim 2.

19. A method for controlling the growth of undesired vegetation which comprises applying to the locus to be protected an effective amount of a compound of claim 3.

20. A method for controlling the growth of undesired vegetation which comprises applying to the locus to be protected an effective amount of a compound of claim 4.

21. A method for controlling the growth of undesired vegetation which comprises applying to the locus to be protected an effective amount of a compound of claim 5.

22. A method for controlling the growth of undesired vegetation which comprises applying to the locus to be protected an effective amount of a compound of claim 6.

23. A method for controlling the growth of undesired vegetation which comprises applying to the locus to be protected an effective amount of a compound of claim 7.

24. A method for controlling the growth of undesired vegetation which comprises applying to the locus to be protected an effective amount of the compound of claim 8.

* * * * *

UNITED STATES PATENT AND TRADEMARK OFFICE
CERTIFICATE OF CORRECTION

PATENT NO. : 4,927,453
DATED : May 22, 1990
INVENTOR(S) : Stephen Kenneth Gee

It is certified that error appears in the above-identified patent and that said Letters Patent is hereby corrected as shown below:

Column 6, line 35, "$R_{17}$ is H, $C_1$-$C_2$ alkyl, CN, Cl, $OCH_3$, $SCH_3$ or" should read --$R_{17}'$ is H, $C_1$-$C_2$ alkyl, CN, Cl, $OCH_3$, $SCH_3$ or--.

Column 109, line 67, "$R_3$ is $C_1$-$C_4$ alkyl, $C_3$-$C_4$ alkenyl, $C_3$-$C_4$ or alkynyl," should read --$R_3$ is $C_1$-$C_4$ alkyl, $C_3$-$C_4$ alkenyl, $C_3$-$C_4$ alkynyl,--.

Signed and Sealed this

Thirtieth Day of June, 1992

Attest:

DOUGLAS B. COMER

Attesting Officer    Acting Commissioner of Patents and Trademarks